(12) United States Patent
Yaghi et al.

(10) Patent No.: US 9,669,098 B2
(45) Date of Patent: *Jun. 6, 2017

(54) METAL-ORGANIC FRAMEWORKS WITH EXCEPTIONALLY LARGE PORE APERATURES

(71) Applicant: The Regents of the University of California, Oakland, CA (US)

(72) Inventors: Omar M. Yaghi, Berkeley, CA (US); Hiroyasu Furukawa, Berkeley, CA (US); Hexiang Deng, Albany, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/797,312

(22) Filed: Jul. 13, 2015

(65) Prior Publication Data

US 2016/0008472 A1 Jan. 14, 2016

Related U.S. Application Data

(63) Continuation of application No. 13/650,232, filed on Oct. 12, 2012, now Pat. No. 9,078,922.

(Continued)

(51) Int. Cl.
*A61K 38/00* (2006.01)
*A61K 47/24* (2006.01)
(Continued)

(52) U.S. Cl.
CPC ............ *A61K 47/24* (2013.01); *A61K 38/00* (2013.01); *B01D 53/02* (2013.01); *B01J 20/0225* (2013.01); *B01J 20/226* (2013.01); *B01J 20/28016* (2013.01); *B01J 20/28066* (2013.01); *B01J 20/28073* (2013.01); *B01J 20/28076* (2013.01); *C02F 1/285* (2013.01);
(Continued)

(58) Field of Classification Search
CPC ..... A61K 47/24; A61K 38/00; B01J 20/0225; B01J 20/28076; B01J 20/28066; B01J 20/28016; B01J 20/28073; C07F 3/02; C07F 3/06
USPC .......................... 514/1.1, 492; 424/489, 499
See application file for complete search history.

(56) References Cited

U.S. PATENT DOCUMENTS 2,684,967 A 7/1954 Berg
4,532,225 A 7/1985 Tsao et al.
(Continued)

FOREIGN PATENT DOCUMENTS

DE 102005023856 A1 11/2006
DE 102005054523 A1 5/2007
(Continued)

OTHER PUBLICATIONS

Stallmach et al., "NMR Studies on the Diffusion of Hydrocarbons on the Metal-Organic Framework Material MOF-5," Angew. Chem. Int. Ed. 45:2123-2126 (2006).

(Continued)

*Primary Examiner* — Porfirio Nazario Gonzalez
(74) *Attorney, Agent, or Firm* — Gavrilovich, Dodd & Lindsey LLP

(57) ABSTRACT

The disclosure relates to metal organic frameworks or isoreticular metal organic frameworks, methods of production thereof, and methods of use thereof.

16 Claims, 34 Drawing Sheets

Related U.S. Application Data

(60) Provisional application No. 61/547,031, filed on Oct. 13, 2011.

(51) Int. Cl.

| | | |
|---|---|---|
| *C07F 3/02* | (2006.01) | |
| *C07F 3/06* | (2006.01) | |
| *B01J 20/22* | (2006.01) | |
| *B01D 53/02* | (2006.01) | |
| *C02F 1/28* | (2006.01) | |
| *C07F 5/02* | (2006.01) | |
| *C07K 14/435* | (2006.01) | |
| *C07F 7/22* | (2006.01) | |
| *B01J 20/28* | (2006.01) | |
| *B01J 20/02* | (2006.01) | |

(52) U.S. Cl.
CPC .............. *C07F 3/02* (2013.01); *C07F 3/06* (2013.01); *C07F 5/025* (2013.01); *C07F 7/2224* (2013.01); *C07K 14/435* (2013.01); *B01D 2253/204* (2013.01); *B01J 2220/58* (2013.01)

(56) References Cited

U.S. PATENT DOCUMENTS

| | | |
|---|---|---|
| 5,064,804 A | 11/1991 | Soo et al. |
| 5,160,500 A | 11/1992 | Chu et al. |
| 5,208,335 A | 5/1993 | Ramprasad et al. |
| 5,648,508 A | 7/1997 | Yaghi et al. |
| 5,733,505 A | 3/1998 | Goldstein et al. |
| 6,479,447 B2 | 11/2002 | Bijl et al. |
| 6,501,000 B1 | 12/2002 | Stilbrany et al. |
| 6,617,467 B1 | 9/2003 | Mueller et al. |
| 6,624,318 B1 | 9/2003 | Mueller et al. |
| 6,893,564 B2 | 5/2005 | Mueller et al. |
| 6,929,679 B2 | 8/2005 | Mueller et al. |
| 6,930,193 B2 | 8/2005 | Yaghi et al. |
| 7,196,210 B2 | 3/2007 | Yaghi et al. |
| 7,202,385 B2 | 4/2007 | Mueller et al. |
| 7,279,517 B2 | 10/2007 | Mueller et al. |
| 7,309,380 B2 | 12/2007 | Mueller et al. |
| 7,343,747 B2 | 3/2008 | Mueller et al. |
| 7,411,081 B2 | 8/2008 | Mueller et al. |
| 7,524,444 B2 | 4/2009 | Hesse et al. |
| 7,582,798 B2 | 9/2009 | Yaghi et al. |
| 7,637,983 B1 | 12/2009 | Liu et al. |
| 7,652,132 B2 | 1/2010 | Yaghi et al. |
| 7,662,746 B2 | 2/2010 | Yaghi et al. |
| 7,799,120 B2 | 9/2010 | Yaghi et al. |
| 7,815,716 B2 | 10/2010 | Mueller et al. |
| 9,078,922 B2 * | 7/2015 | Yaghi ............... A61K 47/24 |
| 2003/0004364 A1 | 1/2003 | Yaghi et al. |
| 2003/0078311 A1 | 4/2003 | Mueller et al. |
| 2003/0148165 A1 | 8/2003 | Mueller et al. |
| 2003/0222023 A1 | 12/2003 | Mueller et al. |
| 2004/0081611 A1 | 4/2004 | Mueller et al. |
| 2004/0225134 A1 | 11/2004 | Yaghi et al. |
| 2004/0249189 A1 | 12/2004 | Mueller et al. |
| 2004/0265670 A1 | 12/2004 | Mueller et al. |
| 2005/0004404 A1 | 1/2005 | Mueller et al. |
| 2005/0014371 A1 | 1/2005 | Tsapatsis |
| 2005/0124819 A1 | 6/2005 | Yaghi et al. |
| 2005/0154222 A1 | 7/2005 | Mueller et al. |
| 2005/0192175 A1 | 9/2005 | Yaghi et al. |
| 2006/0057057 A1 | 3/2006 | Mueller et al. |
| 2006/0135824 A1 | 6/2006 | Mueller et al. |
| 2006/0154807 A1 | 7/2006 | Yaghi et al. |
| 2006/0185388 A1 | 8/2006 | Mueller et al. |
| 2006/0252641 A1 | 11/2006 | Yaghi et al. |
| 2006/0252972 A1 | 11/2006 | Pilliod et al. |
| 2006/0287190 A1 | 12/2006 | Eddaoudi et al. |
| 2007/0068389 A1 | 3/2007 | Yaghi et al. |
| 2007/0202038 A1 | 8/2007 | Yaghi et al. |
| 2007/0248575 A1 | 10/2007 | Conner et al. |
| 2008/0017036 A1 | 1/2008 | Schultink et al. |
| 2008/0184883 A1 | 8/2008 | Zhou et al. |
| 2009/0155588 A1 | 6/2009 | Hesse et al. |
| 2010/0132549 A1 | 6/2010 | Yaghi et al. |
| 2010/0143693 A1 | 6/2010 | Yaghi et al. |
| 2010/0186588 A1 | 7/2010 | Yaghi et al. |
| 2010/0286022 A1 | 11/2010 | Yaghi et al. |
| 2011/0137025 A1 | 6/2011 | Yaghi et al. |

FOREIGN PATENT DOCUMENTS

| | | |
|---|---|---|
| EP | 1674555 A1 | 6/2006 |
| WO | 2004101575 A2 | 11/2004 |
| WO | 2006047423 A2 | 5/2006 |
| WO | 2006072573 A2 | 7/2006 |
| WO | 2006110740 A2 | 10/2006 |
| WO | 2006116340 A1 | 11/2006 |
| WO | 2007101241 A2 | 9/2007 |
| WO | 2007111739 A2 | 10/2007 |
| WO | 2008091976 A1 | 7/2008 |
| WO | 2008138989 A1 | 11/2008 |
| WO | 2008140788 A1 | 11/2008 |
| WO | 2009020745 A9 | 2/2009 |
| WO | 2009042802 A1 | 4/2009 |
| WO | 2009056184 A1 | 5/2009 |
| WO | 2009149381 A3 | 12/2009 |
| WO | 2010056092 A9 | 5/2010 |
| WO | 2010078337 A1 | 7/2010 |
| WO | 2010080618 A1 | 7/2010 |
| WO | 2010083418 A1 | 7/2010 |
| WO | 2010088629 A1 | 8/2010 |
| WO | 2010090683 A1 | 8/2010 |
| WO | 2010148276 A3 | 12/2010 |
| WO | 2010148296 A3 | 12/2010 |
| WO | 2010148374 A2 | 12/2010 |
| WO | 2011014503 A1 | 2/2011 |
| WO | 2011038208 A2 | 3/2011 |
| WO | 2011146155 A9 | 11/2011 |
| WO | 2012012495 A2 | 1/2012 |
| WO | 2012082213 A2 | 6/2012 |
| WO | 2012100224 A3 | 7/2012 |
| WO | 2012106451 A2 | 8/2012 |

OTHER PUBLICATIONS

Sudik et al., "Design, Synthesis, Structure, and Gas (N2, Ar, CO2, CH4 and H2) Sorption Properties of Porous Metal-Organic Tetrahedral and Heterocuboidal Polyhedra," J. Am. Chem. Soc. 127:7110-7118 (2005).

Sudik et al., "Metal-Organic Frameworks Based on Trigonal Prismatic Building Blocks and the New "acs" Topology," Inorg. Chem. 44:2998-3000 (2005).

Sudik et al., "A Metal-Organic Framework with a Hierarchical System of Pores and Tetrahedral Bbuilding Blocks," Angew. Chem. Int. Ed. 45:2528-2533 (2006).

Tranchemontagne et al. "Metal-Organic Frameworks with High Capacity and Selectivity for Harmful Gases," Proc. Natl. Acad. Sci. USA 105:11623-11627 (2008).

Tranchemontagne et al., "Reticular Chemistry of Metal-Organic Polyhedra," Angew. Chem. Int. Ed., 2008, 47:5136-5147 (2008).

Tranchemontagne et al., "Room Temperature Synthesis of Metal-organic Frameworks: MOF-5, MOF-74, MOF-177, MOF-199, and IRMOF-0," Tetrahedron 64:8553-8557 (2008).

Tranchemontagne et al. "Secondary Building Units, Nets and Bonding in the Chemistry of Metal-Organic Frameworks," Chem. Soc. Rev. 38:1257-1283 (2009).

Uribe-Romo et al., "A Crystalline Imine-Linked 3-D Porous Covalent Organic Framework," J. Am. Chem. Soc. 131:4570-4571 (2009).

Uribe-Romo et al., "Crystalline Covalent Organic Frameworks with Hydrazone Linkages," J. Am. Chem. Soc. 133:11478-11481 (2011).

Vairaprakash et al., "Synthesis of Metal-Organic Complex Arrays," J. Am. Chem. Soc. 133:759-761 (2011).

(56) References Cited

OTHER PUBLICATIONS

Valente et al., "Metal-organic Frameworks with Designed Chiral Recognition Sites," Chem. Commun. 46: 4911-4913 (2010).
Vodak et al., "Metal-Organic Frameworks Constructed from Pentagonal Antiprismatic and Cuboctahedral Secondary Building Units," Chem. Commun. 2534-2535 (2001).
Vodak et al., "One-Step Synthesis and Structure of an Oligo(spiro-orthocarbonate)," J. Am. Chem. Soc.124 (18):4942-4943 (2002).
Vodak et al., "Computation of Aromatic C3N4 Networks and Synthesis of the Molecular Precursor N(C3N3)3C16," Chem. Eur. J. 9:4197-4201 (2003).
Walton et al., "Understanding Inflections and Steps in Carbon Dioxide Adsorption Isotherms in Metal-Organic Frameworks," J. Am. Chem. Soc.130:406-407 (2008).
Wang et al., "Colossal Cages in Zeolitic Imidazolate Frameworks as Selective Carbon Dioxide Reservoirs," Nature 453:207-211 (2008).
Wong-Foy, Ag et al., "Exceptional H2 saturation uptake in microporous metal-organic frameworks" J. Am. Chem. Soc., 2006, 128, pp. 3494-3495.
Yaghi et al., "Selective binding and removal of guests in a microporous metal-organic framework," Nature, Dec. 1995, pp. 703-706, vol. 378.
Yaghi et al., "Conversion of Hydrogen-Bonded manganese(II) and zinc(II) squarate (C4O42-) molecules, Chains, and Sheets to 3-D Cage Networks," J. Chem. Soc., Dalton Trans., 1995, 727-732.
Yaghi et al., "Presence of Mutually Interpenetrating Sheets and Channels in the Extended Structure of Cu(4,4'-Bipyndine)Cl," Angew. Chem. Int. Ed. Engl., 1995, 34, 207-209.
Yaghi et al., "The Utility of Polymeric Matrices in the Preparation of Single Crystals of Coordination Solids: Synthesis and Structure of CuII(1,4-C4H4N2)(C4O4)(OH2)4," J. Solid State Chem., 1995, 117, 256-260.
Yaghi et al., "Open-Framework Solids with Diamond-Like Structures Prepared from Clusters and Metal-Organic Building Blocks,"Mater. Res. Soc. Symp. Proc., 1995, 371, 15.
Yaghi et al., "Hydrothermal Synthesis of a Metal-Organic Framework Containing Large Rectangular Channels," J. Am. Chem. Soc., 1995, 117, 10401-10402.
Yaghi et al., "Construction of Microporous Materials from Molecular Building Blocks," Fundamental Materials Research, T. J. Pinnavaia and M. F. Thorpe, eds., vol. II, Plenum: New York, p. 111 (1995).
Yaghi et al., "T-Shaped Molecular Building Units in the Porous Structure of Ag(4,4'-bpy) NO3," J. Am. Chem. Soc., 1996, 118, 295-296.
Yaghi et al., "Construction of Porous Solids from Hydrogen-Bonded Metal Complexes of 1,3,5-Benzenetricarboxylic Acid," J. Am. Chem. Soc., 1996, 118, 9096-9101.
Yaghi et al., "Conversion of Molecules and Clusters to Extended 3-D Cage and Channel Networks," Metal Containing Polymeric Materials, C. U. Pittman, C. E. Carraher, B. M. Culbertson, M. Zeldin, J. E. Sheets, Eds., Plenum: New York, p. 219 (1996).
Yaghi et al., "Selective Guest Binding by Tailored Channels in a 3-D Porous Zinc(II)-1,3,5-Benzenetricarboxylate Network," J. Am. Chem. Soc., 1997, 119, 2861-2868.
Yaghi et al., "Crystal Growth of Extended Solids by Nonaqueous Gel Diffusion," Chem. Mater., 1997, 9, 1074-1076.
Yaghi et al., "A Molecular Railroad with Large Pores: Synthesis and Structure of Ni(4,4'-bpy)2.5(H2O)2(ClO4)2·1.5 (4,4'-bpy)2(H2O)," Inorg. Chem., 1997, 36, 4292-4293.
Yaghi et al., "Construction of a New Open-Framework Solid form 1,3,5-Cyclohexanetricarboxylate and Zinc(II) Building Blocks," J. Chem. Soc. Dalton Trans. 2383-2384 (1997).
Yaghi et al., "Synthesis and Structure of a Metal-Organic Solid Having the Cadmium (II) Sulfate Net," Mater. Res. Soc. Symp. Proc. 453:127 , (1997).
Yaghi et al., "Designing Microporosity in Coordination Solids," Modular Chemistry, J. Michl, Ed., Kluwer: Boston, p. 663 (1997).

Yaghi et al., "Synthetic Strategies, Structure Patterns, and Emerging Properties in the Chemistry of Modular Porous Solids," Acc. Chem. Res. 31:474-484 (1998).
Yaghi et al., "Transformation of Germanium Dioxide to 4-Connected Porous Germanate Net," J. Am. Chem. Soc., 20:10569-10570 (1998).
Yaghi et al., "Design of Solids from Molecular Building Blocks: Golden Opportunities for Solid State Chemistry," J. Solid State Chem. 152, 1-2 (2000).
Yaghi et al., "A Molecular World Full of Holes," Chem. Innov. p. 3 (2000).
Yaghi et al., "Reticular Synthesis and the Design of New Materials," Nature 423:705-714 (2003).
Yaghi et al., "Metal-Organic Frameworks: A Tale of Two Entanglements," Nature materials 6:92-93 (2007).
Yaghi et al., "Reticular Chemistry and Metal-Organic Frameworks for Clean Energy," MRS Bulletin 34:682-690 (2009).
Young, Lee W., International Search Report and Written Opinion, Date of Mailing of Report: May 7, 2008, International Application No. PCT/US08/51859.
Young, Lee W., "International search Report and Written Opinion," PCT/US08/06008, United States Patent & Trademark Office, Aug. 20, 2008.
Young, Lee W., International Search Report and Written Opinion, Date of Mailing: Dec. 2, 2008, International Application No. PCT/US08/77741.
Young, Lee W., International Search Report and Written Opinion, Date of Mailing: Jan. 12, 2009, International Application No. PCT/US08/70149.
Young, Jung Doo. International Search Report for PCT/US2010/050170. Date of Mailing: Jun. 8, 2011.
Zhang et al., "Docking in Metal-Organic Frameworks," Science 325:855-859 (2009).
Zhao et al., "Rigid-Strut-Containing Crown Ethers and [2]Catenanes for Incorporation into Metal-Organic Frameworks," Chem. Eur. J. 15:13356-13380 (2009).
Zhao, Wei. The First Office Action for Chinese Application No. 200880003157.2. The State Intellectual Property Office of the People's Republic of China. Issue Date: Aug. 5, 2011.
Zhofu et al., "A Nearly Planar Water Sheet Sandwiched between Strontium-Imidazolium Carboxylate Coordination Polymers," Inorg. Chem. 44:5200-5202 (2005).
Costa et al., "Chemical Modification of a Bridging Ligand Inside a Metal-Organic Framework while Maintaining the 3D Structure," Eur. J. Inorg. Chem. 10:1539-1545 (2008).
Cui et al., "Iln Situ Hydrothermal Growth of Metal-Organic Framework 199 Films on Stainless Steel Fibers for Solid-Phase Microextraction of Gaseous Benzene Homologues," Anal. Chem. 81(23):9771-9777 (2009).
Dugan et al., "Covalent modification of a metal-organic framework with isocyanates: probing substrate scope and reactivity," 29:3366-3368 (2008).
Luo et al., "Two new metal-triazole-benzenedicarboxylate frameworks affording an uncommon 3,4-connected net and unique 4,6-connected rod packing: hydrothermal synthesis, structure, thermostability and luminescence studies," CrystEngComm 11(6):1097-1102 (2009).
Galli et al., "Adsorption of Harmful Organic Vapors by Flexible Hydrophobic Bis-pyrazolate Based MOFs," Chem. Mater. 22(5):1664-1672 (2010).
Ingleson et al., "Framework fractionalization triggers metal complex binding," Chem. Comm. 23:2680-2682 (2008).
Li et al., "Synthesis and Structural Characterization of a New 3D Lead Coordination Polymer with a Tetrazole-1- acetate Ligand, " Chinese J. Struct. Chem. 30(7):1049-1053 (2011).
Ling et al., "A zinc(II) metal-organic framework based on triazole and dicarboxylate ligands for selective adsorption of hexane isomers," Chem. Comm. 47:7197-7199 (2011).
Natarajan et al., "Non-carboxylate based metal-organic frameworks (MOFs) and related aspects," Current Opinion in Solid State and Materials Science 13(3-4):46-53 (2009).

(56) References Cited

OTHER PUBLICATIONS

Nickitas-Etienne, Athina, International Preliminary Report on Patentability for PCT/US2009/068731. Date of Issuance of the Report: Jun. 21, 2011.
Peterson et al., "Ammonia Vapor Removal by Cu3(BTC)2 and Its Characterization by MAS NMR," J. Phys. Chem. C. 113(32):13906-13917 (2009).
Seo et al., "A homochiral metal-organic porous material for enantioselective separation and catalysis," Nature 404:982-986 (2000).
Sigma-Aldrich, Basolite C300 (MOF-199), catalog No. 688614; http://www.sigmaaldrich.com/catalog/ProductDetail.do?D7=0 &N5=SEARCH_CONCAT_PNO%7CBRAND_KEY &N4=688614%7CALDRICH&N25=0&QS=ON&F=SPEC.
Song et al., "Hydrothermal Synthesis and Structural Characterization of Three-dimensional Metal-organic Framework [Zn3(C2H2N3)2(C7H5O2)4]," Chem. Res. Chinese Universities 25(1):1-4 (2009).
Tanabe et al., "Systematic Functionalization of a Metal-Organic Framework via a Postsynthetic Modification Approach," J. Am. Chem. Soc. 130(26):8508-8517 (2008).
Vitillo et al., "Role of Exposed Metal Sites in Hydrogen Storage in MOFs," J. Am. Chem. Soc. 130(26):8386-8396 (2008).
Wang et al., "Postsynthetic Covalent Modification of a Neutral Metal-Organic Framework," J. Am. Chem. Soc. 129 (41):12368-12369 (2007).
Wang et al., "Tandem Modification of Metal-Organic Frameworks by a Postsynthetic Approach," Angew. Chem. Int. 47:4699-4702 (2008).
Yaghi, Omar., "Porous Crystals for Carbon Dioxide Storage," slide presentation at the Fifth Annual Conference on Carbon Capture & Sequestration, US Department of Energy on May 10, 2006 http://www.netl.doe.gov/publications/proceedings/06/carbon-seq/Tech %20Session%20193.pdf.
Yaghi, Omar, "Hydrogen Storage in Metal-Organic Frameworks," slide presentation to DOE Hydrogen Program 2007 Annual Merit Review, US Department of Energy, on May 15, 2007 at http://www.hydrogen.energy.gov/pdfs/review07/st_10_yaghi.pdf.
Yang et al., "Four Novel Three-Dimensional Triazole-Based Zinc(II) Metal-Organic Frameworks Controlled by the Spacers of Dicarboxylate Ligands: Hydrothermal Synthesis, Crystal Structure, and Luminescence Properties," Crystal Growth Design 7(10):2009-2015 (2007).
Yang et al. "Two Novel Triazole-Based Metal-Organic Frameworks Consolidated by a Flexible Dicarboxylate Co-ligand: Hydrothermal Synthesis, Crystal Structure, and Luminiescence Properties," Australian Journal of Chemistry 61(10):813-820 (2008).
Zhang et al., "Crystal engineering of binary metal imidazolate and triazolate frameworks," Chem. Comm. 1689-1699 (2006).
Zhang et al., "Syntheses, Structures, and Porous/Luminescent Properties of Silver 3-Alkyl-1,2,4-Triazolate Frameworks with Rare 3-Connected Topologies," Crystal Growth and Design 11:796-802 (2011).
Adkins, Chinessa T. Nonfinal Office Action for U.S. Appl. 12/524,205. Mail Date Apr. 17, 2012.
Adkins, Chinessa T. Final Office Action for U.S. Appl. 12/524,205. Mail Date Sep. 27, 2012.
Barman et al., "Incorporation of active metal sites in MOFs via in situ generated ligand deficient metal-linker complexes" Chem. Commun. 47:11882-11884 (Oct. 11, 2011).
Bork, Ana-Marie., International Search Report for PCT/US2011/24671, European Patent Office, Nov. 30, 2011.
Chen et al., "Noncovalently Netted, Photoconductive Sheets with Extremely High Carrier Mobility and Conduction Anisotropy from Triphenylene-Fused Meetal Trigon Conjugates," In. J. Am. Chem. Soc. 131:7287-7297 (2009).
Choi et al., "Reversible Interpenetration in a Metal-Organic Framework Triggered by Ligand Removal and Addition," Angew. Chem. Int. Ed. 51:8791-8795 (2012).
Coskun et al., "Metal-Organic Frameworks Incorporating Copper-Complexed Rotaxanes," Angew. Chem. Int. Ed., 51:2160-2163 (2012).
Chun et al., "Concomitant Formation of N-Heterocyclic Carbene-Copper Comlexies within a Supramolecular Network in the Self-Assembly of Immidzolium Dicarboxylate with Metal Ions," Inorganic Chemistry, Jul. 20, 2009, pp. 6353-6355, vol. 48, No. 14.
Chun et al., "Cu2O: A versatile Reagent for Base-Free Direct Synthesis of NHC-Copper Complexes and Decoration of 3D-MOF with Coordinatively Unsaturated NHC-Copper Species," Organometallics, Mar. 16, 2010, pp. 1518-1521, vol. 29, No. 7.
Cordero Garcia, Marcela M. Nonfinal Office Action for U.S. Appl. No. 12/680,141. Mail Date Nov. 2, 2012.
Crees et al., "Synthesis of a Zinc(II) Imidazolium Dicarboxylate Logand Metal-Organic Framework (MOF): a Potential Precursor to MOF-Tethered N-Heterocyclic Carbene Compounds," Inorganic Chemistry, pp. 1712-1719, vol. 49, No. 4.
Fei et al., "A Nearly Planar Water Sheet Sandwiched between Strontium-Imidazolium Carboxylate Coordination Polymers," Inorg. Chem., 2005, pp. 5200-5202, vol. 44.
Fracaroli et al., "Isomers of Metal-Organic Complex Arrays," Inorg. Chem. 51: 6437-6439 (Jun. 5, 2012).
Furukawa et al., "Isoreticular Expansion of MetalOrganic Frameworks with Triangular and Square Building Units and the Lowest Calculated Density for Porous Crystals," Inorg. Chem. 50:9147-9152 (2011).
Gadzikwa, T. et al., "Selective Bifunctional Modification of a Non-catenated Metal-Organic Framework Material via Click Chemistry," J. Am. Chem. Soc. 131:13613-13615 (2009).
Gandara et al., "Porous, Conductive Metal-Triazolates and Their Structural Elucidation by the Charge-Flipping Method," Chem. Eur. J. 18:10595-10601 (2012).
Gassensmith et al., "Strong and Reversible Binding of Carbon Dioxide in a Green Metal-Organic Framework," J. Am. Chem. Soc. 133:15312-15315 (Aug. 30, 2011).
Goto, Y et al., "Clickable Metal-Organic Framework," J. Am. Chem. Soc. 130:14354-14355 (2008).
Hmadeh et al., "New Porous Crystals of Extended Metal-Catecholates," J. Chem. Mater. 24:3511-3513 (Aug. 28, 2012).
Jones, Christopher. Nonfinal Office Action for U.S. Appl. No. 12/598,855. Mail Date Jun. 14, 2012.
Jones, Christopher. Nonfinal Office Action for U.S. Appl. 12/598,855. Mail Date Oct. 12, 2012.
Koh et al., "A Crystalline Mesoporous Coordination Copolymer with High Microporosity," Angew Chem Int'l, 2008, pp. 677-680, vol. 47.
Deng, H. et al., "Large-Pore Apertures in a Series of Metal-Organic Frameworks," Science, vol. 336, No. 6084, May 12, 2012, pp. 1018-1023.
Doonan, Christian et al., "Hydrogen Storage in Metal-Organic Frameworks," Annual Merit Review Proceedings of DOE Hydrogen Program, May 22, 2009, pp. 1-27, XP008154814.
Eberhard, Michael, International Search Report and Written Opinion, PCT/US2012/059877, European Patent Office, Oct. 15, 2013.
Jeong, Kyung Seok et al., "Asymmetric catalytic reactions by NbO-type chiral metal-organic frameworks," Chemical Science, vol. 2, No. 5, Feb. 25, 2011, p. 877.
McDonald, Thomas M. et al., "Capture of Carbon Dioxide from Air and Flue Gas in the Alkylamine-Appended Metal-Organic Framework mmen-Mg 2 (dobpdc)", Journal of the American Chemical Society, vol. 134, No. 16, Apr. 4, 2012, pp. 7056-7065.
Rosi, Nathaniel L. et al., "Rod Packings and Metal-Organic Frameworks Constructed from Rod-Shaped Secondary Building Units", Journal of the American Chemical Society, vol. 127, No. 5, Jan. 13, 2005, pp. 1504-1518.
Wang, Feng et al., "Six new metal-organic frameworks with multi-carboxylic acids and imidazole-based spacers: syntheses, structures and properties", Dalton Transactions, vol. 40, No. 44, Oct. 5, 2011, p. 11856.
Weng, Danfeng et al., "Low pH hydrothermal synthesis and properties of lanthanide-organic frameworks with (410,65) (49,66) topology constructed from Ln-Hbptc building blocks," Dalton Transactions, No. 42, Jan. 1, 2007, p. 4822.

(56) References Cited

OTHER PUBLICATIONS

Andrew et al., "Post-Synthetic Modification of Tagged MOFs," Angew. Chem. Int. Ed. 47:8482-8486 (2008).
Ashton, Peter R. et al., "Hydrogen-Bonded Complexes of Aromatic Crown Ethers with (9-Anthracenyl) methylammonium Derivatives" J. Am. Chem. Soc., 1997, 119 (44), pp. 10641-10651.
Baharlou, Simin. International Preliminary Report on Patentability for PCT/US2009/046463. Date of Mailing: Dec. 16, 2010.
Banerjee et al., "High-Throughput Synthesis of Zeolitic Imidazolate Frameworks and Application to CO2 Capture," Science 319:939-943 (2008).
Banerjee et al., "Control of Pore Size and Functionality in Isoreticular Zeolitic Imidazolate Frameworks and their Carbon Dioxide Selective Capture Properties," J. Am. Chem. Soc. 131:3875-3877 (2009).
Barman et al., "Azulene Based Metal-Organic Frameworks for Strong Adsorption of H2," Chem. Commun. 46:7981-7983 (2010).
Barton et al., "Tailored Porous Materials," Chem. Mater. 11:2633-2656 (1999).
Bloch et al., "Metal Insertion in a Microporous Metal-Organic Framework Lined with 2,2'-Bipyridine" J. Am. Chem. Soc. 132:14382-14384 (2010).
Braun et al., "1,4-Benzenedicarboxylate Derivatives as Links in the Design of Paddle-Wheel Units and Metal-Organic Frameworks," Chem. Commun. 24:2532-2533 (2001).
Britt et al., "Highly efficient separation of carbon dioxide by a metal-organic framework replete with open metal sites," Proc. Natl. Acad. Sci. USA 106:20637-20640 (2009).
Britt et al., "Ring-Opening Reactions Within Metal-Organic Frameworks," Inorg. Chem. 49:6387-6389 (2010).
Carlucci et al., "Nanoporous three-dimensional networks topologically related to cooperite from the self-assembly of copper(I)centres and 1,2,4,5-tetracyanobenzene," New J. Chem. 23(23):397-401 (1999).
Carlucci, Lucia et al., "Polycatenation, polythreading and polyknotting in coordination network chemistry" Coordination Chemistry Reviews 246, 2003, pp. 247-289.
Caskey et al., "Dramatic Tuning of CO2 Uptake via Metal Substitution in a Coordination Polymer with Cylindrical Pores," JACS 130(33):10870-10871 (2008).
Caskey et al., "Selected Applications of Metal-Organic Frameworks in Sustainable Energy Technologies," Material Matters 4.4:111 (2009).
Centrone et al., "Raman Spectra of Hydrogen and Deuterium Adsorbed on a Metal-Organic Framework," Chem. Phys. Lett. 411:516-519 (2005).
Chae et al., "Tertiary Building Units: Synthesis, Structure, and Porosity of a Metal-Organic Dendrimer Framework (MOD-1)," J. Am. Chem. Soc. 123:11482-11483 (2001).
Chae et al., "Design of Frameworks with Mixed Triangular and Octahedral Building Blocks Exemplified by the Structure of [Zn4O(TCA)2] Having the Pyrite Topology," Angew. Chem. Int. Ed. 42:3907-3909 (2003).
Chae et al., "A Route to High Surface Area, Porosity and Inclusion of Large Molecules in Crystals," Nature427, 523-527 (2004); Featured in (1) Chemical & Engineering News magazine, Feb. 9, 2004, (2) BBC World Service, Feb. 4, (3) New Scientist, Feb. 4.
Chen et al., "Cu2(ATC)6H2O: Design of Open Metal Sites in Porous Metal-Organic Crystals (ATC: 1,3,5,7- adamantane tetracarboxylate)," J. Am. Chem. Soc. 122:11559-11560 (2000).
Chen et al., "Interwoven Metal-Organic Framework on a Periodic Minimal Surface with Extra-Large Pores," Science 291:1021-1023 (2001); Featured in Chemical and Engineering News, Feb. 21, 2001.
Chen et al., "Transformation of a Metal-Organic Framework from the NbO to PtS Net," Inorg. Chem. 41:181-183 (2005).
Chen et al., "High H2 Adsorption in a Microporous Metal-Organic Framework with Open-Metal Sites," Angew. Chem. Int. Ed. 44:4745-4749 (2005).
Chen et al., "A Microporous Metal-Organic Framework for Gas-Chomatographic Separation of Alkanes," Angew. Chem. Int. Ed. 45:1390-1393 (2006).
Cho et al., "A metal-organic framework material that functions as an enantioselective catalyst for olefin epoxidation," Chem. Comm. 24:2563-2565 (2006).
Choi et al., "Heterogeneity within Order in Crystals of a Porous Metal Organic Framework," J. Am. Chem. Soc. 133:11920-11923 (2011).
Cote et al., "Porous, Crystalline, Covalent Organic Frameworks," Science 310:1166-1170 (2005).
Cote et al., "Reticular Synthesis of Microporous and Mesoporous 2D Covalent Organic Frameworks," J. Am. Chem. Soc. 129:12914-12915 (2007).
Czaja et al., "Industrial applications of metal-organic frameworks," Chemical Society Reviews 38(5):1284-1293 (2009).
Delgado-Friedrichs et al., "Three-Periodic Nets and Tilings: Regular and Quasiregular Nets," Acta Cryst. A59:22-27 (2003).
Delgado-Friedrichs et al., "Three-Periodic Nets and Tilings: Semiregular Nets," Acta Cryst. A59:515-525 (2003).
Delgado-Friedrichs et al., "The CdSO4, Rutile, Cooperate and Quartz Dual Nets: Interpenetration and Catenation," Solid State Sciences 5:73-78 (2003).
Delgado-Friedrichs et al., "Reticular Chemistry: Occurrence and Taxonomy of Nets, and Grammar for the Design of Frameworks," Acc. Chem. Res. 38:176-182 (2005).
Delgado-Friedrichs et al. "What Do We Know About Three-Periodic Nets?," J. Solid State Chem. 178:2533-2554 (2005).
Delgado-Friedrichs et al. "Three-Periodic Nets and Tilings: Edge-Transitive Binodal Structures," Acta Cryst. 62:350-355 (2006).
Delgado-Friedrichs et al., "Taxonomy of Periodic Nets and the Design of Materials," Phys. Chem. 9:1035-1043 (2007).
Demessence, A et al., "Strong CO2 Binding in a Water-Stable, Triazolate-Bridged Metal-Organic Framework Funcionalized with Etylenediamine," J. Am. Chem. Soc. 131:8784-8786 (2009).
Demir et al., "Role of Copper Species in the Oxidative Dimerization of Arylboronic Acids: Synthesis of Symmetrical Biaryls," Journal of Organic Chemistry 68(26):10130-10134 (2003).
Deng et al., "Multiple Functional Groups of Varying Ratios in Metal-Organic Frameworks," Science 327:846-850 (2010).
Deng et al., "Robust dynamics" Nature Chem. 2:439-443 (2010).
Doonan et al., "Isoreticular Metalation of Metal-Organic Frameworks," J. Am. Chem. Soc. 131:9492-9493 (2009).
Doonan et al., "Exceptional ammonia uptake by a covalent organic framework," Nature Chem. 2:235-238 (2010).
Duren et al., "Design of New Materials for Methane Storage," Langmuir 20:2683-2689 (2004).
Eddaoudi et al., "Design and Synthesis of Metal-Organic Frameworks with Permanent Porosity," In Topics in Catalysis, G. A. Somorjai and J. M. Thomas, Eds., 9:105 (1999).
Eddaoudi et al., "Highly Porous and Stable Metal-Organic Framework: Structure Design and Sorption Properties," J. Am. Chem. Soc. 121:1391-1397 (2000).
Eddaoudi et al., "Porous Metal-Organic Polyhedra: 25 Å Cuboctahedron Constructed from Twelve Cu2(CO2)4 Paddle-Wheel Building Blocks," J. Am. Chem. Soc. 123:4368-4369 (2001).
Eddaoudi et al., "Modular Chemistry: Secondary Building Units as a Basis for the Design of Highly Porous and Robust Metal-Organic Carboxylate Frameworks" Acc. Chem. Res. 34:319-330 (2001).
Eddaoudi et al., "Geometric Requirements and Examples of Important Structures in the Assembly of Square Building Blocks," Proc. Natl. Acad. Sci. 99:4900-4904 (2002).
Eddaoudi et al., "Systematic Design of Pore Size and Functionality in Isoreticular Metal-Organic Frameworks and Application in Methane Storage," Science 295:469-472 (2002): Featured in (1) Chemical and Engineering News, Jan. 21, 2002, and (2) Chemical Insight magazine, Nov. 15, 2002.
Eddaoudi et al., "Cu2[o-Br-C6H3(CO2)2]2(H2O)2·(DMF)8(H2O)2: A Framework Deliberately Designed to have the NbO Structure Type," J. Am. Chem. Soc.124:376-377 (2002).

(56) References Cited

OTHER PUBLICATIONS

Becamel, Philippe, International Preliminary Report on Patentability, PCT/US2012/059877, The International Bureau of WIPO, Date of Mailing: Sep. 18, 2014.
Llabres et al., "MOFs as catalysts: Activity, reusability and shape-selectivity of a Pd-containing MOF," JOurnal of Catalysis 250(2):294-298.
Loeb, SJ, "Rotaxanes as ligands: from molecules to materials" Chemical Society reviews, 2007, 36, pp. 226-235.
Long et al., "The Pervasive Chemistry of Metal-Organic Frameworks," Chem. Soc. Rev. 38:1213-1214 (2009).
Lu et al., "Synthesis and Structure of Chemically Stable Metal-Organic Polyhedra," J. Am. Chem. Soc. 131:(35) 12532-12533 (2009).
Mendoza-Cortes et al., "Adsorption Mechanism and Uptake of Methane in Covalent Organic Frameworks: Theory and Experiment," J. Phys. Chem. 114:10824-10833 (2010).
Michalitsch, Richard. International Search Report and Written Opinion for PCT/US2009/069700. Date of Mailing: May 7, 2010.
Millward et al., "Metal-Organic Frameworks with Exceptionally High Capacity for Storage of Carbon Dioxide at Room Temperature," J. Am. Chem. Soc. 127:17998-17999 (2005).
Morris et al., "Crystals as Molecules: Postsynthesis Covalent Functionalization of Zeolitic Imidazolate Frameworks," J. Am. Chem. Soc. 130:12626-12627 (2008).
Morris et al., "A Combined Experimental—Computational Investigation of Carbon Dioxide Capture in a Series of Isoreticular Zeolitic Imidazolate Frameworks," J. Am. Chem. Soc. 132:11006-11008 (2010).
Morris et al., "Postsynthetic Modification of a Metal-Organic Framework for Stabilization of a Hemiaminal and Ammonia Uptake," Inorg. Chem. 50:6853-6855 (2011).
Moyse, Ellen, International Preliminary Report on Patentability and Written Opinion, Date of Issuance of Report: Nov. 17, 2009, International Application No. PCT/US08/006008.
Mulhausen, Dorothee. International Preliminary Report on Patentability for PCT/US2009/069700. Date of Mailing: Jul. 7, 2011.
Mulhausen, Dorothee. International Preliminary Report on Patentability for PCT/US2010/021201. Date of Mailing Jul. 28, 2011.
Ni et al,. "Porous Metal-Organic Truncated Octahedron Constructed from Paddle-Wheel Squares and Terthiophene Links," J. Am. Chem. Soc. 127:12752-12753 (2005).
Nickitas-Etienne, Athina, International Preliminary Report on Patentability and Written Opinion, Date of Issuance of Report: Jan. 19, 2010, International Application No. PCT/US08/70149.
Nickitas-Etienne, Athina. International Preliminary Report on Patentability for PCT/US2008/07741. Date of issuance of this report: Mar. 30, 2010.
Nickitas-Etienne, Athina. International Preliminary Report on Patentability for PCT/US2009/068849. Date of Mailing: Jun. 30, 2011.
Niu et al., "Synthesis and structural characterization of the one dimensional polymers [Rh2(OAc)4(NCPhCN)S, S=CH3COCH3, CH3OH, C2H5OH, C4H8O, and C6H6," Polyhedron 17(23-24):4079-89 (1998).
Novoa, Carlos, International Search Report and Written Opinion for PCT/US2010/021201, European Patent Office. Date of Mailing: Apr. 27, 2010.
Oisaki et al., "A Metal-Organic Framework with Covalently Bound Organometallic Complexes," J. Am. Chem. Soc. 132:9262-9264 (2010).
Wu et al., "Structural Study of New Hydrocarbon Nano-Crystals by Energy-Filtered Electron Diffraction," Ultramicroscopy 98:145-150 (2004).
O'Keefe et al., "Germanate Zeolites: Contrasting the Behavior of Germanate and Silicate Structures Built from Cubic T8O20 units (T=Si or Ge)," Chem. Eur. J. 5:2796-2801 (1999).
O'Keeffe et al., "Frameworks for Extended Solids: Geometrical Design Principles," J. Solid State Chem. 152:3-20 (2000).
O'Keeffe et al., "Reticular Chemistry—Present and Future Prospects—Introduction,"J. Solid State Chem.178:V-VI (2005).

O'Keeffe et al., "The Reticular Chemistry Structure Resource (RSCR) Database of, and Symbols for, Crystal Nets," Acc. Chem. Res. 41:1782-1789 (2008).
Park, Kyo Sung et al., "Exceptional chemical and thermal stability of zeolitic imidazolate frameworks," Proc. Natl. Acad. Sci., Jul. 5, 2006, pp. 10186-10191, vol. 103, No. 27.
Park, Jae Woo. International Search Report for PCT/US2010/039123. Date of Mailing: Feb. 24, 2011.
Patteux, Claudine. International Search Report for PCT/US2010/043373. Date of Mailing: Oct. 10, 2010.
Pawsey et al., "Hyperpolarized 129Xe Nuclear Magnetic Resonance Studies of Isoreticular Metal-Organic Frameworks," Phys. Chem. 111:6060-6067 (2007).
Phan et al., "Synthesis, Structure, and Carbon Dioxide Capture Properties of Zeolitic Imidazolate Frameworks," Acc. Chem. Res 43:58-67 (2009).
Phan et al., "Metal-Organic Frameworks of Vanadium as Catalysts for Conversion of Methane to Acetic Acid," Inorg. Chem. 50:7388-7390 (2011).
Plevert et al., "A Flexible Germanate Structure Containing 24-Ring Channels With Very Low Framework Density," J. Am. Chem. Soc. 123:12706-12707 (2001).
Plevert et al., "Synthesis and Characterization of Zirconogermanates," Inorg. Chem., 42:5954-5959 (2003).
Plevert et al., "Layered Structures Constructed from New Linkages of Ge7(O,Oh,F)19 Clusters," Chem. Mater. 15:714-718 (2003).
Reineke et al., "From Condensed Lanthanide Coordination Solids to Microporous Frameworks Having Accessible Metal Sites," J. Am. Chem. Soc 121:1651-1657 (1999).
Reineke et al., "A Microporosity of Lanthanide-Organic Frameworks," Angew. Chem. Int. Ed. 38:2590-2594 (1999).
Reineke et al., "Large Free Volume in Interpenetrating Networks: The Role of Secondary Building Units Exemplified by Tb2(ADB)3[(CH3)2SO]4-16[(CH3)2SO]," J. Am. Chem. Soc. 122:4843-4844 (2000); Featured in Science Magazine, Editors Choice (Nov. 2000).
Rosi et al., "Infinite Secondary Building Units and Forbidden Catenation in Metal-Organic Frameworks," Angew. Chem. Int. Ed. 41:294-297 (2002).
Rosi et al., "Advances in the Chemistry of Metal-Organic Frameworks," CrystEngComm 4:401-404 (2002).
Rosi et al., "Hydrogen Storage in Microporous Metal-Organic Frameworks," Science 300:1127-1129 (2003); Featured in (1) Chemical & Engineering News magazine, May 19, 2004, and (2) Technology Research News Magazine, May 21, 2003.
Rosi et al., "Rod-Packings and Metal-Organic Frameworks Constructed from Rod-Shaped Secondary Building Units," J. Am. Chem. Soc. 127:1504-1518 (2005).
Rowsell et al., "Hydrogen Sorption in Functionalized Metal-Organic Frameworks," J. Am. Chem. Soc.126: 5666-5667 (2004).
Rowsell et al., "Metal-Organic Frameworks: A New Class of Porous Materials," Microporous Mesoporous Mater. 73:3-14 (2004).
Rowsell et al., "Strategies for Hydrogen Storage in Metal-Organic Frameworks," Angew. Chem. Int. Ed. 44:4670-4679 (2005).
Rowsell et al., "Gas Adsorption Sites in a Large-Pore Metal-Organic Framework," Science 309:1350-1354 (2005).
Rowsell et al., "Characterization of H2 Binding sites in prototypical metal-organic frameworks by inelastic neutron scattering," J. Am. Chem. Soc. 127:14904-14910 (2005).
Rowsell et al., "Effects of Functionalization, Catenation, and Variation of the Metal Oxide and Organic Linking Units on the Low-Pressure Hydrogen Adsorption Properties of Metal-Organic Frameworks," J. Am. Chem. Soc. 128:1304-1315 (2006).
Siberio-Perez, "Raman Spectroscopic Investigation of CH4 and N2 Adsorption in Metal-Organic Frameworks," Chem. Mater. 19:3681-3685 (2007).
Smaldone et al., "Metal-Organic Frameworks from Edible Nature Products," Angew. Chem. Int. Ed. 49:8630-8634 (2010).
Spencer et al., "Determination of the Hydrogen Absorption Sites in Zn4O(1,4-benzenedicarboxylate) by Single Crystal Neutron Diffraction," Chem. Commun. 3:278-280 (2006); Epub Dec. 6, 2005.
Lawrence, Frank M. Nonfinal Office Action for U.S. Appl. No. 12/699,616. Mail Date Apr. 10, 2012.

(56) References Cited

OTHER PUBLICATIONS

Lawrence, Frank M. Nonfinal Office Action for U.S. Appl. No. 12/699,616. Mail Date Aug. 3, 2012.
Lee et al., "Synthesis and Gas Sorption Properties of a Metal-Azolium Framework (MAF) Material," Inorganic Chemistry, Nov. 2, 2009, pp. 9971-9973, vol. 48, No. 21.
Li, Y et al., "Hydrogen Storage in Metal-Organic and Covalent-Organic Frameworks by Spillover," AIChe Journal 54 (1):269-279 (2008).
McKeown et al., "Phthalocyanine-Based Nanoporous Network Polymers," Chem. Comm. 23:2780-2781 (Oct. 31, 2002).
McKeown et al., "Porphyrin-Based Nanoporous Network Polymers," Chem. Comm. 23:2782-2783 (Oct. 31, 2002).
Morris et al., "Framework mobility in the metal-organic framework crystal IRMOF-3: Evidence for aromatic ring and amine rotation," Journal of Molecular Structure 1004:94-101 (2011).
Morris et al., "NMR and X-ray Study Revealing the Rigidity of Zeolitic Imidazolate Frameworks," J. Phys. Chem. 116 (24):13307-13312 (Jun. 1, 2012).
Morris et al., "Synthesis, Structure, and Metalation of Two New Highly Porous Zirconium Metal-Organic Frameworks," Inorg. Chem. 51:6443-6445 (Jun. 7, 2012).
O'Keeffe et al., "Deconstructing the Crystal Structures of Metal-Organic Frameworks and Related Materials into Their Underlying Nets," Chem. Rev. 112(2):675-702 (Feb. 8, 2012).
Park, H. et al., "Synthesis, Structure Determination and Hydrogen Sorption Studies of New Metal-Organic Frameworks Using Triazole and Naphthalenedicarboxylic Acid," Chem. Natur. 19:1302-1308 (2007).
Queen et al., "Site-Specific CO2 Adsorption and Zero Thermal Expansion in an Anisotropic Pore Network," J. Phys. Chem. C, 115:24915-24919 (Nov. 8, 2011).
Rinkel, Bert. Extended European Search Report for European Patent Application EP08713961. Mail Date Jan. 2, 2012.
Rouseau-Jager, Nadia, International Search Report and Written Opinion, PCT/US2011/024671, European Patent Office, Dec. 13, 2011.
Sines, Brian J. Nonfinal Office Action for U.S. Appl. No. 13/142,564. Mail Date Jul. 9, 2012.
Song et al., "A Multiunit Catalyst with Synergistic Stability and Reactivity: A PolyoxometalateMetal Organic Framework for Aerobic Decontamination," J. Am. Chem. Soc. 133(42):16839-16846 (Sep. 13, 2011).
Spitler et al., "Lewis Acid Catalyzed Formation of Two-Dimensional Phthalocyanine Covalent Organic Framewokrs." Nature Chem. 2:672-677 (Jun. 20, 2010).
Tilford et al., "Facile Synthesis of a Highly Crystalline, Covalently Porous Boronate Network," 18(22):5296-5301 (Oct. 11, 2006).
Tranchemontagne et al., "Hydrogen Storage in New Metal-Organic Frameworks," J. Phys. Chem. C 116 (24):13143-13151 (May 24, 2012).
Wan et al, "A Belt-Shaped, Blue Luminescent, and Semiconducting Covalent Organic Framework." Angew. Chem. Int. Ed. 47:8826-8830 (2008).
Wan et al., "Covalent Organic Frameworks with High Charge Carrier Mobility," Chem. Mater. 23:4094-4097 (Aug. 22, 2011).
Young, Jung Doo. International Search Report and Written Opinion for PCT/US2011/053423. Date of mailing of ISR Jul. 23, 2012.
Young, Jung Doo. International Search Report and Written Opinion for PCT/US2012/022114. Date of mailing of ISR Aug. 22, 2012.
Young, Jung Doo, "International Search Report and Written Opinion for PCT/2012/023516." Date of mailing of the International Search Report Oct. 19, 2012.
Zhang, J. et al., "Exceptional Framework Flexibility and Sorption Behavior of a Multifunctional Porous Cuprous Triazolate Framework," J. Am. Chem. Soc. 130:6010-6017 (2008).
Zhou, X et al., "Hydrothermal Syntheses and Structures of Three Novel Coordination Polymers Assembled from 1,2,3-Triazolate Ligands," CrystEngComm. 11:1964-1970 (2009).
Zhou et al., "Introduction to Metal-Organic Frameworks," Chemical Reviews 112:673-674 (Jan. 26, 2012).
Zhu, A. et al., "Isomeric Zinc(II) Triazolate Frameworks with 3-Connected Networks: Syntheses, Structures, and Sorption Properties," Inorg. Chem. 48:3882-3889 (2009).
Ferragut et al., "Positronium Formation in Porous Materials for Antihydrogen Production,"J. Phys. Conf. Ser. 225:1-8 (2010).
Furukawa et al., "Crystal Structure, Dissolution, and Deposition of a 5 nm Functionalized Metal-Organic Great Rhombicuboctahedron," J. Am. Chem. Soc. 128:8398-8399 (2006).
Furkawa et al., "Independent verification of the saturation hydrogen uptake in MOF-177 and establishment of a benchmark for hydrogen adsorption in metal-organic frameworks," J. Mater. Chem. 17:3197-3204 (2007).
Furukawa et al., "Control of Vertex Geometry, Structure Dimensionality, Functionality, and Pore Metrics in the Reticular Synthesis of Crystalline Metal-Organic Frameworks and Polyhedra," J. Am. Chem. Soc.130:11650-11661 (2008).
Furukawa et al., "Storage of Hydrogen, Methane, and Carbon Dioxide in Highly Porous Covalent Organic Frameworks for Clean Energy Applications," J. Am. Chem. Soc. 25:8876-8883 (2009).
Furukawa et al., "Ultra-High Porosity in Metal-Organic Frameworks," Science 239:424-428 (2010).
Glover et al., "MOF-74 building unit has a direct impact on toxic gas adsorption," J. Chem. Eng. Sci. 66:163-170 (2011).
Gould et al., "The Amphidynamic Character of Crystalline MOF-5: Rotational Dynamics in a Free-Volume Environment," J. Am. Chem. Soc. 130:3246-3247 (2008).
Goebel, Matthias, Supplemental European Search Report and Written Opinion for EP08826913. Date of Completion of Search and Written Opinion: Nov. 10, 2010.
Goebel, Matthias, Supplemental European Search Report and Written Opinion for EP08754337. Date of Completion of Search and Written Opinion: Dec. 3, 2010.
Gonzalez-Arellano et al., "Homogeneous and heterogeneous Au(III) Schiff base-complexes as selective and general catalysts for self-coupling of aryl boronic acids," Chem. Comm. 15:1990-1992 (2005).
Grzesiak et al., "Polymer-Induced Heteronucleation for the Discovery of New Extended Solids," Angew. Chem. Int. Ed. 45:2553-2556 (2006).
Halper et al., "Topological Control in Heterometallic Metal-Organic Frameworks by Anion Templating and Metalloligand Design," J. Am. Chem. Soc. 128:15255-15268 (2006).
Han, SS et al., "Improved designs of metal-organic frameworks for hydrogen storage" Angew. Chem. Int. Ed. 2007, 46, pp. 6289-6292.
Han et al., "Covalent Organic Frameworks as Exceptional Hydrogen Storage Materials," J. Am. Chem. Soc. 130:11580-11581 (2008).
Hayashi et al., "Zeolite A Imidazolate Frameworks," Nature Materials 6:501-506 (2007).
Hexiang et al., "Multiple Functional Groups of Varying Rations in Metal-Organic Frameworks," Science 327 (5967):846-850 (2010).
Holler et al., "The first dinitrile frameworks of the rare earth elements: [LnCl3(1,4-Ph(Cn)2] and [Ln2CI6(1,4Ph(Cn) 2], Ln = Sm, Gd, Tb, Y; Access to novel metal-organic frameworks by solvent free synthesis in molten 1,4-benodinitrile," Inorganic Chemistry 47(21): 10141-9 (2008).
Honda, Masashi, International Preliminary Report on Patentability for PCT/US2008/051859. Date of Issuance of the Report: Jul. 28, 2009.
Howe, Patrick. International Search Report and Written Opinion for PCT/US2009/068849. Date of Mailing of the Search Report: 06/04/ 201.
Howe, Patrick. International Search Report and Written Opinion for PCT/US2010/022777. Date of Mailing: Jun. 7, 2010.
Huang et al., "Thermal Conductivity of Metal-Organic Framework 5 (MOF-5): Part II. Measurement," Int. J. Heat Mass Transfer 50:405-411 (2007).
Hunt et al., "Reticular Synthesis of Covalent Organic Borosilicate Frameworks," J. Am. Chem. Soc. 130: 11872-11873 (2008).

(56) References Cited

OTHER PUBLICATIONS

Isaeva et al., "Metal-organic frameworks-new materials for hydrogen storage," Russian Journal of General Chemistry 77(4):721-739 (2007).
Jeong et al., "Asymmetric Catalytic Reactions by NbO-Type Chiral Metal-Organic Frameworks," Chem. Sci. 2:877-882 (2011).
Kaderi et al., "Designed Synthesis of 3D Covalent Organic Frameworks," Science 316:268-272 (2007).
Kaye et al., "Impact of Preparation and Handling on the Hydrogen Storage Properties of Zn4O(1,4-benzenedicarboxylate)3 (MOF-5)," J. Am. Chem. Soc. 129:14176-14177 (2007).
Kim et al., "Assembly of Metal-Organic Frameworks From Large Organic and Inorganic Secondary Building Units: New Examples and Simplifying Principles for Complex Structures," J. Am. Chem. Soc. 123:8239-8247 (2001).
Kim, Su Mi, International Search Report and Written Opinion for PCT/US2009/068731. Date of Mailing: Aug. 19, 2010.
Kim, Su Mi, International Search Report and Written Opinion, Date of Mailing: Feb. 24, 2010, International Application No. PCT/US09/46463.
Kim, Su Mi. International Search Report for PCT/US2010/039154. Date of Mailing: Feb. 23, 2011.
Kirai et al., "Homocoupling of arylboronic acids catalyzed by 1,10-phenanthroline—ligated copper complexes in air," European Journal of Organic Chemistry 12:1864-1867 (2009).
Klaes, Daphne. International Search Report and Written Opinion for PCT/US2010/021201. Date of Mailing: Apr. 27, 2010.
Koza et al., "An efficient High Yielding Approach for the Homocoupling of Aryl Boronic Acids," Synthesis 15:2183-2186 (2002).
Kyoungmoo et al., "A Crystalline Mesoporous Coordination Copolymer with High Microporosity," Angew. Chem. Int. Ed. 47(4):677-680 (2008).
Lee, Ji Min. International Search Report for PCT/US2010/039284. Date of Mailing: Feb. 22, 2011.
Li et al., "Coordinatively Unsaturated Metal Centers in the Extended Porous Framewokr of Zn3(BDC)3·6CH3OH (BDC=1,4-Benzenedicarboxylate)," J. Am. Chem. Soc. 2186-2187 (1998).
Li et al., "Establishing Microporosity in Open Metal-Organic Frameworks: Gas Sorption Isotherms for Zn(BDC) (BDC=1,4-Benzenedicaroxylate)," J. Am. Chem. Soc. 120:8571-8572 (1998).
Li et al., "Porous Germanates: Synthesis, Structure and Inclusion Properties of Ge7O14.5F2-[(CH3)2NH2]3(H2O)O.86," J. Am. Chem. Soc. 120:8567-8568 (1998).
Li et al., "Transformation of Germanium Dioxide to 4-Connected Porous Germanate Net," J. Am. Chem. Soc. 10569-10570 (1998).
Li et al., "An Open-Framework Germanate with Polycubane-Like Topology," Angew. Chem. INt. Ed., 38:653-655 (1999).
Li et al., "Supertetrahedral Sulfide Crystals with Giant Cavities and Channels," Science 283:1145-1147 (1999).
Li et al., "Non-interpenetrating Indium Sulfide with a Supertetrahedral Cristobalite Famework," J. Am. Chem. Soc. 121:6096-6097 (1999).
Li et al., "Design and Synthesis of an Exceptionally Stable and Highly Porous Metal-Organic Framework," Science 402:276-279 (1999); Featured in (1) Chemical and Engineering News (Nov. 22, 19999) and (2) Science News (Nov. 20, 1999).
Li et al., "Ge2ZrO6F2 (H2DAB)H2O: A 4-Connected Microporous Material with "Bow Tie" Building Units and an Proportion of 3-Rings," J. Am. Chem. Soc. 122:12409-12410 (2000).
Li et al., "20 A [Cd4In16S35]14- Supertetrahedral T4 Clusters as Building Units in Decorated Cristobalite Frameworks," J. Am. Chem Soc. 123:4867-4868 (2001).
Li et al., "[Cd16In64S134]44-: 31-Å Tetrahedron with a Large Cavity," Angew. Chem. Int. Ed., 42:1819-1821 (2003).
Li et al., "A metal-organic framework replete with ordered donor-acceptor catenanes," Chem. Commun. 46:380-382 (2010).
Li et al., "A Catenated Strut in a Catenated Metal-Organic Framework," Angew. Chem. Int. Ed. 49:6751-6755 (2010).
Linder, Nora. International Preliminary Report on Patentability for PCT/US2010/022777. Date of Mailing: Aug. 11, 2011.

\* cited by examiner

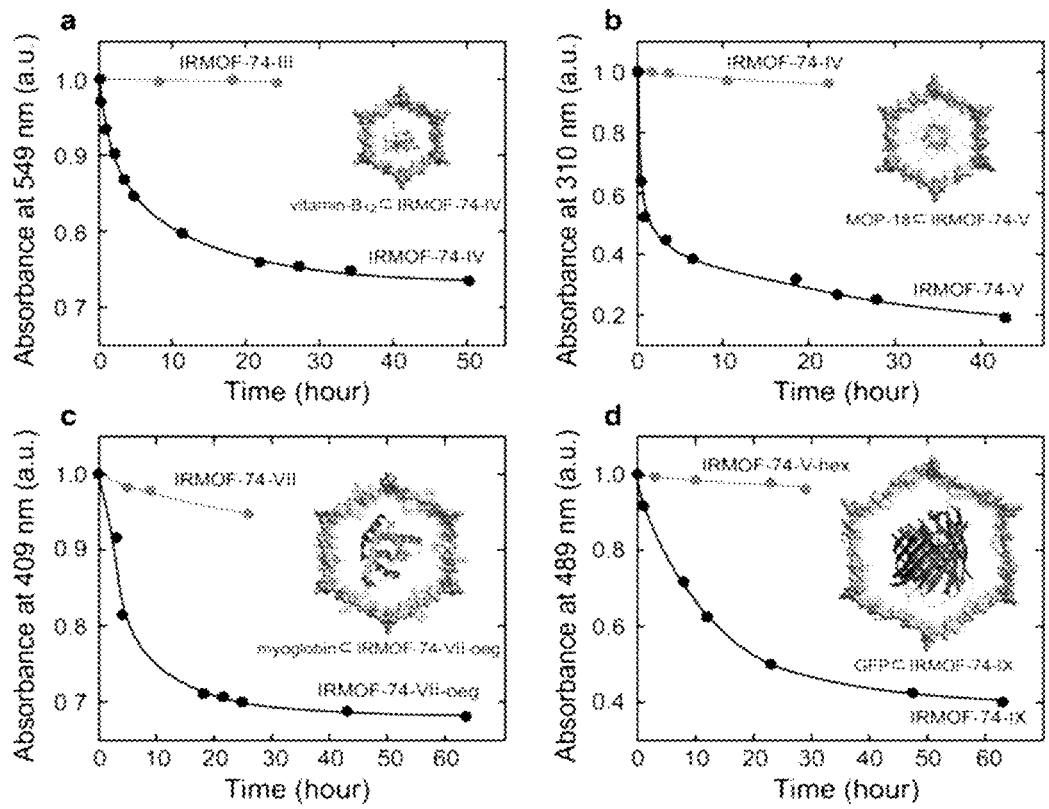
Figure 6A-D
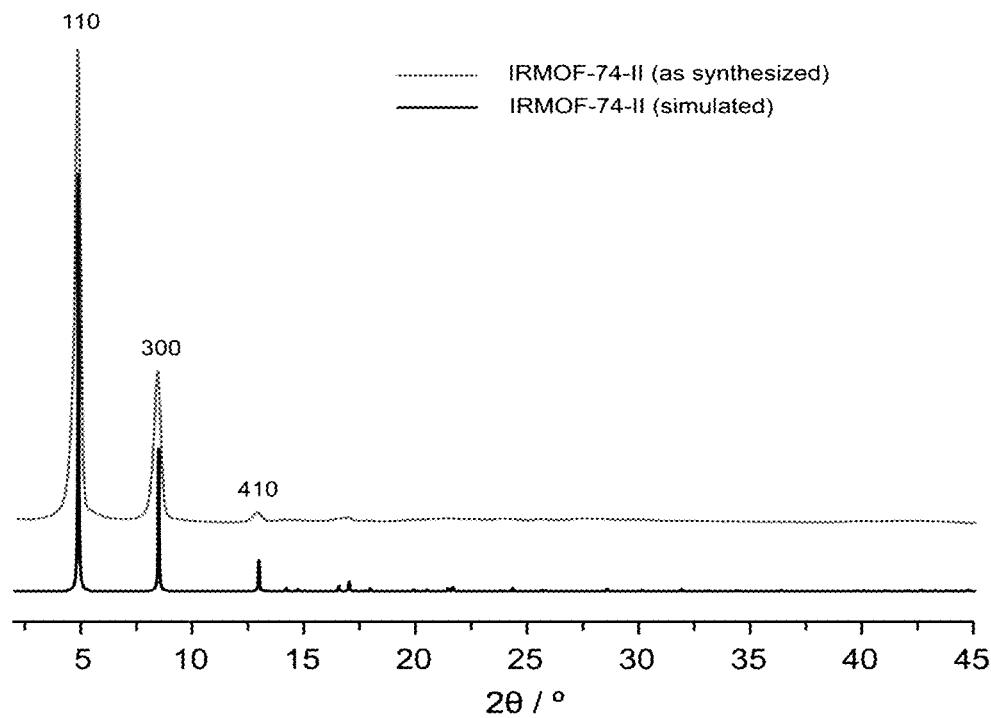
Figure 7

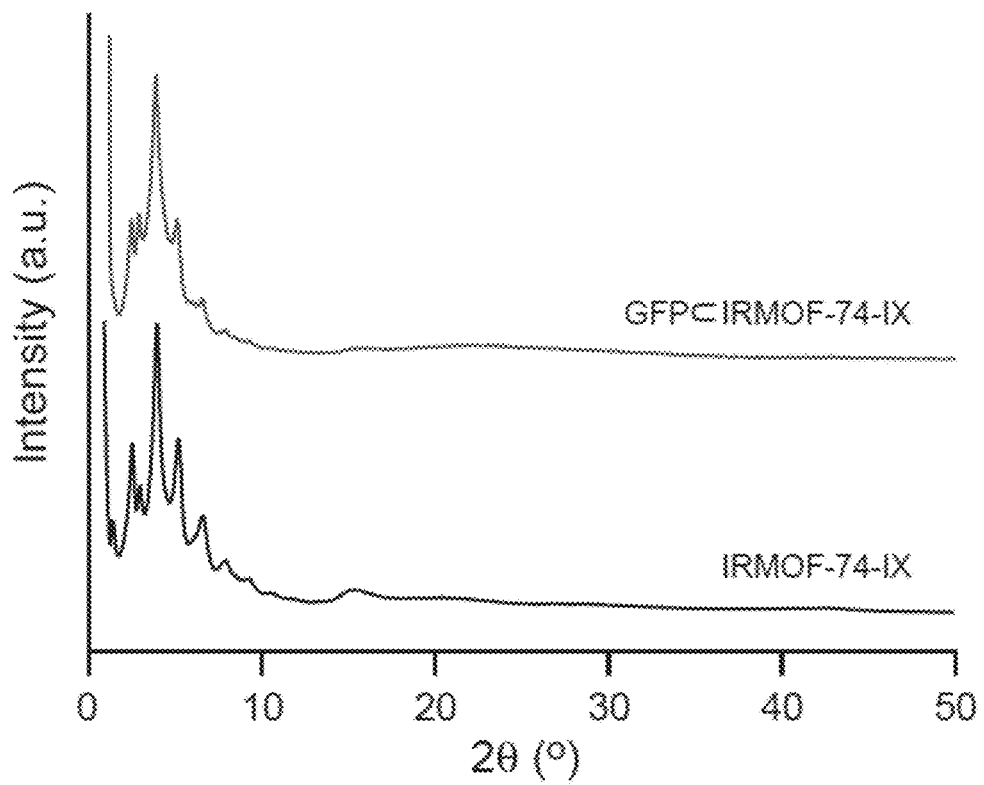
Figure 67
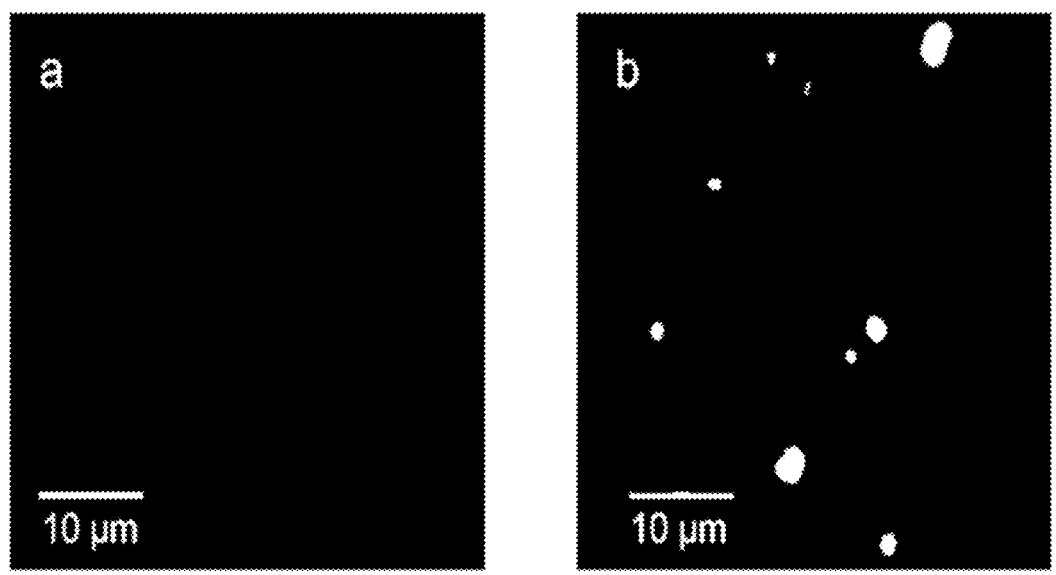
Figure 68A-B

METAL-ORGANIC FRAMEWORKS WITH EXCEPTIONALLY LARGE PORE APERATURES

CROSS REFERENCE TO RELATED APPLICATIONS

This application is a continuation of U.S. application Ser. No. 13/650,232, filed Oct. 12, 2012 (now U.S. Pat. No. 9,078,922), which application claims priority to U.S. Provisional Application Ser. No. 61/547,031, filed Oct. 13, 2011, the disclosure of which are incorporated herein by reference.

STATEMENT REGARDING FEDERALLY SPONSORED RESEARCH

This invention was made with Government support under Grant No. DE-FG02-08ER15935, awarded by the U.S. Department of Energy, and Grant No. W911NF-06-1-0405, awarded by the U.S. Army, Army Research Office. The Government has certain rights in the invention.

TECHNICAL FIELD

The invention relates to methods to produce porous crystals, such as metal organic frameworks (MOFs) or isoreticular metal organic frameworks (IRMOFs), the MOFs or IRMOFs produced thereof, and use of the MOFs or IRMOFs for various applications, including drug delivery, gas storage, gas separation, inorganic and/or organic molecule storage, chemical sensors, conductors, water decontamination, and water purification.

BACKGROUND

The largest reported pore aperture and internal pore diameter are 32×24 Å$^2$ and 47 Å, respectively; both of which are found in metal-organic frameworks (MOFs). Attempts to use long links in the synthesis of MOFs to allow for large pore apertures have failed. The resulting structures either yield interpenetrating structures, thereby restricting the size of the pore aperture, or produce fragile frameworks that collapse upon removal of guest species.

SUMMARY

The following disclosure presents novel methods to produce porous crystal structures with exceptionally large pore apertures that have not been previously presented. Moreover, the disclosure provides characterization of these porous crystals, and methods of use thereof.

The disclosure provides a MOF or IRMOF comprising the general structure M-L-M, wherein M comprises a metal and L is a linking moiety of Formula I:

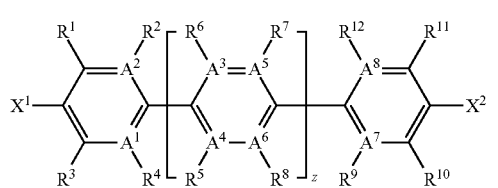

(I)

wherein,
$A^1$-$A^8$ are independently either N or C;
$X^1$ and $X^2$ are FG;
$R^1$-$R^{12}$ are independently selected from the group comprising H, FG, $(C_1$-$C_{12})$alkyl, substituted $(C_1$-$C_{12})$alkyl, $(C_1$-$C_{12})$alkenyl, substituted $(C_1$-$C_{12})$alkenyl, $(C_1$-$C_{12})$alkynyl, substituted $(C_1$-$C_{12})$alkynyl, hetero-$(C_1$-$C_{12})$alkyl, substituted hetero-$(C_1$-$C_{12})$alkyl, hetero-$(C_1$-$C_{12})$alkenyl, substituted hetero-$(C_1$-$C_{12})$alkenyl, hetero-$(C_1$-$C_{12})$alkynyl, substituted hetero-$(C_1$-$C_{12})$alkynyl, $(C_1$-$C_{12})$cycloalkyl, substituted $(C_1$-$C_{12})$cycloalkyl, aryl, substituted aryl, heterocycle, substituted heterocycle, —C($R^{13}$)$_3$, —CH($R^{13}$)$_2$, —CH$_2$$R^{13}$, —C($R^{13}$)$_3$, —CH($R^{14}$)$_2$, —CH$_2$$R^{14}$, —OC($R^{13}$)$_3$, —OCH($R^{13}$)$_2$, —OCH$_2$$R^{14}$, —OC($R^{14}$)$_3$, —OCH($R^{14}$)$_2$, —OCH$_2$$R^{14}$,

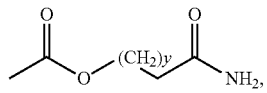

wherein $R^1$ and $R^2$ are linked together to form a substituted or unsubstituted ring selected from the group comprising cycloalkyl, aryl and heterocycle, and wherein $R^3$ and $R^4$ are linked together to form a substituted or unsubstituted ring selected from the group comprising cycloalkyl, aryl and heterocycle;
$R^{13}$ is selected from the group comprising FG, $(C_1$-$C_{12})$ alkyl, $(C_1$-$C_{12})$ substituted alkyl, $(C_1$-$C_{12})$alkenyl, substituted $(C_1$-$C_{12})$alkenyl, $(C_1$-$C_{12})$alkynyl, substituted $(C_1$-$C_{12})$alkynyl, hetero-$(C_1$-$C_{12})$alkyl, substituted hetero-$(C_1$-$C_{12})$alkyl, hetero-$(C_1$-$C_{12})$alkenyl, substituted hetero-$(C_1$-$C_{12})$alkenyl, hetero-$(C_1$-$C_{12})$alkynyl, substituted hetero-$(C_1$-$C_{12})$alkynyl, hemiacetal, hemiketal, acetal, ketal, and orthoester;
$R^{14}$ is one or more substituted or unsubstituted rings selected from the group comprising cycloalkyl, aryl, and heterocycle;
y is a number from 0 to 3;
z is a number from 0 to 20; and
with the proviso that R is absent when bound to an A that is N. In one embodiment, M is either a transition metal or an alkaline earth metal. For example, M is either Mg or Zn. In another embodiment, $X^1$ and $X^2$ are carboxylic acids. In yet a further embodiment, $A^1$-$A^8$ are C. In yet a further embodiment of any of the foregoing, $R^1$ to $R^{10}$ are hydroxyls; $R^2$-$R^5$, $R^2$, $R^9$, $R^{11}$ and $R^{12}$ are hydrogen; and $R^6$ and $R^8$ are selected from the group consisting of $(C_1$-$C_{12})$alkyl, $(C_1$-$C_{12})$alkenyl, substituted $(C_1$-$C_{12})$alkenyl, $(C_1$-$C_{12})$alkynyl, substituted $(C_1$-$C_{12})$alkynyl, hetero-$(C_1$-$C_{12})$alkyl, substituted hetero-$(C_1$-$C_{12})$alkyl, hetero-$(C_1$-$C_{12})$alkenyl, substituted hetero-$(C_1$-$C_{12})$alkenyl, hetero-$(C_1$-$C_{12})$alkynyl, and substituted hetero-$(C_1$-$C_{12})$alkynyl. In yet still further embodiments, $R^6$ and $R^8$ are $(C_1$-$C_6)$alkyls. In yet further embodiments, z is a number from 1 to 15. In another embodiment, the MOF or IRMOF further comprises a post-framework reactant. In yet a further embodiment, the post-framework reactant decreases the hydrophobicity of the framework. In another embodiment, at least one linking moiety comprises Formula I(a):

Formula I(a)

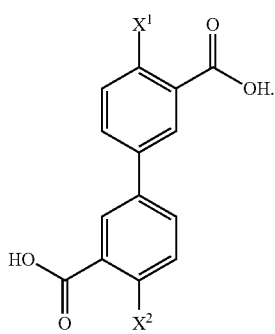

In another embodiment, the MOF or IRMOF comprises the general structure M-L-M, wherein M comprises a metal and L is a linking moiety, and wherein at least one linking moiety comprises Formula IV(a):

Formula IV(a)

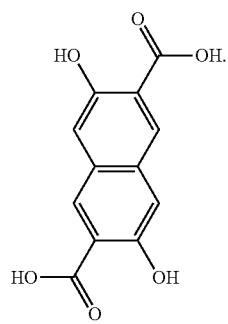

In yet another embodiment, the IRMOF or MOF further comprises at least one linking moiety having Formula IV(a):

Formula IV(a)

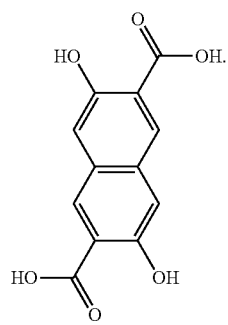

The disclosure also provides a MOF or IRMOF comprising the general structure M-L-M, wherein M comprises a metal and L is a linking moiety, and wherein at least one linking moiety comprises Formula IV(b):

Formula IV(b)

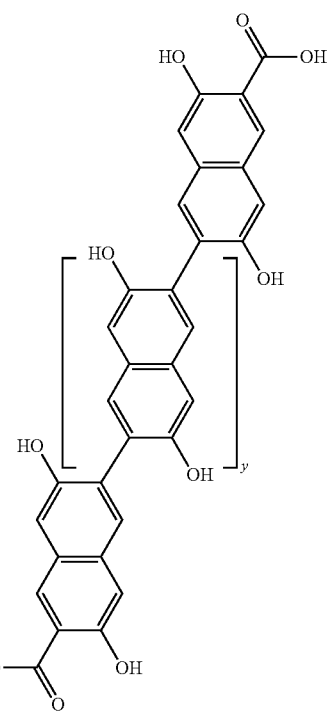

wherein, y is a number from 0 to 20. In another embodiment, the MOF or IRMOF further comprises at least one linking moiety having Formula IV(b):

Formula IV(b)

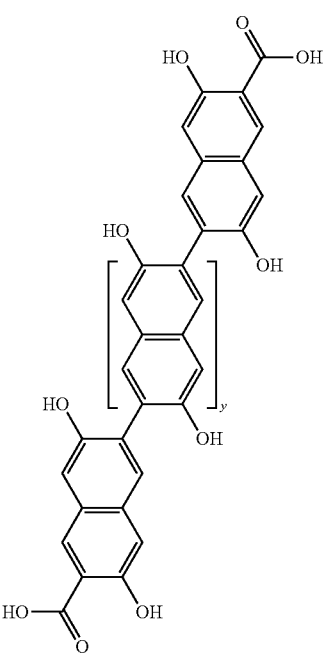

wherein, y is a number from 0 to 20.

The disclosure also provides a method of making the MOF or IRMOF as described above comprising a reaction at an elevated temperature comprising a solvent, metal containing salt, and a linking moiety of Formula I:

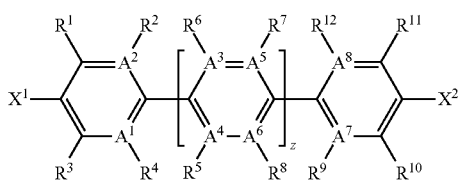

(I)

wherein,

A¹-A⁸ are independently either N or C;

X¹ and X² are FG;

R¹-R¹² are independently selected from the group comprising H, FG, $(C_1-C_{12})$alkyl, substituted $(C_1-C_{12})$alkyl, $(C_1-C_{12})$alkenyl, substituted $(C_1-C_{12})$alkenyl, $(C_1-C_{12})$alkynyl, substituted $(C_1-C_{12})$alkynyl, hetero-$(C_1-C_{12})$alkyl, substituted hetero-$(C_1-C_{12})$alkyl, hetero-$(C_1-C_{12})$alkenyl, substituted hetero-$(C_1-C_{12})$alkenyl, hetero-$(C_1-C_{12})$alkynyl, substituted hetero-$(C_1-C_{12})$alkynyl, $(C_1-C_{12})$cycloalkyl, substituted $(C_1-C_{12})$cycloalkyl, aryl, substituted aryl, heterocycle, substituted heterocycle, —C(R¹³)₃, —CH(R¹³)₂, —CH₂R¹³, —C(R¹³)₃, —CH(R¹⁴)₂, —CH₂R¹⁴, —OC(R¹³)₃, —OCH(R¹³)₂, —OCH₂R¹⁴, —OC(R¹⁴)₃, —OCH(R¹⁴)₂, —OCH₂R¹⁴,

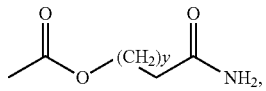

wherein R¹ and R² are linked together to form a substituted or unsubstituted ring selected from the group comprising cycloalkyl, aryl and heterocycle, and wherein R³ and R⁴ are linked together to form a substituted or unsubstituted ring selected from the group comprising cycloalkyl, aryl and heterocycle;

R¹³ is selected from the group comprising FG, $(C_1-C_{12})$ alkyl, $(C_1-C_{12})$ substituted alkyl, $(C_1-C_{12})$alkenyl, substituted $(C_1-C_{12})$alkenyl, $(C_1-C_{12})$alkynyl, substituted $(C_1-C_{12})$alkynyl, hetero-$(C_1-C_{12})$alkyl, substituted hetero-$(C_1-C_{12})$alkyl, hetero-$(C_1-C_{12})$alkenyl, substituted hetero-$(C_1-C_{12})$alkenyl, hetero-$(C_1-C_{12})$alkynyl, substituted hetero-$(C_1-C_{12})$alkynyl, hemiacetal, hemiketal, acetal, ketal, and orthoester;

R¹⁴ is one or more substituted or unsubstituted rings selected from the group comprising cycloalkyl, aryl, and heterocycle;

y is a number from 0 to 3;

z is a number from 0 to 20; and with the proviso that R is absent when bound to an A that is N.

BRIEF DESCRIPTION OF FIGURES

The accompanying Figures, which are incorporated into and constitute a part of this specification, illustrate one or more embodiments of the disclosure and, together with the detailed description, serve to explain the principles and implementations of the disclosure.

FIG. 6A-D presents an inclusion study of selected large molecules in IRMOF-74 series. This process was monitored through the decrease in absorbance at a selected wavelength as a function of contact time. (A) Vitamin-B12 in IRMOF-74-IV with IRMOF-74-III as a control, (B) MOP-18 in IRMOF-74-V with IRMOF-74-IV as a control, (C) Myoglobin in triethylene glycol mono-methyl ether functionalized IRMOF-74-VII, termed IRMOF-74-VII-oeg, with hexyl chain functionalized IRMOF-74-VII, termed IRMOF-74-VII-hex, as a control, (D) Green fluorescent protein (GFP) in IRMOF-74-IX with IRMOF-74-V-hex as a control. For each measurement, the initial absorbance was normalized to 1.0. An illustration of the inclusion complex for each study is shown as an inset in (A)-(D).

FIG. 7 provides a comparison of the experimental PXRD pattern of as synthesized IRMOF-74-II (top) with the simulated IRMOF-74-II diffraction pattern (bottom). The first three most intense reflections are shown.

FIG. 67 provides PXRD patterns of IRMOF-74-IX (bottom line) and Mb $\subset$ IRMOF-74-IX (top line).

FIG. 68A-B presents confocal microscopy images of a) IRMOF-74-IX and b) GFP $\subset$ IRMOF-74-IX.

DETAILED DESCRIPTION

Figure 1:
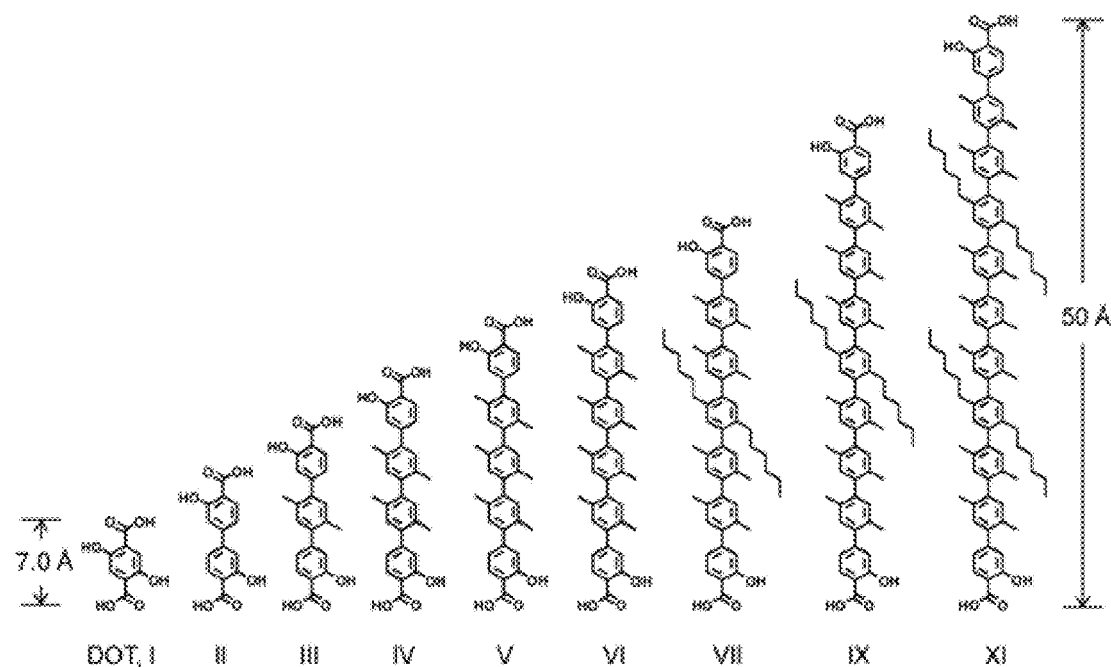
FIG. 1 provides the chemical structure of organic links used in the synthesis of a series of nine IRMOFs. The DOT link (I) with a length of 7 Å is expanded to eleven substituted phenyl rings to make a 50 Å long link DOT link (XI).

As used herein and in the appended claims, the singular forms "a," "and," and "the" include plural referents unless the context clearly dictates otherwise. Thus, for example, reference to "a linking group" includes a plurality of such linking groups and reference to "the pore" includes reference to pores resulting from the process and reaction conditions disclosed herein.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

All publications mentioned herein are incorporated herein by reference in full for the purpose of describing and disclosing the methodologies, which are described in the publications, which might be used in connection with the description herein. The publications discussed above and throughout the text are provided solely for their disclosure prior to the filing date of the present application. Nothing herein is to be construed as an admission that the inventors are not entitled to antedate such disclosure by virtue of prior disclosure. Moreover, with respect to similar or identical terms found in the incorporated references and terms expressly defined in this disclosure, the term definitions provided in this disclosure will control in all respects.

A "metal" refers to a solid material that is typically hard, shiny, malleable, fusible, and ductile, with good electrical and thermal conductivity. "Metals" used herein refer to metals selected from alkali metals, alkaline earth metals, lanthanides, actinides, transition metals, and post transition metals. Unless state otherwise, for the purposes of this disclosure a "metal" is inclusive of any ions in which the metal can form.

The term "cluster" refers to identifiable associations of 2 or more atoms. Such associations are typically established by some type of bond: ionic, covalent, Van der Waal, coordinate and the like.

The term "linking cluster" refers to one or more reactive species capable of condensation comprising an atom capable of forming a bond between a linking moiety parent chain and a metal group or between a linking moiety and another linking moiety. A linking cluster would include a coordination complex defined herein. A linking cluster can be part of the parent chain itself, e.g. imidazoles, or alternatively can arise from functionalizing the parent chain, e.g., adding carboxylic acid groups to aryls. Examples of such reactive species include, but are not limited to, boron, oxygen, carbon, nitrogen, silicon, tin, germanium, arsenic, and phosphorous. In certain embodiments, the linking cluster may comprise one or more different reactive species capable of forming a link with a bridging oxygen atom. For example, a linking cluster can comprise $CO_2H$, $CS_2H$, $NO_2$, $SO_3H$, $Si(OH)_3$, $Ge(OH)_3$, $Sn(OH)_3$, $Si(SH)_4$, $Ge(SH)_4$, $Sn(SH)_4$, $PO_3H$, $AsO_3H$, $AsO_4H$, $P(SH)_3$, $As(SH)_3$, $CH(RSH)_2$, $C(RSH)_3$, $CH(RNH_2)_2$, $C(RNH_2)_3$, $CH(ROH)_2$, $C(ROH)_3$, $CH(RCN)_2$, $C(RCN)_3$, $CH(SH)_2$, $C(SH)_3$, $CH(NH_2)_2$, $C(NH_2)_3$, $CH(OH)_2$, $C(OH)_3$, $CH(CN)_2$, and $C(CN)_3$, wherein R is an alkyl group having from 1 to 5 carbon atoms, or an aryl group comprising 1 to 2 phenyl rings and wherein the phenyl ring is optionally substituted with $CH(SH)_2$, $C(SH)_3$, $CH(NH_2)_2$, $C(NH_2)_3$, $CH(OH)_2$, $C(OH)_3$, $CH(CN)_2$, and $C(CN)_3$. Typically linking clusters for binding metals in the generation of MOFs contain carboxylic acid functional groups. Linking clusters are generally Lewis bases, and therefore have lone pair electrons available and/or can be deprotonated to form stronger Lewis bases. The deprotonated version of the linking clusters, therefore, is encompassed by the disclosure and anywhere a linking cluster that is depicted in a nondeprotenated form, the deprotenated form should be presumed to be included, unless stated otherwise. For example, although the structural Formulas presented herein are illustrated as having carboxylic acid ligands, for the purposes of this disclosure, these illustrated structures should be interpreted as including both carboxylic acid and/or carboxylate ligands.

The term "coordination number" refers to the number of atoms, groups of atoms, or linking clusters that bind to a central metal or metal ion where only the sigma bond between each atom, groups of atoms, or linking cluster and the central atom counts.

A "linking moiety" refers to an organic compound which can form a coordination complex with one or more metals. Generally, a linking moiety comprises a parent chain of a hydrocarbon, hetero-alkane, hetero-alkene, hetero-alkyne, or heterocycles; where this parent chain may be substituted with one or more functional groups, including additional substituted or unsubstituted hydrocarbons, and heterocycles, or a combination thereof; and wherein the linking moiety contains at least one linking cluster. In the case of heterocycles, hetero-alkanes, hetero-alkenes, and hetero-alkynes, one or more heteroatoms can function as linking clusters or alternatively as ligands. Examples of such heteroatoms include, but are not limited to, nitrogen, oxygen, sulfur, boron, phosphorus, silicon or aluminum atoms making up the ring. Moreover, a heterocycle, hetero-alkane, hetero-alkene, or hetero-alkyne, can also be functionalized with one or more linking clusters. Moreover, a heterocycle, hetero-alkane, hetero-alkene, or hetero-alkyne, can also be functionalized with one or more ligands to add or increase denticity of the hetero-based parent chain. In the case of hydrocarbons, typically one or more of the linking clusters of the hydrocarbon-based linking moiety can arise from functionalizing the hydrocarbon parent chain with one or more functional groups that can then act as a linking cluster. Examples of such groups, include, but are not limited to, carboxylic acids, hydroxyls, amines, imines, thiols, phosphines, ketones, aldehydes, halides, cyanos, and nitros. In certain cases, portions of a hydrocarbon itself can function as ligand, for example by forming carbenes and carbocations. It is also well known that functional groups that can be ligands are generally Lewis bases, and therefore have lone pair electrons available and/or can be deprotonated to form stronger Lewis bases. The deprotonated version of the ligand, therefore, is encompassed by the disclosure and anywhere a ligand that is depicted in a nondeprotenated form, the deprotenated form should be presumed to be included, unless stated otherwise. For example, although the structural Formulas presented herein are illustrated as having carboxylic acid ligands, for the purposes of this disclosure, those illustrated structures should be interpreted as including both carboxylic acid and/or carboxylate ligands.

The term "alkyl" refers to an alkyl group that contains 1 to 30 carbon atoms. Where if there is more than 1 carbon, the carbons may be connected in a linear manner, or alternatively if there are more than 2 carbons then the carbons may also be linked in a branched fashion so that the parent chain contains one or more secondary, tertiary, or quaternary carbons. An alkyl may be substituted or unsubstituted, unless stated otherwise.

The term "alkenyl" refers to an alkenyl group that contains 1 to 30 carbon atoms. While a $C_1$-alkenyl can form a double bond to a carbon of a parent chain, an alkenyl group of three or more carbons can contain more than one double bond. It certain instances the alkenyl group will be conjugated, in other cases an alkenyl group will not be conjugated, and yet other cases the alkenyl group may have stretches of conjugation and stretches of nonconjugation. Additionally, if there is more than 1 carbon, the carbons may be connected in a linear manner, or alternatively if there are more than 3 carbons then the carbons may also be linked in a branched fashion so that the parent chain contains one or more secondary, tertiary, or quaternary carbons. An alkenyl may be substituted or unsubstituted, unless stated otherwise.

The term "alkynyl" refers to an alkynyl group that contains 1 to 30 carbon atoms. While a $C_1$-alkynyl can form a triple bond to a carbon of a parent chain, an alkynyl group of three or more carbons can contain more than one triple bond. Where if there is more than 1 carbon, the carbons may be connected in a linear manner, or alternatively if there are more than 4 carbons then the carbons may also be linked in a branched fashion so that the parent chain contains one or more secondary, tertiary, or quaternary carbons. An alkynyl may be substituted or unsubstituted, unless stated otherwise.

The term "cycloalkyl" refers to an alkyl that contains at least 3 carbon atoms but no more than 12 carbon atoms connected so that it forms a ring. A "cycloalkyl" for the purposes of this disclosure encompass from 1 to 7 cycloalkyl rings, wherein when the cycloalkyl is greater than 1 ring, then the cycloalkyl rings are joined so that they are linked, fused, or a combination thereof. A cycloalkyl may be substituted or unsubstituted, or in the case of more than one cycloalkyl ring, one or more rings may be unsubstituted, one or more rings may be substituted, or a combination thereof.

The term "aryl" refers to a conjugated planar ring system with delocalized pi electron clouds that contain only carbon as ring atoms. An "aryl" for the purposes of this disclosure encompass from 1 to 7 aryl rings wherein when the aryl is greater than 1 ring the aryl rings are joined so that they are linked, fused, or a combination thereof. An aryl may be substituted or unsubstituted, or in the case of more than one aryl ring, one or more rings may be unsubstituted, one or more rings may be substituted, or a combination thereof.

The term "heterocycle" refers to ring structures that contain at least 1 non-carbon ring atom. A "heterocycle" for the purposes of this disclosure encompass from 1 to 7 heterocycle rings wherein when the heterocycle is greater than 1 ring, the heterocycle rings are joined so that they are linked, fused, or a combination thereof. A heterocycle may be aromatic or nonaromatic, or in the case of more than one heterocycle ring, one or more rings may be nonaromatic, one or more rings may be aromatic, or a combination thereof. A heterocycle may be substituted or unsubstituted, or in the case of more than one heterocycle ring then one or more rings may be unsubstituted, one or more rings may be substituted, or a combination thereof. Typically, the non-carbon ring atom is either N, O, S, Si, Al, B, or P. In cases where there is more than one non-carbon ring atom, these non-carbon ring atoms can either be the same element, or combination of different elements, such as N and O. Examples of heterocycles include, but are not limited to: a monocyclic heterocycle such as, aziridine, oxirane, thiirane, azetidine, oxetane, thietane, pyrrolidine, pyrroline, imidazolidine, pyrazolidine, pyrazoline, dioxolane, sulfolane 2,3-dihydrofuran, 2,5-dihydrofuran tetrahydrofuran, thiophane, piperidine, 1,2,3,6-tetrahydro-pyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, and hexamethylene oxide; and polycyclic heterocycles such as, indole, indoline, isoindoline, quinoline, tetrahydroquinoline, isoquinoline, tetrahydroisoquinoline, 1,4-benzodioxan, coumarin, dihydrocoumarin, benzofuran, 2,3-dihydrobenzofuran, isobenzofuran, chromene, chroman, isochroman, xanthene, phenoxathiin, thianthrene, indolizine, isoindole, indazole, purine, phthalazine, naphthyridine, quinoxaline, quinazoline, cinnoline, pteridine, phenanthridine, perimidine, phenanthroline, phenazine, phenothiazine, phenoxazine, 1,2-benzisoxazole, benzothiophene, benzoxazole, benzthiazole, benzimidazole, benztriazole, thioxanthine, carbazole, carboline, acridine, pyrolizidine, and quinolizidine. In addition to the polycyclic heterocycles described above, heterocycle includes polycyclic heterocycles wherein the ring fusion between two or more rings includes more than one bond common to both rings and more than two atoms common to both rings. Examples of such bridged heterocycles include, but are not limited to, quinuclidine, diazabicyclo[2.2.1]heptane and 7-oxabicyclo[2.2.1]heptane.

The terms "heterocyclic group", "heterocyclic moiety", "heterocyclic", or "heterocyclo" used alone or as a suffix or prefix, refers to a heterocycle that has had one or more hydrogens removed therefrom.

The term "heterocyclyl" used alone or as a suffix or prefix, refers a monovalent radical derived from a heterocycle by removing one hydrogen therefrom. Heterocyclyl includes, for example, monocyclic heterocyclyls, such as, aziridinyl, oxiranyl, thiiranyl, azetidinyl, oxetanyl, thietanyl, pyrrolidinyl, pyrrolinyl, imidazolidinyl, pyrazolidinyl, pyrazolinyl, dioxolanyl, sulfolanyl, 2,3-dihydrofuranyl, 2,5-dihydrofuranyl, tetrahydrofuranyl, thiophanyl, piperidinyl, 1,2,3,6-tetrahydro-pyridinyl, piperazinyl, morpholinyl, thiomorpholinyl, pyranyl, thiopyranyl, 2,3-dihydropyranyl, tetrahydropyranyl, 1,4-dihydropyridinyl, 1,4-dioxanyl, 1,3-dioxanyl, dioxanyl, homopiperidinyl, 2,3,4,7-tetrahydro-1H-azepinyl, homopiperazinyl, 1,3-dioxepanyl, 4,7-dihydro-1,3-dioxepinyl, and hexamethylene oxidyl. In addition, heterocyclyl includes aromatic heterocyclyls or heteroaryl, for example, pyridinyl, pyrazinyl, pyrimidinyl, pyridazinyl, thienyl, furyl, furazanyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4 oxadiazolyl. Additionally, heterocyclyl encompasses polycyclic heterocyclyls (including both aromatic or non-aromatic), for example, indolyl, indolinyl, isoindolinyl, quinolinyl, tetrahydroquinolinyl, isoquinolinyl, tetrahydroisoquinolinyl, 1,4-benzodioxanyl, coumarinyl, dihydrocoumarinyl, benzofuranyl, 2,3-dihydrobenzofuranyl, isobenzofuranyl, chromenyl, chromanyl, isochromanyl, xanthenyl, phenoxathiinyl, thianthrenyl, indolizinyl, isoindolyl, indazolyl, purinyl, phthalazinyl, naphthyridinyl, quinoxalinyl, quinazolinyl, cinnolinyl, pteridinyl, phenanthridinyl, perimidinyl, phenanthrolinyl, phenazinyl, phenothiazinyl, phenoxazinyl, 1,2-benzisoxazolyl, benzothiophenyl, benzoxazolyl, benzthiazolyl, benzimidazolyl, benztriazolyl, thioxanthinyl, carbazolyl, carbolinyl, acridinyl, pyrolizidinyl, and quinolizidinyl. In addition to the polycyclic heterocyclyls described above, heterocyclyl includes polycyclic heterocyclyls wherein the ring fusion between two or more rings includes more than one bond common to both rings and more than two atoms common to both rings. Examples of such bridged heterocycles include, but are not limited to, quinuclidinyl, diazabicyclo[2.2.1]heptyl; and 7-oxabicyclo[2.2.1]heptyl.

The term "hetero-aryl" used alone or as a suffix or prefix, refers to a heterocyclyl having aromatic character. Examples of heteroaryls include, but are not limited to, pyridine, pyrazine, pyrimidine, pyridazine, thiophene, furan, furazan, pyrrole, imidazole, triazole, oxazole, pyrazole, isothiazole, isoxazole, 1,2,3-triazole, tetrazole, 1,2,3-thiadiazole, 1,2,3-oxadiazole, 1,2,4-triazole, 1,2,4-thiadiazole, 1,2,4-oxadiazole, 1,3,4-triazole, 1,3,4-thiadiazole, and 1,3,4-oxadiazole.

The term "hetero-" when used as a prefix, such as, hetero-alkyl, hetero-alkenyl, hetero-alkynyl, or hetero-hydrocarbon, for the purpose of this disclosure refers to the specified hydrocarbon having one or more carbon atoms replaced by non carbon atoms as part of the parent chain. Examples of such non-carbon atoms include, but are not limited to, N, O, S, Si, Al, B, and P. If there is more than one non-carbon atom in the hetero-hydrocarbon chain then this atom may be the same element or may be a combination of different elements, such as N and O.

The term "unsubstituted" with respect to hydrocarbons, heterocycles, and the like, refers to structures wherein the parent chain contains no substituents.

The term "substituted" with respect to hydrocarbons, heterocycles, and the like, refers to structures wherein the parent chain contains one or more substituents.

The term "substituent" refers to an atom or group of atoms substituted in place of a hydrogen atom. For purposes of this invention, a substituent would include deuterium atoms.

The term "hydrocarbons" refers to groups of atoms that contain only carbon and hydrogen. Examples of hydrocarbons that can be used in this invention include, but is not limited to, alkanes, alkenes, alkynes, arenes, and benzyls.

The term "functional group" or "FG" refers to specific groups of atoms within molecules that are responsible for the characteristic chemical reactions of those molecules. While the same functional group will undergo the same or similar chemical reaction(s) regardless of the size of the molecule it is a part of, its relative reactivity can be modified by nearby functional groups. The atoms of functional groups are linked to each other and to the rest of the molecule by covalent bonds. Examples of FG that can be used in this disclosure, include, but are not limited to, substituted or unsubstituted alkyls, substituted or unsubstituted alkenyls, substituted or unsubstituted alkynyls, substituted or unsubstituted aryls, substituted or unsubstituted hetero-alkyls, substituted or unsubstituted hetero-alkenyls, substituted or unsubstituted hetero-alkynyls, substituted or unsubstituted heteroaryls, substituted or unsubstituted heterocycles, halos, hydroxyls, anhydrides, carbonyls, carboxyls, carbonates, carboxylates, aldehydes, haloformyls, esters, hydroperoxy, peroxy, ethers, orthoesters, carboxamides, amines, imines, imides, azides, azos, cyanates, isocyanates, nitrates, nitriles, isonitriles, nitrosos, nitros, nitrosooxy, pyridyls, sulfhydryls, sulfides, disulfides, sulfinyls, sulfos, thiocyanates, isothiocyanates, carbonothioyls, phosphinos, phosphonos, phosphates, $Si(OH)_3$, $Ge(OH)_3$, $Sn(OH)_3$, $Si(SH)_4$, $Ge(SH)_4$, $AsO_3H$, $AsO_4H$, $P(SH)_3$, $As(SH)_3$, $SO_3H$, $Si(OH)_3$, $Ge(OH)_3$, $Sn(OH)_3$, $Si(SH)_4$, $Ge(SH)_4$, $Sn(SH)_4$, $AsO_3H$, $AsO_4H$, $P(SH)_3$, and $As(SH)_3$.

As used herein, a "core" refers to a repeating unit or units found in a framework. Such a framework can comprise a homogenous repeating core, a heterogeneous repeating core or a combination of homogenous and heterogeneous cores. A core comprises a metal or a cluster of metals and a linking moiety.

As used herein, a "framework" refers to crystalline structure consisting of plurality of cores to form one-, two-, or three-dimensional structures that may or may not be porous. In some cases, the pores are stable upon elimination of the guest molecules (often solvents).

The term "covalent organic polyhedra" refers to a non-extended covalent organic network. Polymerization in such polyhedra does not occur usually because of the presence of capping ligands that inhibit polymerization. Covalent organic polyhedra are covalent organic networks that comprise a plurality of linking moieties linking together polydentate cores such that the spatial structure of the network is a polyhedron. Typically, the polyhedra of this variation are 2 or 3 dimensional structures.

The term "post framework reactants" refers to all known substances that are directly involved in a chemical reaction. Post framework reactants typically are substances, either elemental or compounds, which have not reached the optimum number of electrons in their outer valence levels, and/or have not reached the most favorable energetic state due to ring strain, bond length, low bond dissociation energy, and the like. Some examples of post framework reactants include, but are not limited to:

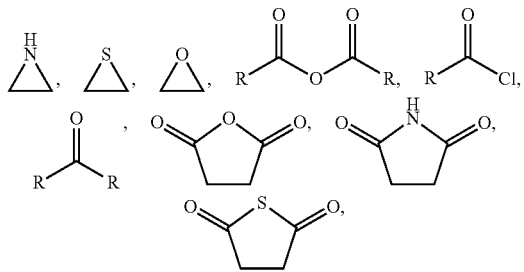

I—R, Br—R, $CR_3$—Mg—Br, $CH_2R$—Li, $CR_3$, Na—R, and K—R; wherein each R is independently selected from the group comprising: H, sulfonates, tosylates, azides, triflates, ylides, alkyl, aryl, OH, alkoxy, alkenes, alkynes, phenyl and substitutions of the foregoing, sulfur-containing groups (e.g., thioalkoxy, thionyl chloride), silicon-containing groups, nitrogen-containing groups (e.g., amides and amines), oxygen-containing groups (e.g., ketones, carbonates, aldehydes, esters, ethers, and anhydrides), halogen, nitro, nitrile, nitrate, nitroso, amino, cyano, ureas, boron-containing groups (e.g., sodium borohydride, and catechol-borane), phosphorus-containing groups (e.g., phosphorous tribromide), and aluminum-containing groups (e.g., lithium aluminum hydride).

As used herein, a wavy line intersecting another line that is connected to an atom indicates that this atom is covalently bonded to another entity that is present but not being depicted in the structure. A wavy line that does not intersect a line but is connected to an atom indicates that this atom is interacting with another atom by a bond or some other type of identifiable association.

A bond indicated by a straight line and a dashed line indicates a bond that may be a single covalent bond or alternatively a double covalent bond. But in the case where an R group defines an atom that is connected to another atom by a straight line and a dashed line which would exceed its maximum valence if the bond was a double covalent bond then the bond would only be a single covalent bond. For example, where R can be hydrogen and is connected to another atom by a straight line and a dashed line, then hydrogen would only form a single bond even though such a bond is indicated as being a single or double bond.

Metals and their associated ions that can be used in the synthesis of the metal organic frameworks disclosed herein are selected from the group comprising alkali metals, alkaline earth metals, transition metals, lanthanoids, actinoids, metalloids, and post transition metals. Metals can be introduced into open frameworks, MOFs, via forming complexes with one or more ligands in a framework or by simple ion exchange. Therefore, it is reasonable to assume that any metal disclosed herein can be introduced. Moreover, post synthesis of the framework, metals may be exchanged by commonly known techniques, and/or additional metal ions can be added to the framework by forming coordination complexes with functional groups arising from post framework reactants.

In an embodiment, one or more metals that can be used in the (1) synthesis of frameworks, (2) exchanged post synthesis of the frameworks, and/or (3) added to a framework by forming coordination complexes with post framework reactant functional group(s) which include, but are not limited to, alkali metals, alkaline earth metals, transition metals, lanthanoids, actinoids, metalloids, and post transition metals.

In a certain embodiment, one or more metals that can be used in the (1) synthesis of frameworks, (2) exchanged post synthesis of the frameworks, and/or (3) added to a framework by forming coordination complexes with post framework reactant functional group(s) include, but are not limited to, $Li^+$, $Na^+$, $K^+$, $Rb^+$, $Cs^+$, $Be^{2+}$, $Mg^{2+}$, $Ca^{2+}$, $Sr^{2+}$, $Ba^{2+}$, $Sc^{2+}$, $Sc^{2+}$, $Sc^+$, $Y^{3+}$, $Y^{2+}$, $Y^+$, $Ti^+$, $Ti^{3+}$, $Ti^{2+}$, $Zr^{4+}$, $Zr^{3+}$, $Zr^{2+}$, $Hf^{4+}$, $Hf^{3+}$, $V^{5+}$, $V^{4+}$, $V^{3+}$, $V^{2+}$, $Nb^{5+}$, $Nb^{4+}$, $Nb^{3+}$, $Nb^{2+}$, $Ta^{5+}$, $Ta^{4+}$, $Ta^{3+}$, $Ta^{2+}$, $Cr^{6+}$, $Cr^{5+}$, $Cr^{4+}$, $Cr^{3+}$, $Cr^{2+}$, $Cr^+$, $Cr$, $Mo^{6+}$, $Mo^{5+}$, $Mo^{4+}$, $Mo^{3+}$, $Mo^{2+}$, $Mo^+$, $Mo$, $W^{6+}$, $W^{5+}$, $W^{4+}$, $W^{3+}$, $W^{2+}$, $W^+$, $W$, $Mn^{7+}$, $Mn^{6+}$, $Mn^{5+}$, $Mn^{4+}$, $Mn^{3+}$, $Mn^{2+}$, $Mn^+$, $Re^{7+}$, $Re^{6+}$, $Re^{5+}$, $Re^{4+}$, $Re^{3+}$, $Re^{2+}$, $Re^+$, $Re$, $Fe^{6+}$, $Fe^{4+}$, $Fe^{3+}$, $Fe^{2+}$, $Fe^+$, $Fe$, $Ru^{8+}$, $Ru^{7+}$, $Ru^{6+}$, $Ru^{4+}$, $Ru^{3+}$, $Ru^{2+}$, $Os^{8+}$, $Os^{7+}$, $Os^{6+}$, $Os^{5+}$, $Os^{4+}$, $Os^{3+}$, $Os^{2+}$, $Os^+$, $Os$, $Co^{5+}$, $Co^{4+}$, $Co^{3+}$, $Co^{2+}$, $Co^+$, $Rh^{6+}$, $Rh^{5+}$, $Rh^{4+}$, $Rh^{3+}$, $Rh^{2+}$, $Rh^+$, $Ir^{6+}$, $Ir^{5+}$, $Ir^{4+}$, $Ir^{3+}$, $Ir^{2+}$, $Ir^+$, $Ir$, $Ni^{3+}$, $Ni^{2+}$, $Ni^+$, $Ni$, $Pd^{6+}$, $Pd^{4+}$, $Pd^{2+}$, $Pd^+$, $Pd$, $Pt^{6+}$, $Pt^{5+}$, $Pt^{4+}$, $Pt^{3+}$, $Pt^{2+}$, $Pt^+$, $Cu^{4+}$, $Cu^{3+}$, $Cu^{2+}$, $Cu^+$, $Ag^{3+}$, $Ag^{2+}$, $Ag^+$, $Au^{5+}$, $Au^{4+}$, $Au^{3+}$, $Au^{2+}$, $Au^+$, $Zn^{2+}$, $Zn^+$, $Zn$, $Cd^{2+}$, $Cd^+$, $Hg^{4+}$, $Hg^{2+}$, $Hg^+$, $B^{3+}$, $B^{2+}$, $B^+$, $Al^{3+}$, $Al^{2+}$, $Al^+$, $Ga^{3+}$, $Ga^{2+}$, $Ga^+$, $In^{3+}$, $In^{2+}$, $In^{1+}$, $Tl^{3+}$, $Tl^+$, $Si^{4+}$, $Si^{3+}$, $Si^{2+}$, $Si^+$, $Ge^{4+}$, $Ge^{3+}$, $Ge^{2+}$, $Ge^+$, $Ge$, $Sn^{4+}$, $Sn^{2+}$, $Pb^{4+}$, $Pb^{2+}$, $As^{5+}$, $As^{3+}$, $As^{2+}$, $As^+$, $Sb^{5+}$, $Sb^{3+}$, $Bi^{5+}$, $Bi^{3+}$, $Te^{6+}$, $Te^{5+}$, $Te^{4+}$, $Te^{2+}$, $La^{3+}$, $La^{2+}$, $Ce^{4+}$, $Ce^{3+}$, $Ce^{2+}$, $Pr^{4+}$, $Pr^{3+}$, $Pr^{2+}$, $Nd^{3+}$, $Nd^{2+}$, $Sm^{3+}$, $Sm^{2+}$, $Eu^{3+}$, $Eu^{2+}$, $Gd^{3+}$, $Gd^{2+}$, $Gd^+$, $Tb^{4+}$, $Tb^{3+}$, $Tb^{2+}$, $Tb^+$, $Db^{3+}$, $Db^{2+}$, $Ho^{3+}$, $Er^{3+}$, $Tm^{4+}$, $Tm^{3+}$, $Tm^{2+}$, $Yb^{3+}$, $Yb^{2+}$, $Lu^{3+}$, and any combination thereof, along with corresponding metal salt counter-anions.

In another embodiment, one or more metal ions in the (1) synthesis of frameworks, (2) exchanged post synthesis of the frameworks, and/or (3) added to a framework by forming coordination complexes with post framework reactant functional group(s), is a metal selected from the group comprising Mg and Zn.

In a certain embodiment, the metal used in the synthesis of the metal organic framework is Mg or Zn.

Linking moiety ligands and/or post frameworks reactants ligands can be selected based on Hard Soft Acid Base theory (HSAB) to optimize the interaction between the ligands and a metal or metal ion disclosed herein. In certain cases the metal and ligands are selected to be a hard acid and hard base, wherein the ligands and the metals will have the following characteristics: small atomic/ionic radius, high oxidation state, low polarizability, hard electronegativity (bases), highest-occupied molecular orbitals (HOMO) of the hard base is low in energy, and lowest unoccupied molecular orbitals (LUMO) of the hard acid are of high energy. Generally hard base ligands contain oxygen. Typical hard metal and metal ions include alkali metals, and transition metals such as Fe, Cr, and V in higher oxidation states. In other cases the metal and ligands are selected to be a soft acid and a soft base, wherein the ligands and the metal or metal ions will have the following characteristics: large atomic/ionic radius, low or zero oxidation state, high polarizability, low electronegativity, soft bases have HOMO of higher energy than hard bases, and soft acids have LUMO of lower energy than hard acids. Generally soft base ligands contain sulfur, phosphorous, and larger halides. In other cases the metal and ligands are selected to be a borderline acid and a borderline base. In certain cases, the metal and ligands are selected so that they are hard and soft, hard and borderline, or borderline and soft.

In an embodiment, the metal that can be used in the (1) synthesis of the metal organic frameworks, (2) exchanged post synthesis of the metal organic frameworks, and/or (3) added to the metal organic framework by forming coordination complexes with post framework reactant functional group(s) is a HSAB hard metal. In yet further embodiments, the metal that can be used in the (1) synthesis of frameworks, (2) exchanged post synthesis of the frameworks, and/or (3) added to a framework by forming coordination complexes with post framework reactant functional group(s) is a HSAB soft metal. In even further embodiments, the metal that can be used in the (1) synthesis of the metal organic frameworks, (2) exchanged post synthesis of the metal organic frameworks, and/or (3) added to the metal organic framework by forming coordination complexes with post framework reactant functional group(s) is a HSAB borderline metal. In the case that there is a plurality of metals used in the (1) synthesis of the metal organic frameworks, (2) exchanged post synthesis of the metal organic frameworks, and/or (3) added to the metal organic framework by forming coordination complexes with post framework reactant functional group(s) then there can be any combination of hard, soft and borderline metals that can be used in or attached to the metal organic framework.

In a further embodiment, one or more metals that can be used in the (1) synthesis of the frameworks, (2) exchanged post synthesis of the frameworks, and/or (3) added to the frameworks by forming coordination complexes with post framework reactant functional group(s) has a coordination number selected from the following: 2, 4, 6, and 8. In another embodiment, one or more metals has a coordination number of 4 and 8. In yet another embodiment, the metal has a coordination number of 8.

In a further embodiment, the metal used in the synthesis of the metal organic frameworks can be coordinated with atoms, groups of atoms, or ligands so that the coordination complex or cluster has a molecular geometry including, but not limited to, trigonal planar, tetrahedral, square planar, trigonal bipyramidal, square pyramidal, octahedral, trigonal prismatic, pentagonal bipyramidal, paddle-wheel and square antiprismatic. In a further embodiment, the metal ion used in the synthesis of the metal organic frameworks can form a coordination complex or cluster that has a molecular geometry including, but not limited to, tetrahedral, paddle-wheel and octahedral molecular geometry. In a further embodiment, the metal used in the synthesis of the metal organic framework can form a coordination complex or cluster that has octahedral molecular geometry. In another embodiment, the coordination complex with octahedral geometry can exist as various isomers depending on whether two or more types of ligands are coordinated to a metal ion. Examples of such isomers that can result, include, but are not limited to, cis, trans, fac, mer, and any combination thereof for coordination complexes that have three or more different ligands. In a yet further embodiment, the coordination complex or cluster disclosed herein may have chirality. In another embodiment, the coordination complex or cluster disclosed herein may not have chirality.

In one embodiment, the linking moiety comprises an organic-based parent chain comprising alkyl, hetero-alkyl, alkenyl, hetero-alkenyl, alkynyl, hetero-alkynyl, one or more cycloalkyl rings, one or more cycloalkenyl rings, one or more cycloalkynyl rings, one of more aryl rings, one or more heterocycle rings, or any combination of the preceding groups, including larger ring structures composed of linked and/or fused ring systems of different types of rings; wherein this organic-based parent chain may be further substituted with one or more functional groups, including additional substituted or unsubstituted hydrocarbons and heterocycle groups, or a combination thereof; and wherein the linking moiety contains at least one (e.g. 1, 2, 3, 4, 5, 6, . . . ) linking cluster.

In a yet further embodiment, the linking moiety of the metal organic framework has an organic-based parent chain that is comprised of one or more substituted or unsubstituted rings; wherein one or more of these rings is further substituted with one or more functional groups, including additional substituted or unsubstituted hydrocarbons and heterocycle groups, or a combination thereof; and wherein the linking moiety contains at least one (e.g., 1, 2, 3, 4, 5, 6, . . . ) linking cluster.

In a yet further embodiment, the linking moiety of the metal organic framework has an organic-based parent chain that is comprised of one or more substituted or unsubstituted rings; wherein one or more of these rings are further substituted with one or more functional groups, including additional substituted or unsubstituted hydrocarbons and heterocycle groups, or a combination thereof; and wherein the linking moiety contains at least one (e.g., 1, 2, 3, 4, 5, 6, or more) linking cluster that is either a carboxylic acid, amine, thiol, cyano, nitro, hydroxyl, or heterocycle ring heteroatom, such as the N in pyridine.

In another embodiment, the linking moiety of the metal organic framework has an organic-based parent chain that is comprised of one or more substituted or unsubstituted rings; wherein one or more of these rings are further substituted with one or more functional groups, including additional substituted or unsubstituted hydrocarbons and heterocycle groups, or a combination thereof; and wherein the linking moiety contains at least one (e.g. 1, 2, 3, 4, 5, 6, or more) linking cluster that is either a carboxylic acid, amine, hydroxyl, or heterocycle ring heteroatom, such as the N in pyridine.

In another embodiment, the linking moiety of the metal organic framework has an organic-based parent chain that is comprised of one or more substituted or unsubstituted rings; wherein one or more of these rings are further substituted with one or more functional groups, including additional substituted or unsubstituted hydrocarbons and heterocycle groups, or a combination thereof; and wherein the linking moiety contains at least one (e.g., 1, 2, 3, 4, 5, 6, or more) carboxylic acid linking cluster.

In another embodiment, the linking moiety of the metal organic framework has an organic-based parent chain that is comprised of one or more substituted or unsubstituted rings; wherein one or more of these rings are further substituted with two or more functional groups, including additional substituted or unsubstituted hydrocarbon and heterocycle groups, or a combination thereof; and wherein the linking moiety contains at least two (e.g., 2, 3, 4, 5, 6, or more) carboxylic acid linking clusters.

In a further embodiment, the metal organic framework is generated from a linking moiety comprising Formula I:

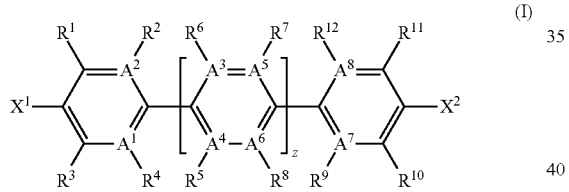

(I)

wherein, $A^1$-$A^8$ are independently either N or C;

$X^1$ and $X^2$ are FG;

$R^1$-$R^{12}$ are independently selected from the group comprising H, FG, ($C_1$-$C_{12}$)alkyl, substituted ($C_1$-$C_{12}$)alkyl, ($C_1$-$C_{12}$)alkenyl, substituted ($C_1$-$C_{12}$)alkenyl, ($C_1$-$C_{12}$)alkynyl, substituted ($C_1$-$C_{12}$)alkynyl, hetero-($C_1$-$C_{12}$)alkyl, substituted hetero-($C_1$-$C_{12}$)alkyl, hetero-($C_1$-$C_{12}$)alkenyl, substituted hetero-($C_1$-$C_{12}$)alkenyl, hetero-($C_1$-$C_{12}$)alkynyl, substituted hetero-($C_1$-$C_{12}$)alkynyl, ($C_1$-$C_{12}$)cycloalkyl, substituted ($C_1$-$C_{12}$)cycloalkyl, aryl, substituted aryl, heterocycle, substituted heterocycle, —C($R^{13}$)$_3$, —CH($R^{13}$)$_2$, —CH$_2$$R^{13}$, —C($R^{13}$)$_3$, —CH($R^{14}$)$_2$, —CH$_2$$R^{14}$, —OC($R^{13}$)$_3$, —OCH($R^{13}$)$_2$, —OCH$_2$$R^{14}$, —OC($R^{14}$)$_3$, —OCH($R^{14}$)$_2$, —OCH$_2$$R^{14}$,

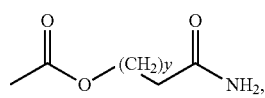

wherein $R^1$ and $R^2$ are linked together to form a substituted or unsubstituted ring selected from the group comprising cycloalkyl, aryl and heterocycle, and wherein $R^3$ and $R^4$ are linked together to form a substituted or unsubstituted ring selected from the group comprising cycloalkyl, aryl and heterocycle;

$R^{13}$ is selected from the group comprising FG, ($C_1$-$C_{12}$) alkyl, ($C_1$-$C_{12}$) substituted alkyl, ($C_1$-$C_{12}$)alkenyl, substituted ($C_1$-$C_{12}$)alkenyl, ($C_1$-$C_{12}$)alkynyl, substituted ($C_1$-$C_{12}$)alkynyl, hetero-($C_1$-$C_{12}$)alkyl, substituted hetero-($C_1$-$C_{12}$)alkyl, hetero-($C_1$-$C_{12}$)alkenyl, substituted hetero-($C_1$-$C_{12}$)alkenyl, hetero-($C_1$-$C_{12}$)alkynyl, substituted hetero-($C_1$-$C_{12}$)alkynyl, hemiacetal, hemiketal, acetal, ketal, and orthoester;

$R^{14}$ is one or more substituted or unsubstituted rings selected from the group comprising cycloalkyl, aryl, and heterocycle;

y is a number from 0 to 3;

z is a number from 0 to 20; and with the proviso that R is absent when bound to an A that is N.

In a certain embodiment, the disclosure provides for a metal organic framework comprising a linking moiety having Formula I(a):

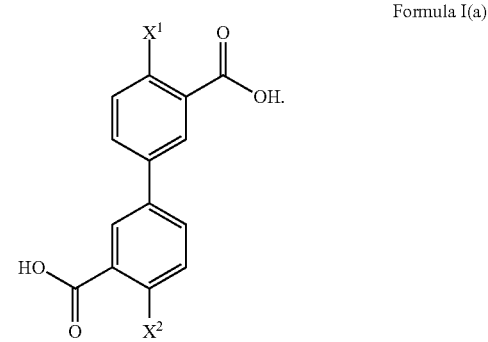

Formula I(a)

In a further embodiment, the metal organic framework is generated from a linking moiety comprising Formula I, II, III, IV, V, and VI:

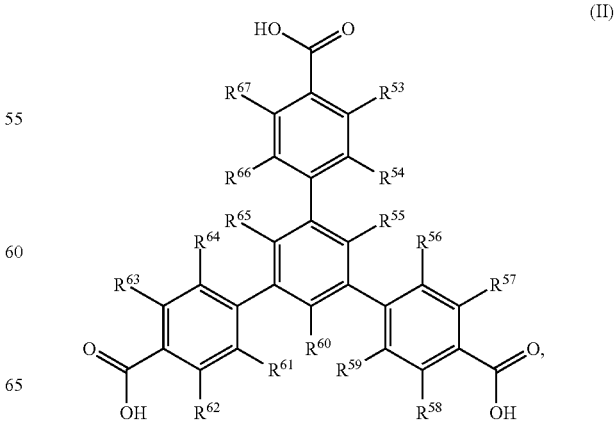

(II)

-continued (III)
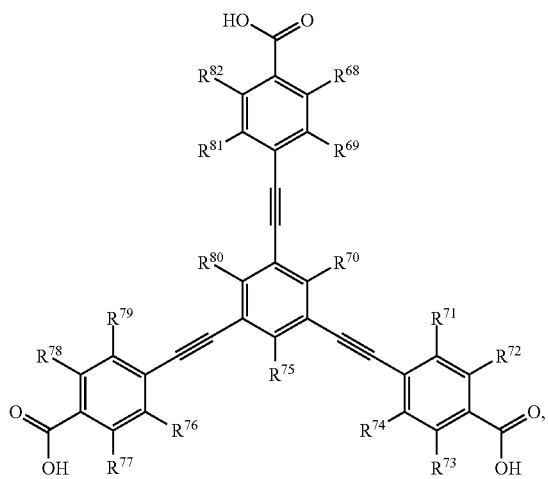

(IV)
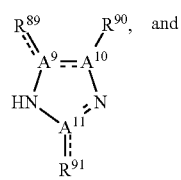

(V)
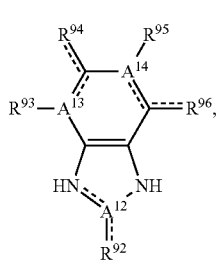

(VI)
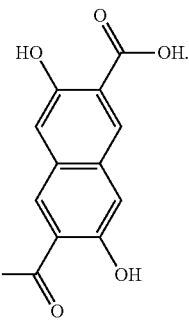

wherein:

$A^9$-$A^{14}$ are independently either N or C;

$R^{53}$-$R^{96}$ are independently selected from the group comprising H, FG, ($C_1$-$C_{12}$)alkyl, substituted ($C_1$-$C_{12}$)alkyl, ($C_1$-$C_{12}$)alkenyl, substituted ($C_1$-$C_{12}$)alkenyl, ($C_1$-$C_{12}$)alkynyl, substituted ($C_1$-$C_{12}$)alkynyl, hetero-($C_1$-$C_{12}$)alkyl, substituted hetero-($C_1$-$C_{12}$)alkyl, hetero-($C_1$-$C_{12}$)alkenyl, substituted hetero-($C_1$-$C_{12}$)alkenyl, hetero-($C_1$-$C_{12}$)alkynyl, substituted hetero-($C_1$-$C_{12}$)alkynyl, ($C_1$-$C_{12}$)cycloalkyl, substituted ($C_1$-$C_{12}$)cycloalkyl, aryl, substituted aryl, heterocycle, substituted heterocycle, —C($R^{13}$)$_3$, —CH($R^{13}$)$_2$, —CH$_2R^{13}$, —C($R^{13}$)$_3$, —CH($R^{14}$)$_2$, —CH$_2R^{14}$, —OC($R^{13}$)$_3$, —OCH($R^{13}$)$_2$, —OCH$_2R^{13}$, —OC($R^{14}$)$_3$, —OCH($R^{14}$)$_2$, —OCH$_2R^{14}$,

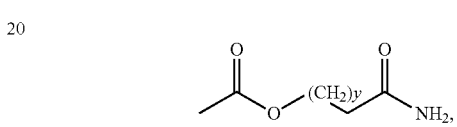

$R^{13}$ is selected from the group comprising FG, ($C_1$-$C_{12}$) alkyl, ($C_1$-$C_{12}$) substituted alkyl, ($C_1$-$C_{12}$)alkenyl, substituted ($C_1$-$C_{12}$)alkenyl, ($C_1$-$C_{12}$)alkynyl, substituted ($C_1$-$C_{12}$)alkynyl, hetero-($C_1$-$C_{12}$)alkyl, substituted hetero-($C_1$-$C_{12}$)alkyl, hetero-($C_1$-$C_{12}$)alkenyl, substituted hetero-($C_1$-$C_{12}$)alkenyl, hetero-($C_1$-$C_{12}$)alkynyl, substituted hetero-($C_1$-$C_{12}$)alkynyl, hemiacetal, hemiketal, acetal, ketal, and orthoester;

$R^{14}$ is one or more substituted or unsubstituted rings selected from the group comprising cycloalkyl, aryl, and heterocycle;

y is a number from 0 to 3; and with the proviso that R is absent when bound to an A that is N.

In a particular embodiment, the disclosure provides for a metal organic framework comprising a linking moiety having Formula IV(a):

Formula IV(a)

[structure of 3,7-dihydroxynaphthalene-2,6-dicarboxylic acid]

In a further embodiment, the disclosure provides for a metal organic framework comprising a linking moiety having Formula IV(b):

Formula IV(b)

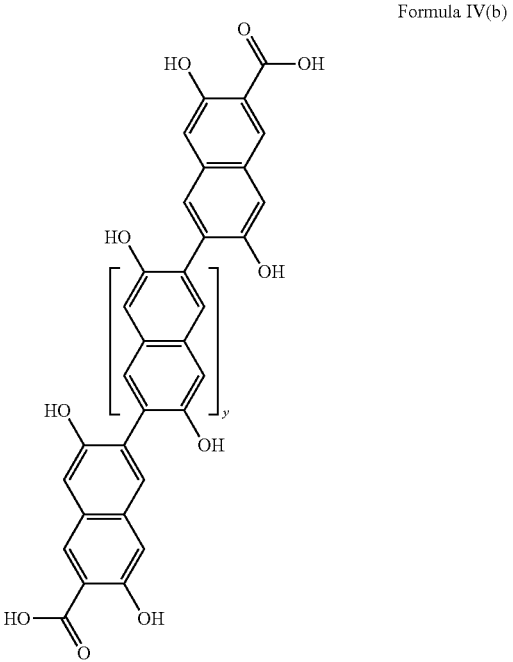

wherein, y is a number from 0 to 20.

In another embodiment, the disclosure provides for a metal organic framework comprising at least two linking moieties having Formula I(a) and Formula IV(a).

In yet another embodiment, the disclosure provides for a metal organic framework comprising at least two linking moieties having Formula I(a) and Formula IV(b).

In a certain embodiment, a metal organic framework disclosed herein comprising one or more linking moieties of Formula (I) further comprises at least one linking moiety of Formula IV(a).

In a particular embodiment, a metal organic framework disclosed herein comprising one or more linking moieties of Formula (I) further comprises at least one linking moiety of Formula IV(b).

The preparation of the frameworks of the disclosure can be carried out in either an aqueous or non-aqueous solvent system. The solvent may be polar or non-polar, or a combination thereof, as the case may be. The reaction mixture or suspension comprises a solvent system, linking moiety or moieties, and a metal or a metal/salt complex. The reaction solution, mixture or suspension may further contain a templating agent, catalyst, or combination thereof. The reaction mixture may be heated at an elevated temperature or maintained at ambient temperature, depending on the reaction components.

Examples of non-aqueous solvents that can be used in the reaction to make the framework and/or used as non-aqueous solvent for a post synthesized framework reaction, include, but is not limited to: n-hydrocarbon based solvents, such as pentane, hexane, octadecane, and dodecane; branched and cyclo-hydrocarbon based solvents, such as cycloheptane, cyclohexane, methyl cyclohexane, cyclohexene, cyclopentane; aryl and substituted aryl based solvents, such as benzene, toluene, xylene, chlorobenzene, nitrobenzene, cyanobenzene, naphthalene, and aniline; mixed hydrocarbon and aryl based solvents, such as, mixed hexanes, mixed pentanes, naptha, and petroleum ether; alcohol based solvents, such as, methanol, ethanol, n-propanol, isopropanol, propylene glycol, 1,3-propanediol, n-butanol, isobutanol, 2-methyl-1-butanol, tert-butanol, 1,4-butanediol, 2-methyl-1-pentanol, and 2-pentanol; amide based solvents, such as, dimethylacetamide, dimethylformamide (DMF), formamide, N-methylformamide, N-methylpyrrolidone, and 2-pyrrolidone; amine based solvents, such as, piperidine, pyrrolidine, collidine, pyridine, morpholine, quinoline, ethanolamine, ethylenediamine, and diethylenetriamine; ester based solvents, such as, butylacetate, sec-butyl acetate, tert-butyl acetate, diethyl carbonate, ethyl acetate, ethyl acetoacetate, ethyl lactate, ethylene carbonate, hexyl acetate, isobutyl acetate, isopropyl acetate, methyl acetate, propyl acetate, and propylene carbonate; ether based solvents, such as, di-tert-butyl ether, diethyl ether, diglyme, diisopropyl ether, 1,4-dioxane, 2-methyltetrahydrofuran, tetrahydrofuran (THF), and tetrahydropyran; glycol ether based solvents, such as, 2-butoxyethanol, dimethoxyethane, 2-ethoxyethanol, 2-(2-ethoxyethoxy)ethanol, and 2-methoxyethanol; halogenated based solvents, such as, carbon tetrachloride, chlorobenzene, chloroform, 1,1-dichloroethane, 1,2-dichloroethane, 1,2-dichloroethene, dichloromethane (DCM), diiodomethane, epichlorohydrin, hexachlorobutadiene, hexafluoro-2-propanol, perfluorodecalin, perfluorohexane, tetrabromomethane, 1,1,2,2-tetrachloroethane, tetrachloroethylene, 1,3,5-trichlorobenzene, 1,1,1-trichloroethane, 1,1,2-trichloroethane, trichloroethylene, 1,2,3-trichloropropane, trifluoroacetic acid, and 2,2,2-trifluoroethanol; inorganic based solvents, such as hydrogen chloride, ammonia, carbon disulfide, thionyl chloride, and phosphorous tribromide; ketone based solvents, such as, acetone, butanone, ethylisopropyl ketone, isophorone, methyl isobutyl ketone, methyl isopropyl ketone, and 3-pentanone; nitro and nitrile based solvents, such as, nitroethane, acetonitrile, and nitromethane; sulfur based solvents, dimethyl sulfoxide (DMSO), methylsulfonylmethane, sulfolane, isocyanomethane, thiophene, and thiodiglycol; urea, lactone and carbonate based solvents, such as 1-3-dimethyl-3,4,5,6-tetrahydro-2(1H)-pyrimidinone (DMPU), 1-3-dimethyl-2-imidazolidinone, butyrolactone, cis-2,3-butylene carbonate, trans-2,3-butylene carbonate, 2,3-butylene carbonate; carboxylic acid based solvents, such as formic acid, acetic acid, chloracetic acid, trichloroacetic acid, trifluoroacetic acid, propanoic acid, butanoic acid, caproic acid, oxalic acid, and benzoic acid; boron and phosphorous based solvents, such as triethyl borate, triethyl phosphate, trimethyl borate, and trimethyl phosphate; deuterium containing solvents, such as deuterated acetone, deuterated benzene, deuterated chloroform, deuterated dichloromethane, deuterated DMF, deuterated DMSO, deuterated ethanol, deuterated methanol, and deuterated THF; and any appropriate mixtures thereof.

In another embodiment, the nonaqueous solvent used as the solvent system in synthesizing the framework has a pH less than 7. In a further embodiment, the solvent system used to synthesize the framework is an aqueous solution that has a pH less than 7. In yet a further embodiment, the solvent system used to synthesize the frameworks contains water. In another embodiment, the solvent system used to synthesize the frameworks contains water and hydrochloric acid.

Those skilled in the art will be readily able to determine an appropriate solvent or appropriate mixture of solvents based on the starting reactants and/or where the choice of a particular solvent(s) is not believed to be crucial in obtaining the materials of the disclosure.

Templating agents can be used in the methods of the disclosure. Templating agents employed in the disclosure are added to the reaction mixture for the purpose of occupying the pores in the resulting crystalline base frameworks. In some variations of the disclosure, space-filling agents, adsorbed chemical species and guest species increase the surface area of the metal-organic framework. Suitable space-filling agents include, for example, a component selected from the group consisting of: (i) alkyl amines and their corresponding alkyl ammonium salts, containing linear, branched, or cyclic aliphatic groups, having from 1 to 20 carbon atoms; (ii) aryl amines and their corresponding aryl ammonium salts having from 1 to 5 phenyl rings; (iii) alkyl phosphonium salts, containing linear, branched, or cyclic aliphatic groups, having from 1 to 20 carbon atoms; (iv) aryl phosphonium salts, having from 1 to 5 phenyl rings; (v) alkyl organic acids and their corresponding salts, containing linear, branched, or cyclic aliphatic groups, having from 1 to 20 carbon atoms; (vi) aryl organic acids and their corresponding salts, having from 1 to 5 phenyl rings; (vii) aliphatic alcohols, containing linear, branched, or cyclic aliphatic groups, having from 1 to 20 carbon atoms; or (viii) aryl alcohols having from 1 to 5 phenyl rings.

In certain embodiments templating agents are used with the methods disclosed herein, and in other embodiments templating agents are not used with the methods disclosed herein.

Crystallization of the frameworks can be carried out by maintaining the solution, mixture, or suspension at ambient temperature or by maintaining the solution, mixture, or suspension at an elevated temperature; adding a diluted base to the solution; diffusing the diluted base throughout the solution; and/or transferring the solution to a closed vessel and heating to a predetermined temperature.

In a certain embodiment, crystallization of the frameworks can be improved by adding an additive that promotes nucleation.

In a certain embodiment, the solution, mixture or suspension is maintained at ambient temperature to allow for crystallization. In another embodiment, the solution, mixture, or suspension is heated in isothermal oven for up to 300° C. to allow for crystallization. In yet another embodiment, activated frameworks can be generated by calcination. In a further embodiment, calcination of the frameworks can be achieved by heating the frameworks at 350° C. for at least 1 hour.

It is further contemplated that a framework of the disclosure may be generated by first utilizing a plurality of linking moieties having different functional groups, wherein at least one of these functional groups may be modified, substituted, or eliminated with a different functional group post-synthesis of the framework. In other words, at least one linking moiety comprises a functional group that may be post-synthesized reacted with a post framework reactant to further increase the diversity of the functional groups in the organic framework.

After the frameworks are synthesized, the frameworks may be further modified by reacting with one or more post framework reactants that may or may not have denticity. In a certain embodiment, the frameworks as-synthesized are not reacted with a post framework reactant. In another embodiment, the frameworks as-synthesized are reacted with at least one post framework reactant. In yet another embodiment, the frameworks as-synthesized are reacted with at least two post framework reactants. In a further embodiment, the frameworks as-synthesized are reacted with at least one post framework reactant that will result in adding denticity to the framework.

It is contemplated by this disclosure that chemical reactions that modify, substitute, or eliminate a functional group post-synthesis of the framework with post framework reactant may use one or more similar or divergent chemical reaction mechanisms depending on the type of functional group and/or post framework reactant used in the reaction. Examples of chemical reaction mechanisms contemplated by this invention include, but is not limited to, radical-based, unimolecular nucleophilic substitution (SN1), bimolecular nucleophilic substitution (SN2), unimolecular elimination (E1), bimolecular elimination (E2), E1cB elimination, nucleophilic aromatic substitution (SnAr), nucleophilic internal substitution (SNi), nucleophilic addition, electrophilic addition, oxidation, reduction, cycloadition, ring closing metathesis (RCM), pericylic, electrocylic, rearrangement, carbene, carbenoid, cross coupling, and degradation.

All the aforementioned linking moieties that possess appropriate reactive functionalities can be chemically transformed by a suitable reactant post framework synthesis to add further functionalities to the pores. By modifying the organic links within the framework post-synthetically, access to functional groups that were previously inaccessible or accessible only through great difficulty and/or cost is possible and facile.

It is yet further contemplated by this disclosure that to enhance chemoselectivity it may be desirable to protect one or more functional groups that would generate unfavorable products upon a chemical reaction desired for another functional group, and then deprotect this protected group after the desired reaction is completed. Employing such a protection/deprotection strategy could be used for one or more functional groups.

Other agents can be added to increase the rate of the reactions disclosed herein, including adding catalysts, bases, and acids.

In another embodiment, the post framework reactant is selected to have a property selected from the group comprising, binds a metal ion, increases the hydrophobicity of the framework, decreases the hydrophobicity of the framework, modifies the chemical sorption of the framework, modifies the pore size of the framework, and tethers a catalyst to the framework.

In one embodiment, the post framework reactant can be a saturated or unsaturated heterocycle.

In another embodiment, the post framework reactant has 1-20 carbons with functional groups including atoms such as N, S, and O.

In yet another embodiment, the post framework reactant is selected to modulate the size of the pores in the framework.

In another embodiment, the post framework reactant is selected to increase the hydrophobicity of the framework. In an alternative embodiment, the post framework reactant is selected to decrease the hydrophobicity of the framework.

In yet another embodiment, the post framework reactant is selected to modulate chemical, inorganic and/or organic, sorption of the framework.

In yet another embodiment, the post framework reactant is selected to modulate gas separation of the framework. In a certain embodiment, the post framework reactant creates an electric dipole moment on the surface of the framework when it chelates a metal ion.

In a further embodiment, the post framework reactant is selected to modulate the gas sorption properties of the framework. In another embodiment, the post framework reactant is selected to promote or increase hydrocarbon gas sorption of the framework.

In yet a further embodiment, the post framework reactant is selected to increase or add catalytic efficiency to the framework.

In another embodiment, a post framework reactant is selected so that organometallic complexes can be tethered to the framework. Such tethered organometallic complexes can be used, for example, as heterogeneous catalysts.

In a certain embodiment the pore aperture is controlled by the length of the linking moiety.

By allowing access of molecules through their pore apertures for storage, separation, or conversion, porous crystals are very useful structures. While the pore apertures govern the size of the molecules that may enter through the pores, the crystal framework provides surface and space to carry out many functions. A long-standing challenge, however, is to make crystals whose pore apertures are of a size suitable for the inclusion of large organic, inorganic and biological molecules. The largest reported pore aperture and internal pore diameter are 32×24 Å$^2$ and 47 Å, respectively; both of which are found in metal-organic frameworks (MOFs). While in principle it should be possible to use long links in the synthesis of MOFs to allow for large pore apertures, attempts to do so have been met with failure. The resulting structures are either interpenetrating structures, thereby restricting the size of the pore aperture, or are fragile, wherein the frameworks collapse upon removal of guest species. Disclosed herein are methods that solve this long standing problem, by presenting the synthesis of a stable non-interpenetrating isoreticular (having the same topology) series of MOF-74 like structures (termed IRMOF-74-I to XI) that have pore apertures ranging from 14 to 98 Å.

The novel compounds disclosed herein share properties with MOF-74, $M_2$ (2,5-DOT) (M=$Zn^{2+}$, $Mg^{2+}$; DOT=dioxidoterephthalate, I, FIG. 1), but utilize methods to link DOTs of two (II), three (III), four (IV), five (V), six (VI), seven (VII), nine (IX) and eleven (XI) to give the compounds of the disclosure. Six members of this series (IRMOF-74-IV to XI) have the largest pore apertures ever reported for a crystalline material, and one member (IRMOF-74-XI), in its guest-free form, has the lowest density (0.195 g·cm$^{-3}$) ever known for a crystal at ambient temperature. All members of this series have non-interpenetrating structures and exhibit robust architectures as evidenced by their permanent porosity and high thermal stability (up to 300° C.). The disclosure also provides that large molecules, such as vitamin-$B_{12}$, metal-organic polyhedron-18, myoglobin, and green fluorescent protein, can readily pass through the pore apertures of IRMOF-74-IV, V, VII, and IX, respectively.

Mesoporous silica, porous carbon, and other related materials are known to have very large apertures (up to 100 nm); however, unlike porous crystals of MOFs, they are amorphous with either irregular structures and/or inhomogeneous pores. In contrast, the MOF pore apertures reported herein are homogenous and precisely controlled on the Angstrom level. These features, coupled with the flexibility in which MOFs' composition and structure metrics can be varied, make these MOFs highly desirable for specific inclusion processes which distinguish them from amorphous materials.

Figure 2:
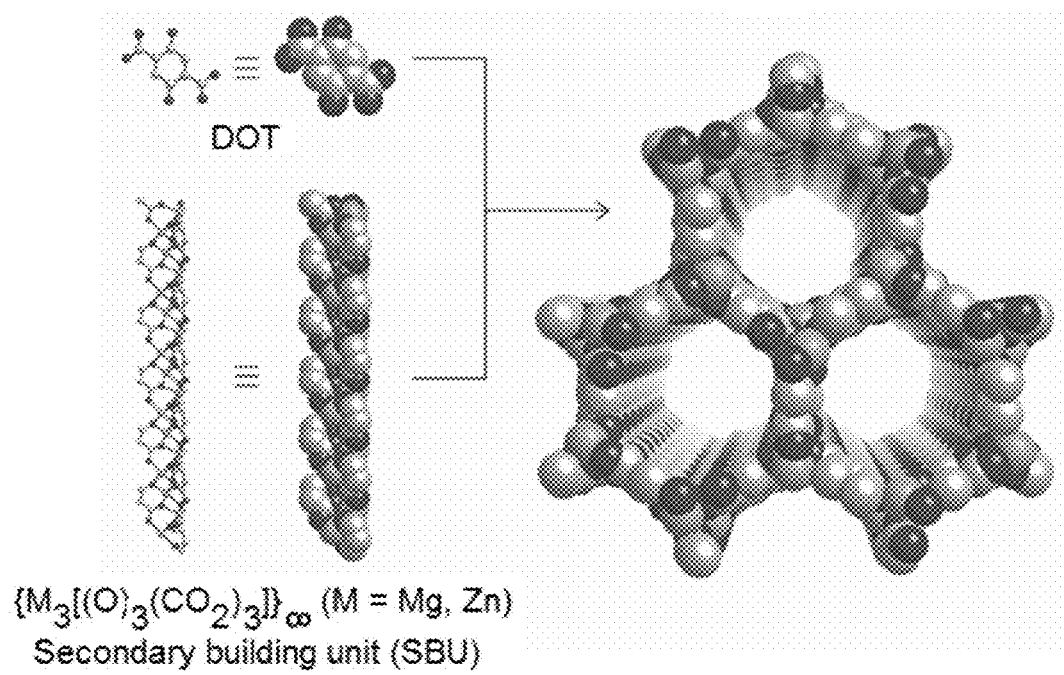
FIG. 2 provides a single crystal structure of IRMOF-74. The DOT link is joined with a metal oxide secondary building unit (SBU) to make the three dimensional IRMOF-74 structure with one dimensional hexagonal channels. C atoms are shown in light grey, 0 atoms in black, 5-coordinate Mg or Zn atoms with open metal site are shown in dark grey, H atoms and terminal ligands protruding into the pores have been omitted for clarity.

One strategy disclosed herein for making MOFs with large pore apertures and avoiding the problem of interpenetration is to start with a framework in which one can maintain a short axis with the long organic links placed inclined to that axis. The short axis effectively eliminates the possibility of interpenetration of those links. Ideal in this regard are the frameworks built from infinite rod-shaped metal oxide secondary building units (SBUs) as exemplified in the structure of MOF-74 (FIG. 2). Here, the zinc oxide rod SBUs are in a rhombohedral arrangement joined along the short and long axes by zinc-oxygen bonds and organic DOT links, respectively; a construction that forbids interpenetration regardless of the link's length.

Initially, models of a MOF-74 like structure were produced with progressively longer links II to XI assuming $R\bar{3}$ symmetry. From which, calculations for X-ray powder diffraction patterns, their expected cell parameters, pore aperture, and other related porosity information were produce for the IRMOF compounds are disclosed herein in the Examples. This initial analysis was followed by the preparation of the links as well as, carrying out the synthesis and characterization of the IRMOFs, and comparing the observed and calculated structural data to verify that the entire IRMOF series had MOF-74 like topology (Table 23).

The organic links disclosed herein utilize a homologous series of palindromic oligo-phenyl derivatives that terminate with α-hydroxy-carboxylic acid groups. The low solubility of the parent oligo-phenyl derivatives were circumvented by substituting (III to VI) the phenyls with para-methyl substituents, except for the terminal phenyls. By doing so, torsional twists were introduced into the previously planar structures. This stereoelectronic control breaks inter-ring conjugation and reduces π-π stacking, thereby enhancing the solubility of the building blocks for IRMOF production (see Examples). In the syntheses of even longer links (VII to XI) solubility's were maintained by replacing, in a corresponding symmetrical manner, selected pairs of methyl groups with hexyl substituents on certain phenyls. By using these substituted phenyls, coupled with a modular synthetic strategy, based on transition metal catalyzed cross-coupling reactions, enabled the efficient elaboration of a series of slender and robust organic links with lengths ranging from 7 (I) to 50 Å (XI) (FIG. 1). Gram quantities of soluble organic links II-XI were synthesized in 5-16 steps as disclosed herein in the Examples.

Figure 3:
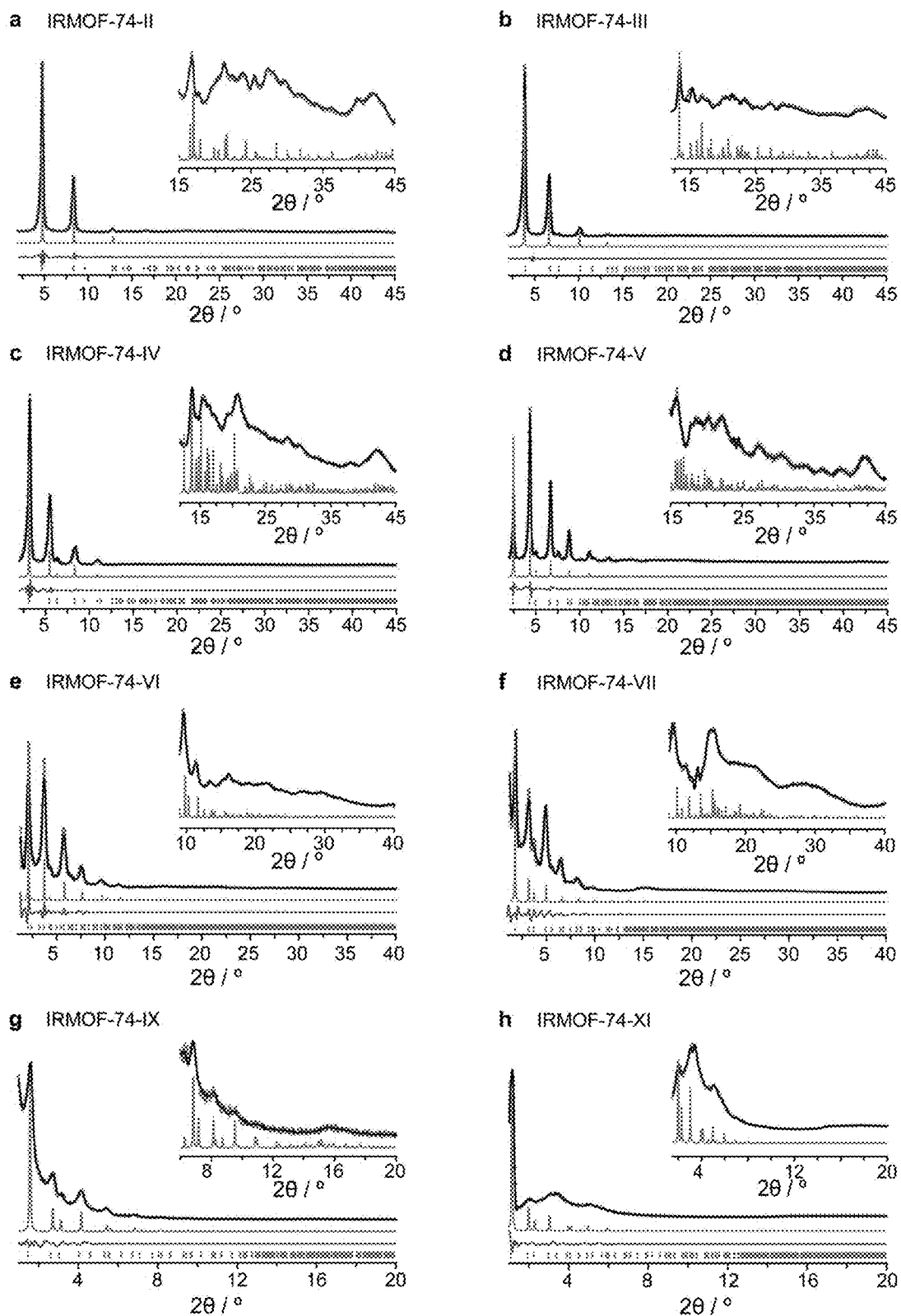
FIG. 3A-H provides X-ray diffraction patterns of the IRMOF-74 series. Overlays of experimental and refined (top; note the lines overlap), and simulated (second from top) X-ray diffraction patterns are also presented. The difference of the experimental and refined patterns (second from bottom) and the Bragg positions (bottom) are shown in (A)-(H) for IRMOF-74-II to XI, respectively.
Figure 4:
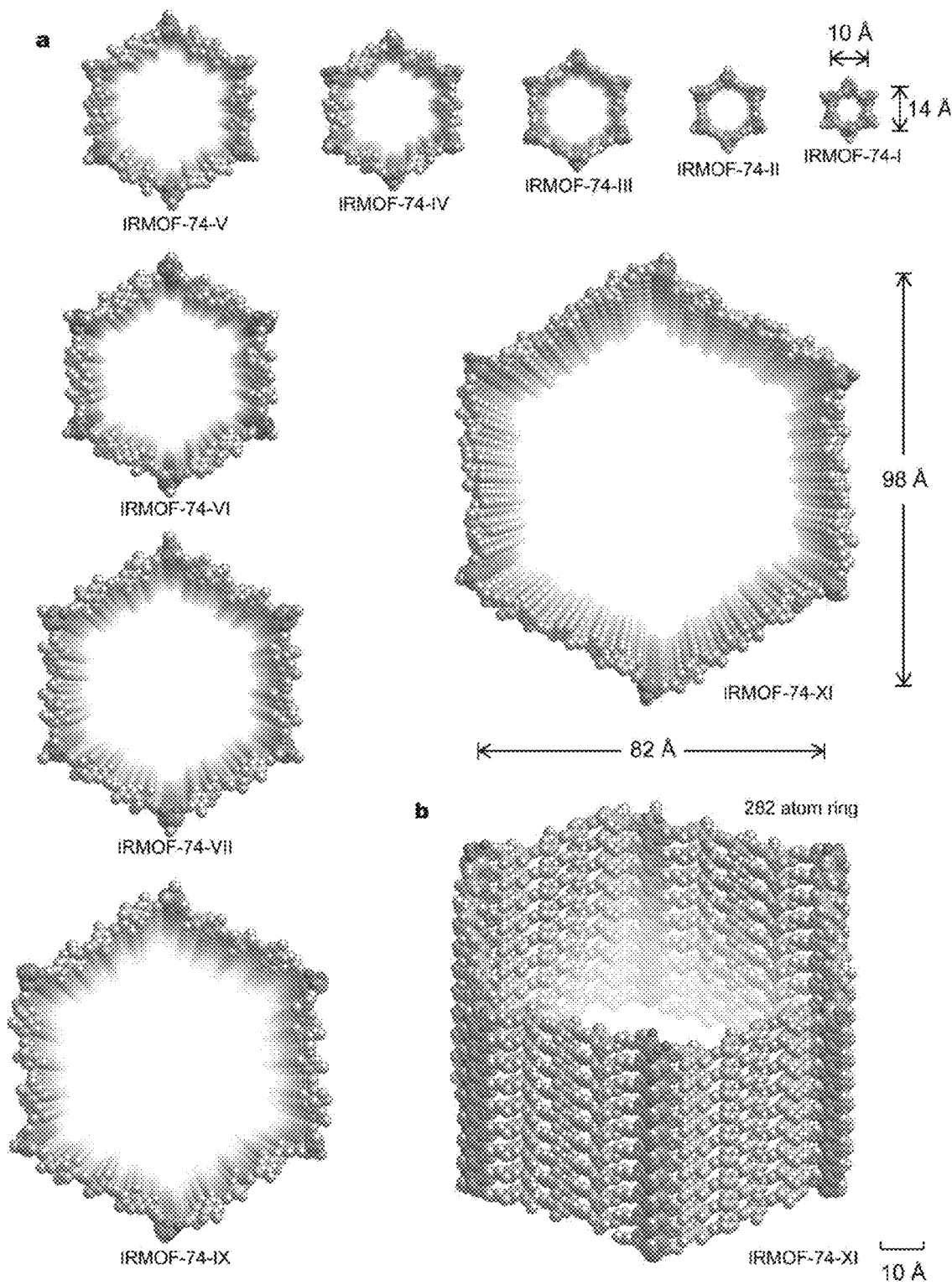
FIG. 4A-B provides crystal structures of the IRMOF-74 series. (A) Perspective views of a single one dimensional channel shown for each member of IRMOF series starting from the smallest (upper most right). Pore aperture is described by the length of the diagonal and the distance between the two opposite edges in the regular hexagonal cross section. Hexyl chains are omitted for clarity as well as hydrogen atoms. C atoms are shown in light grey, O atoms in black, Mg and ZN atoms dark grey. (B) Perspective side view of the hexagonal channel showing the ring of 282 atoms defining the pore aperture of the largest member of the series, IRMOF-74-XI.

All the crystals of the IRMOF-74 family were synthesized under similar, if not identical, conditions to those previously used in the synthesis of MOF-74. Colorless, needle-shaped crystals were obtained for all the IRMOFs. The phase purity of each material was confirmed by their singular crystal morphology as observed in the scanning electron microscopy (SEM) images (see FIGS. 17-25). The materials are highly crystalline, as demonstrated by their sharp X-ray diffraction peaks observed for the entire series of IRMOF-74 (FIG. 3). Comparison of the experimental powder X-ray diffraction (PXRD) patterns with those calculated from the crystal models was in good agreement with regard to both the position and relative intensities of the peaks, confirming that the predicted IRMOF-74 structures were obtained (FIG. 4a). For each IRMOF, a full pattern profile refinement was then performed to obtain the lattice parameters, using the unit cell parameters of the geometrically optimized models as the initial input data. All the refinements resulted in acceptable convergence residuals. IRMOF-74-IX and XI display broad peaks, indicative of small crystals, a situation that precludes distinguishing the peaks with low intensities in the high angle area. Nevertheless, the patterns clearly show the most intense diffraction peaks, corresponding to the largest d-spacings, at their expected 2θ positions.

The unit cell, void volume, and pore aperture cover a wide range as the size of the organic link is increased (Table 2 and 23). The void volume calculated using the crystal structure data increases from 48.5% to 85.0% for IRMOF-74-I to XI. The pore aperture is defined as the length of the diagonal and the distance between the two opposite edges in the regular hexagonal cross section (atom to atom distance, FIG. 4a, see Examples). This method is consistent with that previously used for referring to the pore aperture and it is deployed here to facilitate comparison with those in the literature. The diagonal dimension of the pore aperture, based on the refined unit cell, increases from 19 Å in IRMOF-74-II to 98 Å in IRMOF-74-XI with a discrete increment of nearly 6 Å as each phenyl unit is added. Furthermore, upon the addition of each phenyl unit, there is an increase by 24 atoms in the ring size defining the pore aperture, leading to rings of 282 atoms in IRMOF-74-XI (FIG. 4b). This far exceeds the number of atoms defining the most open zeolites, and it exceeds any previously presented uncatenated crystalline material (see Examples). In this series of IRMOFs, eight out of nine members (IRMOF-74-II to XI) have pore dimensions falling in the mesoporous region (i.e. >20 Å). While several other MOFs have been reported whose pore sizes are in this mesoporous region, their pore apertures are all exceeded by IRMOF-74-IV to XI.

Figure 5:
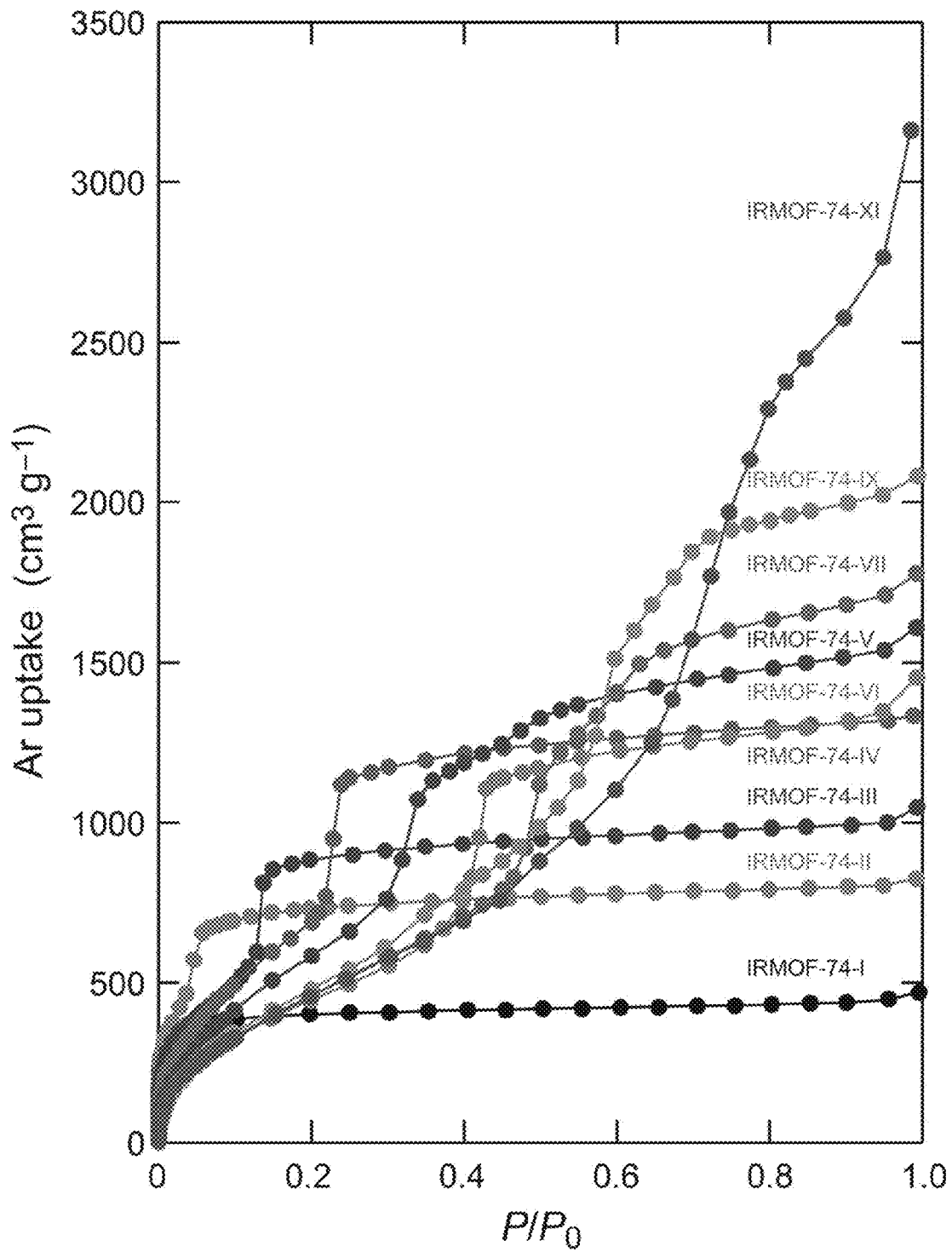
FIG. 5 provides Ar adsorption isotherms for the IRMOF-74 series at 87K. Ar uptake capacity, which reflects the pore volume of the framework, increases systematically from IRMOF-74-I to XI, corresponding to the increasing length of the organic links. IRMOF-74-VI shows lower uptake than IRMOF-74-V due to the use of Zn instead of Mg in the SBU. Only the adsorption branch of the Ar isotherms is displayed for clearance. $P/P_0$ is relative pressure. Instrument uncertainty is ±5%.
Figure 46:
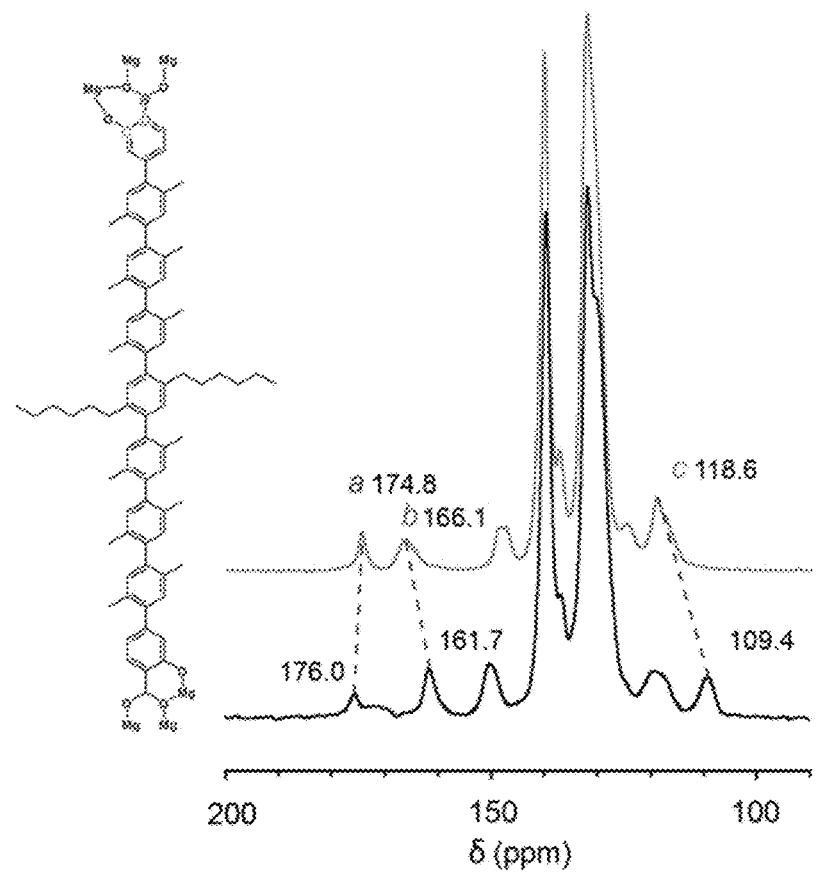
FIG. 46 presents $^{13}C$ CP/MAS NMR spectra of activated IRMOF-74-IX (top line) and its counterpart free organic link (bottom line).

In order to assess the porosity of the IRMOFs and their architectural stability, Ar gas adsorption measurements at 87 K were performed. Initially, activation procedures and characterization were performed to ensure that the pores were activated and free of any guests molecules. The solids of the IRMOFs were subjected to solvent exchange followed by evacuation, and in some cases treated by supercritical carbon dioxide, to obtain porous samples (see Examples). These samples were studied by thermal gravimetric analysis, which showed no weight loss up to 300° C., confirming the high thermal stability of all the IRMOFs and indicating the absence of organic solvents from their pores. Successful removal of unreacted starting materials and organic solvent was further confirmed by $^{13}C$ cross-polarization/magic angle spinning nuclear magnetic resonance, elemental analysis, and Fourier transform infrared spectroscopy (FIG. 46). FIG. 5 shows the gas adsorption isotherms performed on the evacuated samples of IRMOF-74-I to XI. Two types of behavior are observed: IRMOF-74-I exhibits a Type I isotherm indicative of a microporous material, while the other IRMOFs display Type IV isotherms typical of mesoporous materials. The effect of pore size expansion is observed in the relative pressure of the second steps in the Type IV isotherms. IRMOF-74-II, III, and IV have a steep step is observed at $P/P_0$=0.04, 0.13 and 0.23, and a broad step is observed in IRMOF-74-VII, IX, and XI around $P/P_0$=0.46-0.66, 0.54-0.72, and 0.60-0.82, respectively. The gradual shift of the step position from IRMOF-74-II to XI corresponds closely to the pore size expansion trend in the series.

The pore volume in the frameworks is reflected in their Ar uptake capacity, which increases systematically from IRMOF-74-I to XI as longer organic links are incorporated (440, 800, 990, 1310, 1520, 1320, 1680, 2000, and 2580 cm·g$^{-1}$ at $P/P_0$=0.9, respectively; slightly lower uptake is observed in IRMOF-74-VI due to the use of Zn instead of Mg). The largest calculated pore volume in the series is for IRMOF-74-XI (3.3 cm·g$^{-1}$), which is close to that of the recently reported ultra-highly porous MOF-210 (3.6 cm$^3$·g$^{-1}$). Applying the Langmuir model to the pressure regions after the second step, apparent surface areas of IRMOF-74-I to XI were calculated to be 1600, 2940, 3750, 5370, 6940, 5880, 8320, 9410, and 9880 m$^2$·g$^{-1}$, respectively. In contrast, the highest BET surface area among the IRMOFs was observed in IRMOF-74-II and the BET surface areas for IRMOFs with longer organic links showed even lower values because of the smaller geometric surface per volume (1350, 2510, 2440, 2480, 2230, 1600, 1800, 1920, and 1760 m$^2$·g$^{-1}$ for IRMOF-74-I to XI). Nevertheless, the surface areas are still much higher compared to those found in mesoporous silica, porous carbon, and zeolites, thus providing more readily available surfaces for interaction with large guest molecules. The low density, which was also achieved in this IRMOF series, is not only attributable to the increase of open space, but is a consequence of the use of magnesium, a metal with light weight, for the formation of the SBU. Seven of the eight new IRMOFs were constructed with Mg, including IRMOF-74-XI, which has the crystal density of 0.195 g·cm$^{-3}$; the lowest known so far for a guest-free crystal at ambient temperature.

Given the remarkable stability, ultrahigh porosity, and extremely large pore aperture characteristic of the IRMOF-74 series, the frameworks of the disclosure give access to a new size regime for the inclusion of large organic, inorganic and biological molecules inside the pores of the IRMOF crystals. The disclosure demonstrates the inclusion of large molecules into the IRMOFs with appropriate pore apertures; specifically, vitamin-$B_{12}$ (largest size dimension of 27 Å) in IRMOF-74-IV, MOP-18 (inorganic spherical cluster with diameter of 34 Å) in IRMOF-74-V, myoglobin (globular protein with spherical dimensions of 21 Å×35 Å×44 Å) in IRMOF-74-VII-oeg, and green fluorescent protein (barrel structure with diameter of 34 Å and length of 45 Å) in IRMOF-74-IX.

Typically, crystals of the desired IRMOF-74 were immersed in a solution containing the particular guest compound to be included. Activated crystals of IRMOF-74-IV were immersed in a 0.11 mM solution of vitamin-$B_{12}$. The amount of vitamin-$B_{12}$ in the supernatant was measured by UV-Vis spectrophotometry and the characteristic absorbance at 480 nm was monitored over a period of 48 hours. The results are plotted in FIG. 6a, which clearly shows a continuous decrease of the amount of vitamin-$B_{12}$ in the supernatant. The same experiment was carried out, as a control, with IRMOF-74-III whose pore aperture is smaller than IRMOF-74-IV and therefore was not expected to show any uptake of vitamin-$B_{12}$. This is confirmed to be the case as no decrease in absorbance was observed (FIG. 6a). Similar experiments were done for the inclusion of MOP-18 in IRMOF-74-V, myoglobin in IRMOF-74-VII, and GFP in IRMOF-74-IX (FIG. 6b-d). For the solid resulting from the inclusion of MOP-18, an Ar adsorption isotherm at 87 K of a dried sample displayed a decrease in the step pressure as a result of inclusion into the pore (FIG. 6l). Myoglobin is very hydrophilic. Consequently, the IRMOF-74-VII pores were functionalized with a hydrophilic group (triethylene glycol mono-methyl ether, oeg) and upon testing, significant uptake of myoglobin was observed. However, negligible amount of myoglobin inclusion was observed in the control experiment where the pores were functionalized with hydrophobic hexyl chains, IRMOF-74-VII (FIG. 6c). For the control experiment in the GFP inclusion study, IRMOF-74-V was functionalized with hexyl chains (IRMOF-74-V-hex), to provide a similarly hydrophobic pore environment as IRMOF-74-IX (FIG. 6d). GFP retained its folded structure when included in IRMOF-74-IX, as evidenced by confocal microscopy, which showed an unaltered characteristic fluorescence of GFP (FIG. 68). It is remarkable that the crystallinity of the IRMOF materials were fully maintained throughout the inclusion process: the diffraction lines in the PXRD patterns of the included samples were coincident with those of the starting materials (See Examples).

Examples

Crystal Modeling

Crystal models were generated through modification of the reported crystal structure of Mg-MOF-74 (IRMOF-74-

I). The atomic connectivity within the inorganic SBU remained the same. A water molecule was included to complete the octahedral coordination environment of the Mg atoms. The appropriate number of phenyl rings, with their substituent groups, was added in the links for each IRMOF. An energetic minimization was then performed to optimize the geometry of the molecules, employing a smart algorithm and the universal force field implemented in the Forcite module of Materials Studio (Materials Studio v. 5.0.0.0, 2009, Accelrys Software Inc.). The unit cell parameters were also optimized until convergence was reached (energy convergence criteria: $10^{-4}$ kcal/mol). The powder X-ray diffraction patterns of the crystal structures were then calculated and compared with the experimental ones. The unit cell parameters and pore aperture dimensions of the initial structural models are presented in Table 1.

TABLE 1

| Compound | Space group | a (Å) | (Å) | Unit cell Volume (Å$^3$) | Pore aperture metrics (Å$^2$) | Number of atoms in the ring* |
|---|---|---|---|---|---|---|
| IRMOF-74-II | $\bar{3}$ | 36.060 | .464 | 7279.2 | 16.3 × 20.0 | 66 |
| IRMOF-74-III | $\bar{3}$ | 45.113 | .432 | 11336.5 | 22.4 × 26.5 | 90 |
| IRMOF-74-IV | $\bar{3}$ | 5.778 | .434 | 17335.5 | 28.1 × 33.7 | 114 |
| IRMOF-74-V | $\bar{3}$ | 68.787 | .449 | 26426.3 | 36.6 × 42.3 | 138 |
| IRMOF-74-VI | $\bar{3}$ | 78.239 | .501 | 34463.3 | 40.7 × 48.6 | 162 |
| IRMOF-74-VII | $\bar{3}$ | 92.059 | .497 | 47684.4 | 48.7 × 57.8 | 186 |
| IRMOF-74-IX | $\bar{3}$ | 116.01 | .668 | 77717.2 | 62.4 × 72.5 | 234 |
| IRMOF-74-XI | $\bar{3}$ | 145.75 | .677 | 122837.0 | 82.2 × 95.4 | 282 |

*The smallest hexagonal ring defining the pore aperture

General Experimental (Links):

Anhydrous tetrahydrofuran (THF), dichloromethane ($CH_2Cl_2$) and acetonitrile (MeCN) were obtained from an EMD Chemicals DrySolv® system. Anhydrous p-dioxane and $Me_2SO$ were purchased from Aldrich and stored under an atmosphere of argon. $CDCl_3$, $C_6D_6$, $CD_2Cl_2$ and $(CD_3)_2CO$ were purchased from Aldrich and used without further purification. All other reagents and solvents were purchased from commercial sources and were used without further purification, unless indicated otherwise. All reactions were carried out under an atmosphere of $N_2$ in flame-dried flasks using anhydrous solvents, unless indicated otherwise. Thin-layer chromatography (TLC) was carried out using glass or aluminium plates, pre-coated with silica-gel 60 containing fluorescent indicator (Whatman LK6F). The plates were inspected by UV light (254 nm) and/or $KMnO_4$ stain. Column chromatography was carried out using the flash technique using silica-gel 60F (230-400 mesh). $^1H$ and $^{13}C$ NMR spectra were recorded on a Bruker ARX500 (500 MHz) spectrometer. VT-NMR spectra were recorder on a BrukerAdvance 600 MHz spectrometer, which was temperature-calibrated using neat ethylene glycol. The chemical shifts (δ) for $^1H$ spectra, given in ppm, are referenced to the residual proton signal of the deuterated solvent. The chemical shifts (δ) for $^{13}C$ spectra are referenced relative to the signal from the carbon of the deuterated solvent. High-resolution mass spectra were measured on a Finnigan LCQ ion-trap mass spectrometer (HR-ESI).

Suzuki-Miyaura Cross-Couplings:

A p-dioxane/$H_2O$ mixture (2:1 v/v, 0.12 M based on aryl halide) was purged with $N_2$ and transferred subsequently via cannula to a round-bottomed flask charged with the aryl halide (1.00 equiv.), the boronic acid pinacol ester (1.05 equiv. per halide), CsF (3.00 equiv. per halide) and $PdCl_2$(dppf) (2.5 mol % per halide). The resulting mixture was transferred to an oil bath pre-warmed to 90° C. and the reaction mixture was stirred vigorously for 24 h. It was then cooled to RT, and the products were purified using techniques outlined with specific measures per individual reactions as noted below.

Saponifications:

A solution of NaOH (10.0 equiv.) in $H_2O$ was added to a solution of the requisite diester (1.0 equiv.) in THF to make a final 0.2 M solution (equal volumes of $H_2O$ and THF). The resulting biphasic solution was stirred vigorously at 50° C. for 24 h, before being cooled subsequently to RT. The THF was removed in vacuo to provide typically an insoluble white solid in $H_2O$. While stirring, the aqueous layer was acidified with concentrated HCl until a pH<2 was attained and the resulting precipitate was collected by vacuum filtration, washed with ample $H_2O$ and air-dried for 24 h to provide the target compound as typically a white powder.

Synthesis of the Organic Links

The synthetic strategy to build up the oligo-phenyl backbone of all the oligo-para-xylene (OPX) links II-VII, and IX and XI were based on palladium-catalysed Suzuki-Miyaura cross-coupling. The general strategy was to couple two equivalents of a terminal boronic ester building block, bearing carboxyl and hydroxyl groups to a di-halide midriff. The carboxylic acid was protected as its methyl ester, and the phenolic hydroxyl group was protected as its benzylic ether. Suzuki-Miyaura cross-coupling conditions, employing CsF as base with $PdCl_2$(dppf) as the catalyst in a p-dioxane/$H_2O$ (2:1 v/v) mixture, were found not to effect the protection groups, providing the oligo-phenyls in good yields. The benzylic protection groups were cleaved by hydrogenolysis and subsequently the methyl ester functions were saponified to provide the target compounds, usually in quantitative yields over the two consecutive steps with no purification required other than filtration.

The synthesis scheme of OPX links III-VI are presented in Scheme 1:

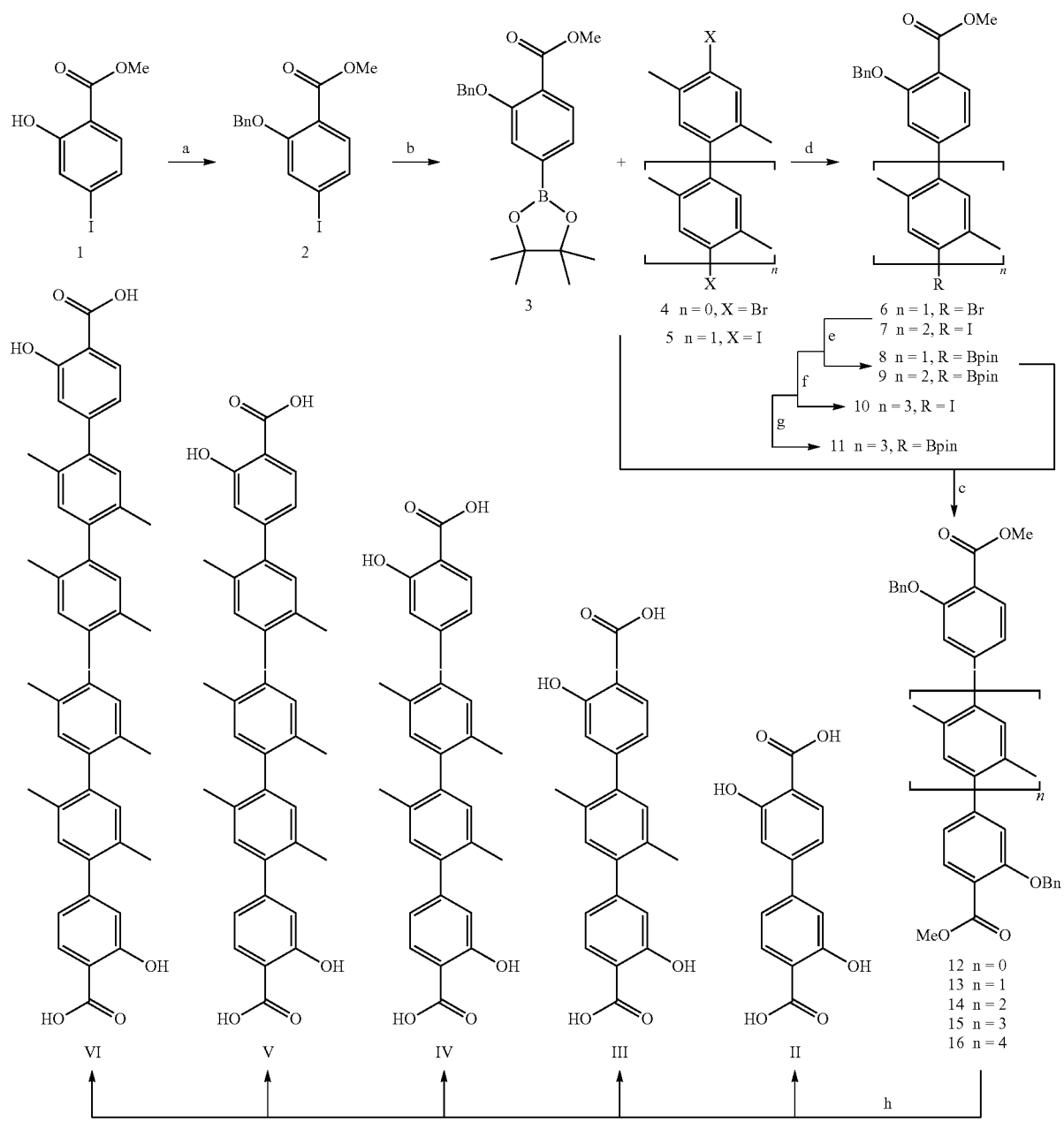

Scheme 1

Scheme 1, reagents and conditions: a) K$_2$CO$_3$, BnBr, MeCN, 80° C. b) (Bpin)$_2$, KOAc, (PPh$_3$)$_2$PdCl$_2$, p-dioxane, 106° C. c) CsF, PdCl$_2$(dppf), p-dioxane/H$_2$O, 90° C. d) CsF, PdCl$_2$(dppf), p-dioxane/H$_2$O, 90° C. e) KOAc, PdCl$_2$(dppf), (Bpin)$_2$, Me$_2$SO, 80° C. f) 5, CsF, PdCl$_2$(dppf), p-dioxane/H$_2$O, 90° C. g) KOAc, PdCl$_2$(dppf), (Bpin)$_2$, Me$_2$SO, 80° C. h) i) Pd/C or Raney Ni, H$_2$, THF, 50° C.; ii) NaOH, THF/H$_2$O, 50° C.

The boronic ester 3 key building block was synthesized on a 100-g scale. By coupling two equivalents of 3 with 2,5-dibromo-para-xylene (4) or 4,4'-diiodo-2,2',5,5'-tetramethyl-1,1'-biphenyl (5), III and IV, respectively, were obtained after deprotection. If one equivalent of the boronic ester 3 is coupled to an excess of the dihalide 4 or 5, the mono-coupled products can be obtained in 70% yields, thus providing building blocks 6 and 7, respectively. The halides of building blocks 6 and 7 were subsequently converted (e in Scheme 1) in a palladium-catalyzed coupling with pinacol diboron into the boronic acid pinacol esters 8 and 9, respectively. The building block 10 was further extended with two additional 2,5-dimethyl-para-phenylene units by exposing it once again to a Suzuki-Miyaura coupling with an excess of 5. After borylation of the iodide of 10 the building block 11 was obtained in good yields. Two equivalents of the biphenyl boronic ester derivative 8 were coupled with the 2,5-dibromo-para-xylene (4) and 4,4'-diiodo-2,2',5,5'-tetramethyl-1,1'-biphenyl (5) to provide, after deprotection, V and VI, respectively.

Synthesis scheme of the hexyl-doped OPX links V-hex, VII, and IX are presented Scheme 2:

Scheme 2

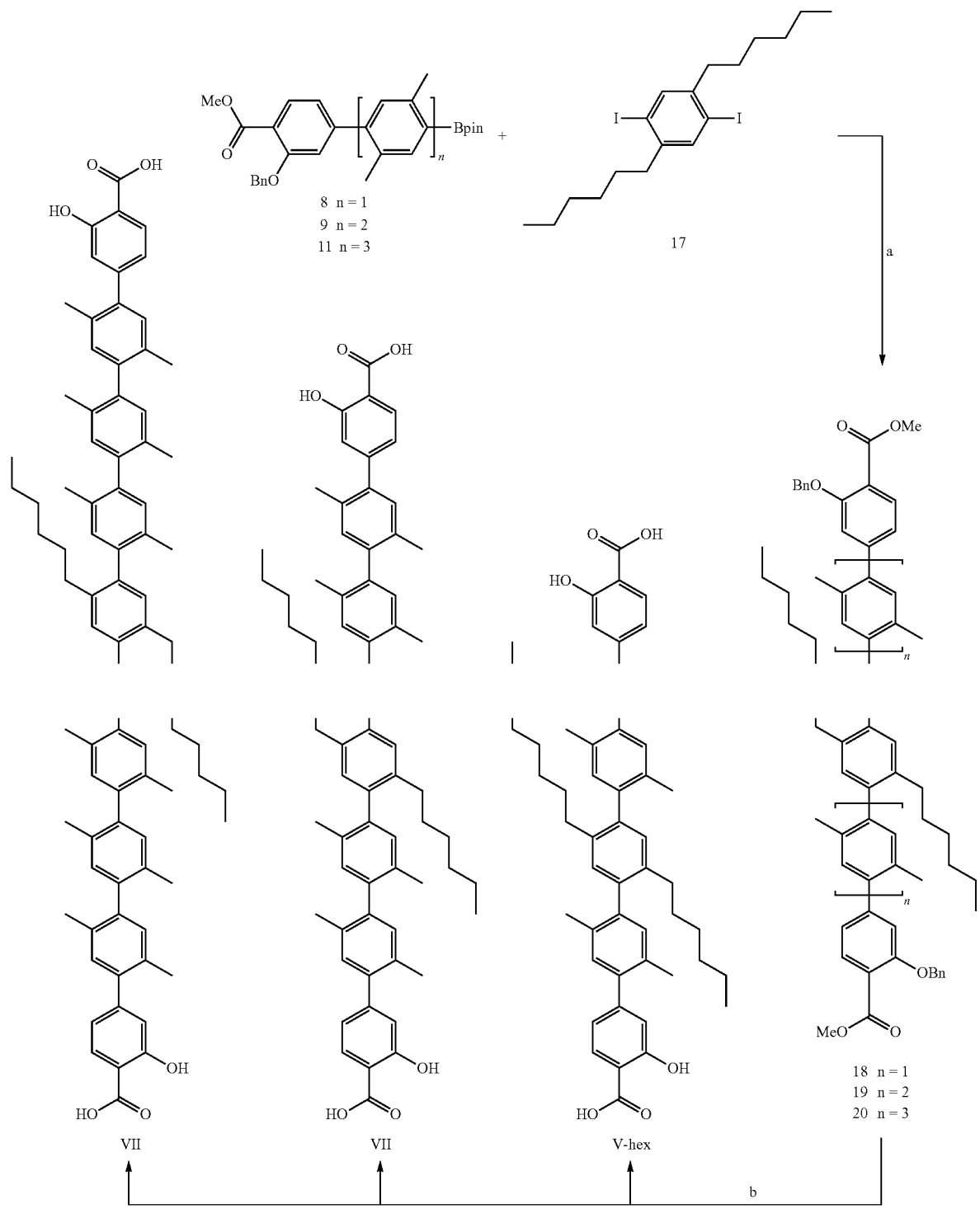

Scheme 2, reagents and conditions: a) CsF, PdCl$_2$(dppf), p-dioxane/H$_2$O, 90° C. b) i) Pd/C or Raney Ni, H$_2$, THF, 50° C.; ii) NaOH, THF/H$_2$O, 50° C.

For the synthesis of the dihexyl-substituted series, 1,4-dihexyl-2,5-diiodobenzene (17) was required as a key building block: it was obtained in three steps starting from 1,4-diiodobenzene. Coupling two equivalents of the boronic ester building blocks 8, 9, and 11 to the dihexyl-paraphenylene building block 17, followed by hydrogenolysis and saponification, yielded (Scheme 2) the dihexyl-substituted OPX links V-hex, VII, and IX, in turn.

Synthesis scheme of the hexyl-doped OPX link XI is presented in Scheme 3:

Scheme 3

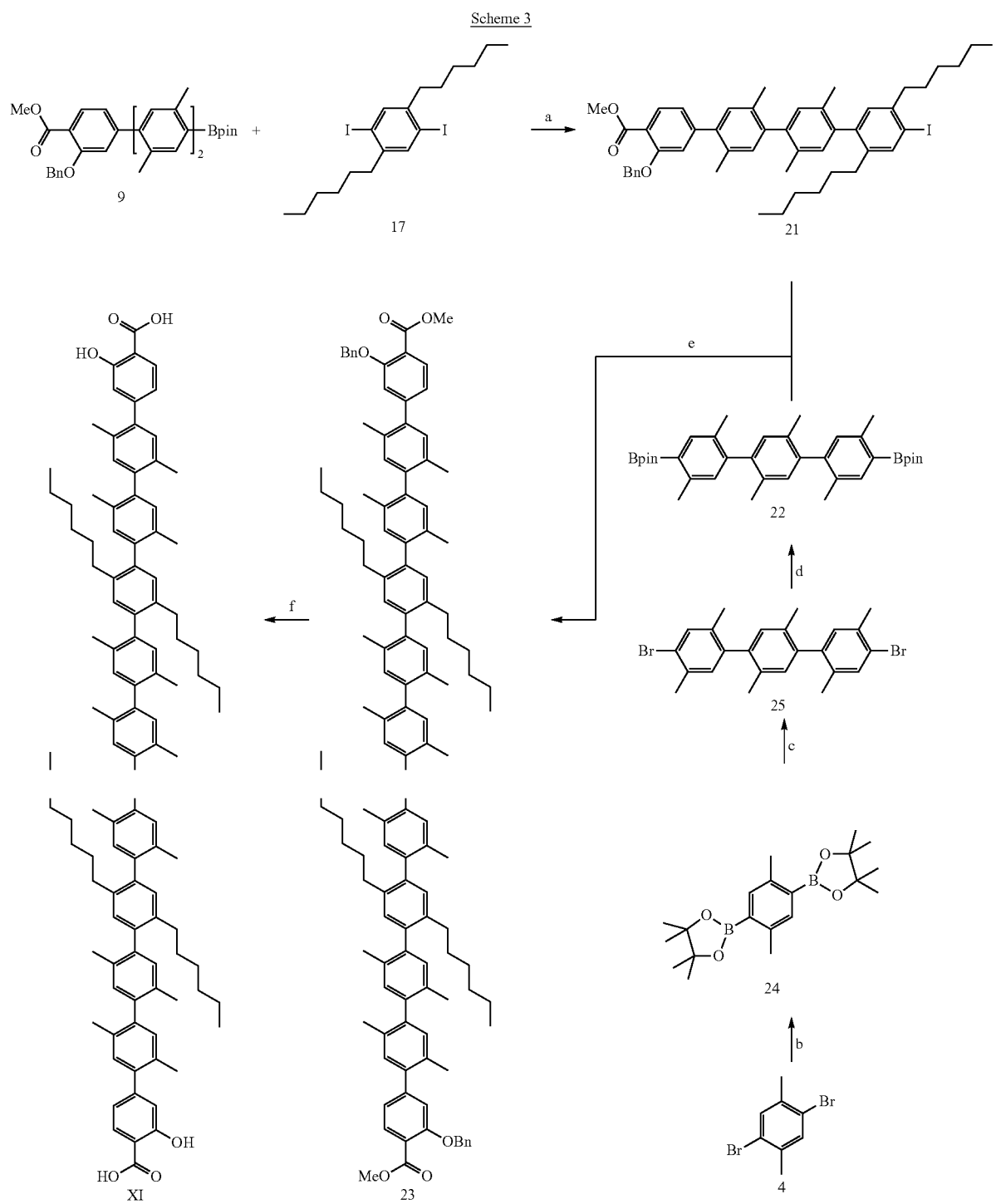

Scheme 3, reagents and conditions, a) CsF, PdCl$_2$(dppf), p-dioxane/H$_2$O, 100° C. b) (Bpin)$_2$, KOAc, PdCl$_2$(dppf), Me$_2$SO, 100° C. c) CsF, PdCl$_2$(dppf), p-dioxane/H$_2$O, 100° C. d) (Bpin)$_2$, KOAc, PdCl$_2$(dppf), Me$_2$SO, 100° C. e) CsF, PdCl$_2$(dppf), p-dioxane/H$_2$O, 100° C. f) i) Raney Ni, H$_2$, THF, 50° C.; ii) NaOH, THF/H$_2$O, 50° C.

In order to confer solubility on the longer OPX links such as the XI, two para-xylene residues had to be substituted with 2,5-dihexylphenylenes. The boronic ester building block 9 was therefore extended in a Suzuki-Miyaura reaction with an excess of 1,4-dihexyl-2,5-diiodobenzene (17) to provide the iodide 21. Two equivalents of 21 were then coupled with the diboronic ester building block 22, obtained in three steps, to provide the 11-ring backbone 23. After hydrogenolysis and saponification the XI was obtained (Scheme 3).

Synthesis scheme of the ethylene glycol-substituted OPX link VII-oeg is presented in Scheme 4:

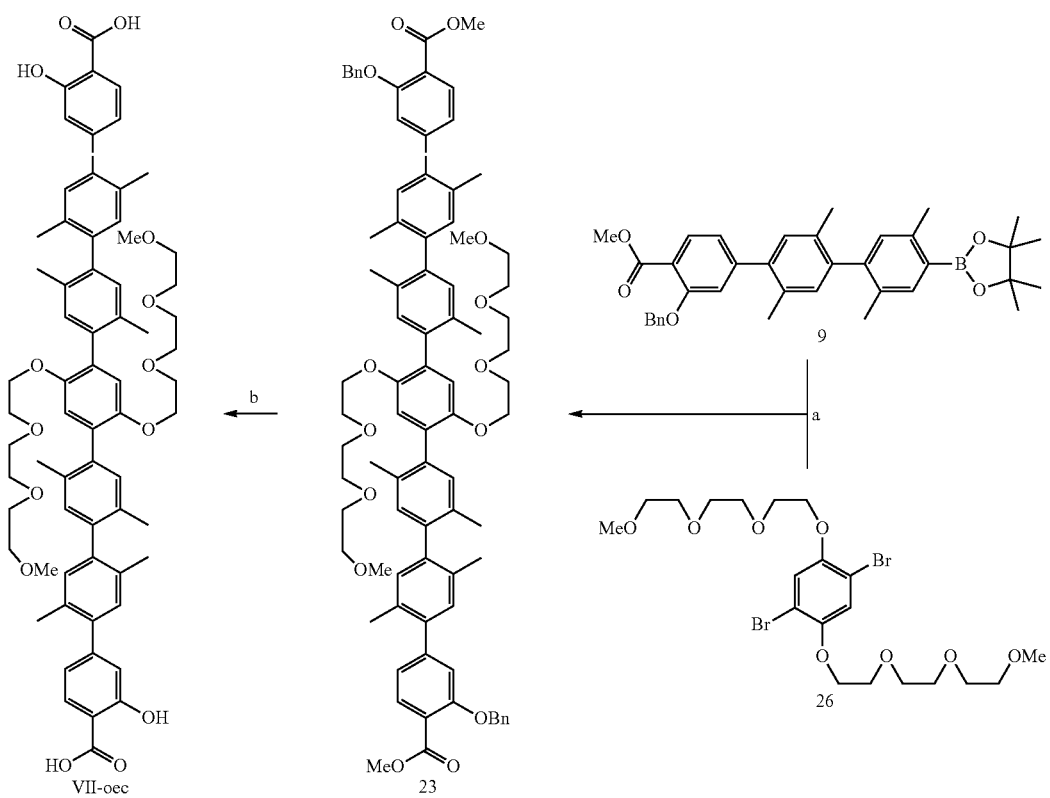

Scheme 4, reagents and conditions: a) CsF, PdCl$_2$(dppf), p-dioxane/H$_2$O, 100° C. b) i) Raney Ni, H$_2$, THF, 50° C.; ii) NaOH, THF/H$_2$O, 50° C.

The triethylene glycol mono methyl ether substituted derivative VII-oeg was obtained by reacting the boronic ester building block 9 with the dibromide 26, which itself was observed in two steps starting from commercially available 2,5-dibromohydroquinone following a reported procedure.[3] The benzylic ether protection groups were then cleaved by hydrogenolysis using Raney Ni as a catalyst. Subsequently the methyl ester groups were saponified to yield the target compound VII-oeg as a colourless solid (Scheme 4).

Synthesis of Compound Building Blocks for Link Syntheses

Methyl 2-(benzyloxy)-4-iodobenzoate (2)

Solid K$_2$CO$_3$ (76.1 g, 0.55 mol) was added to a solution of methyl 4-iodosalicylate (1) (76.5 g, 0.28 mol) in MeCN (550 mL) at RT. Benzyl bromide (32.7 mL, 0.28 mol) was added via syringe, and the resulting reaction mixture was warmed to 80° C. and stirred overnight. The reaction mixture was then cooled to RT and filtered subsequently to remove insoluble salts, which were washed further with EtOAc. The filtrate was concentrated in vacuo, before re-dissolving the residue in fresh EtOAc and filtering a second time. The filtrate was concentrated in vacuo to provide an oil which solidified upon standing to yield 2 (99%, 100.5 g) as a beige solid that required no further purification. $^1$H NMR (500 MHz, CDCl$_3$, 25° C.): δ=7.54 (d, J=8.0 Hz, 1H), 7.49 (d, J=7.5 Hz, 2H), 7.43-7.35 (m, 4H), 7.33 (t, J=7.5 Hz, 1H), 5.15 (s, 2H), 3.89 (s, 3H) ppm. $^{13}$C NMR (126 MHz, CDCl$_3$, 25° C.): δ=166.3, 158.4, 136.2, 133.1, 130.1, 128.8, 128.1, 127.0, 123.3, 120.3, 100.0, 71.0, 52.3 ppm. HRMS (ESI) calculated for C$_{15}$H$_{14}$IO$_3$: m/z=367.9909 ([M+H]$^+$). Found m/z=367.9893.

Synthesis of Compound (3)

Anhydrous p-dioxane (1.35 L) was added to a three-neck round-bottomed flask equipped with a reflux condenser and charged with methyl 2-(benzyloxy)-4-iodobenzoate (2) (100.2 g, 0.27 mol), bis(pinacolato)diboron (76.0 g, 0.30 mol), KOAc (80.1 g, 0.82 mol) and (Ph$_3$P)$_2$PdCl$_2$ (3.8 g, 5.4 mmol). The reaction mixture was purged at RT with dry N$_2$ (approx. 30 min) and the flask was subsequently transferred to an oil bath pre-warmed to 130° C. The reaction mixture was heated under reflux for 16 h, before being cooled to RT and filtered subsequently to remove insoluble salts which were washed further with EtOAc. The filtrate was concentrated in vacuo before re-dissolving the residue in EtOAc. Ample activated carbon was added to the typically dark brown/black solution and the EtOAc solution was warmed to reflux for 15 min. The insoluble material was removed by hot filtration through a pad of Celite to provide typically a yellow solution that was concentrated in vacuo to provide an oil. To facilitate solidification, hexanes (200 mL) were added and the solution was subsequently concentrated in vacuo. The dilution of the residue with hexanes and subsequent concentration in vacuo was repeated a further two times so as to remove any residual p-dioxane and/or EtOAc. Typically, this process yields a light brown solid that is insoluble in hexanes at RT. Hexanes (500 mL) was added to the solid and warmed to reflux to provide a homogeneous solution that was removed from the heat source and left to stand overnight to crystallize. Filtration provided 3 (78%, 78.1 g) as yellow needles. $^1$H NMR (500 MHz, CDCl$_3$, 25° C.): δ=7.80 (d, J=7.5 Hz, 1H), 7.53 (d, J=7.5 Hz, 2H), 7.48 (s, 1H), 7.44 (dd, J=7.5, 1.0 Hz, 1H), 7.40 (t, J=8.0 Hz, 2H), 7.31 (t, J=7.5 Hz, 1H), 5.22 (s, 2H), 3.90 (s, 3H), 1.36 (s, 12H) ppm. $^{13}$C NMR (126 MHz, CDCl$_3$, 25° C.): δ=166.9, 157.4, 136.9, 134.7 (br.), 130.9, 128.5, 127.7, 127.0, 126.9, 123.1, 119.3, 84.3, 70.6, 52.1, 24.9 ppm. HRMS (ESI) calculated for C$_{21}$H$_{25}$B$_1$O$_5$: m/z=369.1873 ([M+H]$^+$). found m/z=369.1884; m/z=391.1693 ([M+Na]$^+$). found m/z=369.1702.

Synthesis of Compound (6)

The boronic ester 3 (9.20 g, 25.0 mmol, 1.0 equiv.) and the bromide 4 (35.9 g, 135.8 mmol, 5.4 equiv.) were dissolved in a degassed 2:1 p-dioxane/H$_2$O mixture (300 mL). CsF (11.4 g, 75.0 mmol, 3.0 equiv.) and PdCl$_2$(dppf) (1.11 g, 1.36 mmol, 5 mol %) were added and it was heated under reflux for 14 h. The reaction mixture was cooled to RT, before being extracted with CH$_2$Cl$_{12}$ and H$_2$O. The aqueous phase was washed twice with CH$_2$Cl$_2$. The combined organic phases were dried (MgSO$_4$), filtrated and evaporated. The crude product was absorbed on silica-gel and subjected to column chromatography (SiO$_2$:hexanes: CH$_2$Cl$_2$=1:1→1:10) to give the compound 6 as a yellowish oil (7.75 g, 18.2 mmol, 67%). $^1$H NMR (500 MHz, CDCl$_3$, 25° C.): δ=7.87 (d, J=7.9 Hz, 1H), 7.48 (m, 2H), 7.43 (s, 1H), 7.40 (m, 2H), 7.31 (m, 1H), 7.03 (s, 1H), 6.91 (dd, J=7.9, 1.5 Hz, 1H), 6.89 (d, J=1.3 Hz, 1H), 5.21 (s, 2H), 3.93 (s, 3H), 2.38 (s, 3H), 2.08 (s, 3H) ppm. $^{13}$C NMR (126 MHz, CDCl$_3$, 25° C.): δ=166.7, 157.8, 146.4, 140.0, 136.6, 135.2, 134.5, 133.9, 131.8, 131.5, 128.6, 127.8, 126.8, 124.2, 121.3, 119.2, 114.9, 70.6, 52.1, 22.3, 19.5 ppm. HRMS (ESI) calculated for C$_{23}$H$_{22}$BrO$_3$: m/z=425.0747 ([M+H]$^+$). found m/z=425.0755.

Synthesis of Compound (7)

The boronic ester 3 (1.08 g, 2.92 mmol, 1.0 equiv.) and the iodide 5 (5.40 g, 11.7 mmol, 4.0 equiv.) were dissolved in degassed p-dioxane (150 mL) and H$_2$O (50 mL). CsF (1.33 g, 8.76 mmol, 3.0 equiv.) and PdCl$_2$(dppf) (120 mg, 0.147 mmol, 5 mol %) were added and the reaction mixture was heated under reflux for 14 h. It was then cooled to RT before being extracted with CH$_2$Cl$_2$ and H$_2$O. The aqueous phase was washed twice with CH$_2$Cl$_2$. The combined organic phases were dried (MgSO$_4$), filtrated and evaporated. The crude product was absorbed on silica-gel and subjected to column chromatography (SiO$_2$:hexanes: EtOAc=5:1) to give the compound 7 as a colourless solid (1.11 g, 1.93 mmol, 66%). $^1$H NMR (500 MHz, CDCl$_3$, 25° C.): δ=7.90 (d, J=8.2 Hz, 1H), 7.74 (s, 1H), 7.51 (d, J=8.5 Hz, 2H), 7.40 (t, J=7.6 Hz, 2H), 7.32 (t, J=7.3 Hz, 1H), 7.07 (s, 1H), 7.02-7.00 (m, 3H), 6.95 (s, 1H), 5.24 (s, 2H), 3.94 (s, 3H), 2.41 (s, 3H), 2.15 (s, 3H), 2.04 (m, 6H) ppm. $^{13}$C NMR (126 MHz, CDCl$_3$, 25° C.): δ=166.8, 157.8, 147.3, 141.4, 140.2, 139.88, 139.81, 138.5, 136.8, 135.4, 133.2, 132.3, 131.7, 131.3, 130.9, 130.5, 128.6, 127.8, 126.8, 121.6, 118.9, 115.0, 99.6, 70.6, 52.1, 27.5, 19.8, 19.3, 19.0 ppm. HRMS (ESI) calculated for C$_{34}$H$_{30}$ IO$_3$: m/z=577.1234 ([M+H]$^+$). found m/z=577.1229.

Synthesis of Compound (8)

The bromide 6 (7.75 g, 18.2 mmol, 1.0 equiv.) was dissolved in dry and degassed Me$_2$SO (80 mL). Bis(pinacolata)diboron (5.08 g, 20.0 mmol, 1.1 equiv.), KOAc (5.36 g, 54.6 mmol, 3.0 equiv.) and PdCl$_2$(dppf) (743 mg, 0.91 mmol, 5 mol %) were added and it was heated to 80° C. for 14 h. The reaction mixture was then cooled to RT and extracted with CH$_2$Cl$_2$ and H$_2$O. The aqueous phase was washed twice with CH$_2$Cl$_2$. The combined organic phases were washed with H$_2$O, dried (MgSO$_4$), filtrated and evaporated. The crude product was absorbed on silica-gel and subjected to column chromatography (SiO$_2$:hexanes: EtOAc=5:1) to give compound 8 as a colourless oil (8.04 g, 17.0 mmol, 94%). $^1$H NMR (500 MHz, CDCl$_3$, 25° C.): δ=7.91 (d, J=7.8 Hz, 1H), 7.68 (s, 1H), 7.51 (m, 2H), 7.41 (m, 2H), 7.33 (m, 1H), 7.02 (s, 1H), 6.98-6.95 (m, 2H), 5.23 (s, 2H), 3.96 (s, 3H), 2.55 (s, 3H), 2.14 (s, 3H), 1.39 (s, 12H) ppm. $^{13}$C NMR (126 MHz, CDCl$_3$, 25° C.): δ=166.7, 157.8, 147.4, 143.1, 142.4, 138.1, 136.7, 131.7, 131.3, 130.8, 128.6, 127.8, 126.8, 121.3, 119.0, 114.9, 83.5, 70.6, 52.1, 25.1, 24.9, 21.7, 19.5 ppm. HRMS (ESI) calculated for C$_{29}$H$_{34}$BO$_6$: m/z=472.2544 ([M+H]$^+$). found m/z=472.2530.

Synthesis of Compound (9)

The iodide 7 (971 mg, 1.68 mmol, 1.0 equiv.) was dissolved in dry and degassed Me$_2$SO (7 mL). Bis(pinacolata)diboron (470 mg, 1.85 mmol, 1.1 equiv.), KOAc (494 mg, 5.04 mmol, 3.0 equiv.) and PdCl$_2$(PPh$_3$)$_2$ (69 mg, 0.084 mmol, 5 mol %) were added and the reaction mixture was heated to 80° C. for 15 h. After cooling to RT, the reaction mixture was extracted with H$_2$O and CH$_2$Cl$_2$. The aqueous phase was washed twice with CH$_2$Cl$_2$. The combined organic phases were washed with H$_2$O, dried (MgSO$_4$), evaporated and subjected to column chromatography (SiO$_2$: hexanes:EtOAc=9:1), to give compound 9 as a colourless foam (810 mg, 1.41 mmol, 84%). $^1$H NMR (500 MHz, CDCl$_3$, 25° C.): δ=7.93 (d, J=8.2 Hz, 1H), 7.70 (s, 1H), 7.54 (d, J=8.0 Hz, 2H), 7.42 (t, J=7.5 Hz, 2H), 7.35 (t, J=7.3 Hz, 1H), 7.10 (s, 1H), 7.05 (m, 2H), 6.99 (s, 1H), 6.98 (s, 1H), 5.27 (s, 2H), 3.97 (s, 3H), 2.55 (s, 3H), 2.17 (s, 3H), 2.10 (s, 3H), 2.06 (s, 3H), 1.39 (s, 12H) ppm. $^{13}$C NMR (126 MHz, CDCl$_3$, 25° C.): δ=166.8, 157.8, 147.5, 143.8, 142.0, 141.3, 139.5, 137.4, 136.8, 133.2, 132.1, 132.0, 131.7, 131.2, 130.9, 130.7, 128.6, 127.8, 126.8, 121.7, 118.8, 115.1, 83.5, 70.6, 52.1, 34.7, 31.6, 25.3, 24.98, 24.95, 22.7, 21.8, 20.8, 19.8, 19.3, 19.2, 14.3 ppm. HRMS (ESI) calculated for C$_{37}$H$_{41}$BO$_5$: m/z=576.3156 ([M+H]$^+$). found m/z=576.3169.

Synthesis of Compound (10)

The boronic ester 8 (2.60 g, 5.50 mmol, 1.0 equiv.), the iodide 5 (10.2 g, 22.1 mmol, 4.0 equiv.), and CsF (2.50 g, 16.5 mmol, 3.0 equiv.) were dissolved in a degassed mixture of p-dioxane (500 mL) and H$_2$O (200 mL) at 80° C. Then PdCl$_2$(dppf) (225 mg, 0.276 mmol, 5 mol %) was added and the reaction mixture was heated under reflux for 14 h. After cooling to RT, the reaction mixture was extracted with CH$_2$Cl$_2$ (400 mL) and H$_2$O (1000 mL). The aqueous phase was washed twice with CH$_2$Cl$_2$ (2×200 mL). The combined organic phases were washed with brine, dried (MgSO$_4$) and evaporated. The crude product was subjected to column chromatography (SiO$_2$:hexanes:EtOAc=5:1) to give the product 10 as a colourless oil (2.34 g, 3.44 mmol, 63%). $^1$H NMR (500 MHz, CDCl$_3$, 25° C.): δ=7.94 (d, J=8.2 Hz, 1H), 7.77 (s, 1H), 7.55 (d, J=7.4 Hz, 2H), 7.43 (t, J=7.6 Hz, 2H), 7.35 (t, J=7.3 Hz, 1H), 7.13 (s, 1H), 7.09-7.03 (m, 5H), 6.99 (m, 1H), 5.27 (s, 2H), 3.97 (s, 3H), 2.45 (s, 3H), 2.20 (s, 3H), 2.14-2.06 (m, 12H) ppm. $^{13}$C NMR (126 MHz, CDCl$_3$, 25° C.): δ=166.8, 157.9, 147.5, 141.83, 141.77, 141.20, 141.14, 141.00, 140.1, 139.8, 139.53, 139.50, 139.41, 139.36, 138.39, 138.36, 136.8, 135.56, 135.49, 133.45, 133.39, 132.92, 132.83, 132.66, 132.56, 132.1, 131.66, 131.60, 131.54, 130.78, 130.73, 130.69, 130.62, 130.48, 130.45, 128.6, 127.8, 126.8, 121.7, 118.8, 115.1, 99.4, 70.6, 52.1, 34.70, 34.57, 27.4, 25.3, 20.7, 19.83, 19.79, 19.47, 19.44, 19.37, 19.31, 18.98, 18.85 ppm. HRMS (ESI) calculated for C$_{29}$H$_{28}$IO$_2$: m/z=681.1860 ([M+H]$^+$). found m/z=681.1848.

Synthesis of Compound (11)

The iodide 10 (2.06 g, 3.02 mmol, 1.0 equiv.) was dissolved in dry and degassed Me$_2$SO (20 mL). Bis(pinacolato)diboron (843 mg, 3.32 mmol, 1.1 equiv.), KOAc (888 mg, 9.06 mmol, 3.0 equiv.) and PdCl$_2$(dppf) (123 mg, 0.151 mmol, 5 mol %) were added and it was heated to 80° C. for 14 h. The reaction mixture was cooled to RT and extracted with CH$_2$Cl$_2$ and H$_2$O. The aqueous phase was washed twice with CH$_2$Cl$_2$. The combined organic phases were washed with H$_2$O, dried (MgSO$_4$), filtrated and evaporated. The crude product was absorbed on silica-gel and subjected to column chromatography (SiO$_2$:hexanes:EtOAc=7:1) to give compound 11 as a colourless solid (1.50 g, 2.2 mmol, 72%). $^1$H NMR (500 MHz, CDCl$_3$, 25° C.): δ=7.94 (d, J=8.3 Hz, 1H), 7.71 (s, 1H), 7.55 (d, J=7.7 Hz, 2H), 7.44-7.41 (m, 2H), 7.35 (m, 1H), 7.12 (s, 1H), 7.10-6.99 (m, 6H), 5.27 (s, 2H), 3.97 (s, 3H), 2.57 (s, 3H), 2.20 (s, 3H), 2.14-2.06 (m, 12H), 1.39 (s, 12H) ppm. $^{13}$C NMR (126 MHz, CDCl$_3$, 25° C.): δ=166.8, 157.9, 147.6, 144.25, 144.19, 141.95, 141.93, 141.38, 141.31, 140.49, 140.44, 139.87, 139.82, 139.44, 139.41, 137.3, 136.8, 133.52, 133.46, 132.72, 132.65, 132.62, 132.55, 132.19, 132.14, 132.06, 132.04, 131.66, 131.60, 131.04, 130.96, 130.75, 130.61, 130.59, 130.40, 130.38, 128.6, 127.8, 126.8, 121.7, 118.8, 115.11, 115.10, 83.4, 77.1, 70.6, 52.1, 31.6, 25.06, 24.98, 24.96, 21.76, 21.73, 19.82, 19.78, 19.49, 19.45, 19.36, 19.31, 19.21, 19.08 ppm. HRMS (ESI) calculated for C$_{45}$H$_{50}$BO$_5$: m/z=680.3782 ([M+H]$^+$). found m/z=680.3776.

Synthesis of Compound (12)

Following the General Coupling Procedure (based on 4.00 g of the aryl iodide), compound 2 and 3 were reacted, and the desired product precipitated out of solution. The aqueous (bottom) layer of the biphasic solution was removed via syringe, and the product was collected by filtration of the remaining dark brown p-dioxane layer. The collected product was washed with EtOAc and allowed to air dry to provide 12 (83%, 4.35 g) as an off-white powder which required no further purification. $^1$H NMR (500 MHz, CDCl$_3$, 25° C.): δ=7.91 (d, J=8.0 Hz, 2H), 7.52 (d, J=7.5 Hz, 4H), 7.42 (t, J=7.5 Hz, 4H), 7.34 (t, J=7.5 Hz, 2H), 7.16 (dd, J=8.0, 1.5 Hz, 2H), 7.08 (d, J=1.5 Hz, 2H), 5.23 (s, 4H), 3.93 (s, 6H) ppm. $^{13}$C NMR (125 MHz, CDCl$_3$, 25° C.): δ=166.5, 158.6, 145.4, 136.7, 132.6, 128.8, 128.1, 127.0, 120.2, 119.6, 113.1, 70.9, 52.3 ppm. MS (ESI) calculated for C$_{30}$H$_{16}$O$_6$: m/z=483.2 ([M+H]$^+$), 505.2 ([M+Na]$^+$) and 987.3 ([2M+Na]$^+$. found m/z=483.4 ([M+H]$^+$), 505.4 ([M+Na]$^+$) and 987.1 ([2M+Na]$^+$).

Synthesis of Compound (13)

Following the General Coupling Procedure (based on 2.00 g of the aryl dibromide), compound 3 and 4 were reacted, and the desired product precipitated out of solution. The aqueous (bottom) layer of the biphasic solution was removed via syringe, and the product was collected by filtration of the remaining dark brown p-dioxane layer. The collected product was washed with EtOAc and left to air dry to provide 13 (96%, 4.29 g) as an off-white powder that required no further purification. $^1$H NMR (500 MHz, THF-d$_8$, 25° C.): δ=7.96 (d, J=7.5 Hz, 2H), 7.66 (d, J=7.5 Hz, 4H), 7.48 (t, J=7.5 Hz, 4H), 7.39 (t, J=7.5 Hz, 2H), 7.24 (s, 2H), 7.22 (s, 2H), 7.10 (dd, J=8.0, 1.0 Hz, 2H), 5.36 (s, 4H), 3.98 (s, 6H), 2.30 (s, 6H) ppm. $^{13}$C NMR (125 MHz, THF-d$_8$, 25° C.): δ=167.0, 159.3, 148.2, 141.8, 138.8, 133.7, 132.6, 132.6, 129.5, 128.6, 127.9, 122.2, 120.8, 116.1, 71.4, 52.2, 20.3 ppm. MS (ESI) calculated for C$_{38}$H$_{34}$O$_6$: m/z=587.2 ([M+H]$^+$), 609.2 ([M+Na]$^+$) and 1195.5 ([2M+Na]$^+$). found m/z=587.4 ([M+H]$^+$), 609.5 ([M+Na]$^+$) and 1195.1 ([2M+Na]$^+$).

Synthesis of Compound (14)

The boronic ester 3 (4.78 g, 13.0 mmol, 3.0 equiv.) and the iodide 5 (2.00 g, 4.33 mmol, 1.0 equiv.) were dissolved in a degassed 2:1 p-dioxane/H$_2$O mixture (420 mL). CsF (3.95 g, 26.0 mmol, 6.0 equiv.) and PdCl$_2$(dppf) (354 mg, 0.433 mmol, 10 mol %) were added and the reaction mixture was heated under reflux for 14 h. It was cooled to RT, before being extracted with CH$_2$Cl$_2$ and H$_2$O. The aqueous phase was washed twice with CH$_2$Cl$_2$. The combined organic phases were dried (MgSO$_4$), filtrated and evaporated. The crude product was absorbed on silica-gel and subjected to column chromatography (SiO$_2$:hexanes:EtOAc=5:1) to give the compound 14 as a colourless solid (2.60 g, 3.82 mmol, 87%). $^1$H NMR (500 MHz, CD$_2$Cl$_2$, 25° C.): δ=7.86 (d, J=7.9 Hz, 2H), 7.51 (m, 4H), 7.40 (m, 4H), 7.33 (m, 2H), 7.13 (m, 2H), 7.06 (d, J=1.3 Hz, 2H), 7.03 (dd, J=7.9, 1.5 Hz, 2H), 7.01 (s, 2H), 5.29 (s, 4H), 3.89 (s, 6H), 2.20 (s, 6H), 2.09 (s, 6H) ppm. $^{13}$C NMR (126 MHz, CD$_2$Cl$_2$, 25° C.): rS=166.8, 158.2, 147.7, 141.2, 140.0, 137.3, 133.7, 132.6, 131.9, 131.8, 131.2, 128.9, 128.2, 127.4, 121.9, 119.5, 115.4, 71.0, 52.3, 20.0, 19.5 ppm. HRMS (ESI) calculated for C$_{46}$H$_{43}$O$_6$: m/z=691.3051 ([M+H]$^+$). found m/z=691.3067.

Synthesis of Compound (15)

The boronic ester 8 (1.77 g, 3.75 mmol, 3.0 equiv.) and the 1,4-diiodo-2,5-dimethylbenzene$^4$ (447 mg, 1.25 mmol, 1.0 equiv.) were dissolved in a degassed 2:1 p-dioxane/H$_2$O mixture (150 mL). CsF (1.14 g, 7.50 mmol, 6.0 equiv.) and PdCl$_2$(dppf) (102 mg, 0.125 mmol, 10 mol %) were added and the reaction mixture was heated under reflux for 14 h. It was then cooled to RT before being extracted with CH$_2$Cl$_2$ and H$_2$O. The aqueous phase was washed twice with CH$_2$Cl$_2$. The combined organic phases were dried (MgSO$_4$), filtrated and evaporated. The crude product was absorbed on silica-gel and subjected to column chromatography (SiO$_2$:hexanes:EtOAc=5:1) to give the compound 15 as a colourless solid (765 mg, 0.962 mmol, 77%). $^1$H NMR (500 MHz, CDCl$_3$, 25° C.): δ=7.92 (d, J=8.2 Hz, 2H), 7.53 (m, 4H), 7.41 (m, 4H), 7.32 (m, 2H), 7.11 (s, 2H), 7.09 (m, 2H), 7.05-7.03 (m, 6H), 5.25 (s, 4H), 3.95 (s, 6H), 2.19 (s, 6H), 2.13 (s, 3H), 2.12 (s, 3H), 2.11 (m, 6H) ppm. $^{13}$C NMR (126 MHz, CDCl$_3$, 25° C.): δ=166.8, 157.9, 147.6, 141.30, 141.23, 140.03, 139.98, 139.50, 139.47, 136.8, 133.50, 133.44, 132.84, 132.74, 132.10, 132.08, 131.67, 131.60, 130.79, 130.72, 130.70, 128.6, 127.8, 126.8, 121.7, 118.8, 115.11, 115.10, 70.6, 52.1, 19.84, 19.80, 19.51, 19.47, 19.34 ppm. HRMS (ESI) calculated for $C_{54}H_{51}O_6$: m/z=795.3680 ([M+H]$^+$). found m/z=795.3659.

Synthesis of Compound (16)

The boronic ester 8 (600 mg, 1.27 mmol, 3.0 equiv.) and the iodide 5 (196 mg, 0.423 mmol, 1.0 equiv.) were dissolved in a degassed 2:1 p-dioxane/$H_2O$ mixture (45 mL). CsF (386 mg, 2.54 mmol, 6.0 equiv.) and PdCl$_2$(dppf) (35 mg, 0.043 mmol, 10 mol %) were added and the reaction mixture was heated under reflux for 14 h. It was cooled to RT before being extracted with $CH_2Cl_2$ and $H_2O$. The aqueous phase was washed twice with $CH_2Cl_2$. The combined organic phases were dried (MgSO$_4$), filtrated and evaporated. The crude product was absorbed on silica-gel and subjected to column chromatography (SiO$_2$:hexanes:EtOAc=5:1) to give the compound 16 as a colourless solid (229 mg, 0.255 mmol, 60%). $^1$H NMR (500 MHz, CDCl$_3$, 25° C.): δ=7.93 (d, J=8.3 Hz, 2H), 7.53 (m, 4H), 7.40 (m, 4H), 7.33 (m, 2H), 7.12-7.04 (m, 12H), 5.26 (s, 4H), 3.95 (s, 6H), 2.19 (s, 6H), 2.15-2.12 (m, 18H) ppm. $^{13}$C NMR (126 MHz, CDCl$_3$, 25° C.): δ=166.8, 157.9, 147.6, 141.4, 141.3, 140.8, 140.5, 140.44, 140.43, 140.38, 139.9, 139.83, 139.82, 139.78, 139.7, 139.5, 139.4, 136.81, 136.78, 133.54, 133.48, 133.9, 132.93, 132.88, 132.82, 132.75, 132.72, 132.65, 132.6, 132.08, 132.06, 131.71, 131.67, 131.5, 130.9, 130.83, 130.78, 130.7, 128.6, 127.8, 126.8, 121.7, 118.8, 115.1, 70.6, 52.1, 19.9, 19.8, 19.53, 1949, 19.47, 19.46, 19.38, 19.36 ppm. HRMS (ESI) calculated for $C_{62}H_{59}O_6$: m/z=899.4306 ([M+H]$^+$). found m/z=899.4330.

Synthesis of Compound (18)

The boronic ester 8 (697 mg, 1.48 mmol, 2.2 eq.) and the iodide 17 (334 mg, 0.670 mmol, 1.0 equiv.) were dissolved in a degassed mixture of p-dioxane (15 mL) and $H_2O$ (7.5 mL). CsF (610 mg, 4.02 mmol, 6.0 equiv.) and PdCl$_2$(dppf) (55 mg, 0.067 mmol, 10 mol %) were added and the reaction mixture was heated under reflux for 15 h. It was cooled to RT and extracted with $H_2O$ and $CH_2Cl_2$. The aqueous phase was washed twice with $CH_2Cl_2$. The combined organic phases were dried (MgSO$_4$) and evaporated. The crude product was subjected to column chromatography (SiO$_2$: CH$_2$Cl$_2$:hexanes=1:1→1:0) to give compound 18 as a colourless solid (465 mg, 0.497 mmol, 74%). $^1$H-NMR (500 MHz; CDCl$_3$): δ=7.95 (d, J=8.2 Hz, 2H), 7.56 (d, J=7.5 Hz, 4H), 7.44 (t, J=7.6 Hz, 4H), 7.35 (t, J=7.4 Hz, 2H), 7.14 (m, 4H), 7.09-7.06 (m, 6H), 5.28 (s, 4H), 3.98 (s, 6H), 2.49 (m, 2H), 2.40-2.35 (m, 2H), 2.22 (s, 6H), 2.15 (d, J=3H), 2.14 (s, 3H), 1.48 (m, 4H), 1.22 (m, 12H), 0.85 (t, J=7.0 Hz, 6H) ppm. $^{13}$C NMR (126 MHz, CDCl$_3$, 25° C.): δ=166.8, 157.9, 147.6, 141.34, 141.25, 139.51, 139.49, 139.40, 139.37, 137.41, 137.36, 136.8, 133.64, 133.58, 132.00, 131.93, 131.82, 131.81, 131.66, 130.77, 130.74, 130.06, 130.00, 128.6, 127.8, 126.8, 121.7, 118.8, 115.1, 70.6, 52.1, 32.51, 32.46, 31.6, 30.75, 30.66, 29.00, 28.95, 22.5, 19.85, 19.81, 19.72, 19.58, 14.1 ppm. HRMS (ESI) calculated for $C_{64}H_{21}O_6$: m/z=935.5245 ([M+H]$^+$). found m/z=935.5213.

Synthesis of Compound (19)

The boronic ester 9 (641 mg, 1.11 mmol, 2.2 equiv.) and the iodide 17 (252 mg, 0.505 mmol, 1.0 equiv.) were dissolved in a degassed mixture of p-dioxane (11 mL) and $H_2O$ (5.5 mL). CsF (460 mg, 43.03 mmol, 6.0 equiv.) and PdCl$_2$(dppf) (41 mg, 0.050 mmol, 10 mol %) were added and the reaction mixture was heated under reflux for 15 h. It was cooled to RT and extracted with $H_2O$ and $CH_2Cl_2$. The aqueous phase was washed twice with $CH_2Cl_2$. The combined organic phases were dried (MgSO$_4$) and evaporated. The crude product was subjected to column chromatography (SiO$_2$:CH$_2$Cl$_2$) to give compound 19 as a colourless solid (527 mg, 0.460 mmol, 91%). $^1$H-NMR (500 MHz; CDCl$_3$): δ=7.95 (d, J=8.2 Hz, 2H), 7.56 (d, J=7.6 Hz, 4H), 7.44 (t, J=7.6 Hz, 4H), 7.35 (t, J=7.4 Hz, 2H), 7.17-7.06 (m, 15H), 5.28 (s, 4H), 3.98 (s, 6H), 2.51 (m, 2H), 2.39 (m, 2H), 2.22 (s, 6H), 2.18 (s, 3H), 2.15-2.12 (m, 15H), 1.50-1.45 (m, 4H), 1.28-1.17 (m, 12H), 0.85 (m, 6H) ppm. $^{13}$C NMR (126 MHz, CDCl$_3$, 25° C.): δ=166.8, 157.9, 147.6, 141.50, 141.40, 140.5, 139.72, 139.64, 139.44, 139.40, 137.56, 137.51, 136.8, 133.55, 133.48, 133.25, 133.20, 133.14, 133.12, 133.02, 132.96, 132.95, 132.45, 132.43, 132.31, 132.09, 132.03, 131.76, 131.67, 131.58, 131.26, 131.21, 131.18, 131.12, 130.77, 130.58, 130.26, 130.17, 130.13, 128.6, 127.8, 126.8, 121.7, 118.8, 115.1, 70.6, 52.1, 32.8, 32.58, 32.53, 31.64, 31.59, 31.48, 31.08, 30.95, 30.85, 30.70, 29.15, 29.10, 29.07, 22.71, 22.58, 22.55, 19.86, 19.79, 19.62, 19.52, 19.49, 19.44, 19.2, 14.16, 14.08 ppm. HRMS (ESI) calculated for $C_{96}H_{103}O_6$: m/z 1350.7676 ([M+H]$^+$). found m/z=1351.7733.

Synthesis of Compound (20)

The boronic ester 11 (916 mg, 1.35 mmol, 2.2 equiv.) and the iodide 17 (305 mg, 0.612 mmol, 1.0 equiv.) were dissolved in a degassed mixture of p-dioxane (18 mL) and $H_2O$ (9 mL). PdCl$_2$(dppf) (50.0 mg, 0.061 mmol, 10 mol %) and CsF (558 mg, 3.67 mmol, 6.0 equiv.) were added and the reaction mixture was heated to 106° C. for 13 h. The reaction mixture was cooled to RT and the precipitate was filtered off, washed with $H_2O$ and MeOH, dried under vacuum and subjected to column chromatography (SiO$_2$:CH$_2$Cl$_2$) to give compound 20 as a colourless solid (700 mg, 0.518 mmol, 85%). $^1$H NMR (500 MHz, CDCl$_3$, 25° C.): S=7.93 (d, J=8.3 Hz, 2H), 7.54 (d, J=7.2 Hz, 4H), 7.42 (t, J=7.6 Hz, 4H), 7.33 (t, J=7.4 Hz, 2H), 7.17-7.10 (m, 12H), 7.07-7.05 (m, 6H), 5.27 (s, 4H), 3.96 (s, 6H), 2.53-2.37 (m, 4H), 2.20 (s, 6H), 2.14 (m, 30H), 1.48 (m, 4H), 1.21 (m, J=6.7 Hz, 12H), 0.88-0.81 (m, 6H) ppm. $^{13}$C NMR (126 MHz; CDCl$_3$, 25° C.): δ=166.8, 157.9, 147.6, 141.45, 141.39, 140.71, 140.63, 140.56, 140.46, 140.37, 140.28, 140.18, 140.13, 140.09, 140.03, 139.93, 139.90, 139.81, 139.76, 139.70, 139.45, 139.43, 137.63, 137.60, 137.56, 137.54, 137.51, 136.8, 133.56, 133.51, 133.10, 133.05, 132.98, 132.94, 132.88, 132.73, 132.67, 132.64, 132.57, 132.53, 132.45, 132.39, 132.08, 132.06, 131.73, 131.68, 131.22, 131.13, 130.98, 130.95, 130.73, 130.65, 130.35, 130.30, 130.22, 130.17, 130.07, 130.03, 128.6, 127.8, 126.8, 121.7, 118.8, 115.1, 70.6, 52.1, 32.90, 32.85, 32.79, 32.67, 32.62, 32.57, 31.61, 31.49, 31.11, 31.02, 30.98, 30.88, 30.86, 30.72, 29.23, 29.18, 29.15, 29.12, 29.10, 29.05, 22.59, 22.57, 19.85, 19.81, 19.78, 19.76, 19.64, 19.60, 19.55, 19.50, 19.47, 19.40, 19.37, 19.33, 19.28, 14.17, 14.09 ppm. HRMS (ESI) calculated for $C_{96}H_{103}O_6$: m/z=1351.7749 ([M+H]$^+$). found m/z=1351.7758.

Synthesis of Compound (21)

The boronic ester 9 (1.50 g, 2.61 mmol, 1.0 equiv.) and the iodide 17 (5.20 g, 10.4 mmol, 4.0 equiv.) were dissolved in a degassed mixture of dioxane (100 mL) and $H_2O$ (50 mL) at 80° C. PdCl$_2$(dppf) (106 mg, 0.131 mmol, 5 mol %) and CsF (1.19 g, 7.83 mmol, 3.0 equiv.) were added and the reaction mixture was heated to 106° C. for 13 h. It was cooled to RT and extracted with $CH_2Cl_2$ and $H_2O$. The aqueous phase was washed twice with $CH_2Cl_2$, the combined organic phases were dried ($MgSO_4$), evaporated, absorbed on silica-gel and subjected to column chromatography ($SiO_2$:hexanes:EtOAc=5:1) in order to afford compound 21 as a colourless solid (856 mg, 1.04 mmol, 40%). $^1$H NMR (500 MHz, $CDCl_3$, 25° C.): δ=7.94 (d, J=8.3 Hz, 1H), 7.76 (s, 1H), 7.55 (d, J=7.2 Hz, 2H), 7.43 (t, J=7.6 Hz, 2H), 7.35 (t, J=7.4 Hz, 1H), 7.13 (s, 1H), 7.10-7.00 (m, 6H), 5.28 (s, 2H), 3.98 (s, 3H), 2.72 (m, 2H), 2.42 (m, 1H), 2.31 (m, 1H), 2.21 (s, 3H), 2.15-2.11 (m, 6H), 2.06 (m, 3H), 1.46-1.14 (m, 16H), 0.93-0.83 (m, 6H) ppm. $^{13}$C NMR (126 MHz, $CDCl_3$, 25° C.): δ=166.8, 157.9, 147.5, 142.3, 141.39, 141.26, 140.55, 140.52, 140.13, 140.08, 139.61, 139.53, 139.48, 139.36, 139.27, 136.8, 133.45, 133.37, 132.82, 132.67, 132.54, 132.13, 132.07, 131.67, 131.47, 130.90, 130.84, 130.78, 130.69, 130.50, 130.40, 128.6, 127.8, 126.8, 121.7, 118.8, 115.1, 99.2, 70.6, 52.1, 40.38, 40.34, 34.7, 32.4, 32.1, 31.7, 31.45, 31.36, 30.81, 30.66, 30.43, 30.30, 29.15, 29.08, 29.00, 25.3, 22.69, 22.50, 19.84, 19.77, 19.62, 19.47, 19.2, 14.15, 14.06 ppm. HRMS (ESI) calculated for $C_{49}H_{58}IO_2$: m/z=821.3425 ([M+H]$^+$). found m/z=821.3424.

Synthesis of Compound (22)

Dibromide 25 (1.00 g, 2.12 mmol, 1.0 equiv.), bis(pinacolato)diboron (1.13 g, 4.45 mmol, 2.1 equiv.), $PdCl_2(dppf)$ (173 mg, 0.212 mmol, 10 mol %), and KOAc (1.25 g, 12.7 mmol, 6.0 equiv.) were added to a flame-dried flask containing anhydrous $Me_2SO$ (50 mL) and the reaction mixture was heated under reflux for 16 h. It was cooled to RT, added to $H_2O$ (25 mL), then extracted three times with $CH_2Cl_2$. The organic layer was then washed extensively with $H_2O$. The organic phase was dried ($MgSO_4$), filtered, and evaporated. The crude product was absorbed on silica-gel and subjected to column chromatography ($SiO_2$:hexanes) to give the compound 22 as a colourless solid (371 mg, 0.655 mmol, 31%). $^1$H NMR (500 MHz, $CD_2Cl_2$, 25° C.): δ=7.66 (s, 2H), 6.99 (m, 4H), 2.54 (s, 6H), 2.10 (s, 6H), 2.04 (s, 6H), 1.39 (s, 24H) ppm. $^{13}$C NMR (126 MHz, $CD_2Cl_2$, 25° C.): δ=144.5, 142.2, 140.7, 137.7, 132.9, 132.8, 132.4, 131.3, 131.2, 130.7, 83.8, 25.1, 21.80, 21.78, 19.4, 19.3, 19.1 ppm. HRMS (ESI) calculated for $C_{36}H_{49}B_2O_4$: m/z=565.3884 ([M+H]$^+$). found m/z=565.3864.

Synthesis of Compound (23)

The boronic ester 22 (151 mg, 0.266 mmol, 1.0 equiv.) and the iodide 21 (480 mg, 0.585 mmol, 2.2 equiv.) were suspended in a degassed mixture of dioxane (12 mL) and $H_2O$ (6 mL). $PdCl_2(dppf)$ (22 mg, 0.0269 mmol, 10 mol %) and CsF (242 mg, 1.60 mmol, 6.0 equiv.) were added and the reaction mixture was heated to 106° C. for 15 h. It was cooled to RT and the precipitate was filtered off, washed with $H_2O$ and MeOH and dried at vacuum. The beige crude product was subjected to column chromatography ($SiO_2$: $CH_2Cl_2$) to yield compound 23 as a colourless solid (373 mg, 0.219 mmol, 82%). $^1$H NMR (500 MHz, $CDCl_3$, 25° C.): δ=7.96 (d, J=8.2 Hz, 2H), 7.57 (d, J=7.6 Hz, 4H), 7.44 (t, J=7.6 Hz, 4H), 7.36 (t, J=7.4 Hz, 2H), 7.19-7.07 (m, 22H), 5.29 (s, 4H), 3.99 (s, 6H), 2.54 (m, 4H), 2.41 (m, 4H), 2.23-2.14 (m, 46H), 1.54-1.46 (m, 8H), 1.28-1.17 (m, 24H), 0.87 (m, 12H) ppm. $^{13}$C NMR (126 MHz, $CDCl_3$, 25° C.): δ=166.8, 157.9, 147.6, 141.53, 141.43, 140.68, 140.65, 140.57, 140.47, 140.33, 140.28, 140.21, 140.18, 140.02, 139.99, 139.90, 139.87, 139.78, 139.71, 139.68, 139.63, 139.60, 139.58, 139.45, 139.40, 137.67, 137.64, 137.61, 137.57, 137.54, 137.51, 137.49, 137.46, 137.44, 136.8, 133.57, 133.50, 133.21, 133.15, 133.05, 132.99, 132.87, 132.82, 132.76, 132.71, 132.66, 132.64, 132.60, 132.51, 132.50, 132.45, 132.42, 132.31, 132.09, 132.04, 131.78, 131.68, 131.60, 131.29, 131.24, 131.20, 131.16, 131.11, 130.90, 130.78, 130.71, 130.67, 130.59, 130.37, 130.32, 130.25, 130.19, 130.13, 130.10, 130.06, 130.04, 130.00, 128.6, 127.8, 121.7, 118.8, 115.1, 70.6, 52.1, 34.7, 32.8, 32.62, 32.61, 31.61, 31.50, 31.10, 31.01, 30.97, 30.87, 30.84, 30.72, 29.23, 29.18, 29.14, 29.10, 29.05, 22.60, 22.57, 20.8, 19.87, 19.80, 19.78, 19.64, 19.61, 19.53, 19.50, 19.48, 19.46, 19.37, 19.31, 19.25, 14.17, 14.09 ppm. HRMS (ESI) calculated for $C_{122}H_{129}O_6$: m/z=1700.0566 ([M+H]$^+$). found m/z=1700.0582.

Synthesis of Compound (24)

1,4-Dibromo-2,5-dimethylbenzene (4) (25.0 g, 94.7 mmol, 1.0 equiv.), bis(pinacolato)diboron (50.5 g, 199 mmol, 2.1 equiv.), $PdCl_2(dppf)$ (3.87 g, 4.74 mmol, 5 mol %), and KOAc (55.8 g, 568 mmol, 6.0 equiv.) were added to a flame-dried flask containing anhydrous $Me_2SO$ (300 mL). The reaction mixture was heated under reflux for 16 h. It was then cooled tort, added to $H_2O$ (100 mL) before being extracted three times with $CH_2Cl_2$. The organic layer was then washed extensively with $H_2O$. The organic phase was dried ($MgSO_4$), filtered, and evaporated. EtOAc (250 mL) was added to the crude mixture, along with activated carbon (10 g) and the reaction mixture was refluxed for 3 h. It was cooled to RT, filtered through Celite, and the Celite was washed thoroughly with $CH_2Cl_2$. The $CH_2Cl_2$ layer was evaporated, causing the product to precipitate from the EtOAc as fine off-white needles, which were isolated by vacuum filtration (14.6 g, 40.8 mmol, 43%). $^1$H NMR (500 MHz, $CDCl_3$, 25° C.): δ=7.53 (s, 2H), 2.48 (s, 6H), 1.34 (s, 24H) ppm. $^{13}$C NMR (126 MHz, $CDCl_3$, 25° C.): δ=140.7, 137.0, 83.5, 25.0, 21.6 ppm. HRMS (ESI) calculated for $C_{20}H_{33}B_2O_4$: m/z=357.2632 ([M+H]$^+$). found m/z=357.2614.

Synthesis of Compound (25)

The diboronic ester 24 (5.00 g, 13.9 mmol, 1.0 equiv.) and 1,4-dibromo-2,5-dimethylbenzene (4) (18.4 g, 69.8 mmol, 5.0 equiv.) were dissolved in a degassed 2:1 dioxane/$H_2O$ mixture (75 mL). CsF (12.7 g, 83.8 mmol, 6.0 equiv.) and $PdCl_2(dppf)$ (1.14 g, 1.40 mmol, 10 mol %) were added and it was heated under reflux for 16 h. The reaction mixture was cooled to RT before being extracted with $CH_2Cl_2$ and $H_2O$. The aqueous phase was washed twice with $CH_2Cl_2$. The combined organic phases were dried ($MgSO_4$), filtered and evaporated. The crude product was absorbed on silica-gel and subjected to column chromatography ($SiO_2$:hexanes) to give the compound 25 as a colourless solid (2.18 g, 4.61 mmol, 33% yield). $^1$H NMR (500 MHz, $CD_2Cl_2$, 25° C.): δ=7.47 (s, 2H), 7.04 (m, 2H), 6.95 (s, 2H), 2.39 (s, 6H), 2.05 (m, 6H), 2.02 (s, 6H) ppm. $^{13}$C NMR (126 MHz, $CD_2Cl_2$, 25° C.): δ=141.2, 139.91, 139.89, 135.9, 135.1, 133.5, 133.2, 133.1, 132.1, 132.0, 130.9, 123.4, 22.5, 22.4, 19.4, 19.3, 19.2 ppm.

Synthesis of Compound (27)

The boronic ester 9 (600 mg, 1.04 mmol, 2.2 equiv.) and the dibromide 26 (265 mg, 0.473 mmol, 1.0 equiv.) were dissolved in a degassed mixture of dioxane (10 mL) and $H_2O$ (5 mL). $PdCl_2(dppf)$ (38.4 mg, 0.047 mmol, 10 mol %)

and CsF (431 mg, 2.84 mmol, 6.0 equiv.) were added and the reaction mixture was heated to 106° C. for 16 h. It was then cooled to RT before being extracted with $CH_2Cl_2$ and $H_2O$. The aqueous phase was washed twice with $CH_2Cl_2$. The combined organic phases were dried ($MgSO_4$), filtrated and evaporated. The crude product was absorbed on silica-gel and subjected to column chromatography ($SiO_2$:hexanes: EtOAc=1:1) to give the compound 27 as a colourless solid (485 mg, 0.373 mmol, 79%). $^1$H NMR (500 MHz, $CDCl_3$, 25° C.): δ=7.95 (d, J=8.2 Hz, 2H), 7.56 (d, J=7.6 Hz, 4H), 7.44 (t, J=7.6 Hz, 4H), 7.35 (t, J=7.4 Hz, 2H), 7.21 (s, 2H), 7.14 (s, 2H), 7.11 (s, 2H), 7.08-7.06 (m, 6H), 6.91 (s, 2H), 5.28 (s, 4H), 4.09 (m, 4H), 3.98 (s, 6H), 3.75 (m, 4H), 3.62 (m, 4H), 3.59 (s, 8H), 3.55 (m, 4H), 2.26 (d, 6H), 2.22 (s, 6H), 2.16 (2, 12H) ppm. $^{13}$C NMR (126 MHz, $CDCl_3$, 25° C.): δ=166.8, 157.9, 150.0, 147.6, 141.3, 140.0, 139.5, 137.4, 136.8, 134.0, 133.4, 132.5, 132.1, 131.68, 131.64, 130.86, 130.79, 130.5, 128.6, 127.8, 126.8, 121.7, 118.8, 116.1, 115.1, 71.9, 70.87, 70.79, 70.63, 70.55, 69.8, 69.2, 59.1, 52.1, 19.84, 19.72, 19.49, 19.44 ppm. HRMS (ESI) calculated for $C_{82}H_{91}O_{14}$: m/z=1299.6403 ([M+H]$^+$). found m/z=1299.6454.

Link Synthetic Procedures

Synthesis of Link II

EtOAc (50 mL), THF (50 mL) and 10% by weight Pd/C (0.98 g, 0.90 mmol) were added to a flask charged with 12 (4.35 g, 9.0 mmol). The reaction flask was sealed with a septum and the heterogeneous solution was purged with $H_2$ that was delivered by a balloon attached to an 8" stainless steel needle. A balloon inflated with $H_2$ was attached to the reaction vessel, which was transferred subsequently to an oil bath pre-warmed to 50° C. The reaction mixture was stirred for 24 h to provide an insoluble product. The reaction mixture was then cooled to RT, purged with a stream of $N_2$ and filtered to collect the product that was contaminated with Pd/C. The filter cake was suspended in THF (30 mL) and the suspension was warmed to reflux and subsequently hot-filtered. This process was repeated five times in order to extract all of the product from the Pd/C. The combined organic layers were concentrated in vacuo to provide the product that was used directly in the next step.

Following the General Saponification Procedure, 2.0 g of II (82% over hydrogenolysis and saponification) was collected as a white solid. $^1$H NMR (500 MHz, $CD_3SOCD_3$, 25° C.): δ=7.86 (d, J=9.0 Hz, 2H), 7.30-7.25 (m, 4H) ppm. $^{13}$C NMR (126 MHz, $CD_3SOCD_3$, 25° C.): δ=171.7, 161.4, 145.5, 131.0, 117.9, 115.3, 113.0 ppm. HRMS (ESI) Calculated for $C_{14}H_{10}O_6$: m/z=273.0405 ([M−H]$^−$). Found m/z=273.0397.

Synthesis of Link III

DMF (15 mL), THF (60 mL) and 10% by weight Pd/C (0.78 g, 0.73 mmol) were added to a flask charged with 13 (4.29 g, 7.32 mmol). The reaction flask was sealed with a septum and the heterogeneous solution was purged with $H_2$ that was delivered by a balloon attached to an 8" stainless steel needle. A balloon inflated with $H_2$ was attached to the reaction vessel, which was transferred subsequently to an oil bath, pre-warmed to 50° C. The reaction mixture was stirred for 24 h before being cooled to RT, purged with a stream of $N_2$ and filtered. The filter cake was washed with THF (10 mL) and the combined filtrates were concentrated in vacuo to provide the product that was used directly in the next step.

Following the General Saponification Procedure, 2.4 g of III (87% over hydrogenolysis and saponification) was isolated as a white powder. $^1$H NMR (500 MHz, $CD_3SOCD_3$, 25° C.): δ=14.0 (br. s, 2H), 11.4 (br. s, 2H), 7.85-7.82 (m, 2H), 7.18 (s, 2H), 6.98-6.92 (m, 4H), 2.24 (m, 6H) ppm. $^{13}$C NMR (126 MHz, $CD_3SOCD_3$, 25° C.): δ=171.9, 160.9, 148.3, 139.7, 132.3, 131.3, 130.2, 120.3, 117.4, 111.7, 19.5 ppm. HRMS (ESI) Calculated for $C_{22}H_{17}O_6$: m/z=377.1031 ([M−H]$^−$). Found m/z=377.1031.

Synthesis of Link IV

EtOAc (10 mL), EtOH (10 mL) and 10% by weight Pd/C (0.15 g, 0.15 mmol) were added to a flask charged with 14 (1.00 g, 1.45 mmol). The reaction flask was sealed with a septum and the heterogeneous solution was purged with $H_2$ that was delivered by a balloon attached to an 8" stainless steel needle. A balloon inflated with $H_2$ was attached to the reaction vessel, which was transferred subsequently to an oil bath pre-warmed to 50° C. The reaction mixture was stirred for 24 h before being cooled to RT, purged with a stream of $N_2$ and filtered. The filter cake was washed with THF (10 mL) and the combined filtrates were concentrated in vacuo to provide the product that was used directly in the next step.

Following the General Saponification Procedure, 620 mg of IV (89% over hydrogenolysis and saponification) was collected as a white solid. $^1$H NMR (500 MHz, $CD_3SOCD_3$, 25° C.): δ=7.86-7.83 (m, 2H), 7.19 (s, 2H), 7.06 (s, 2H), 6.98-6.92 (m, 4H), 2.25 (s, 6H), 2.06 (s, 6H) ppm. $^{13}$C NMR (126 MHz, $CD_3SOCD_3$, 25° C.): δ=171.8, 160.9, 148.5, 140.3, 138.9, 132.8, 131.8, 131.3, 130.6, 130.1, 120.3, 117.3, 111.5, 19.6, 19.0 ppm. HRMS (ESI) calculated for $C_{30}H_{26}O_6$: m/z=481.1657 ([M−H]$^−$). Found m/z=481.1654.

Synthesis of Link V

THF (20 mL) and 10% by weight Pd/C (0.29 g, 0.27 mmol) were added to a flask charged with 15 (2.16 g, 2.72 mmol). The reaction flask was sealed with a septum and the heterogeneous solution was purged with $H_2$ that was delivered by a balloon attached to an 8" stainless steel needle. A balloon inflated with $H_2$ was attached to the reaction vessel, which was transferred subsequently to an oil bath pre-warmed to 50° C. The reaction mixture was stirred for 24 h before being cooled to RT, purged with a stream of $N_2$ and filtered. The filter cake was washed with THF (10 mL) and the combined filtrates were concentrated in vacuo to afford the product, which was used directly in the next step.

Following the General Procedure, 1.60 g of V (quantitative over hydrogenolysis and saponification) was collected as an off-white solid. $^1$H NMR (500 MHz, DMF-$d_7$, 25° C.): δ=8.00 (d, J=8.0 Hz, 2H), 7.31 (s, 2H), 7.16-7.12 (m, 4H), 7.07 (dd, J=8.0, 1.5 Hz, 2H), 7.04-7.02 (m, 2H), 2.37 (s, 6H), 2.18-2.16 (m, 6H), 2.15 (s, 6H) ppm. $^{13}$C NMR (126 MHz, DMF-$d_7$, 25° C.): δ=172.6, 149.2, 141.2, 140.20, 140.18, 139.5, 133.38, 133.35, 132.8, 132.2, 131.6, 130.90, 130.88, 130.78, 130.75, 130.3, 120.5, 117.6, 111.9, 19.38, 19.36, 18.82, 18.79, 18.7 ppm. $^1$H NMR (600 MHz; $CD_3SOCD_3$, 100° C.): δ=7.86 (d, J=8.6 Hz, 2H), 7.16 (s, 2H), 7.07 (s, 2H), 7.04 (s, 2H), 6.94-6.93 (m, 4H), 2.26 (s, 6H), 2.08 (s, 6H), 2.07 (s, 6H) ppm. $^{13}$C NMR (151 MHz; $CD_3SOCD_3$, 100° C.): δ=171.8, 161.3, 149.2, 141.2, 140.2, 139.6, 133.3, 132.8, 132.1, 131.8, 130.98, 130.93, 130.6, 120.7, 117.9, 112.6, 19.8, 19.39, 19.27 ppm. HRMS (ESI) calculated for $C_{38}H_{34}O_6$: m/z=585.2283 ([M−H]$^−$). found m/z=585.2299.

Synthesis of Link V-Hex

The starting material 18 (455 mg, 0.467 mmol, 1.0 equiv.) was dissolved in THF (10 mL). Pd/C (10%, 50 mg) was added. The reaction mixture was then stirred under an atmosphere of $H_2$ overnight at 50° C. It was then filtrated through a Celite plug, washed with THF, evaporated and dried at vacuum.

The residue was then dissolved in THF (10 mL) and $H_2O$ (10 mL) and NaOH (300 mg, 7.69 mmol, 16 equiv.) was added. The reaction mixture was stirred at 50° C. overnight. The THF was evaporated and the mixture was acidified to pH 1 with conc. HCl. The precipitate was filtrated off, washed with $H_2O$ and dried to give compound V-hex as a colourless solid (339 mg, 30.467 mmol, quant.). $^1$H NMR (600 MHz, $CD_3SOCD_3$, 100° C.): δ=7.85 (d, J=8.4 Hz, 2H), 7.15 (s, 2H), 7.07 (s, 2H), 7.01 (s, 2H), 6.89 (m, 4H), 2.46 (m, 2H), 2.34 (m, 2H), 2.25 (s, 6H), 2.07 (s, 6H), 1.41 (m, J=7.1 Hz, 4H), 1.15 (m, J=13.9, 7.1 Hz, 12H), 0.78 (t, J=7.1 Hz, 6H) ppm. $^{13}$C NMR (126 MHz, $CD_2Cl_2$, 25° C.): δ=171.8, 161.5, 148.9, 141.1, 139.79, 139.71, 137.5, 133.4, 132.1, 131.9, 130.9, 130.55, 130.44, 120.4, 117.8, 113.1, 32.5, 31.2, 30.4, 28.6, 22.1, 19.8, 19.4, 14.0 ppm. HRMS (ESI) calculated for $C_{48}H_{53}O_6$: m/z=725.3848 ([M−H]$^-$). found m/z=725.3834.

Synthesis of Link VI

THF (60 mL) was added to a flask charged with 16 (2.0 g, 2.22 mmol). Raney Ni (approx. 200 mg, commercially purchased as a slurry in $H_2O$ which was converted to a slurry in THF by successive (5×) dilutions with THF followed by removal of the supernatant) was added to the flask using a pipette. The reaction flask was sealed with a septum and the heterogeneous solution was purged with $H_2$ that was delivered by a balloon attached to an 8" stainless steel needle. A balloon inflated with $H_2$ was affixed to the reaction vessel, which was transferred subsequently to an oil bath prewarmed to 50° C. The reaction mixture was stirred for 48 h before being cooled to RT and purged with a stream of $N_2$. It was decanted into an Erlenmeyer flask (most of the Ni remains bound to the magnetic stir bar) before being diluted with $CHCl_3$ (100 mL). The solution was then brought to reflux and hot-filtered through a well-packed bed of Celite. The filter cake was rinsed further with hot $CHCl_3$. The combined filtrates were combined and concentrated in vacuo to afford the product, which was used directly in the next step.

Following the General Procedure, 1.35 g of VI (90% over hydrogenolysis and saponification) were collected as an off-white solid. $^1$H NMR (500 MHz, THF-$d_8$, 25° C.): δ=8.08 (d, J=8.0 Hz, 2H), 7.36 (s, 2H), 7.28-7.20 (m, 6H), 7.15 (s, 2H), 7.12-7.09 (m, 2H), 2.47 (s, 6H), 2.31 (s, 6H), 2.29 (s, 6H), 2.28 (s, 6H) ppm. $^{13}$C NMR (126 MHz, THF-$d_8$, 25° C.): δ=173.6, 163.7, 151.1, 142.8, 142.1, 141.7, 141.2, 134.6, 134.2, 134.1, 133.4, 133.0, 132.9, 132.2, 132.1, 132.0, 131.4, 121.5, 119.3, 112.5, 20.7, 20.6, 20.19, 20.18, 20.1, 20.0 ppm. $^1$H NMR (600 MHz; $CD_3SOCD_3$, 100° C.): δ=7.88 (d, J=7.8 Hz, 2H), 7.18 (s, 2H), 7.09 (s, 2H), 7.09 (s, 2H), 7.06 (s, 2H), 6.97-6.94 (m, 4H), 2.28 (s, 6H), 2.11 (s, 6H), 2.10 (s, 12H) ppm. $^{13}$C NMR (151 MHz; $CD_3SOCD_3$, 100° C.): δ=171.8, 161.3, 149.2, 141.3, 140.5, 140.1, 139.6, 133.4, 132.88, 132.77, 132.1, 131.8, 131.03, 130.95, 130.93, 130.6, 120.8, 117.9, 112.5, 19.8, 19.38, 19.32, 19.28 ppm. HRMS (ESI) calculated for $C_{46}H_{42}O_6$: m/z=689.2909 ([M−H]$^-$). Found m/z=689.2912.

Synthesis of Link VII

The starting material 19 (1.19 g, 1.04 mmol, 1.0 equiv.) was dissolved in THF (50 mL). Pd/C (10%, 110 mg) was added. The reaction mixture was then stirred under an atmosphere of $H_2$ overnight at 50° C. It was then filtrated through a Celite plug, washed with THF, evaporated and dried at vacuum.

It was then dissolved in THF (130 mL) and $H_2O$ (110 mL) and NaOH (880 mg, 30.4 mmol, 29 equiv.) was added. The reaction mixture was stirred at 50° C. overnight. The THF was evaporated and the mixture was acidified to pH 1 with conc. HCl. The precipitate was filtrated off, washed with $H_2O$ and dried to give compound VII as a colourless solid (973 mg, 1.04 mmol, quant.). $^1$H NMR (600 MHz; $CD_3SOCD_3$, 90° C.): δ=7.86 (d, J=8.0 Hz, 2H), 7.17 (s, 2H), 7.09 (s, 2H), 7.07 (m, 6H), 6.96 (m, 4H), 2.26 (s, 6H), 2.08 (m, 18H), 1.42 (m, 4H), 1.20-1.12 (m, 16H), 0.80 (t, J=6.6 Hz, 6H) ppm. $^{13}$C NMR (151 MHz, $CD_3SOCD_3$, 90° C.): δ=171.9, 161.3, 149.2, 141.3, 140.5, 140.02, 139.96, 139.6, 137.7, 133.3, 133.0, 132.5, 132.1, 131.7, 131.4, 130.95, 130.88, 130.57, 130.51, 120.8, 117.9, 112.4, 32.6, 31.2, 30.9, 30.6, 29.8, 28.7, 22.2, 19.8, 19.4, 14.0 ppm. HRMS (ESI): m/z calculated for $C_{64}H_{96}O_6$ [M−H]$^-$ 934.5172. found 934.5162.

Synthesis of Link VII-oeg

The starting material 27 (590 mg, 0.454 mmol, 1.0 equiv.) was dissolved in THF (40 mL). Raney Ni (~mol 10%) was added. The reaction mixture was then stirred under an atmosphere of $H_2$ overnight at 50° C. It was then filtrated through a Celite plug, washed with THF, evaporated and dried at vacuum.

The residue was then dissolved in THF (20 mL) and $H_2O$ (20 mL) and NaOH (390 mg, 10.0 mmol, 22 equiv.) was added. The reaction mixture was stirred at 50° C. overnight. The THF was evaporated and the mixture was acidified to pH 1 with conc. HCl. The precipitate was filtrated off, washed with $H_2O$ and dried to give VII-oeg as a colourless solid (495 mg, 0.454 mmol, quant.). $^1$H NMR (500 MHz; $CD_3SOCD_3$, 25° C.): δ=7.87 (d, J=8.5 Hz, 2H), 7.20 (d, J=6.6 Hz, 4H), 7.08 (s, 2H), 7.02 (s, 2H), 6.98 (m, 4H), 6.92 (s, 2H), 4.07 (m, 4H), 3.62 (m, 4H), 3.46-3.36 (m, 16H), 2.27 (s, 6H), 2.19 (s, 6H), 2.09 (s, 6H), 2.08 (s, 6H) ppm. $^{13}$C NMR (126 MHz, $CD_3SOCD_3$, 25° C.): δ=171.8, 160.9, 149.3, 148.5, 140.7, 139.4, 138.8, 137.2, 133.5, 132.9, 131.80, 131.67, 131.44, 131.33, 130.6, 130.13, 130.06, 129.89, 120.3, 117.3, 115.4, 111.6, 71.2, 69.98, 69.87, 69.6, 69.0, 68.6, 58.0, 19.6, 19.3, 19.11, 19.02 ppm. HRMS (ESI) calculated for $C_{66}H_{75}O_{14}$: m/z=935.5245 ([M+H]$^+$). found m/z=935.5213.

Synthesis of Link IX

The starting material 20 (827 mg, 0.612 mmol, 1.0 equiv.) was dissolved in THF (50 mL). Raney Ni (~mol 10%) was added. The reaction mixture was stirred under an atmosphere of $H_2$ overnight at 40° C. It was then filtrated through a Celite plug, washed with THF, evaporated and dried under vacuum.

The residue was dissolved in THF (50 mL) and $H_2O$ (50 mL) and NaOH (700 mg, 18.0 mmol, 29 equiv.) was added. The reaction mixture was stirred at 50° C. overnight. The THF was evaporated and the mixture was acidified to pH 1 with conc. HCl. The precipitate was filtrated off, washed with $H_2O$ and dried to give compound IX as a colourless solid (700 mg, 0.612 mmol, quant.). $^1$H NMR (600 MHz, $CD_3SOCD_3$, 100° C.): δ=7.87 (d, J=8.1 Hz, 2H), 7.17 (s, 2H), 7.10 (s, 2H), 7.08 (m, 8H), 7.05 (s, 2H), 6.94 (m, 4H), 2.27 (s, 6H), 2.09 (m, 30H), 1.44 (m, 4H), 1.26 (m, 4H), 1.22-1.14 (m, 12H), 0.81 (t, J=7.1 Hz, 6H). $^{13}$C NMR (151 MHz, THF-d$_8$, 55° C.): δ=170.0, 160.4, 147.9, 139.5, 138.63, 138.55, 138.32, 138.23, 137.9, 131.2, 130.93, 130.86, 130.68, 130.49, 130.0, 129.57, 129.51, 129.2, 128.90, 128.73, 128.71, 128.67, 128.61, 128.0, 123.0, 118.1, 115.9, 109.2, 32.2, 29.62, 29.55, 28.0, 27.7, 27.02, 26.96, 20.5, 17.0, 16.73, 16.68, 16.59, 11.45, 11.38 ppm. HRMS (ESI) calculated for C$_{80}$H$_{85}$O$_6$: m/z=1141.6352 ([M−H]$^-$). found m/z=1141.6295.

Synthesis of Link XI

The starting material 23 (372 mg, 0.219 mmol, 1.0 equiv.) was dissolved in THF (30 mL). Raney Ni (~mol 10%) was added. The reaction mixture was stirred under an atmosphere of H$_2$ overnight at 40° C. It was then filtrated through a Celite plug, washed with THF, and hot CHCl$_3$, evaporated and dried at vacuum.

The residue was dissolved in THF (50 mL) and H$_2$O (50 mL) and NaOH (700 mg, 18.0 mmol, 29 equiv.) was added. The reaction mixture was stirred at 50° C. overnight. The THF was evaporated and the mixture was acidified to pH 1 with conc. HCl. The precipitate was filtrated off, washed with H$_2$O and dried to give compound XI as a colourless solid (326 mg, 0.219 mmol, quant.). $^1$HNMR (600 MHz; CD$_3$SOCD$_3$, 100° C.): δ=7.87 (d, J=7.8 Hz, 2H), 7.17 (s, 2H), 7.11-7.05 (m, 16H), 6.95 (m, 4H), 2.27 (s, 6H), 2.11-2.09 (m, 36H), 1.44 (m, 8H), 1.26-1.15 (m, 32H), 0.81 (m, 12H) ppm. $^1$H NMR (600 MHz; THF, 56° C.): δ=7.92 (d, J=8.0 Hz, 2H), 7.18 (s, 2H), 7.16 (s, 2H), 7.12 (t, J=9.7 Hz, 12H), 7.07 (s, 2H), 6.98 (s, 2H), 6.92 (d, J=7.8 Hz, 2H), 2.56 (m, 4H), 2.45 (m, 4H), 2.30 (s, 6H), 2.16 (s, 18H), 2.15 (s, 12H), 2.13 (s, 6H), 1.53 (m, 8H), 1.26 (s, 24H), 0.87 (m, J=7.6 Hz, 12H) ppm. HRMS (ESI) calculated for C$_{106}$H$_{123}$O$_6$: m/z=1491.9314 ([M+H]$^+$). found 1491.9260. calculated for C$_{106}$H$_{121}$O$_6$: m/z=1489.9169 ([M−H]$^-$). found m/z=1489.9145.

Synthesis of IRMOF-74 Series

General Synthetic Conditions

Magnesium nitrate hexahydrate (Mg(NO$_3$)$_2$.6H$_2$O), magnesium chloride (MgCl$_2$), and potassium bromide (KBr) were purchased from Sigma Aldrich Chemical Co. Zinc nitrate tetrahydrate (Zn(NO$_3$)$_2$.4H$_2$O) and concentrated hydrochloric acid (Certified ACS Plus, 12 M) were purchased from Fisher Scientific International Inc. Anhydrous N,N-dimethylformamide (DMF) and methanol (HPLC grade) were purchased from EMD Science. Ethanol (200 Proof, ACS/USP Grade) was purchased from Pharmco-Aaper Co. All chemicals were used without further purification. Elemental Analysis was performed at UCLA and was carried out on a Thermo Scientific FLASH 2000 Series CHNS/O Analyzer using 2-3 mg of IRMOF-74 sample. FT-IR spectroscopy measurements were performed on an IRAffinity-1/Michelson interferometer (30 degree incident angle), with single-beam optics. The interferometer contains a DLATGS detector equipped with temperature control mechanism, S/N ratio: 30,000:1 or higher (peak-to-peak, 4 cm' resolution, in the neighborhood of 2,100 cm$^{-1}$), and scan range from 7,800 to 350 cm$^{-1}$. All experimental characterization (i.e. EA and FT-IR) operations were performed in air, which led to adsorption of water into the pore of activated samples. The simulated powder diffraction patterns were compared to the as synthesized powder diffraction patterns for IRMOF-74-II to VI. The as synthesized powder diffraction patterns of IRMOF-74-VII to XI are significantly broadened most likely due to the greater dynamic motions of the guest molecule within the larger pore volumes, in addition to, the flexibility of the dangling chains on the links. Therefore, we present the activated powder diffraction patterns for IRMOF-74-VII to XI for comparison with the corresponding simulated powder diffraction patterns.

Syntheses of IRMOF-74 Series (IRMOF-74 series syntheses are exemplified herein by the synthesis of IRMOF74-II). A solid mixture of magnesium nitrate hexahydrate Mg(NO$_3$)$_2$.6H$_2$O (80 mg, 0.31 mmol) and link II (C$_{14}$H$_{10}$O$_6$, 26 mg, 0.095 mmol) was dissolved in 7.5 mL of N,N-dimethylformamide (DMF) in a 20 mL vial. The vial was sealed and sonicated for 20 minutes until the solid was completely dissolved. To this solution, 0.5 mL of ethanol followed by 0.5 mL of deionized water was added drop wise. The vial was then vigorously swirled and shortly sonicated resulting in a clear, colorless solution. This solution was heated in an isothermal oven at 120° C. and allowed to react solvothermally for 24 hrs. The as-synthesized sample was washed three times before the activation procedure was carried out. The purity of the IRMOF74-II product has been confirmed by PXRD analysis. Elemental Analysis (activated): Anal. Calc. for Mg$_2$ (C$_{14}$H$_6$O$_6$) (H$_2$O)$_{6.5}$: C, 38.04; H, 4.49. Found: C, 38.58; H, 4.39. FT-IR (KBr, 3500-400 cm$^{-1}$): 3410 (br), 2924 (w), 2854 (w), 2854 (w), 1604 (m), 1573 (m), 1419 (s), 1381 (m), 1234 (s), 1157 (w), 887 (s), 786 (s), 717 (w), 671 (m), 609 (m).

Synthesis of IRMOF-74-I

The synthesis of IRMOF-74-I was carried out according to Rosi, N. L. et al. "Rod packings and metal-organic frameworks constructed from rod-shaped secondary building units." *J. Am. Chem. Soc.* 127, 1504-1518 (2005), which is incorporated herein.

Synthesis of IRMOF-74-II 80 mg of Mg(NO$_3$)$_2$.6H$_2$O (0.31 mmol) and 26 mg of link II (0.095 mmol) were dissolved with 7.5 mL DMF in a 20 mL vial. The vial was sealed and sonicated for 30 minutes until the solid was completely dissolved. To this solution, 0.5 mL of ethanol followed by 0.5 mL of deionized water was added drop wise. The vial was then vigorously swirled and shortly sonicated resulting in a clear, colorless solution. This solution was heated in an isothermal oven at 120° C. and allowed to react solvothermally for 24 h yielding colorless needle crystals (90% yield based on organic link). The resulting colorless powder's crystallinity was confirmed through comparison and subsequent matching of the as synthesized compound and the simulated powder diffraction pattern (FIG. 7). Gram scale of IRMOF-74-II crystals was obtained by combining products from multiple small-scale reactions. Elemental Analysis (activated sample): Anal. Calculated for Mg$_2$(C$_{14}$H$_6$O$_6$)(H$_2$O)$_{6.5}$: C, 38.04; H, 4.49. Found: C, 38.58; H, 4.39. FT-IR (KBr, 3500-400 cm$^{-1}$): 3410 (br), 2924 (w), 2854 (w), 2854 (w), 1604 (m), 1573 (m), 1419 (s), 1381 (m), 1234 (s), 1157 (w), 887 (s), 786 (s), 717 (w), 671 (m), 609 (m).

Figure 8:
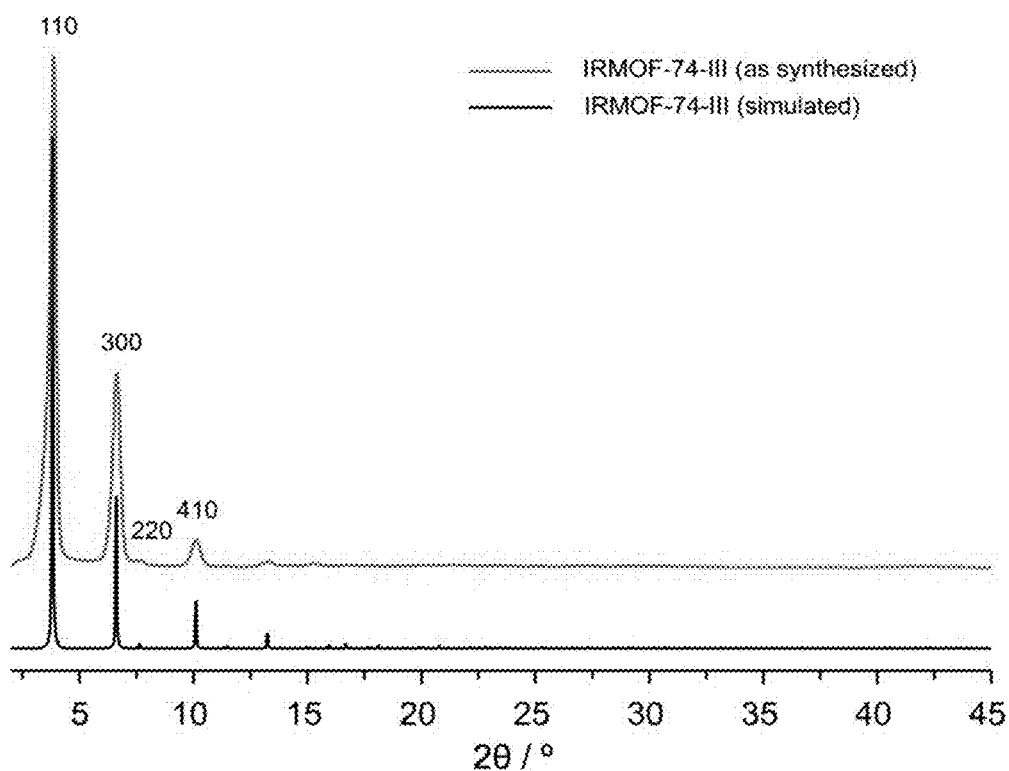
FIG. 8 provides a comparison of the experimental PXRD pattern of as synthesized IRMOF-74-III (top) with the simulated IRMOF-74-III diffraction pattern (bottom). The first four most intense reflections are shown.

Synthesis of IRMOF-74-III 160 mg of Mg(NO$_3$)$_2$.6H$_2$O (0.62 mmol) and 71 mg of link III (0.188 mmol) were dissolved with 15 mL DMF in a 20 mL vial. The vial was sealed and sonicated for 30 minutes until the solid was completely dissolved. To this solution, 1.0 mL of ethanol followed by 1.0 mL of deionized water was added drop wise. The vial was then vigorously swirled and shortly sonicated resulting in a clear, colorless solution. This solution was heated in an isothermal oven at 120° C. and allowed to react solvothermally for 24 h yielding colorless needle crystals (95% yield based on organic link). The resulting colorless powder's crystallinity was confirmed through comparison and subsequent matching of the as synthesized compound and the simulated powder diffraction pattern (FIG. 8). Gram scale of IRMOF-74-III crystals was obtained by combining products from multiple small-scale reactions. Elemental Analysis (activated sample): Anal. Calculated for $Mg_2(C_{22}H_{14}O_6)(H_2O)_3$: C, 55.40; H, 4.23. Found: C, 54.37; H, 4.36. FT-IR (KBr, 3500-400 $cm^{-1}$): 3410 (br), 2924 (w), 1604 (s), 1573 (s), 1512 (m), 1435 (vs), 1373 (s), 1226 (m), 925 (s), 879 (w), 601 (m), 524 (w).

Figure 9:
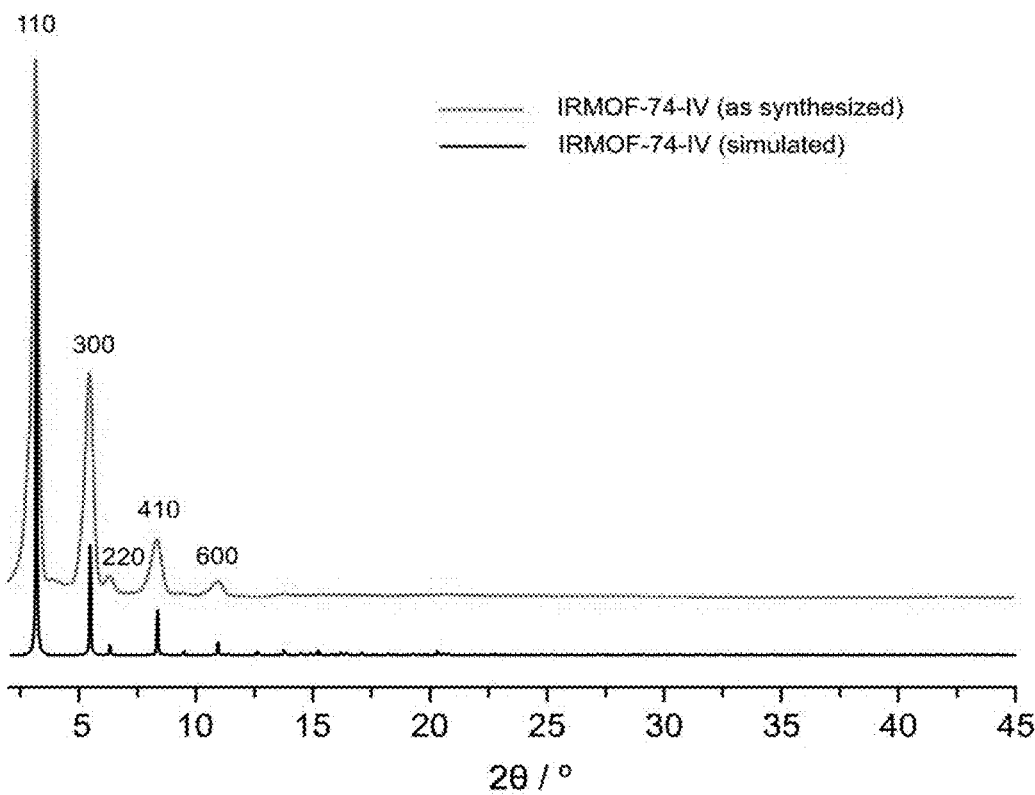
FIG. 9 provides a comparison of the experimental PXRD pattern of as synthesized IRMOF-74-IV (top) with the simulated IRMOF-74-IV diffraction pattern (bottom). The first five most intense reflections are shown.

Synthesis of IRMOF-74-IV 80 mg of $Mg(NO_3)_2.6H_2O$ (0.31 mmol) and 45 mg of link IV (0.093 mmol) were dissolved with 7.5 mL DMF in a 20 mL vial. The vial was sealed and sonicated for 30 minutes until the solid was completely dissolved. To this solution, 0.5 mL of ethanol followed by 0.5 mL of deionized water was added drop wise. The vial was then vigorously swirled and shortly sonicated resulting in a clear, colorless solution. This solution was heated in an isothermal oven at 120° C. and allowed to react solvothermally for 24 h yielding colorless needle crystals (87% yield based on organic link). The resulting colorless powder's crystallinity was confirmed through comparison and subsequent matching of the as synthesized compound and the simulated powder diffraction pattern (FIG. 9). Gram scale of IRMOF-74-IV crystals was obtained by combining products from multiple small-scale reactions. Elemental Analysis (activated sample): Anal. Calculated for $Mg_2(C_{30}H_{22}O_6)(H_2O)_5$: C, 58.06; H, 4.64. Found: C, 58.38; H, 5.23.FT-IR (KBr, 3500-400 $cm^{-1}$): 3410 (br), 3016 (w), 2924 (w), 1604 (s), 1573 (s), 1435 (vs), 1373 (s), 1327 (w), 1273 (m), 1226 (s), 1157 (m), 948 (s), 663 (m), 601 (m).

Figure 10:
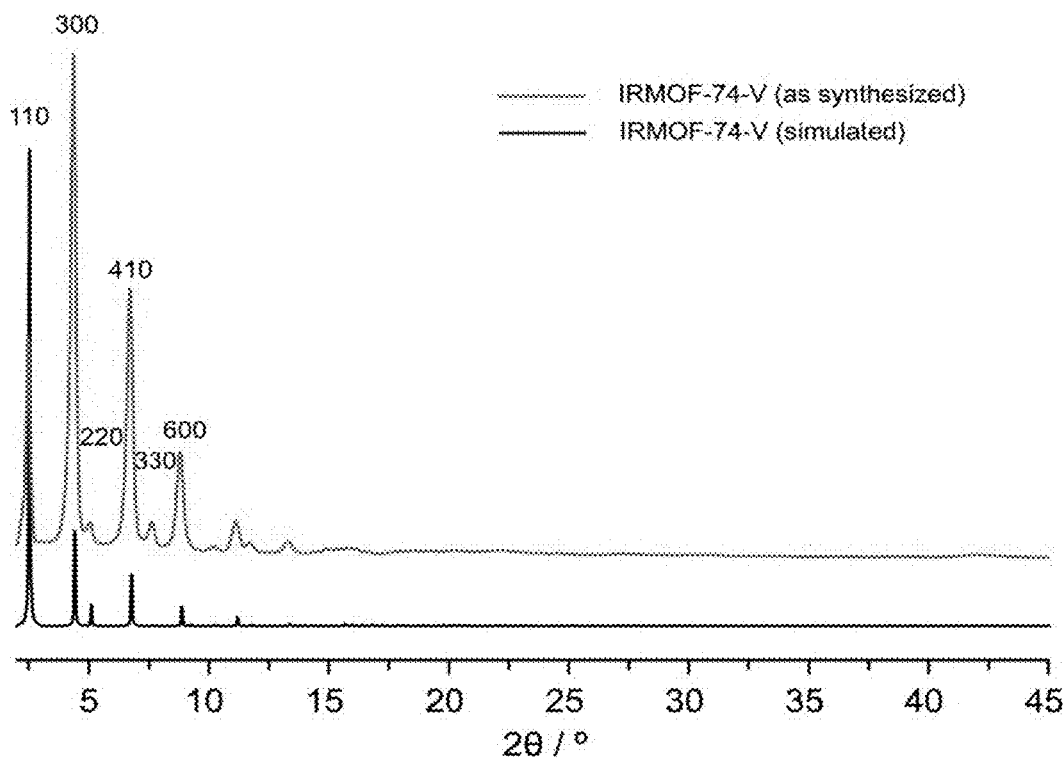
FIG. 10 provides a comparison of the experimental PXRD pattern of as synthesized IRMOF-74-V (top) with the simulated IRMOF-74-V diffraction pattern (bottom). The first six most intense reflections are shown.

Synthesis of IRMOF-74-V 80.0 mg of $Mg(NO_3)_2.6H_2O$ (0.313 mmol) and 52.5 mg of V (0.089 mmol) were dissolved with 7.5 mL DMF in a 20 mL vial. The vial was sealed and sonicated for 20 minutes until the solid was completely dissolved. To this solution, 0.5 mL of ethanol followed by 0.5 mL of deionized water was added drop wise. The vial was then vigorously swirled and shortly sonicated resulting in a clear, colorless solution. This solution was heated in an isothermal oven at 120° C. and allowed to react solvothermally for 24 h yielding colorless needle crystals (63% yield based on organic link). This solution was heated in an isothermal oven at 120° C. and allowed to react solvothermally for 24 h. The resulting white powder's crystallinity was confirmed through comparison and subsequent matching of the as synthesized and the simulated powder diffraction pattern (FIG. 10). Gram scale of IRMOF-74-V crystals was obtained by combining products from multiple small-scale reactions. Elemental Analysis (activated sample): Anal Calculated for $Mg_2(C_{38}H_{30}O_6)(H_2O)_6$: C, 61.26; H, 5.49. Found: C, 61.73; H, 5.73.FT-IR (KBr, 3500-400 $cm^{-1}$): 3394 (br), 3008 (w), 2924 (w), 2862 (w), 1604 (s), 1573 (s), 1512 (w), 1435 (vs), 1381 (vs), 1226 (m), 879 (m), 802 (m), 678 (w), 601 (w), 455 (w).

Figure 11:
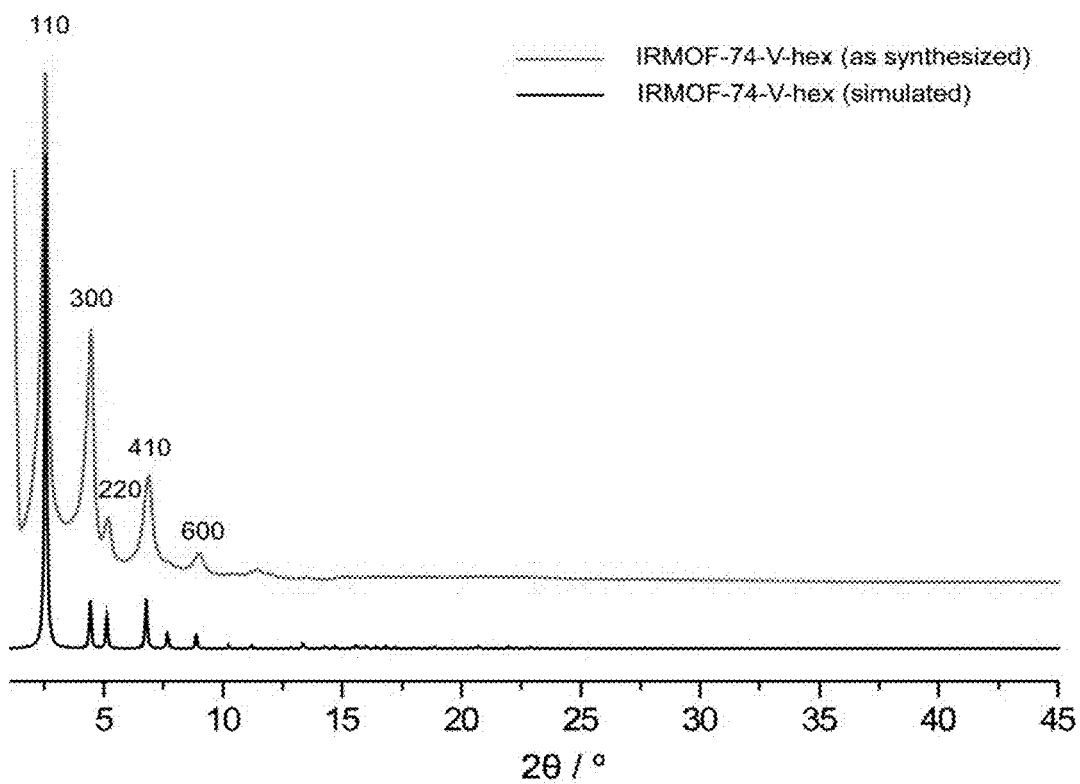
FIG. 11 provides a comparison of the experimental PXRD pattern of as synthesized IRMOF-74-V-hex (top) with the simulated IRMOF-74-V-hex diffraction pattern (bottom). The first five most intense reflections are shown.

Synthesis of IRMOF-74-V-Hex 80.0 mg of $Mg(NO_3)_2.6H_2O$ (0.313 mmol) and 65 mg of V-hex (0.089 mmol) were dissolved with 7.5 mL DMF in a 20 mL vial. The vial was sealed and sonicated for 20 min. To this solution, 0.5 mL of ethanol followed by 0.5 mL of deionized water was added drop wise. The vial was then vigorously swirled and shortly sonicated resulting in a slightly cloudy solution. This solution was heated in an isothermal oven at 120° C. and allowed to react solvothermally for 24 h yielding colorless needle crystals (60% yield based on organic link). The resulting white powder's crystallinity was confirmed through comparison and subsequent matching of the as synthesized and the simulated powder diffraction pattern (FIG. 11). Gram scale of IRMOF-74-V-hex crystals was obtained by combining products from multiple small-scale reactions. Elemental Analysis (activated sample): Anal. Calculated for $Mg_2(C_{48}H_{50}O_6)(H_2O)_{4.5}$: C, 67.62; H, 6.98. Found: C, 67.89; H, 6.96. FT-IR (KBr, 3500-400 $cm^{-1}$): 3417 (br), 3008 (w), 2924 (vs), 2854 (s), 1604 (m), 1581 (m), 1435 (vs), 1373 (m), 1257 (w), 1219 (s), 972 (s), 879 (s), 802 (s), 717 (s), 678 (s), 601 (s).

Figure 12:
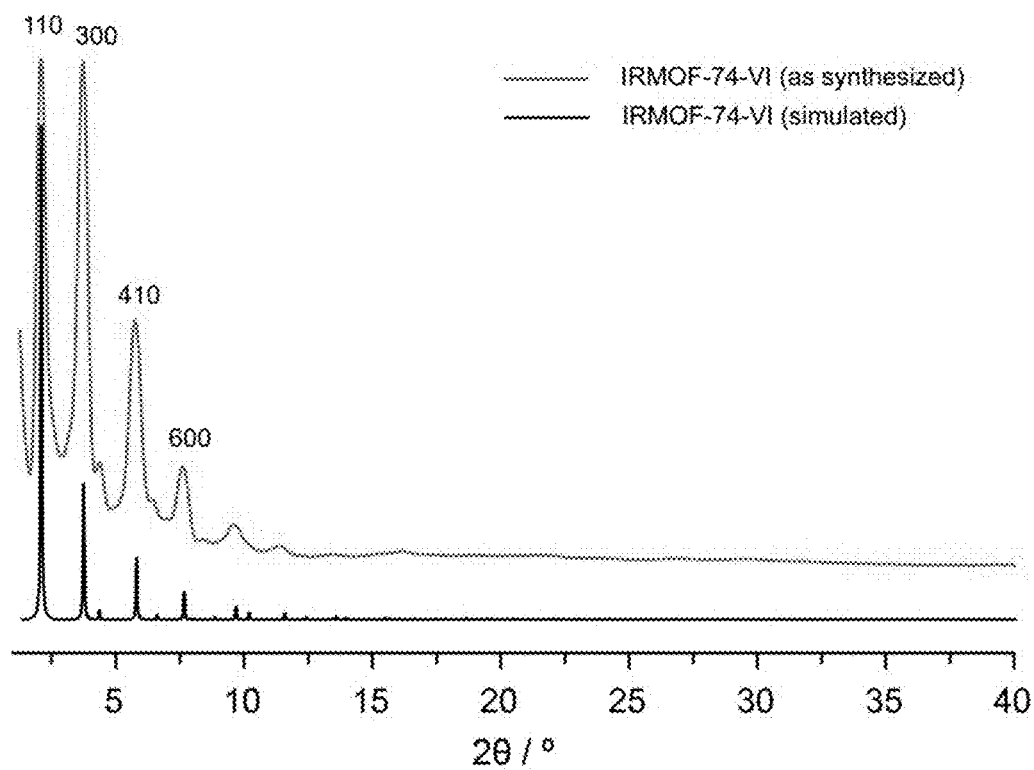
FIG. 12 provides a comparison of the experimental PXRD pattern of as synthesized IRMOF-74-VI (top) with the simulated IRMOF-74-VI diffraction pattern (bottom). The first five most intense reflections are shown.

Synthesis of IRMOF-74-VI 120.0 mg of $Zn(NO_3)_2.4H_2O$ (0.403 mmol) and 79.0 mg of link VI (0.114 mmol) were dissolved with 10 mL DMF in a 20 mL vial. The vial was sealed and sonicated for two hours to ensure maximum solubility of the linker, VI. This white, cloudy solution was heated in an isothermal oven at 100° C. and allowed to react solvothermally for 48 h yielding colorless needle crystals (72% yield based on organic link). The resulting white powder's crystallinity was confirmed through comparison and subsequent matching of the as synthesized and the simulated powder diffraction pattern (FIG. 12). Gram scale of IRMOF-74-VI crystals was obtained by combining products from multiple small-scale reactions. Elemental Analysis (activated sample): Anal. Calculated for $Zn_2(C_{46}H_{36}O_6)(H_2O)_4$: C, 62.10; H, 5.21. Found: C, 61.90; H, 5.28. FT-IR (KBr, 3500-400 $cm^{-1}$): 3425 (br), 3008 (w), 2924 (w), 2862 (w), 1604 (s), 1573 (s), 1435 (vs), 1381 (m), 1211 (m), 887 (m), 665 (w), 570 (w), 524 (w).

Figure 13:
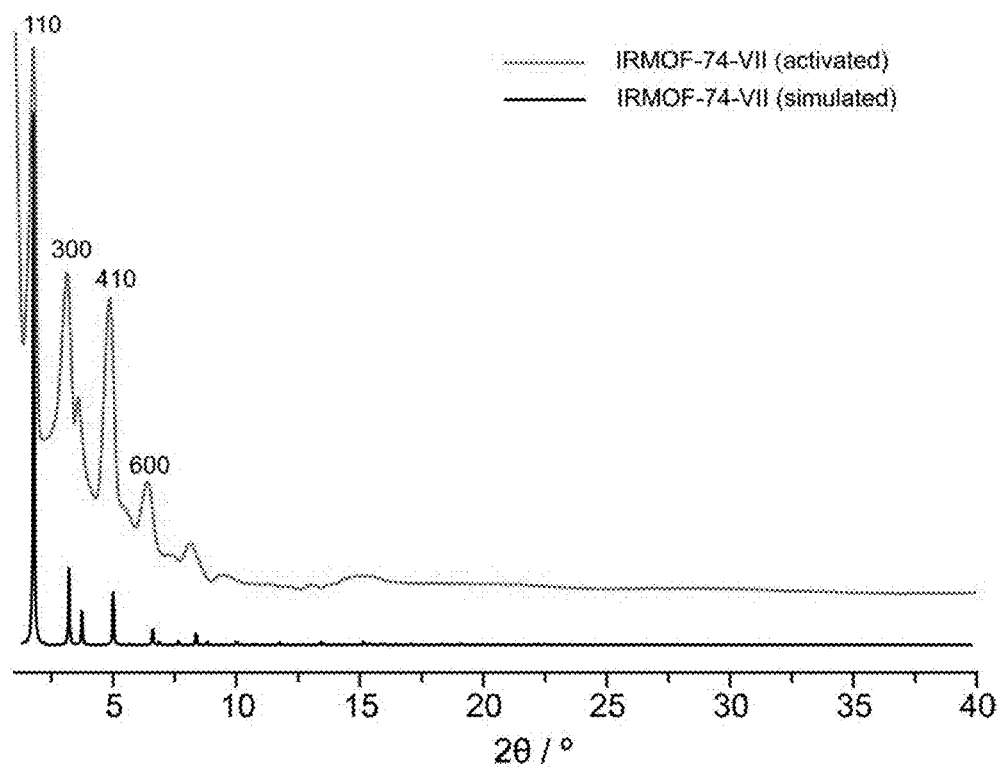
FIG. 13 provides a comparison of the experimental PXRD pattern of activated IRMOF-74-VII (top) with the simulated IRMOF-74-VII diffraction pattern (bottom). The first four most intense reflections are shown.

Synthesis of IRMOF-74-VII 96 mg of $Mg(NO_3)_2.6H_2O$ (0.375 mmol) and 100 mg of link VII (0.107 mmol) were dissolved with 9.0 mL DMF in a 20 mL vial. The vial was sealed and sonicated for 30 minutes, then heat in 100° C. oven until the solid was completely dissolved (usually within 20 minutes). To this hot solution, 0.5 mL of ethanol followed by 0.5 mL of deionized water was added drop wise. The vial was then vigorously swirled and shortly sonicated (2 to 3 seconds, no longer) resulting in a clear, colorless solution. This solution was heated in an isothermal oven at 120° C. and allowed to react solvothermally for 24 h yielding colorless needle crystals (71% yield based on organic link). The resulting colorless powder's crystallinity was confirmed through comparison and subsequent matching of the activated compound and the simulated powder diffraction pattern (FIG. 13). Gram scale of IRMOF-74-VII crystals was obtained by combining products from multiple small-scale reactions.

Elemental Analysis (activated sample): Anal. Calculated for $Mg_2(C_{64}H_{66}O_6)(H_2O)_9$: C, 67.67; H, 6.79. Found: C, 67.91; H, 6.59.FT-IR (KBr, 3500-400 cm$^{-1}$): 3410 (br), 3008 (w), 2924 (s), 2854 (s), 1604 (s), 1573 (s), 1435 (vs), 1381 (s), 1219 (m), 887 (m), 717 (w), 671 (w), 601 (w).

Figure 14:
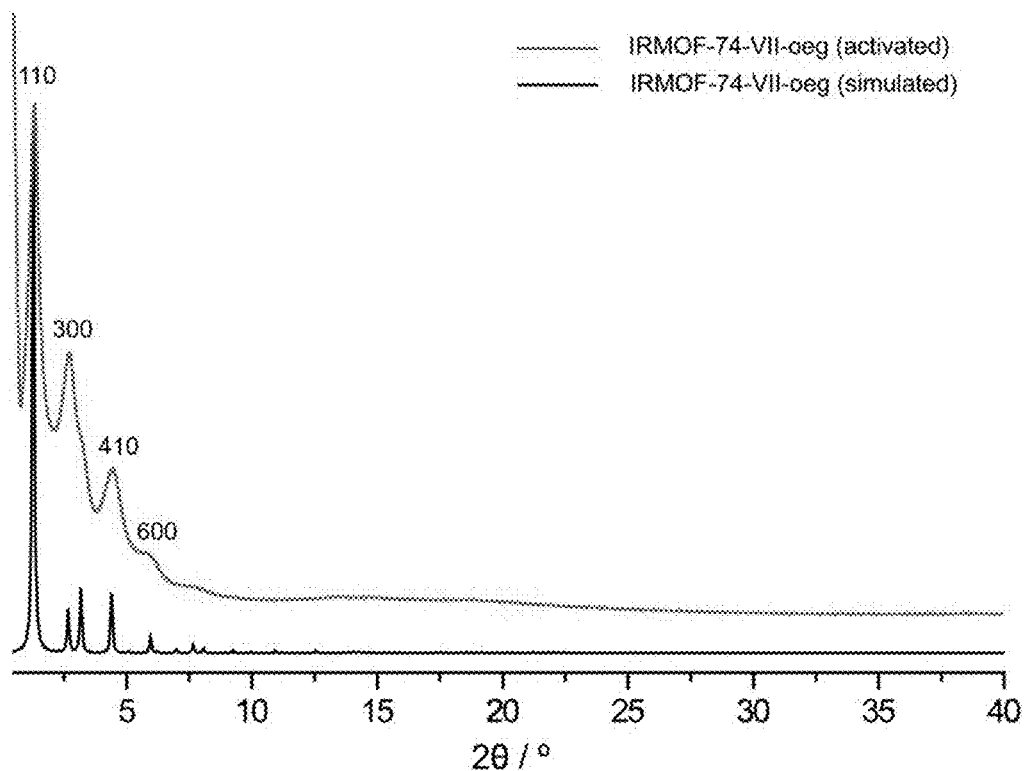
FIG. 14 provides a comparison of the experimental PXRD pattern of activated IRMOF-74-VII-oeg (top) with the simulated IRMOF-74-VII-oeg diffraction pattern (bottom). The first four most intense reflections are shown.

Synthesis of IRMOF-74-VII-oeg 96 mg of $Mg(NO_3)_2.6H_2O$ (0.375 mmol) and 117 mg of link VI-oeg (0.117 mmol) were dissolved with 9.0 mL DMF in a 20 mL vial. The vial was sealed and sonicated for 30 minutes until the solid was completely dissolved. To this solution, 0.6 mL of ethanol followed by 0.6 mL of deionized water was added drop wise. The vial was then vigorously swirled and shortly sonicated resulting in a clear, colorless solution. This solution was heated in an isothermal oven at 120° C. and allowed to react solvothermally for 24 h yielding colorless needle crystals (87% yield based on organic link). The resulting colorless powder's crystallinity was confirmed through comparison and subsequent matching of the compound and the simulated powder diffraction pattern (FIG. 14). Gram scale of IRMOF-74-VII-oeg crystals was obtained by combining products from multiple small-scale reactions. Elemental Analysis (activated sample): Anal. Calculated for $Mg_2(C_{66}H_{20}O_{14})(H_2O)_7$: C, 62.81; H, 6.71. Found: C, 62.82; H, 6.56. FT-IR (KBr, 3500-400 cm$^{-1}$): 3387 (br), 2924 (m), 2870 (m), 1604 (s), 1573 (s), 1435 (m), 1357 (m), 1203 (s), 1103 (m), 933 (m), 879 (w), 717 (w), 671 (w), 601 (w), 455 (w).

Figure 15:
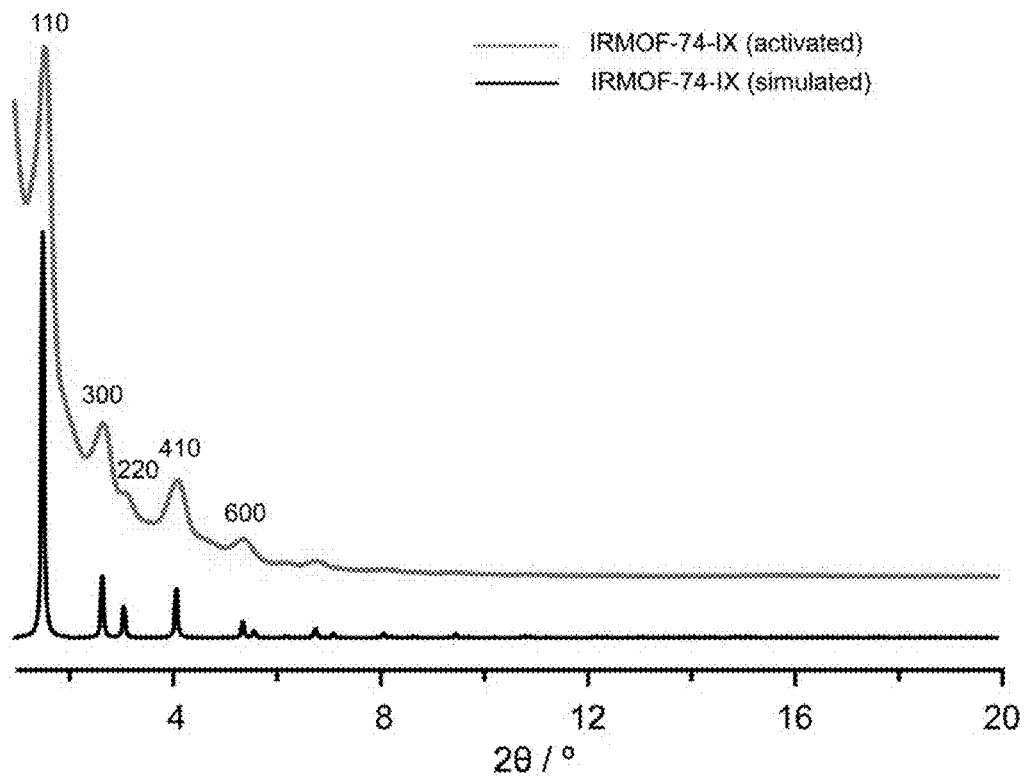
FIG. 15 provides a comparison of the experimental PXRD pattern of activated IRMOF-74-IX (top) with the simulated IRMOF-74-IX diffraction pattern (bottom). The first five most intense reflections are shown.

Synthesis of IRMOF-74-IX 96 mg of $Mg(NO_3)_2.6H_2O$ (0.375 mmol) and 122 mg of link IX (0.107 mmol) were dissolved with 9.0 mL DMF in a 20 mL vial. The vial was sealed and sonicated for 30 minutes, then heated in a 120° C. oven until the solid was completely dissolved (usually 40 minutes). To this hot solution, 0.5 mL of ethanol followed by 0.5 mL of deionized water was added drop wise. The vial was then vigorously swirled and shortly sonicated (2 to 3 seconds, no longer) resulting in a clear, colorless solution. This solution was heated in an isothermal oven at 130° C. and allowed to react solvothermally for 24 h yielding colorless needle crystals (65% yield based on organic link). If the solution did not become clear after 2 h. in 130° C. oven, 10 μL of concentrated HCl (12 M) was added to dissolve the insoluble solid and form a clear solution (Note that if the solution is not clear before the reaction starts, no crystal will yield). The resulting colorless powder's crystallinity was confirmed through comparison and subsequent matching of the activated compound and the simulated powder diffraction pattern (FIG. 15). Gram scale of IRMOF-74-IX crystals was obtained by combining products from multiple small-scale reactions. Elemental Analysis (activated): Anal. Calculated for $Mg_2(C_{80}H_{82}O_6)(H_2O)_{5.5}$: C, 74.65; H, 7.29. Found: C, 74.39; H, 7.11. FT-IR (KBr, 3500-400 cm$^{-1}$): 3379 (br), 3008 (w), 2924 (s), 2854 (s), 1604 (s), 1573 (s), 1435 (vs), 1381 (s), 1265 (m), 1157 (m), 887 (s), 663 (w), 601 (w), 462 (w).

Figure 16:
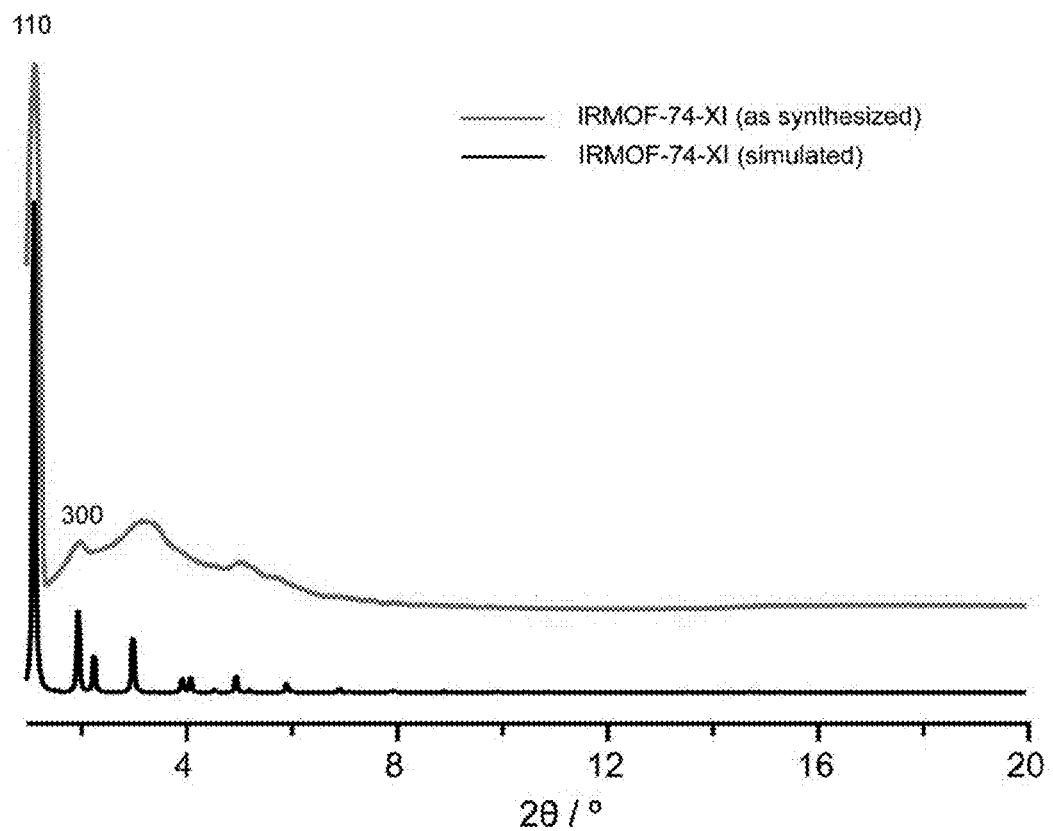
FIG. 16 provides a comparison of the experimental PXRD pattern of activated IRMOF-74-XI (top) with the simulated IRMOF-74-XI diffraction pattern (bottom). The first two most intense reflections are shown.

Synthesis of IRMOF-74-XI 6.0 mg of anhydrous $MgCl_2$ (0.063 mmol) and 11 mg of link XI (0.0074 mmol) were added into a Pyrex tube measuring o.d.×i.d.=10×8 mm$^2$. The tube was evacuated to less than 10 mTorr and then back filled with nitrogen. This process was repeated three times before 3 mL of anhydrous DMF was injected. The solution was then sonicated for 30 min. in the Pyrex tube with the opening tightly capped by septa. The tube was flash frozen at 77 K ($LN_2$ bath), evacuated to an internal pressure of 20 mTorr and flame sealed. Upon sealing the length of the tube was reduced to ca. 18 cm. This solution was heated in sand bath in an isothermal oven at 130° C. and allowed to react solvothermally for 24 h yielding colorless needle crystals (50% yield based on organic link). The resulting colorless powder's crystallinity was confirmed through comparison and subsequent matching of the activated compound and the simulated powder diffraction pattern (FIG. 16). Gram scale of IRMOF-74-XI crystals was obtained by combining products from multiple small-scale reactions. Elemental Analysis (activated): Anal. Calculated for $Mg_2(C_{106}H_{118}O_6)(H_2O)_{6.5}$: C, 76.88; H, 7.98. Found: C 76.88; H, 7.77. FT-IR (KBr, 3500-400 cm$^{-1}$): 3417 (br), 3008 (m), 2924 (vs), 2854 (s), 1604 (m), 1573 (m), 1435 (vs), 1381 (m), 1265 (w), 887 (s), 802 (w), 609 (w), 455 (w).

Scanning Electron Microscopy Imaging (SEM)

Figure 17:
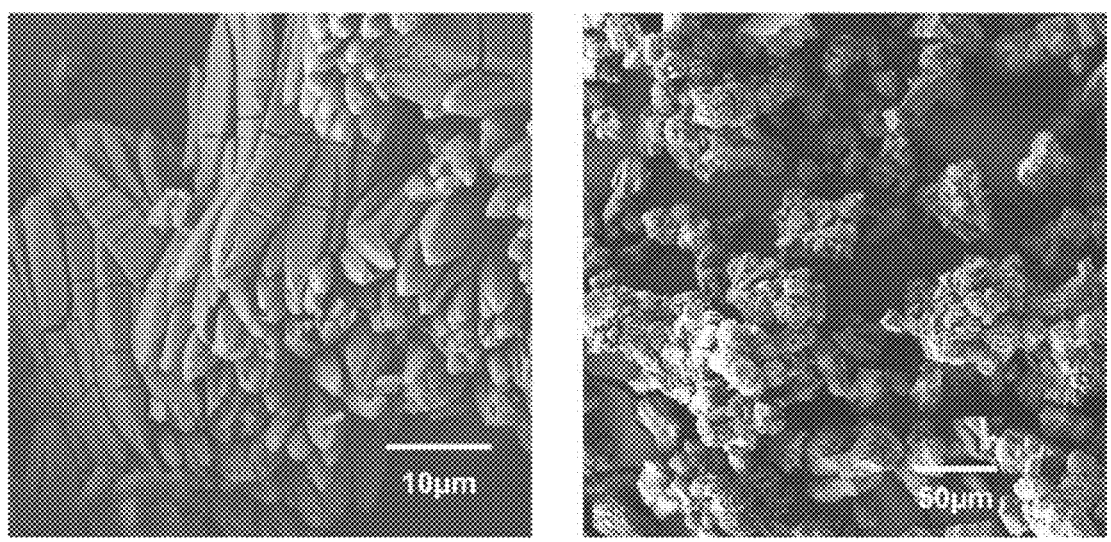
FIG. 17 presents SEM images with different scales, revealing single-phase morphology of IRMOF-74-I.
Figure 18:
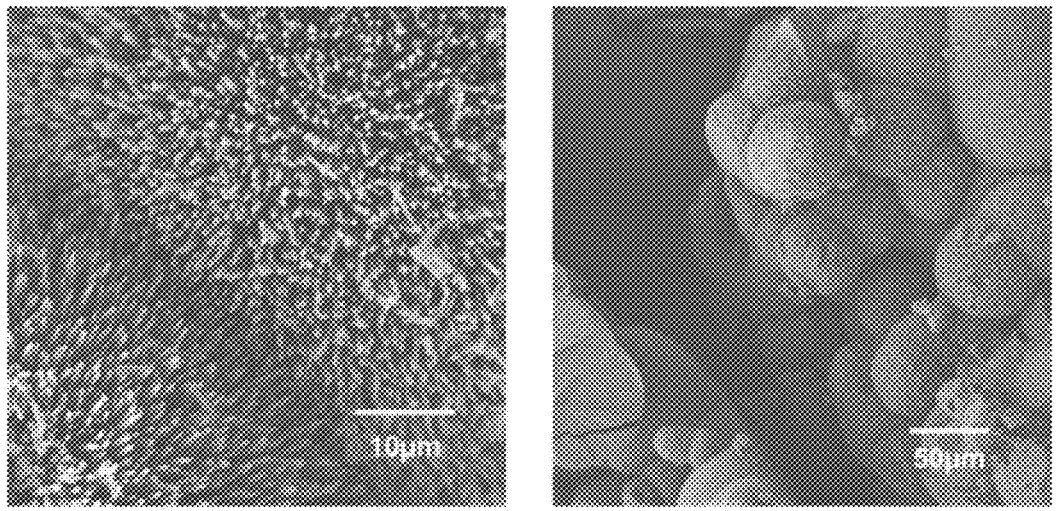
FIG. 18 presents SEM images with different scales, revealing single-phase morphology of IRMOF-74-II.
Figure 19:
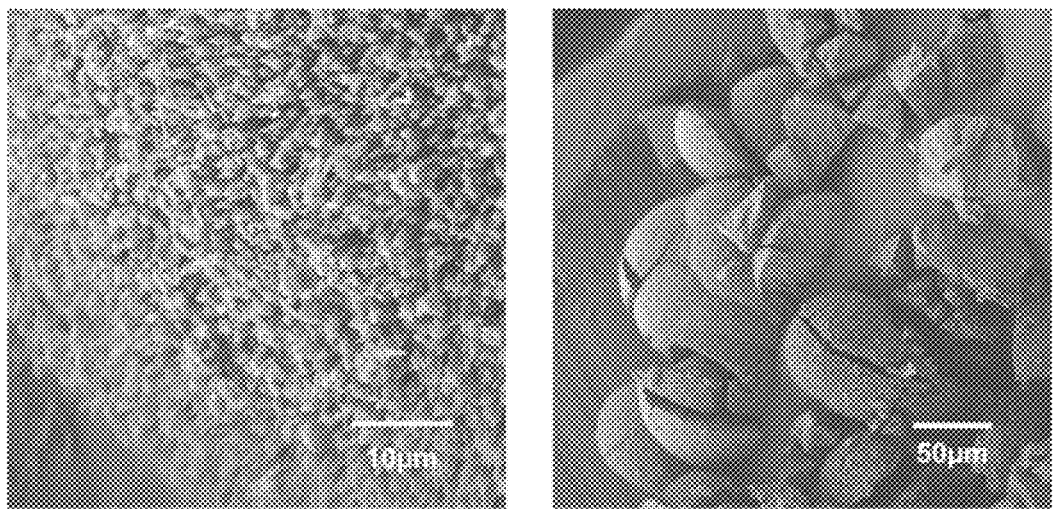
FIG. 19 presents SEM images with different scales, revealing single-phase morphology of IRMOF-74-III.
Figure 20:
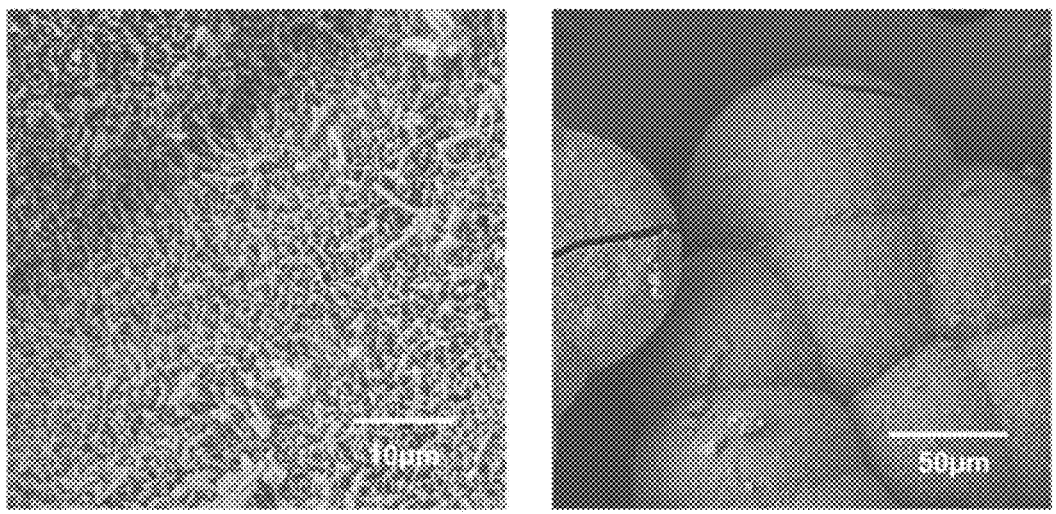
FIG. 20 presents SEM images with different scales, revealing single-phase morphology of IRMOF-74-IV.
Figure 21:
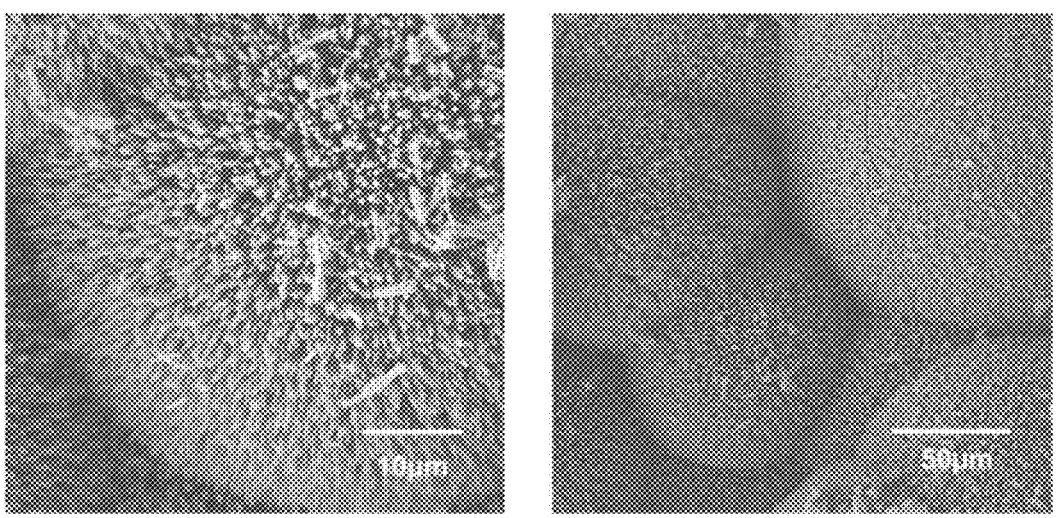
FIG. 21 presents SEM images with different scales, revealing single-phase morphology of IRMOF-74-V.
Figure 22:
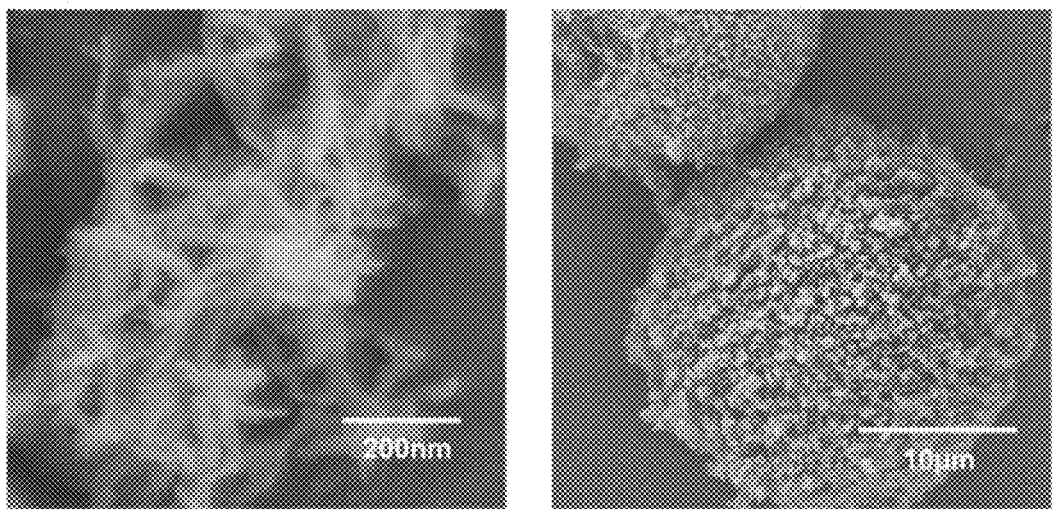
FIG. 22 presents SEM images with different scales, revealing single-phase morphology of IRMOF-74-VI.
Figure 23:
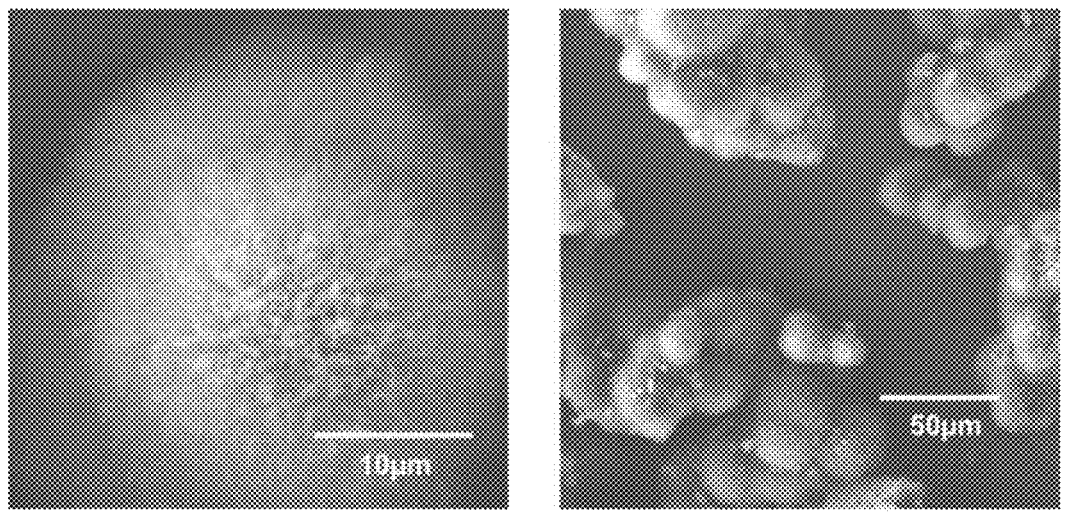
FIG. 23 presents SEM images with different scales, revealing single-phase morphology of IRMOF-74-VII.
Figure 24:
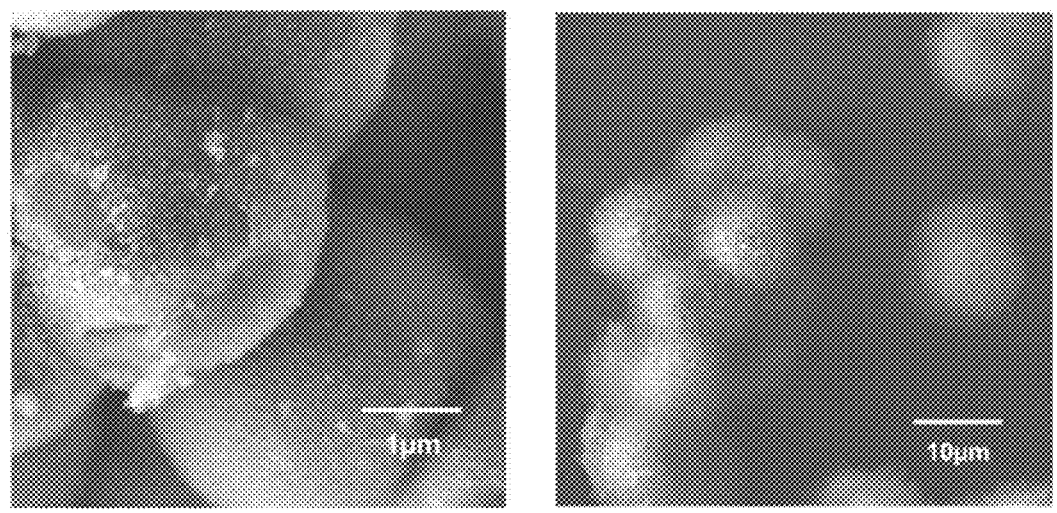
FIG. 24 presents SEM images with different scales, revealing single-phase morphology of IRMOF-74-IX.
Figure 25:
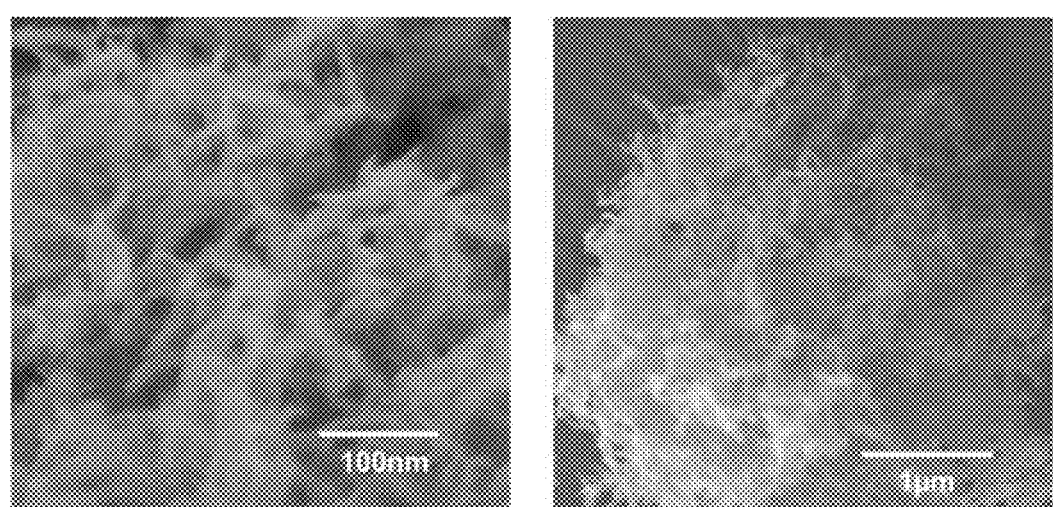
FIG. 25 presents SEM images with different scales, revealing single-phase morphology of IRMOF-74-XI.

General:

Samples of synthesized IRMOF-74 were measured by dispersing the material onto a sticky carbon surface attached to a flat aluminum sample holder. The samples were then gold coated using a Hummer 6.2 Sputter at ambient temperature and a pressure of 70 mTorr in an argon atmosphere for 30 s while maintaining a current of 15 mA. Samples were analyzed using a JEOL JSM-6701F Scanning Electron Microscope using both the SEI and LEI detectors with accelerating voltage of 5 to 10 kV. Multiple samples of each synthesized IRMOF were surveyed. Only a unique morphology was apparent after exhaustive examination of a range of particle sizes that were deposited on the sample holder. No evidence for the presence of other phases was observed in the surveyed samples. SEM images of the IRMOF-74 series, with different scales, are presented in the FIGS. 17 to 25: SEM images of IRMOF-74-I (FIG. 17); IMROF-74-II (FIG. 18); IMROF-74-III (FIG. 19); IMROF-74-IV (FIG. 20); IMROF-74-V (FIG. 21); IMROF-74-VI (FIG. 22); IMROF-74-VII (FIG. 23); IMROF-74-IX (FIG. 24); and IMROF-74-XI (FIG. 25).

X-Ray Powder Diffraction Studies and X-Ray Crystallography

General:

X-ray powder diffraction patterns were collected at ambient temperature and pressure, in reflectance Bragg-Brentano geometry employing Ni filtered Cu K lines focused radiation (1.54059 Å, 1.54439 Å) at 1600 W (40 kV, 40 mA) power. Determination of the final unit cell parameters was conducted by performing full pattern profile refinements. The limited number and broadness of the diffraction peaks precluded from performing Rietveld refinements. Nevertheless, good profiles were obtained from readily convergent refinements.

A 20 parameters polynomial function was selected for background correction. To define the pattern profile, a Thomson-Cox-Hasting pseudo Voigt function was employed, combined with a Finger et al. function for asymmetry correction. Satisfactory residuals were obtained for all the materials employing the initial R $\bar{3}$ space group, with the only exception of IRMOF-74-VI. The reflection conditions in the diffraction pattern suggested P $\bar{3}$ as possible space group for this compound. Therefore, an equivalent crystal model was generated using this space group, and the profile refinement was successfully carried out. Another run of geometry optimization was finally performed for all the compounds using the unit cell parameters obtained from the experimental pattern refinements to generate the final crystal models.

X-Ray Powder Diffraction Studies:

Full pattern profile refinements were carried out for all IRMOF-74 compounds resulting in satisfactory residuals. R$\bar{3}$ space group, same as the initial models, was employed, with the only exception being IRMOF-74-VI, for which P$\bar{3}$ space group was used. IRMOF-74-II: a=36.121(6) Å, c=6.813(4) Å (FIG. 7). IRMOF-74-III: a=46.283(5) Å, c=6.411(2) Å (FIG. 8). IRMOF-74-IV: a=56.19(2) Å, c=6.838(5) Å (FIG. 9). IRMOF-74-V: a=68.668(8) Å, c=6.801(2) Å (FIG. 10). IRMOF-74-VI: a=76.645(3) Å, c=6.317(4) Å (FIG. 12). IRMOF-74-VII: a=93.34(3) Å, c=6.595(2) Å (FIG. 13). IRMOF-74-IX: a=112.82(6) Å, c=6.802(6) Å (FIG. 14). IRMOF-74-XI: a=143.84(6) Å, c=6.563(9) Å (FIG. 15). Molecular formulas, unit cell volume, void space, and density of the refine structures are presented in Table 2.

Figure 26:
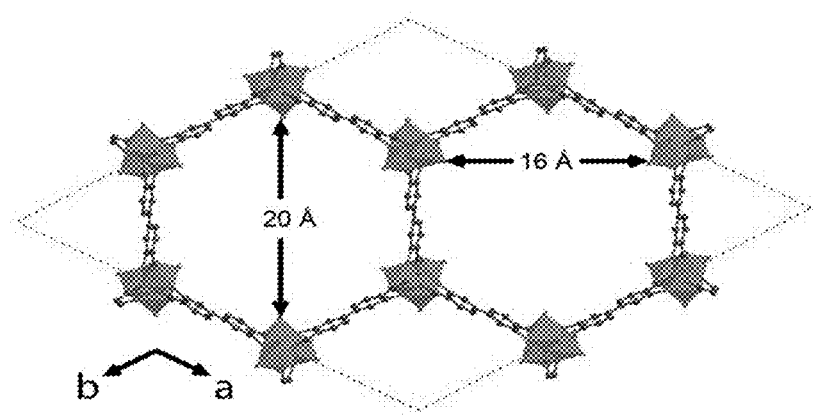
FIG. 26 presents a rhombohedral unit cell of IRMOF-74-II showing hexagonal channels. The pore apertures are measured from opposite $H_2O$ oxygen atoms coordinated to the octahedral magnesium. C atoms are shown as black dots between the Mg atoms, O atoms are shown as dots immediately adjacent to the Mg atom, and octahedral Mg atoms are shown as the large octahedra.

IRMOF-74-II: a=36.121(6) Å, c=6.813(4) Å, Rp=4.44, wRp=6.40 (see Table 3 and 4); pore aperture dimensions (the distance between opposites vertices in the hexagon) (Å)=16.5×19.5 (see FIG. 26).

TABLE 3

Crystallographic data of the refined PXRD for IRMOF-74-II.

| Compound | IRMOF-74-II |
|---|---|
| Empirical Formula | $C_7H_4MgO_4$ |
| Space Group | R$\bar{3}$ |
| Z | 18 |
| a (Å) | 36.121(6) |
| b (Å) | 6.813(4) |
| Unit Cell Volume (Å$^3$) | 7699.36 |
| 2θ range (°) | 2-45 |
| $R_p$ | 4.44 |
| $R_{wp}$ | 6.4 |
| $R_{wp}$ (w/o background) | 8.82 |

TABLE 2

| Compound | Space group | Molecular formula | a (Å) | c (Å) | Unit Cell Volume (Å$^3$) | Void space (%) | Density (g · cm$^{-3}$) | Density with open metal site (g · cm$^{-3}$)* |
|---|---|---|---|---|---|---|---|---|
| IRMOF-74-II | R$\bar{3}$ | $C_7H_4MgO_4$ | 36.121(6) | 6.813(4) | 7699.36 | 66.0 | 0.689 | 0.615 |
| IRMOF-74-III | R$\bar{3}$ | $C_{10}H_6MgO_4$ | 46.283(5) | 6.411(2) | 11893.93 | 70.7 | 0.542 | 0.493 |
| IRMOF-74-IV | R$\bar{3}$ | $C_{15}H_{13}MgO_4$ | 56.19(2) | 6.838(5) | 18700.52 | 73.2 | 0.450 | 0.421 |
| IRMOF-74-V | R$\bar{3}$ | $C_{19}H_{16}MgO_4$ | 68.74(4) | 6.473(3) | 27774.76 | 76.5 | 0.375 | 0.338 |
| IRMOF-74-V-hex | R$\bar{3}$ | $C_{24}H_{26}MgO_4$ | 68.95(8) | 6.461(1) | 26610.98 | 68.1 | 0.452 | 0.432 |
| IRMOF-74-VI | P$\bar{3}$ | $C_{23}H_{16}ZnO_4$ | 76.64(4) | 6.161(1) | 31343.78 | 78.1 | 0.373 | 0.385 |
| IRMOF-74-VII | R$\bar{3}$ | $C_{32}H_{34}MgO_4$ | 93.34(3) | 6.595(4) | 49766.55 | 77.9 | 0.322 | 0.294 |
| IRMOF-74-VII-oeg | R$\bar{3}$ | $C_{33}H_{37}MgO_8$ | 94.39(8) | 6.731(5) | 51947.61 | 76.5 | 0.337 | 0.327 |
| IRMOF-74-IX | R$\bar{3}$ | $C_{40}H_{42}MgO_4$ | 112.82(1) | 6.802(9) | 74990.33 | 82.7 | 0.247 | 0.236 |
| IRMOF-74-XI | R$\bar{3}$ | $C_{53}H_{61}MgO_4$ | 143.84(5) | 6.563(3) | 117610.1 | 85.3 | 0.200 | 0.195 |

*Coordinating water molecules were removed to leave open metal site after activation Crystallographic Studies on IRMOF-74 Series.

Powder x-ray data were collected by using D8-Advance θ-θ diffractometer (Bruker) in reflectance Bragg Brentano geometry employing Ni-filtered CuKα line focused radiation at 1,600 W (40 kV, 40 mA) power and equipped with a Vantec position sensitive detector (PSD) with and electronic window of 6°, and fitted with 0.2 to 0.6 mm radiation entrance slits. Samples were mounted on sample holders by dropping powders from a wide-blade spatula and then leveling the sample surface with a razor blade.

Based on the reported crystal structure of Mg-MOF-74 (IRMOF-74-I), crystal models of IRMOF-74 series were generated by adding the appropriate number of phenyl rings. An energetic minimization was then performed to optimize the geometry of the molecules, employing the universal force field implemented in the Forcite module of Materials Studio (v 5.0.0.0, 2009, Accelrys Software Inc.). The unit cell parameters were also optimized until convergence was reached. Satisfactory residuals were obtained for all the materials employing the initial R-3 space group, with the only exception of IRMOF-74-VI. The reflection conditions suggested P-3 as possible space group for this compound.

TABLE 4

List of the 25 most intense reflections, calculated from the final crystal structures for IRMOF-74-II.

| h | k | l | d (Å) | I/I$_{max}$ |
|---|---|---|---|---|
| 1 | 1 | 0 | 18.0641 | 34.200 |
| 3 | 0 | 0 | 10.4293 | 4.710 |
| 1 | 4 | 0 | 6.8276 | 2.760 |
| 4 | 1 | 0 | 6.8276 | 2.440 |
| 6 | 0 | 0 | 5.2147 | 1.320 |
| 1 | 3 | 1 | 5.3591 | 0.800 |
| 2 | 0 | −1 | 6.2469 | 0.750 |
| 3 | 2 | 1 | 4.9418 | 0.730 |
| 4 | 3 | 1 | 4.1053 | 0.700 |
| 6 | 2 | 1 | 3.6598 | 0.590 |
| 7 | 3 | 1 | 3.1275 | 0.450 |
| 3 | 3 | 0 | 6.0214 | 0.440 |
| 9 | 2 | 1 | 2.8088 | 0.400 |
| 13 | 3 | 1 | 2.0277 | 0.390 |
| 1 | 7 | 0 | 4.1442 | 0.390 |
| 7 | 1 | 0 | 4.1442 | 0.380 |
| 9 | 0 | 0 | 3.4764 | 0.350 |
| 2 | 4 | 1 | 4.4658 | 0.310 |
| 10 | 3 | 1 | 2.4729 | 0.280 |
| 1 | 10 | 0 | 2.9697 | 0.270 |
| 3 | 10 | 2 | 2.0936 | 0.260 |
| 1 | 5 | −1 | 4.3353 | 0.250 |
| 3 | 4 | −1 | 4.1053 | 0.230 |
| 4 | 0 | 1 | 5.1378 | 0.190 |
| 1 | 0 | 1 | 6.6577 | 34.200 |

Figure 27:
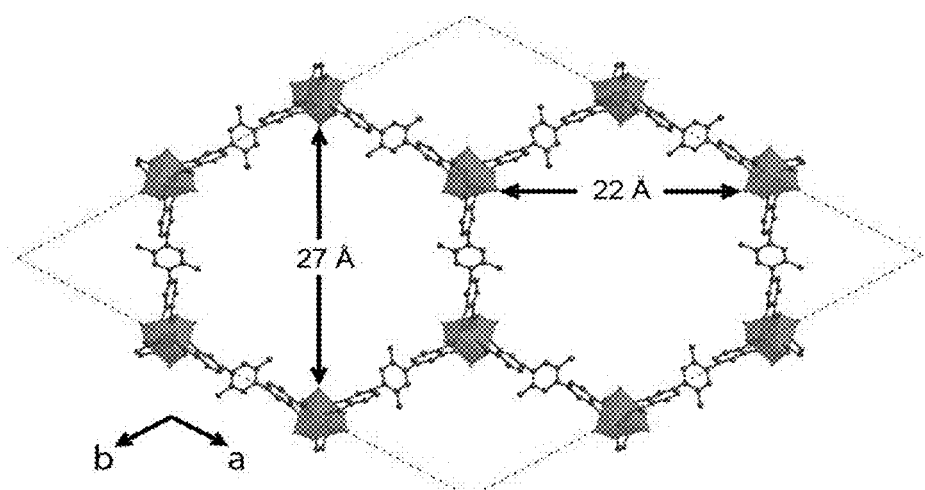
FIG. 27 presents a rhombohedral unit cell of IRMOF-74-III showing hexagonal channels. The pore apertures are measured from opposite $H_2O$ oxygen atoms coordinated to the octahedral magnesium. C atoms are shown as black dots between the Mg atoms, O atoms are shown as dots immediately adjacent to the Mg atom, and octahedral Mg atoms are shown as the large octahedra.

IRMOF-74-III: a=46.283(5) Å, c=6.411(2) Å, Rp=6.26, wRp=8.57 (See Table 5 and 6); pore aperture dimensions (Å)=22.2×27.3 (see FIG. 27).

TABLE 5

Crystallographic data of the refined PXRD for IRMOF-74-III

| Compound | IRMOF-74-III |
|---|---|
| Empirical Formula | $C_{10}H_6MgO_4$ |
| Space Group | $R\bar{3}$ |
| Z | 18 |
| a (Å) | 46.283(5) |
| b (Å) | 6.411(2) |
| Unit Cell Volume (Å$^3$) | 11893.93 |
| 2θ range (°) | 2-45 |
| $R_p$ | 6.26 |
| $R_{wp}$ | 8.57 |
| $R_{wp}$ (w/o background) | 9.01 |

TABLE 6

List of the 25 most intense reflections, calculated from the final crystal structures for IRMOF-74-III.

| h | k | l | d (Å) | $I/I_{max}$ |
|---|---|---|---|---|
| 1 | 1 | 0 | 23.1418 | 100.000 |
| 3 | 0 | 0 | 13.3609 | 24.960 |
| 1 | 4 | 0 | 8.7468 | 6.490 |
| 4 | 1 | 0 | 8.7468 | 2.580 |
| 6 | 0 | 0 | 6.6804 | 2.340 |
| 2 | 2 | 0 | 11.5709 | 1.350 |
| 3 | 3 | 0 | 7.7139 | 1.000 |
| 1 | 2 | −1 | 5.9043 | 0.690 |
| 2 | 4 | 1 | 4.8937 | 0.570 |
| 3 | 1 | −1 | 5.5538 | 0.460 |
| 5 | 0 | −1 | 5.0069 | 0.420 |
| 8 | 1 | 1 | 3.786 | 0.360 |
| 7 | 1 | 0 | 5.3091 | 0.310 |
| 5 | 3 | −1 | 4.2707 | 0.290 |
| 7 | 0 | 1 | 4.2707 | 0.280 |
| 1 | 3 | 1 | 5.5538 | 0.250 |
| 2 | 0 | −1 | 6.1064 | 0.240 |
| 4 | 4 | 0 | 5.7854 | 0.240 |
| 9 | 0 | 0 | 4.4536 | 0.230 |
| 1 | 10 | 0 | 3.8045 | 0.220 |
| 8 | 4 | 1 | 3.2609 | 0.210 |
| 11 | 4 | 1 | 2.7018 | 0.210 |
| 5 | 5 | 0 | 4.6284 | 0.190 |
| 3 | 4 | −1 | 4.5952 | 0.190 |
| 5 | 4 | 1 | 4.0065 | 0.190 |

Figure 28:
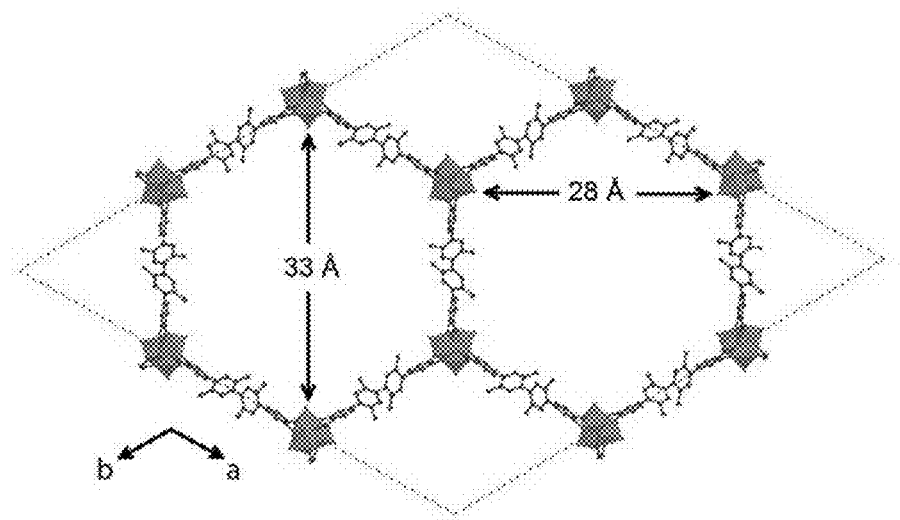
FIG. 28 presents a rhombohedral unit cell of IRMOF-74-IV showing hexagonal channels. The pore apertures are measured from opposite $H_2O$ oxygen atoms coordinated to the octahedral magnesium. C atoms are shown as black dots between the Mg atoms, O atoms are shown as dots immediately adjacent to the Mg atom, and octahedral Mg atoms are shown as the large octahedra.

IRMOF-74-IV: a=56.19(2) Å, c=6.838(5) Å, Rp=5.30, wRp=7.62 (See Table 7 and 8); pore aperture dimensions (Å)=28.0×32.8 (see FIG. 28).

TABLE 7

Crystallographic data of the refined PXRD for IRMOF-74-IV.

| Compound | IRMOF-74-IV |
|---|---|
| Empirical Formula | $C_{15}H_{13}MgO_4$ |
| Space Group | $R\bar{3}$ |
| Z | 18 |
| a (Å) | 56.19(2) |
| b (Å) | 6.838(5) |
| Unit Cell Volume (Å$^3$) | 18700.52 |
| 2θ range (°) | 2-45 |
| $R_p$ | 5.3 |
| $R_{wp}$ | 7.62 |
| $R_{wp}$ (w/o background) | 9.21 |

TABLE 8

List of the 25 most intense reflections, calculated from the final crystal structures for IRMOF-74-IV.

| h | k | l | d (Å) | $I/I_{max}$ |
|---|---|---|---|---|
| 1 | 1 | 0 | 28.0974 | 100.000 |
| 3 | 0 | 0 | 16.222 | 23.370 |
| 4 | 1 | 0 | 10.6198 | 5.290 |
| 1 | 4 | 0 | 10.6198 | 4.270 |
| 6 | 0 | 0 | 8.111 | 2.840 |
| 2 | 2 | 0 | 14.0487 | 2.290 |
| 3 | 3 | 0 | 9.3658 | 0.720 |
| 4 | 4 | 0 | 7.0243 | 0.710 |
| 3 | 2 | 1 | 5.8312 | 0.580 |
| 7 | 1 | 0 | 6.446 | 0.560 |
| 1 | 7 | 0 | 6.446 | 0.500 |
| 4 | 0 | 1 | 5.961 | 0.450 |
| 8 | 1 | 1 | 4.3765 | 0.440 |
| 9 | 0 | 0 | 5.4073 | 0.430 |
| 4 | 3 | 1 | 5.1981 | 0.420 |
| 2 | 3 | −1 | 5.8312 | 0.410 |
| 4 | 2 | −1 | 5.4875 | 0.300 |
| 1 | 8 | −1 | 4.3765 | 0.300 |
| 2 | 4 | 1 | 5.4875 | 0.260 |
| 5 | 0 | −1 | 5.5952 | 0.250 |
| 3 | 5 | 1 | 4.8751 | 0.250 |
| 1 | 2 | −1 | 6.4094 | 0.220 |
| 3 | 1 | −1 | 6.0999 | 0.220 |
| 6 | 3 | 0 | 6.1314 | 0.190 |
| 8 | 5 | 0 | 4.2848 | 0.190 |

Figure 29:
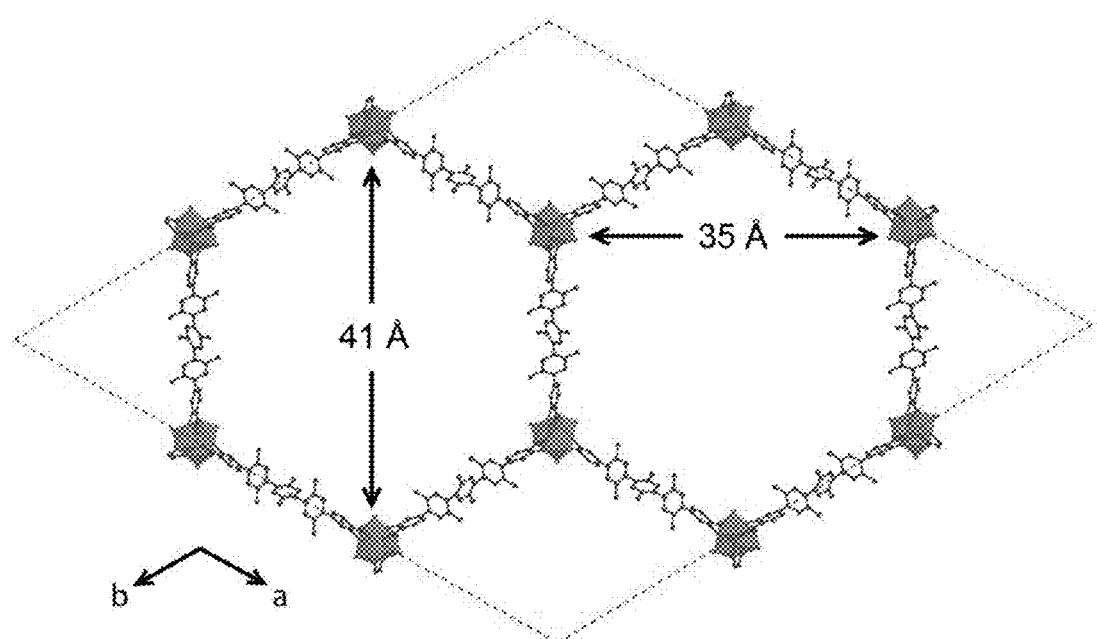
FIG. 29 presents a rhombohedral unit cell of IRMOF-74-V showing hexagonal channels. The pore apertures are measured from opposite $H_2O$ oxygen atoms coordinated to the octahedral magnesium. C atoms are shown as black dots between the Mg atoms, O atoms are shown as dots immediately adjacent to the Mg atom, and octahedral Mg atoms are shown as the large octahedra.

IRMOF-74-V: a=68.668 (8) Å, c=6.801 (2) Å, $R_p$=6.68, w$R_p$=10.34 (See Table 9 and 10); pore aperture dimensions (Å)=35.2×41.1 (see FIG. 29).

TABLE 9

Crystallographic data of the refined PXRD for IRMOF-74-V.

| Compound | IRMOF-74-V |
|---|---|
| Empirical Formula | $C_{19}H_{16}MgO_4$ |
| Space Group | $R\bar{3}$ |
| Z | 18 |
| a (Å) | 68.74(4) |
| b (Å) | 6.473(3) |
| Unit Cell Volume (Å$^3$) | 27774.76 |
| 2θ range (°) | 2-45 |
| $R_p$ | 6.68 |
| $R_{wp}$ | 10.34 |
| $R_{wp}$ (w/o background) | 10.64 |

TABLE 10

List of the 25 most intense reflections, calculated from the final crystal structures for IRMOF-74-V.

| h | k | l | d (Å) | $I/I_{max}$ |
|---|---|---|---|---|
| 1 | 1 | 0 | 34.3342 | 100.000 |
| 3 | 0 | 0 | 19.8229 | 20.800 |
| 1 | 4 | 0 | 12.9771 | 5.700 |
| 4 | 1 | 0 | 12.9771 | 5.200 |
| 2 | 2 | 0 | 17.1671 | 4.310 |
| 6 | 0 | 0 | 9.9114 | 4.160 |
| 7 | 1 | 0 | 7.8768 | 1.290 |
| 1 | 7 | 0 | 7.8768 | 0.630 |
| 9 | 0 | 0 | 6.6076 | 0.590 |
| 1 | 10 | 0 | 5.6445 | 0.360 |
| 4 | 4 | 0 | 8.5835 | 0.340 |
| 6 | 3 | 0 | 7.4923 | 0.290 |
| 4 | 3 | 1 | 5.5833 | 0.280 |
| 3 | 3 | 0 | 11.4447 | 0.270 |
| 1 | 5 | −1 | 5.737 | 0.270 |
| 6 | 1 | −1 | 5.4412 | 0.240 |
| 9 | 2 | 1 | 4.4393 | 0.240 |
| 5 | 1 | 1 | 5.737 | 0.220 |

TABLE 10-continued

List of the 25 most intense reflections, calculated from the final crystal structures for IRMOF-74-V.

| h | k | l | d (Å) | $I/I_{max}$ |
|---|---|---|-------|-------------|
| 4 | 2 | −1 | 5.8189 | 0.210 |
| 2 | 3 | −1 | 6.087 | 0.200 |
| 9 | 4 | −1 | 4.1091 | 0.200 |
| 3 | 4 | −1 | 5.5833 | 0.160 |
| 4 | 6 | 1 | 4.8164 | 0.160 |
| 10 | 0 | 1 | 4.4769 | 0.150 |
| 2 | 5 | 0 | 9.5226 | 0.140 |

Figure 30:
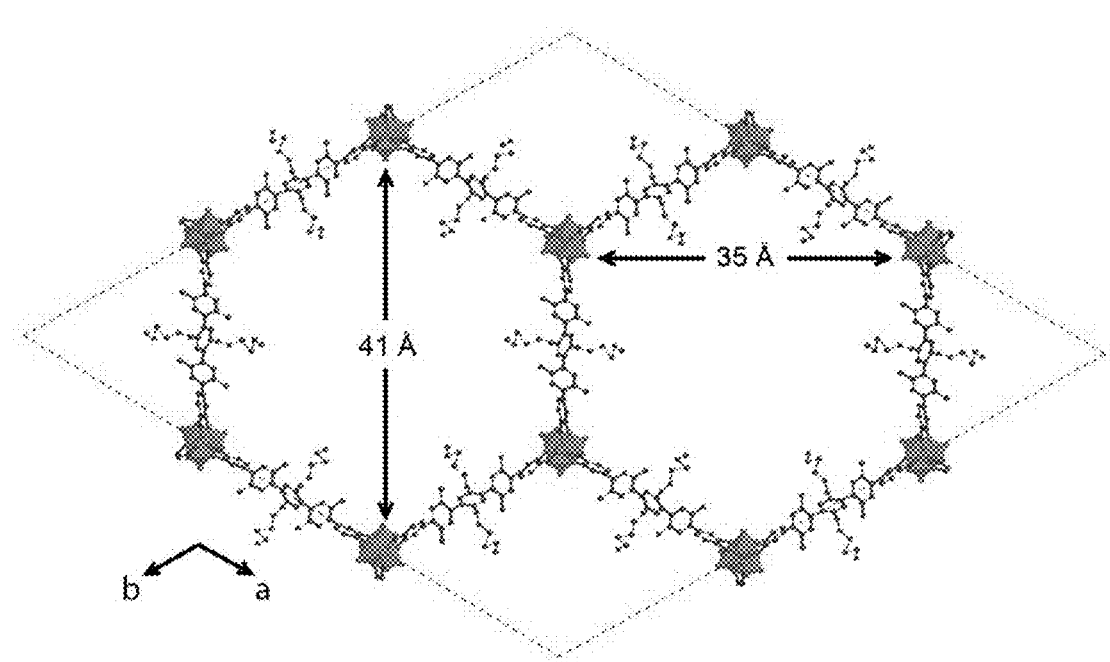
FIG. 30 presents a rhombohedral unit cell of IRMOF-74-V-hex showing hexagonal channels. The pore apertures are measured from opposite $H_2O$ oxygen atoms coordinated to the octahedral magnesium. C atoms are shown as black dots between the Mg atoms, O atoms are shown as dots immediately adjacent to the Mg atom, and octahedral Mg atoms are shown as the large octahedra.

IRMOF-74-V-hex: a=68.95(8) Å, c=6.461(8) Å, Rp=5.01, wRp=6.84 (See Table 11 and 12); pore aperture dimensions (Å)=35.2×41.1 (see FIG. 30).

TABLE 11

Crystallographic data of the refined PXRD for IRMOF-74-V-hex.

| Compound | IRMOF-74-V-hex |
|---|---|
| Empirical Formula | $C_{24}H_{26}MgO_4$ |
| Space Group | $R\bar{3}$ |
| Z | 18 |
| a (Å) | 68.95(8) |
| b (Å) | 6.461(8) |
| Unit Cell Volume (Å³) | 26610.98 |
| 2θ range (°) | 2-45 |
| $R_p$ | 5.01 |
| $R_{wp}$ | 6.84 |
| $R_{wp}$ (w/o background) | 10.20 |

TABLE 12

List of the 25 most intense reflections, calculated from the final crystal structures for IRMOF-74-V-hex.

| h | k | l | d (Å) | $I/I_{max}$ |
|---|---|---|-------|-------------|
| 1 | 1 | 0 | 34.4793 | 100.000 |
| 3 | 0 | 0 | 19.9066 | 9.690 |
| 2 | 2 | 0 | 17.2397 | 6.510 |
| 4 | 1 | 0 | 13.032 | 5.590 |
| 1 | 4 | 0 | 13.032 | 4.410 |
| 3 | 3 | 0 | 11.4931 | 3.070 |
| 6 | 0 | 0 | 9.9533 | 2.590 |
| 9 | 0 | 0 | 6.6355 | 0.990 |
| 4 | 4 | 0 | 8.6198 | 0.580 |
| 1 | 7 | 0 | 7.9101 | 0.380 |
| 1 | 10 | 0 | 5.6684 | 0.360 |
| 3 | 1 | −1 | 6.0199 | 0.350 |
| 4 | 6 | 1 | 4.7006 | 0.330 |
| 5 | 5 | 0 | 6.8959 | 0.310 |
| 1 | 5 | −1 | 5.535 | 0.280 |
| 7 | 1 | 0 | 7.9101 | 0.260 |
| 7 | 4 | 0 | 6.1927 | 0.260 |
| 5 | 0 | −1 | 5.6834 | 0.250 |
| 9 | 4 | −1 | 4.0409 | 0.250 |
| 5 | 7 | 1 | 4.2831 | 0.240 |
| 3 | 4 | −1 | 5.3976 | 0.210 |
| 1 | 6 | 1 | 5.27 | 0.200 |
| 10 | 3 | 1 | 3.9865 | 0.180 |
| 3 | 5 | 1 | 5.1511 | 0.170 |
| 6 | 1 | −1 | 5.27 | 0.160 |

Figure 31:
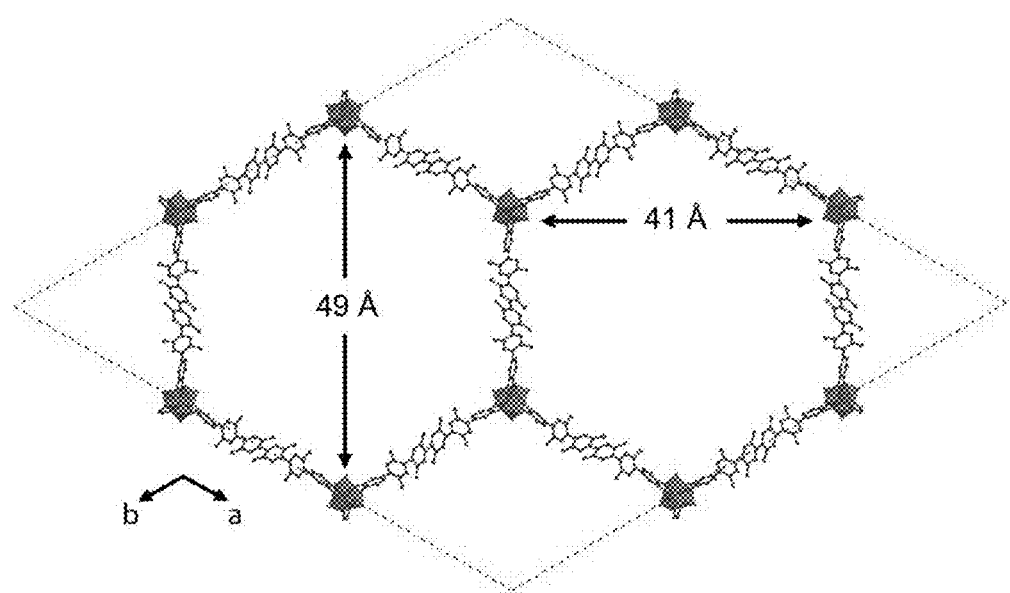
FIG. 31 presents a rhombohedral unit cell of IRMOF-74-VI showing hexagonal channels. The pore apertures are measured from opposite $H_2O$ oxygen atoms coordinated to the octahedral magnesium. C atoms are shown as black dots between the Zn atoms, O atoms are shown as dots immediately adjacent to the Zn atom, and octahedral Zn atoms are shown as the large octahedra.

IRMOF-74-VI: a=76.64(3) Å, c=6.317(4) Å, Rp=7.04, wRp=11.13 (See Table 13 and 14); pore aperture dimensions (Å)=41.1×49.1 (see FIG. 31).

TABLE 13

Crystallographic data of the refined PXRD for IRMOF-74-VI.

| Compound | IRMOF-74-VI |
|---|---|
| Empirical Formula | $C_{39}H_{48}Zn_3O_{12}$ |
| Space Group | $P\bar{3}$ |
| Z | 6 |
| a (Å) | 76.64(4) |
| b (Å) | 6.161(1) |
| Unit Cell Volume (Å³) | 31343.78 |
| 2θ range (°) | 1-40 |
| $R_p$ | 7.04 |
| $R_{wp}$ | 11.13 |
| $R_{wp}$ (w/o background) | 15.85 |

TABLE 14

List of the 25 most intense reflections, calculated from the final crystal structures for IRMOF-74-VI.

| h | k | l | d (Å) | $I/I_{max}$ |
|---|---|---|-------|-------------|
| 1 | 1 | 0 | 39.4089 | 100.000 |
| 3 | 0 | 0 | 22.7527 | 30.000 |
| 1 | 4 | 0 | 14.8952 | 8.100 |
| 6 | 0 | 0 | 11.3764 | 5.540 |
| 4 | 1 | 0 | 14.8952 | 4.480 |
| 1 | 7 | 0 | 9.041 | 1.580 |
| 2 | 2 | 0 | 19.7044 | 1.410 |
| 9 | 0 | 0 | 7.5842 | 1.400 |
| 7 | 1 | 0 | 9.041 | 1.190 |
| 3 | 3 | 0 | 13.1363 | 1.150 |
| 6 | 3 | 0 | 8.5997 | 1.050 |
| 4 | 4 | 0 | 9.8522 | 0.720 |
| 1 | 10 | 0 | 6.4788 | 0.420 |
| 12 | 0 | 0 | 5.6882 | 0.410 |
| 7 | 4 | 0 | 7.078 | 0.390 |
| 6 | 6 | 0 | 6.5681 | 0.360 |
| 1 | 5 | −1 | 5.5634 | 0.340 |
| 3 | 6 | 0 | 8.5997 | 0.330 |
| 9 | 3 | 0 | 6.3105 | 0.300 |
| 2 | 5 | 0 | 10.9301 | 0.230 |
| 5 | 7 | 1 | 4.5153 | 0.220 |
| 3 | 4 | −1 | 5.4557 | 0.180 |
| 10 | 1 | 0 | 6.4788 | 0.170 |
| 11 | 4 | 1 | 3.9374 | 0.170 |
| 4 | 7 | 0 | 7.078 | 0.160 |

Figure 32:
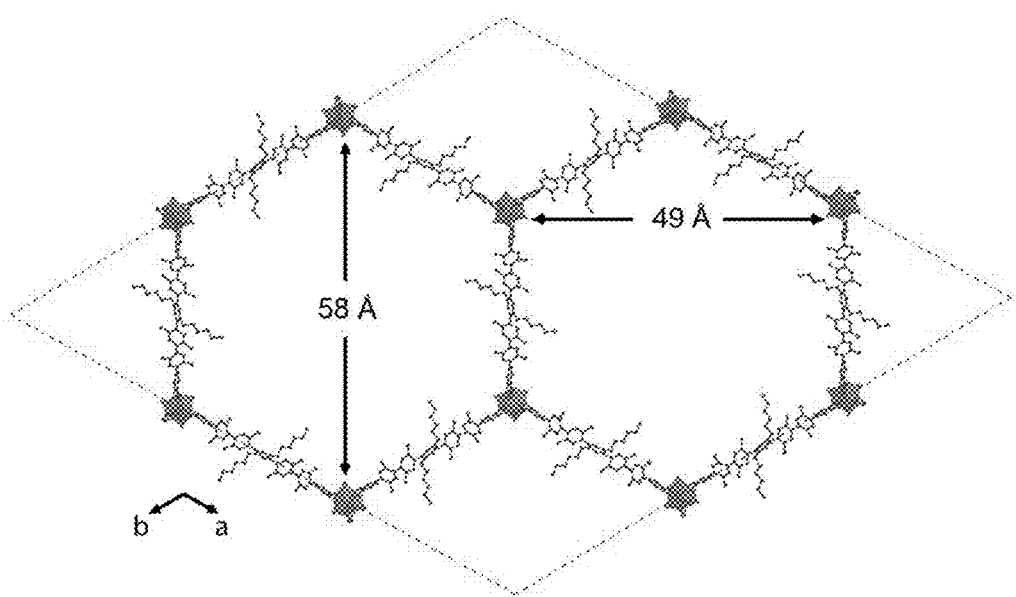
FIG. 32 presents a rhombohedral unit cell of IRMOF-74-VII showing hexagonal channels. The pore apertures are measured from opposite $H_2O$ oxygen atoms coordinated to the octahedral magnesium. C atoms are shown as black dots between the Mg atoms, O atoms are shown as dots immediately adjacent to the Mg atom, and octahedral Mg atoms are shown as the large octahedra.

IRMOF-74-VII: a=93.34(3) Å, c=6.595(2) Å, Rp=7.43, wRp=9.83 (See Table 15 and 16); pore aperture dimensions (Å)=49.4×57.5 (see FIG. 32).

TABLE 15

Crystallographic data of the refined PXRD for IRMOF-74-VII.

| Compound | IRMOF-74-VII |
|---|---|
| Empirical Formula | $C_{32}H_{34}MgO_4$ |
| Space Group | $R\bar{3}$ |
| Z | 18 |
| a (Å) | 93.34(3) |
| b (Å) | 6.595(4) |
| Unit Cell Volume (Å³) | 49766.55 |
| 2θ range (°) | 1-40 |
| $R_p$ | 7.43 |
| $R_{wp}$ | 9.83 |
| $R_{wp}$ (w/o background) | 11.65 |

TABLE 16

List of the 25 most intense reflections, calculated from the final crystal structures for IRMOF-74-VII.

| h | k | l | d (Å) | I/I$_{max}$ |
|---|---|---|---|---|
| 1 | 1 | 0 | 46.6716 | 100.000 |
| 3 | 0 | 0 | 26.9459 | 14.500 |
| 1 | 4 | 0 | 17.6402 | 7.480 |
| 2 | 2 | 0 | 23.3358 | 6.530 |
| 6 | 0 | 0 | 13.4729 | 2.900 |
| 4 | 1 | 0 | 17.6402 | 2.510 |
| 7 | 1 | 0 | 10.7072 | 1.820 |
| 4 | 4 | 0 | 11.6679 | 0.740 |
| 9 | 0 | 0 | 8.982 | 0.620 |
| 6 | 3 | 0 | 10.1846 | 0.460 |
| 12 | 0 | 0 | 6.7365 | 0.440 |
| 2 | 5 | 0 | 12.9444 | 0.430 |
| 6 | 1 | -1 | 5.8154 | 0.390 |
| 1 | 7 | 0 | 10.7072 | 0.290 |
| 1 | 10 | 0 | 7.6728 | 0.230 |
| 6 | 8 | 1 | 4.681 | 0.220 |
| 8 | 0 | -1 | 5.523 | 0.180 |
| 10 | 1 | 0 | 7.6728 | 0.170 |
| 1 | 9 | 1 | 5.2048 | 0.170 |
| 5 | 2 | 0 | 12.9444 | 0.160 |
| 3 | 3 | 0 | 15.5572 | 0.140 |
| 5 | 4 | 1 | 5.5621 | 0.140 |
| 4 | 6 | 1 | 5.3746 | 0.140 |
| 7 | 0 | 1 | 5.7272 | 0.130 |
| 4 | 7 | 0 | 8.3825 | 0.100 |

Figure 33:
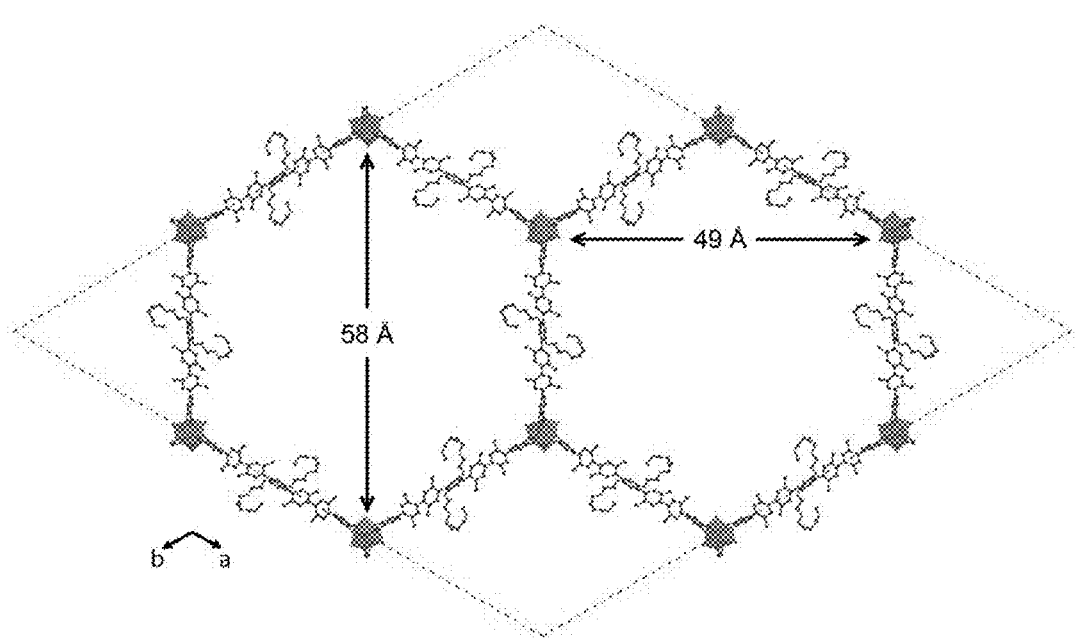
FIG. 33 presents a rhombohedral unit cell of IRMOF-74-VII-oeg showing hexagonal channels. The pore apertures are measured from opposite $H_2O$ oxygen atoms coordinated to the octahedral magnesium. C atoms are shown as black dots between the Mg atoms, O atoms are shown as dots immediately adjacent to the Mg atom, and octahedral Mg atoms are shown as the large octahedra.

IRMOF-74-VII-oeg: a=93.34(3) Å, c=6.595(4) Å, Rp=7.43, wRp=9.83 (See Table 17 and 18); pore aperture dimensions (Å)=49.4×57.5 (see FIG. 33).

TABLE 17

Crystallographic data of the refined PXRD for IRMOF-74-VII-oeg.

| Compound | IRMOF-74-VII-oeg |
|---|---|
| Empirical Formula | $C_{32}H_{34}MgO_4$ |
| Space Group | $R\bar{3}$ |
| Z | 18 |
| a (Å) | 93.34(3) |
| b (Å) | 6.595(4) |
| Unit Cell Volume (Å$^3$) | 49766.55 |
| 2θ range (°) | 1-40 |
| R$_p$ | 7.43 |
| R$_{wp}$ | 9.83 |
| R$_{wp}$ (w/o background) | 11.65 |

TABLE 18

List of the 25 most intense reflections, calculated from the final crystal structures for IRMOF-74-VII-oeg.

| h | k | l | d (Å) | I/I$_{max}$ |
|---|---|---|---|---|
| 1 | 1 | 0 | 47.1988 | 100.000 |
| 2 | 2 | 0 | 23.5994 | 11.590 |
| 1 | 4 | 0 | 17.8395 | 9.250 |
| 3 | 0 | 0 | 27.2503 | 7.690 |
| 6 | 0 | 0 | 13.6251 | 2.810 |
| 7 | 1 | 0 | 10.8282 | 1.480 |
| 4 | 1 | 0 | 17.8395 | 1.470 |
| 6 | 3 | 0 | 10.2996 | 0.790 |
| 4 | 4 | 0 | 11.7997 | 0.700 |
| 9 | 0 | 0 | 9.0834 | 0.420 |
| 1 | 10 | 0 | 7.7594 | 0.420 |
| 12 | 0 | 0 | 6.8126 | 0.390 |
| 3 | 3 | 0 | 15.7329 | 0.380 |
| 1 | 5 | -1 | 6.1191 | 0.290 |
| 2 | 5 | 0 | 13.0906 | 0.270 |
| 4 | 7 | 0 | 8.4772 | 0.170 |
| 3 | 4 | -1 | 6.0188 | 0.160 |
| 1 | 12 | 1 | 4.685 | 0.150 |
| 5 | 5 | 0 | 9.4398 | 0.140 |
| 3 | 9 | 0 | 7.5579 | 0.140 |
| 11 | 0 | -1 | 4.9892 | 0.140 |
| 7 | 12 | 1 | 3.9679 | 0.140 |
| 9 | 6 | 0 | 6.2516 | 0.120 |
| 13 | 1 | 0 | 6.0432 | 0.120 |
| 6 | 8 | 1 | 4.7558 | 0.120 |

Figure 34:
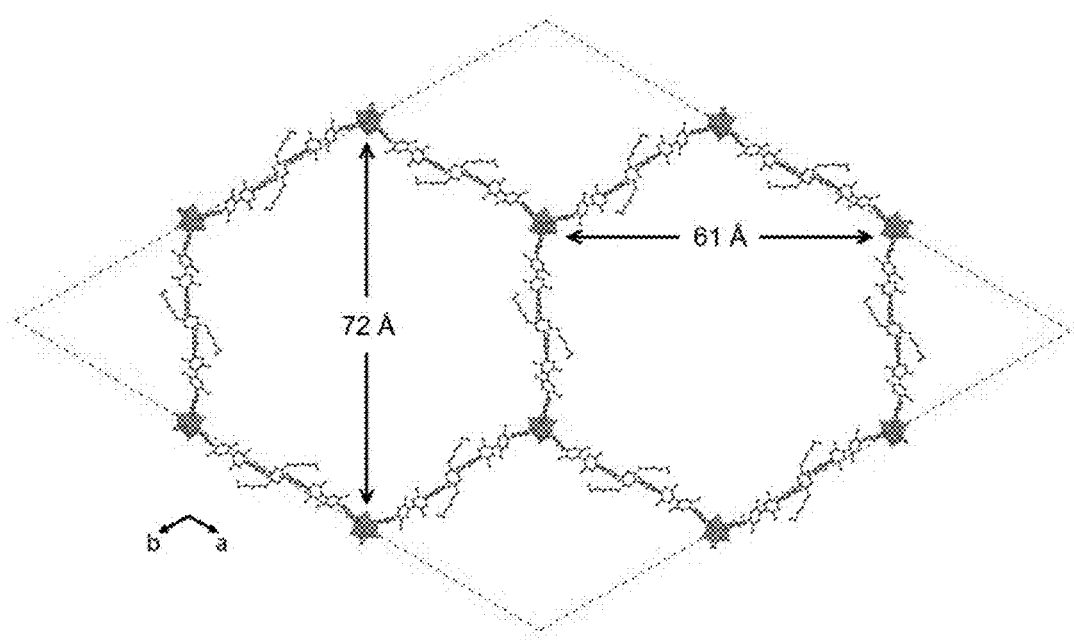
FIG. 34 presents a rhombohedral unit cell of IRMOF-74-IX showing hexagonal channels. The pore apertures are measured from opposite $H_2O$ oxygen atoms coordinated to the octahedral magnesium. C atoms are shown as black dots between the Mg atoms, O atoms are shown as dots immediately adjacent to the Mg atom, and octahedral Mg atoms are shown as the large octahedra.

IRMOF-74-IX: a=112.82(6) Å, c=6.802(6) Å, Rp=2.47, wRp=3.61 (See Table 19 and 20); pore aperture dimensions (Å)=60.5×71.8 (see FIG. 34).

TABLE 19

Crystallographic data of the refined PXRD for IRMOF-74-IX.

| Compound | IRMOF-74-IX |
|---|---|
| Empirical Formula | $C_{40}H_{42}MgO_4$ |
| Space Group | $R\bar{3}$ |
| Z | 18 |
| a (Å) | 112.82(1) |
| b (Å) | 6.802(9) |
| Unit Cell Volume (Å$^3$) | 74990.33 |
| 2θ range (°) | 1-20 |
| R$_p$ | 2.47 |
| R$_{wp}$ | 3.61 |
| R$_{wp}$ (w/o background) | 13.08 |

TABLE 20

List of the 25 most intense reflections, calculated from the final crystal structures for IRMOF-74-IX.

| h | k | l | d (Å) | I/I$_{max}$ |
|---|---|---|---|---|
| 1 | 1 | 0 | 56.4101 | 100.000 |
| 3 | 0 | 0 | 32.5684 | 15.490 |
| 1 | 4 | 0 | 21.321 | 10.110 |
| 2 | 2 | 0 | 28.2051 | 7.760 |
| 6 | 0 | 0 | 16.2842 | 3.900 |
| 4 | 1 | 0 | 21.321 | 2.150 |
| 2 | 5 | 0 | 15.6454 | 1.470 |
| 7 | 1 | 0 | 12.9414 | 1.150 |
| 1 | 7 | 0 | 12.9414 | 1.100 |
| 9 | 0 | 0 | 10.8561 | 0.940 |
| 6 | 3 | 0 | 12.3097 | 0.930 |
| 1 | 10 | 0 | 9.2738 | 0.840 |
| 12 | 0 | 0 | 8.1421 | 0.370 |
| 4 | 4 | 0 | 14.1025 | 0.350 |
| 7 | 4 | 0 | 10.1316 | 0.290 |
| 2 | 8 | 0 | 10.6605 | 0.190 |
| 8 | 1 | 1 | 5.8466 | 0.160 |
| 1 | 13 | 0 | 7.2226 | 0.150 |
| 11 | 2 | 0 | 8.0586 | 0.140 |
| 7 | 2 | -1 | 5.9105 | 0.130 |
| 3 | 4 | -1 | 6.2643 | 0.120 |
| 12 | 3 | 0 | 7.107 | 0.110 |
| 2 | 0 | -1 | 6.738 | 0.100 |
| 1 | 8 | -1 | 5.8466 | 0.090 |
| 3 | 7 | -1 | 5.7848 | 0.090 |

Figure 35:
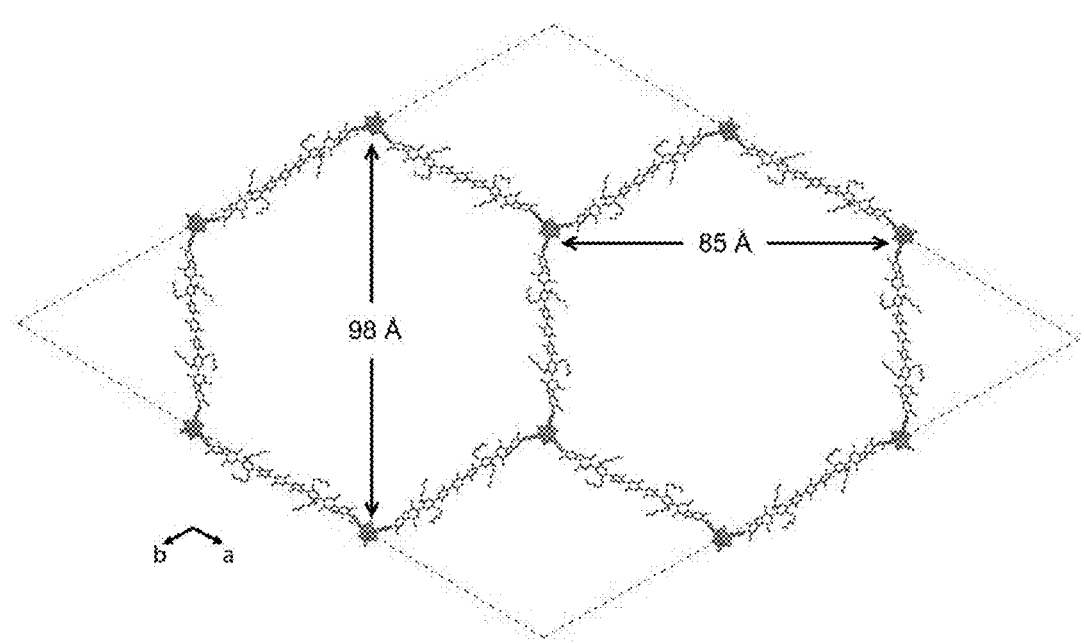
FIG. 35 presents a rhombohedral unit cell of IRMOF-74-XI showing hexagonal channels. The pore apertures are measured from opposite $H_2O$ oxygen atoms coordinated to the octahedral magnesium. C atoms are shown as black dots between the Mg atoms, O atoms are shown as dots immediately adjacent to the Mg atom, and octahedral Mg atoms are shown as the large octahedra.

IRMOF-74-XI: a=143.84(6) Å, c=6.563(9) Å, Rp=3.74, wRp=4.95 (See Table 21 and 22); pore aperture dimensions (Å)=84.5×98.1 (see FIG. 35).

TABLE 21

Crystallographic data of the refined PXRD for IRMOF-74-XI.

| Compound | IRMOF-74-XI |
|---|---|
| Empirical Formula | $C_{53}H_{61}MgO_4$ |
| Space Group | $R\overline{3}$ |
| Z | 18 |
| a (Å) | 143.84(5) |
| b (Å) | 6.563(3) |
| Unit Cell Volume (Å$^3$) | 117610.1 |
| 2θ range (°) | 0.8-20 |
| $R_p$ | 3.74 |
| $R_{wp}$ | 4.95 |
| $R_{wp}$ (w/o background) | 11.65 |

TABLE 22

List of the 25 most intense reflections, calculated from the final crystal structures for IRMOF-74-XI.

| h | k | l | d (Å) | $I/I_{max}$ |
|---|---|---|---|---|
| 1 | 1 | 0 | 77.2682 | 100.000 |
| 3 | 0 | 0 | 44.6108 | 16.780 |
| 1 | 4 | 0 | 29.2046 | 8.230 |
| 2 | 2 | 0 | 38.6341 | 7.410 |
| 4 | 1 | 0 | 29.2046 | 2.860 |
| 6 | 0 | 0 | 22.3054 | 2.810 |
| 2 | 5 | 0 | 21.4303 | 2.570 |
| 1 | 7 | 0 | 17.7265 | 2.460 |
| 9 | 0 | 0 | 14.8703 | 1.880 |
| 7 | 1 | 0 | 17.7265 | 0.820 |
| 1 | 10 | 0 | 12.7028 | 0.620 |
| 4 | 4 | 0 | 19.317 | 0.600 |
| 6 | 3 | 0 | 16.8613 | 0.480 |
| 12 | 0 | 0 | 11.1527 | 0.300 |
| 1 | 13 | 0 | 9.8932 | 0.290 |
| 5 | 2 | 0 | 21.4303 | 0.280 |
| 9 | 3 | 0 | 12.3728 | 0.170 |
| 2 | 11 | 0 | 11.0383 | 0.170 |
| 2 | 8 | 0 | 14.6023 | 0.150 |
| 10 | 1 | 0 | 12.7028 | 0.140 |
| 8 | 2 | 0 | 14.6023 | 0.130 |
| 12 | 6 | 0 | 8.4306 | 0.130 |
| 1 | 16 | 0 | 8.0999 | 0.100 |
| 15 | 0 | 0 | 8.9222 | 0.090 |
| 3 | 3 | 0 | 25.7561 | 0.080 |

The comparison of the unit cell parameters of the initial model with those obtained from the refinement of the PXRD patterns, along with the pore aperture dimensions of the initial and refined crystal models is presented in Table 23.

TABLE 23

| | a (Å) Initial model/refined | c (Å) initial model/refined | Pore aperture metrics (Å$^2$) (initial model/refined) |
|---|---|---|---|
| IRMOF-74-II | 36.060/36.121(6) | 6.464/6.813(4) | 16.3 × 20.0/16.5 × 19.5 |
| IRMOF-74-III | 45.113/46.283(5) | 6.432/6.411(2) | 22.4 × 26.5/22.2 × 27.3 |
| IRMOF-74-IV | 55.778/56.19(2) | 6.434/6.838(5) | 28.1 × 33.7/28.0 × 32.8 |
| IRMOF-74-V | 68.787/68.668(8) | 6.449/6.801(2) | 36.6 × 42.3/35.2 × 41.1 |
| IRMOF-74-VI | 78.239/76.64(3) | 6.501/6.317(4) | 40.7 × 48.6/41.1 × 49.1 |
| IRMOF-74-VII | 92.059/93.34(3) | 6.497/6.595(2) | 48.7 × 57.8/49.4 × 57.5 |
| IRMOF-74-IX | 116.01/112.82(6) | 6.668/6.802(6) | 62.4 × 72.5/60.5 × 71.8 |
| IRMOF-74-XI | 145.75/143.84(6) | 6.677/6.563(9) | 82.4 × 95.4/84.5 × 98.1 |

MAS NMR

Activation of IRMOF-74 Series:

The as-synthesized samples of IRMOF-74-I to IV were washed three times with DMF before being immersed in dry methanol for 3 days; during this exchange the dry methanol was refreshed three times to fully replace the water molecules coordinating to metals. The resulting methanol-exchanged samples were transferred as a suspension to a quartz cell and the solvent was decanted. The IRMOF-74-I to IV samples were then evacuated ($10^{-3}$ Torr) at room temperature for 10 h followed by heating at 130° C. for 12 h to remove methanol and create open metal site on each metal'. Complete removal of coordinating methanol was confirmed by the absence of methanol peak in solid-state $^{13}C$ MAS NMR of the activated samples.

The as-synthesized samples of IRMOF-74-V to XI were immersed in dry methanol for 3 days, respectively, during which the activation solvent was decanted and freshly replenished three times to fully replace the water molecules coordinating to metals. The sample was evacuated with supercritical $CO_2$ in a Tousimis Samdri PVT-3D critical point dryer. For this step, the methanol-containing sample was placed in the chamber and methanol was completely exchanged with liquid $CO_2$. After this exchange, the chamber containing the sample and liquid $CO_2$ was heated up around 40° C. and held constant at the supercritical condition (typically 1300 psi) for 1 h. The $CO_2$ was slowly vented (ca. 8 h) from the chamber at around 40° C., yielding porous material. Before gas adsorption analysis the sample was evacuated with a dynamic $10^{-5}$ Torr vacuum pressure at room temperature for 12 h to remove methanol and create open metal site on each metal. Complete removal of coordinating methanol was confirmed by the absence of methanol peak in solid-state $^{13}C$ MAS NMR of the activated samples.

Thermal Gravimetric Analyses

All samples were run on a TA Instruments Q-500 series thermal gravimetric analyzer with samples held in platinum pans in a continuous airflow atmosphere. Samples were heated at a constant rate of 5° C. min$^{-1}$ during all TGA experiments.

Figure 36:
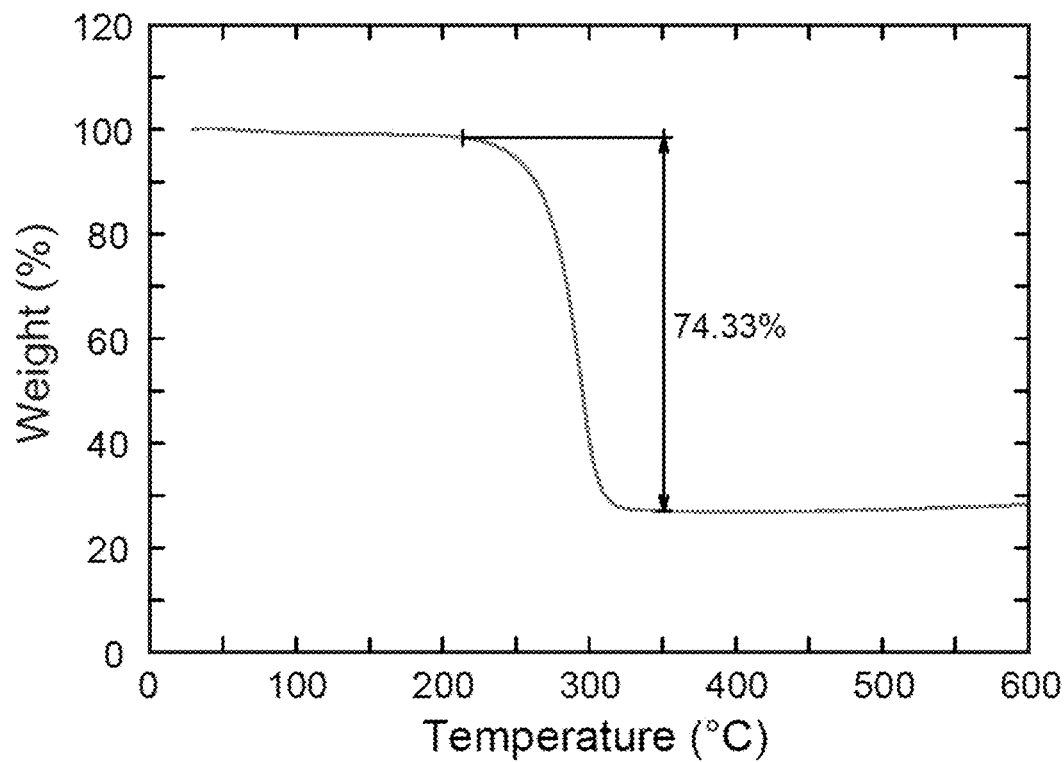
FIG. 36 provides a TGA trace of activated IRMOF-74-II.
Figure 37:
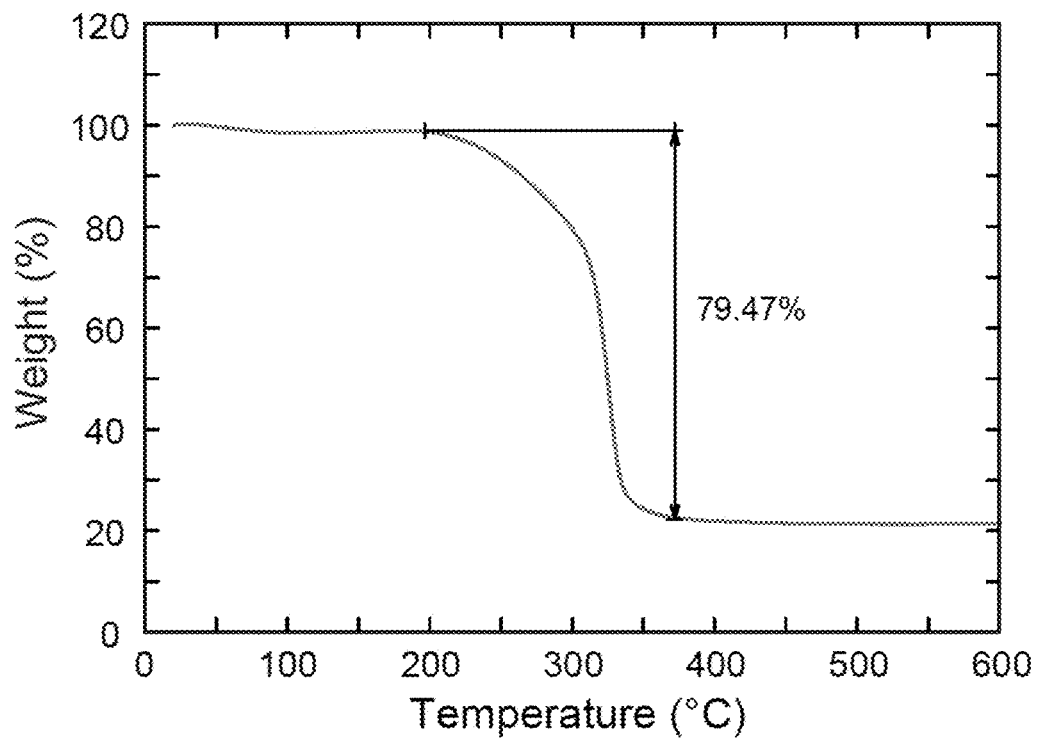
FIG. 37 provides a TGA trace of activated IRMOF-74-III.
Figure 38:
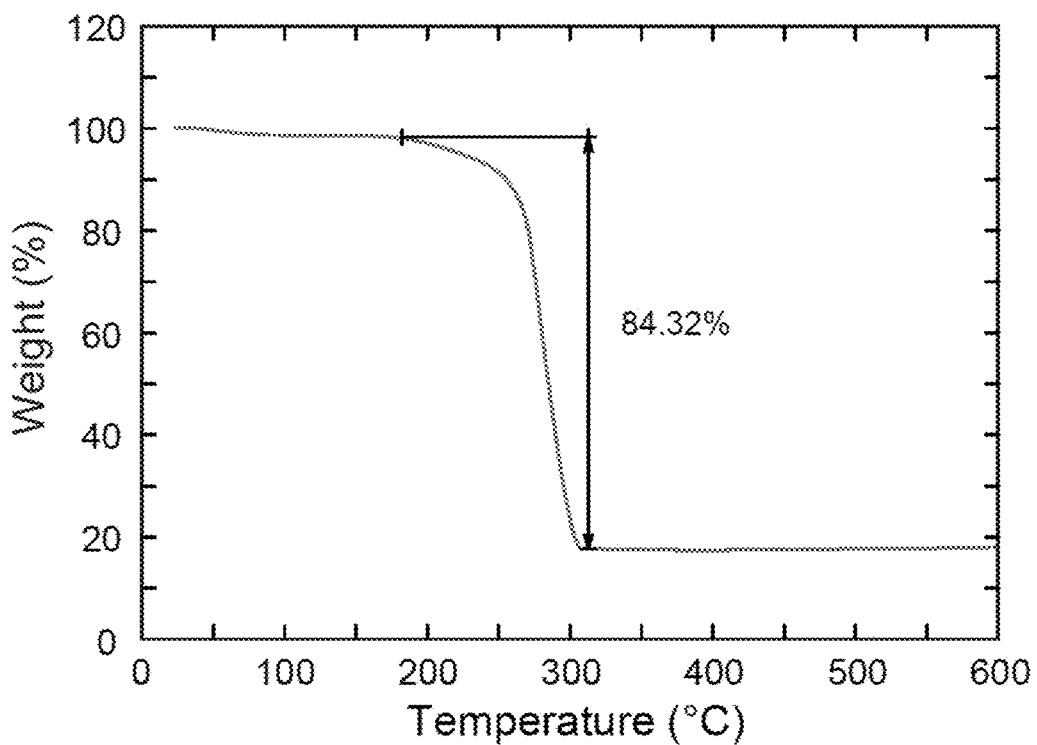
FIG. 38 provides a TGA trace of activated IRMOF-74-IV.
Figure 39:
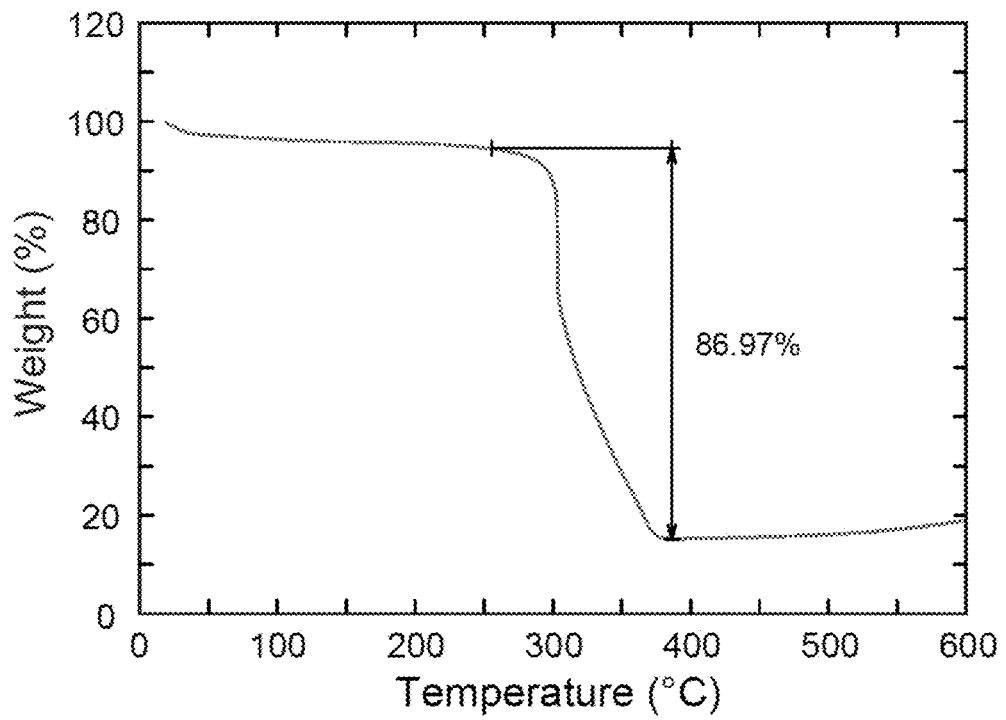
FIG. 39 provides a TGA trace of activated IRMOF-74-V.
Figure 40:
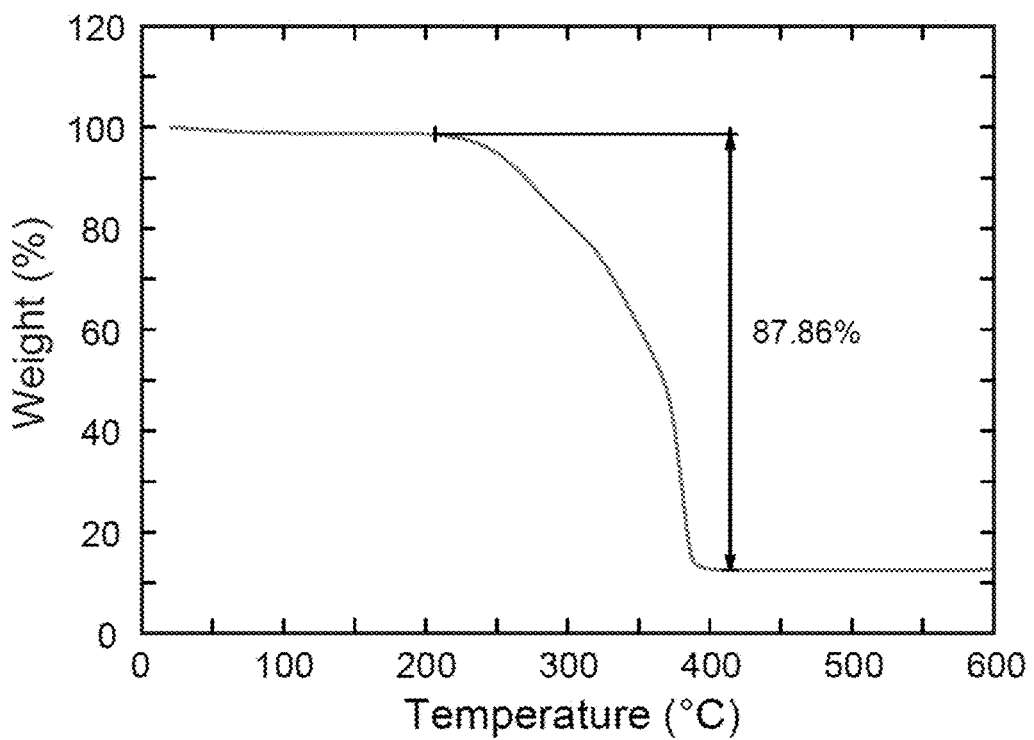
FIG. 40 provides a TGA trace of activated IRMOF-74-V-hex.
Figure 41:
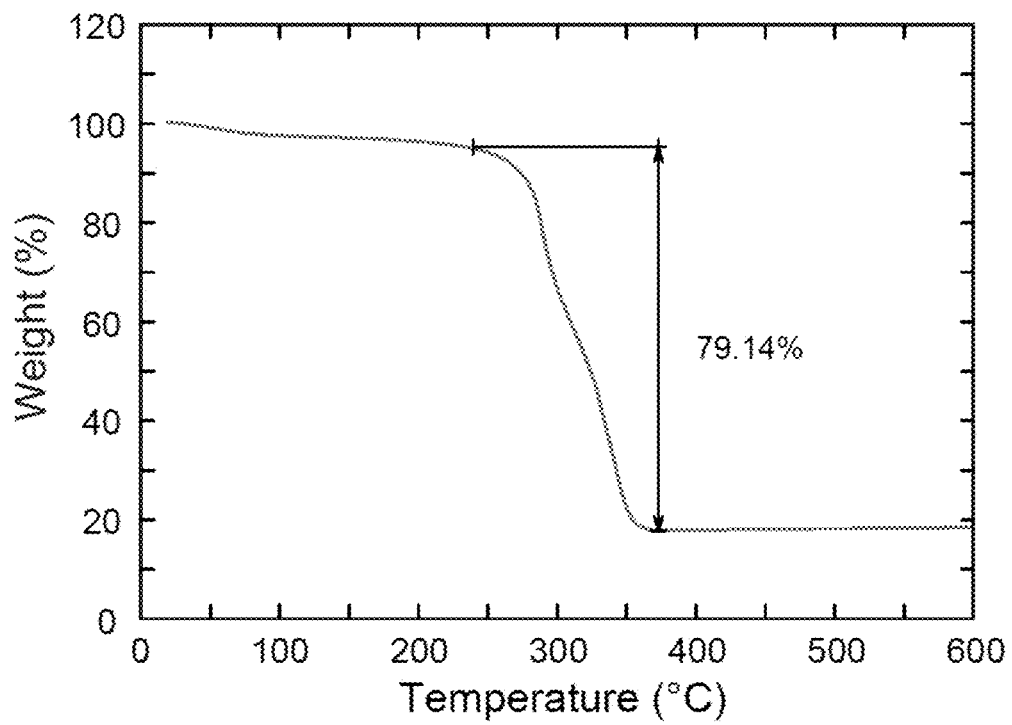
FIG. 41 provides a TGA trace of activated IRMOF-74-VI.
Figure 42:
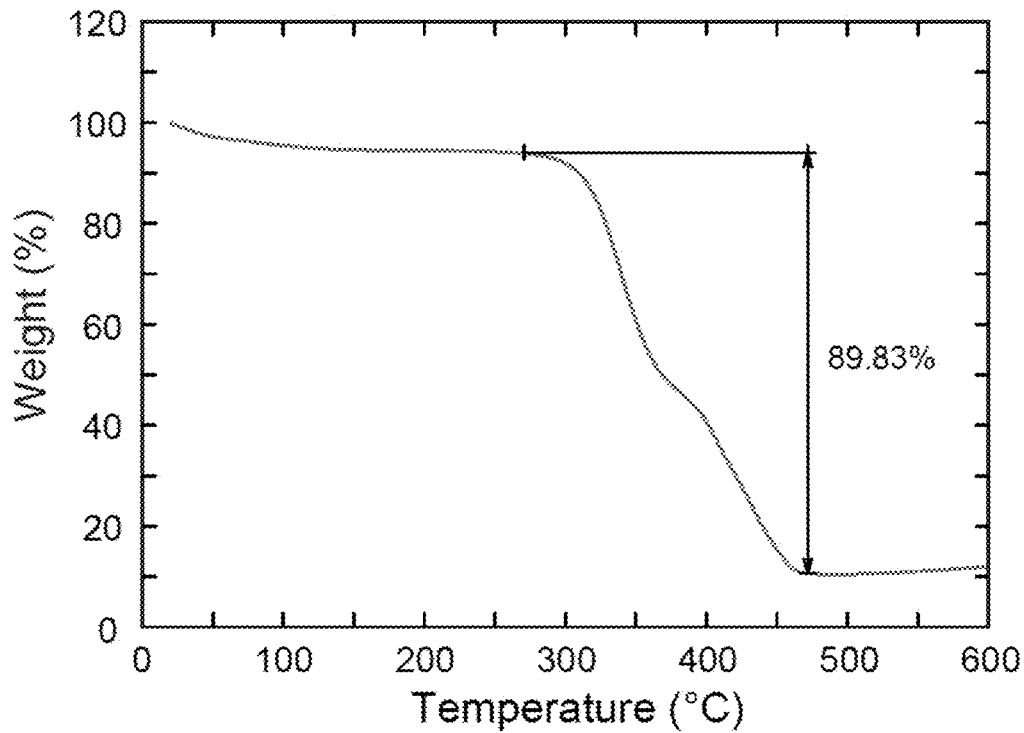
FIG. 42 provides a TGA trace of activated IRMOF-74-VII.
Figure 43:
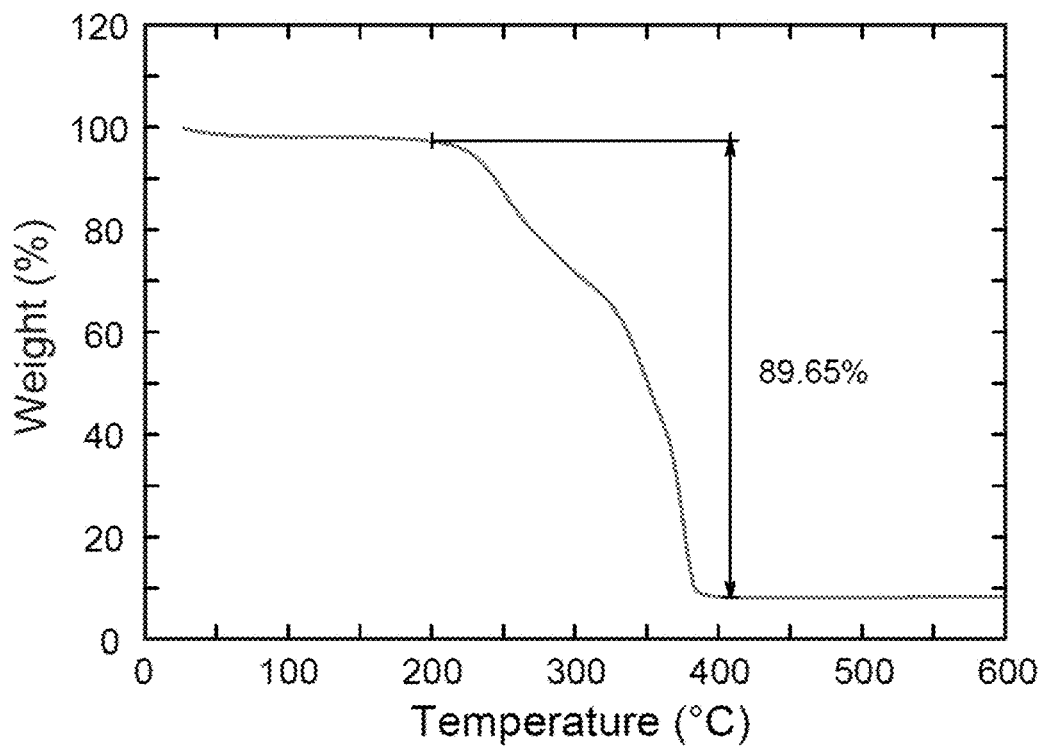
FIG. 43 provides a TGA trace of activated IRMOF-74-VII-oeg
FIG. 44 provides a TGA trace of activated IRMOF-74-IX.
Figure 44:
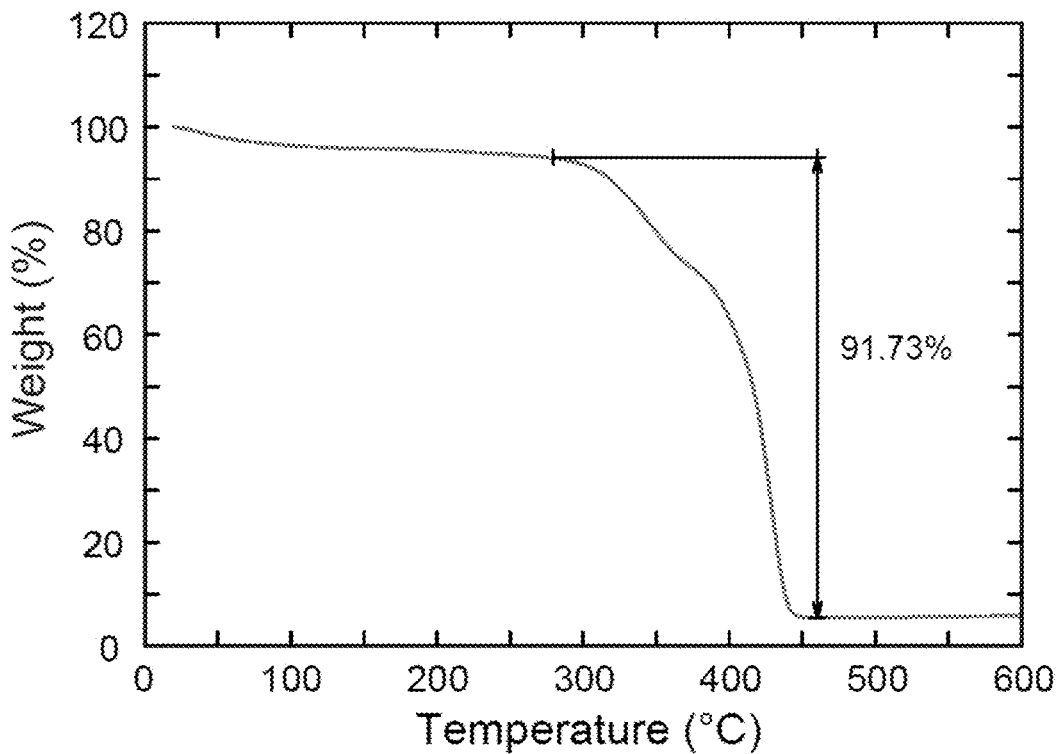
Figure 45:
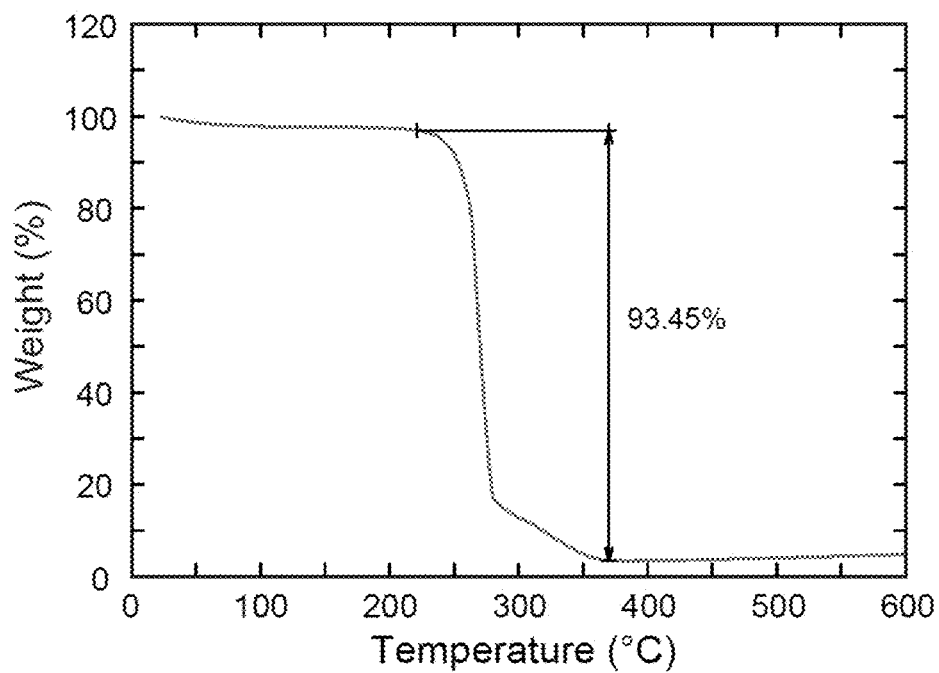
FIG. 45 provides a TGA trace of activated IRMOF-74-XI.

In each TGA, one minor weight loss and one distinguishable weight loss were observed before the final plateau. The first small decrease in weight % is due to the evaporation of water and air contaminants collected by the MOF. The major weight loss evidenced (~300° C. for most all of series) in each TGA was attributed to the framework destruction. TGA traces of the activated IRMOF-74 series is presented in FIGS. 36-45: IRMOF-74-II (FIG. 36); IRMOF-74-III (FIG. 37); IRMOF-74-IV(FIG. 38); IRMOF-74-V (FIG. 39); IRMOF-74-V-hex (FIG. 40); IRMOF-74-VI (FIG. 41); IRMOF-74-VII (FIG. 42); IRMOF-74-VII-oeg (FIG. 43); IRMOF-74-IX (FIG. 44); and IRMOF-74-XI (FIG. 45).

Solid-State $^{13}C$ MAS NMR of Activated IRMOFs

High-resolution solid-state nuclear magnetic resonance (NMR) spectra were recorded at ambient temperature on a Bruker DSX-300 spectrometer using a standard Bruker magic angle-spinning (MAS) probe with 4 mm (outside diameter) zirconia rotors. Cross-polarization with MAS (CP/MAS) was used to acquire $^{13}C$ data at 75.47 MHz. The $^1H$ and $^{13}C$ ninety-degree pulse widths were both 4 µs. The CP contact time was varied at 1.5 ms and 5 ms. High power two-pulse phase modulation (TPPM) $^1$H decoupling was applied during data acquisition. The decoupling frequency corresponded to 72 kHz. The MAS sample spinning rate was 10 kHz. Recycle delays for (CP/MAS) between scans varied between 3 and 20 s, depending upon the compound as determined by observing no apparent loss in the $^{13}$C signal intensity from one scan to the next. The $^{13}$C chemical shifts are given relative to tetramethylsilane as zero ppm, calibrated using the methylene carbon signal of adamantane assigned to 37.77 ppm as a secondary reference.

Figure 47:
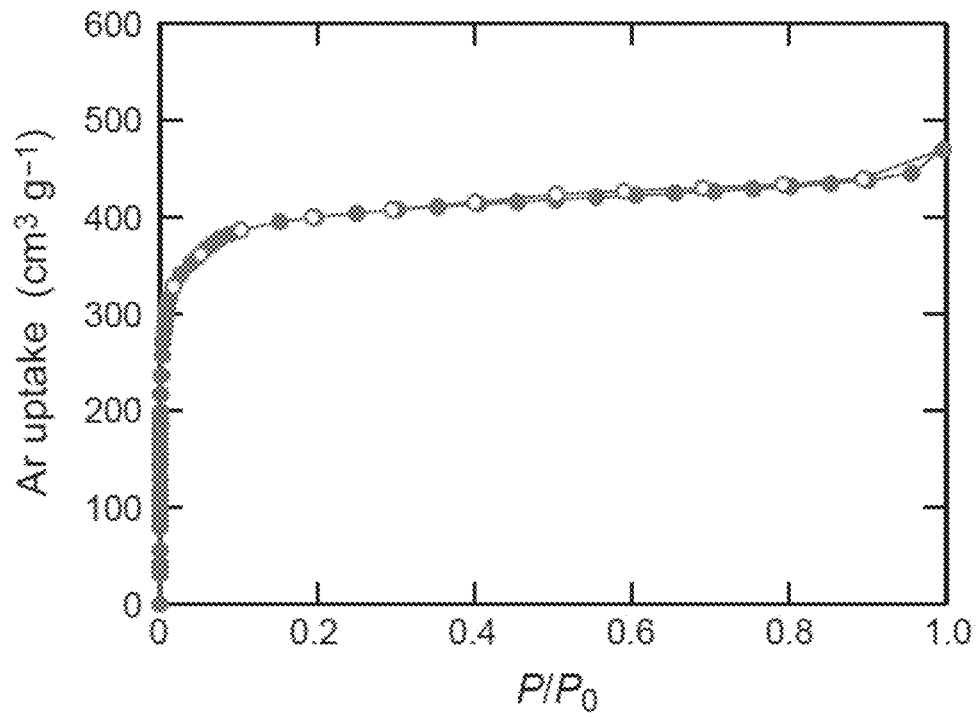
FIG. 47 provides an Ar isotherm of IRMOF-74-I at 87 K. Filled and open symbols represent adsorption and desorption branches, respectively. The connecting curve is presented as a visual guide.
Figure 48:
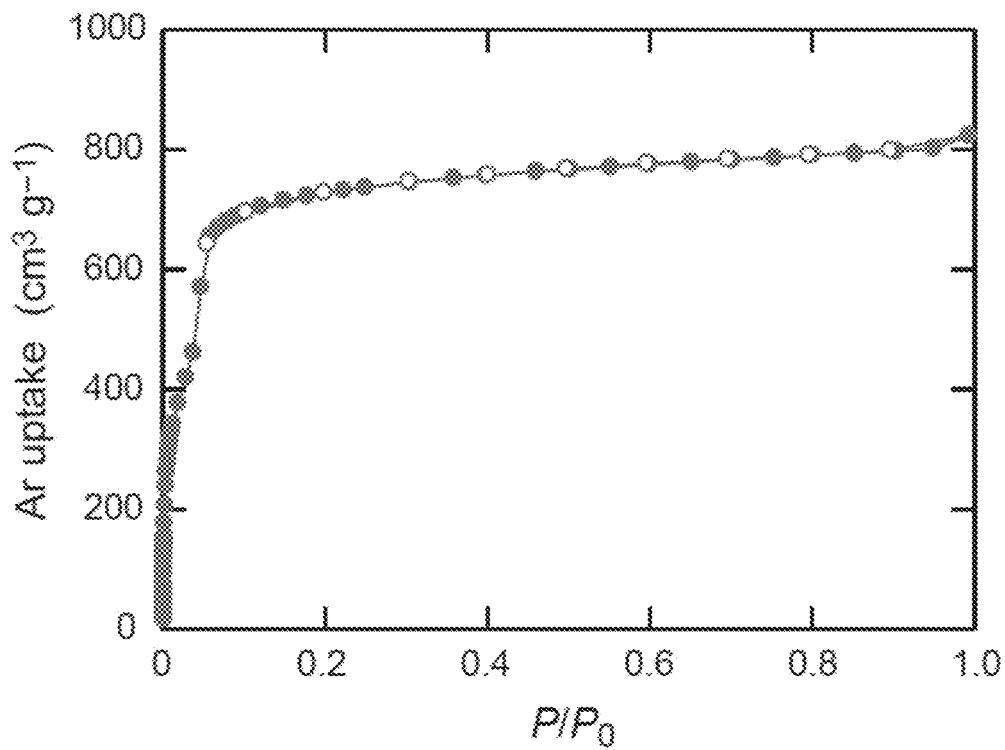
FIG. 48 provides an Ar isotherm of IRMOF-74-II at 87 K. Filled and open symbols represent adsorption and desorption branches, respectively. The connecting curve is presented as a visual guide.
Figure 49:
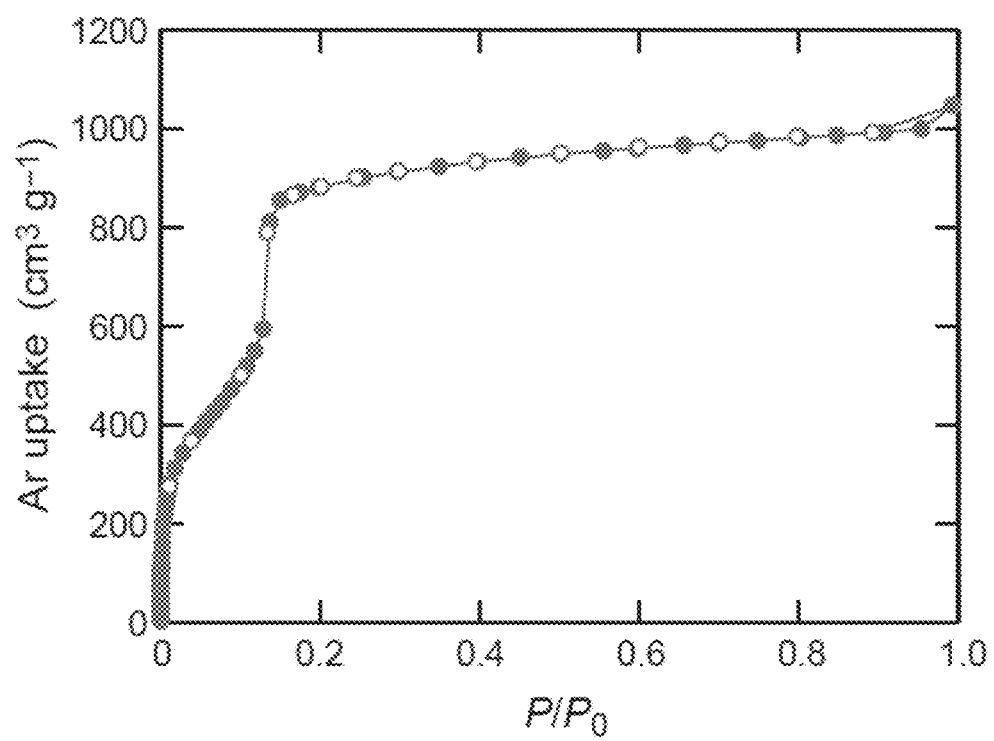
FIG. 49 provides an Ar isotherm of IRMOF-74-III at 87 K. Filled and open symbols represent adsorption and desorption branches, respectively. The connecting curve is presented as a visual guide.
Figure 50:
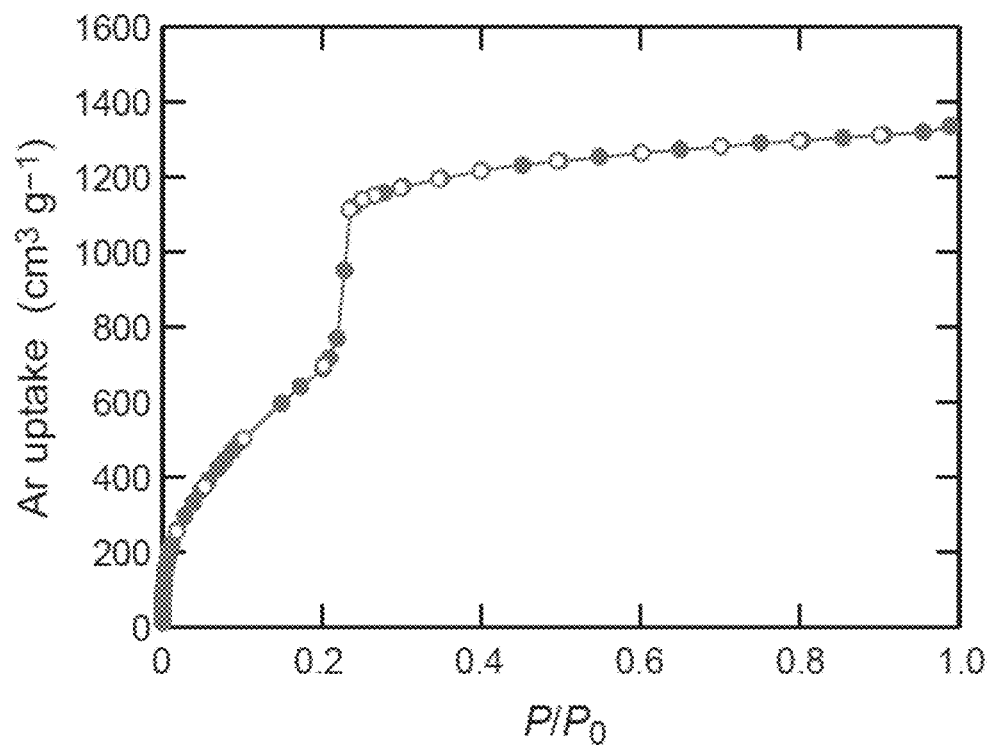
FIG. 50 provides an Ar isotherm of IRMOF-74-IV at 87 K. Filled and open symbols represent adsorption and desorption branches, respectively. The connecting curve is presented as a visual guide.
Figure 51:
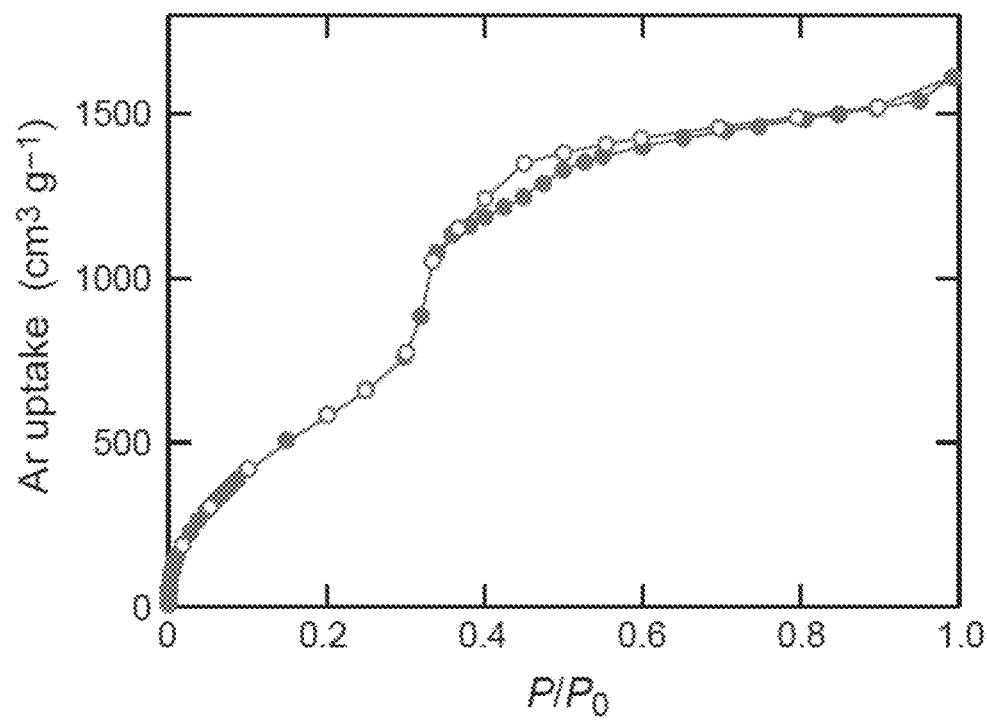
FIG. 51 provides an Ar isotherm of IRMOF-74-V at 87 K. Filled and open symbols represent adsorption and desorption branches, respectively. The connecting curve is presented as a visual guide.
Figure 52:
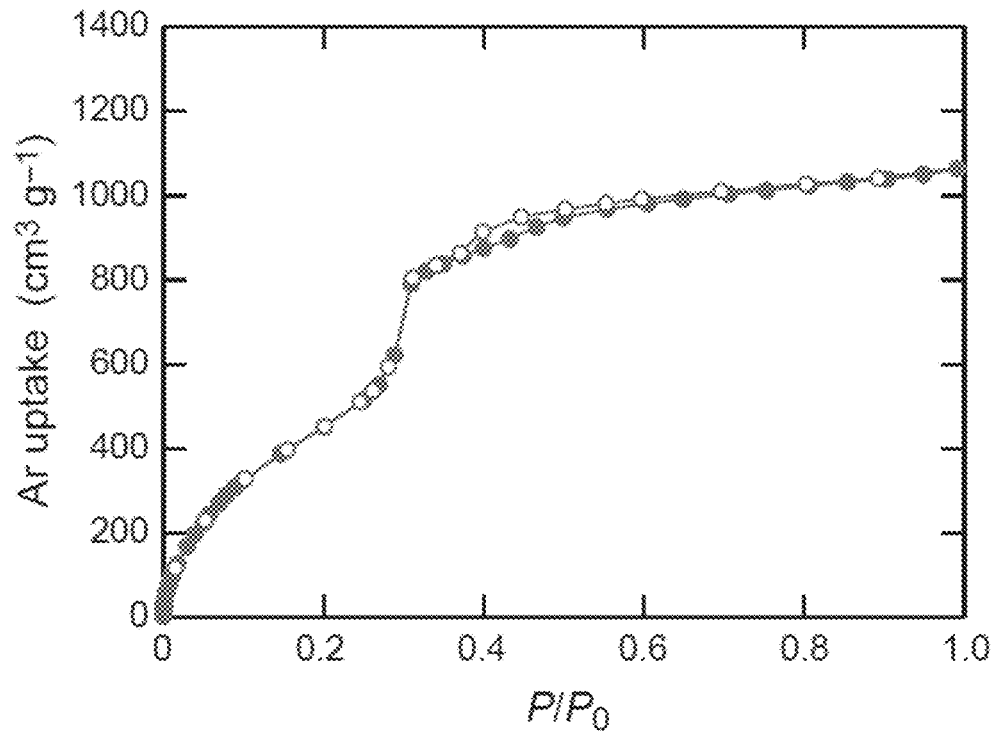
FIG. 52 provides an Ar isotherm of IRMOF-74-V-hex at 87 K. Filled and open symbols represent adsorption and desorption branches, respectively. The connecting curve is presented as a visual guide.
Figure 53:
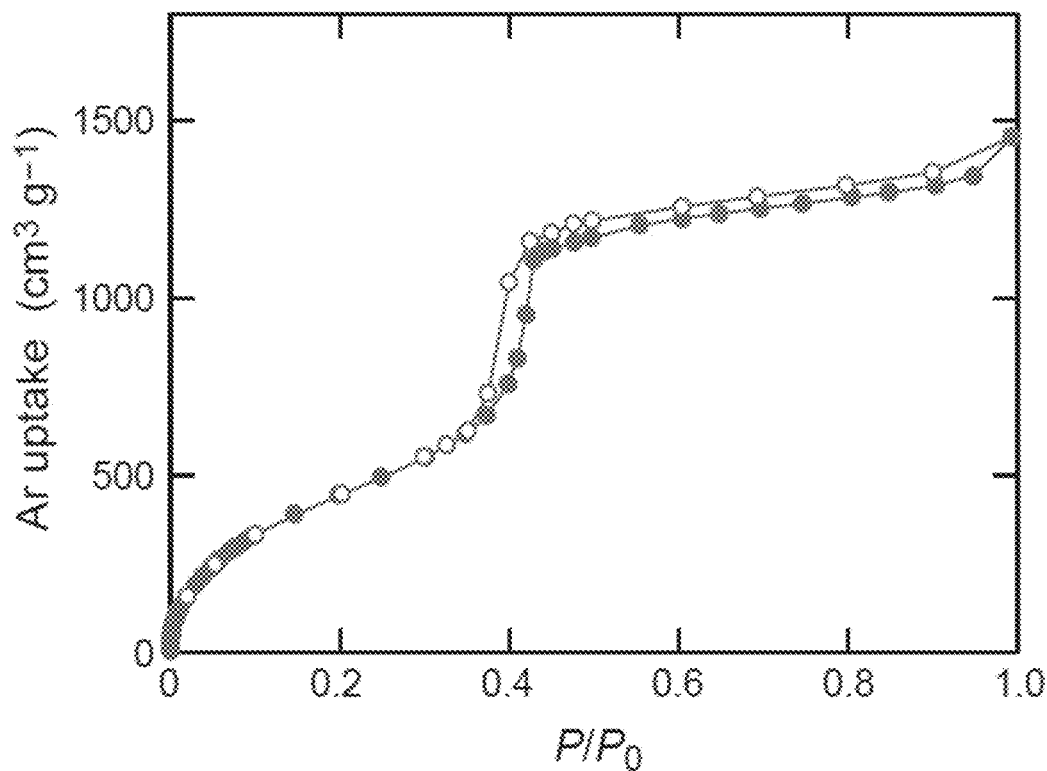
FIG. 53 provides an Ar isotherm of IRMOF-74-VI at 87 K. Filled and open symbols represent adsorption and desorption branches, respectively. The connecting curve is presented as a visual guide.
Figure 54:
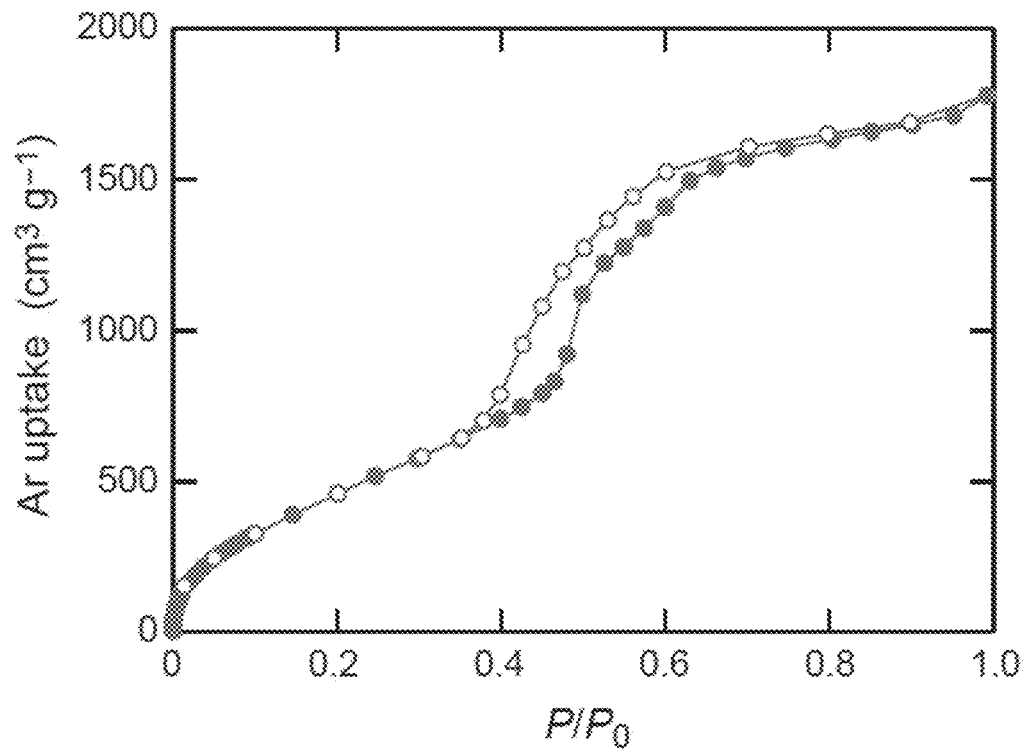
FIG. 54 provides an Ar isotherm of IRMOF-74-VII at 87 K. Filled and open symbols represent adsorption and desorption branches, respectively. The connecting curve is presented as a visual guide.
Figure 55:
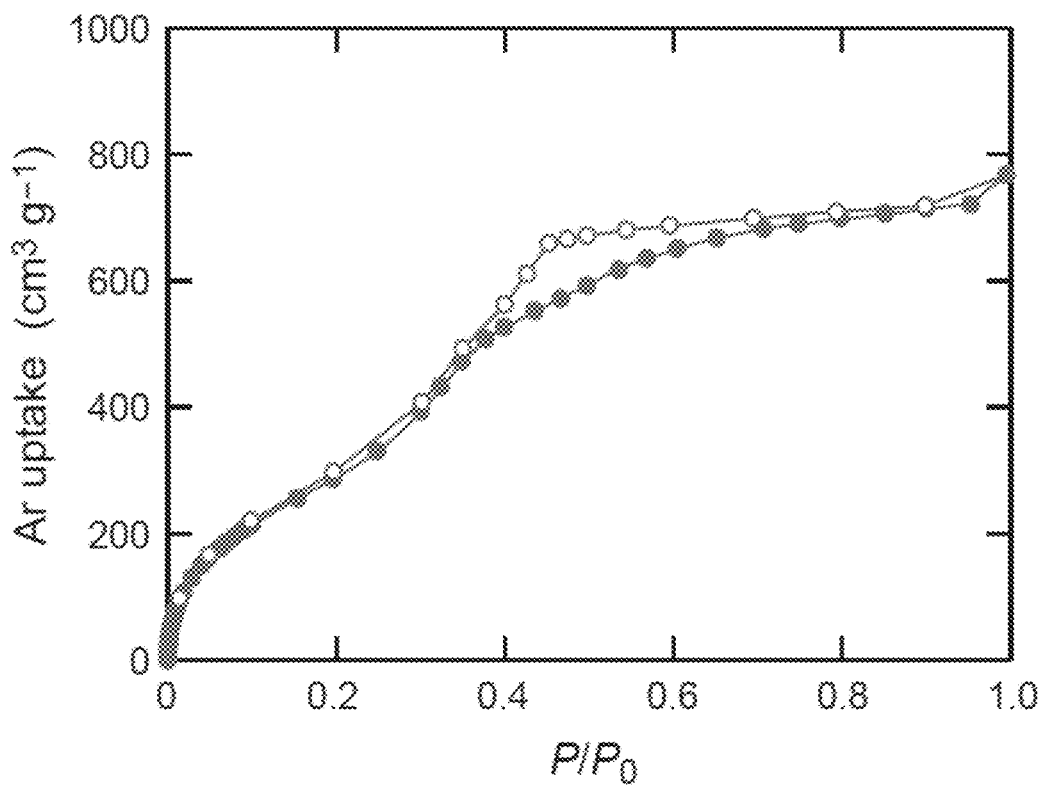
FIG. 55 provides an Ar isotherm of IRMOF-74-VII-oeg at 87 K. Filled and open symbols represent adsorption and desorption branches, respectively. Connecting curve is guide for eye.
Figure 56:
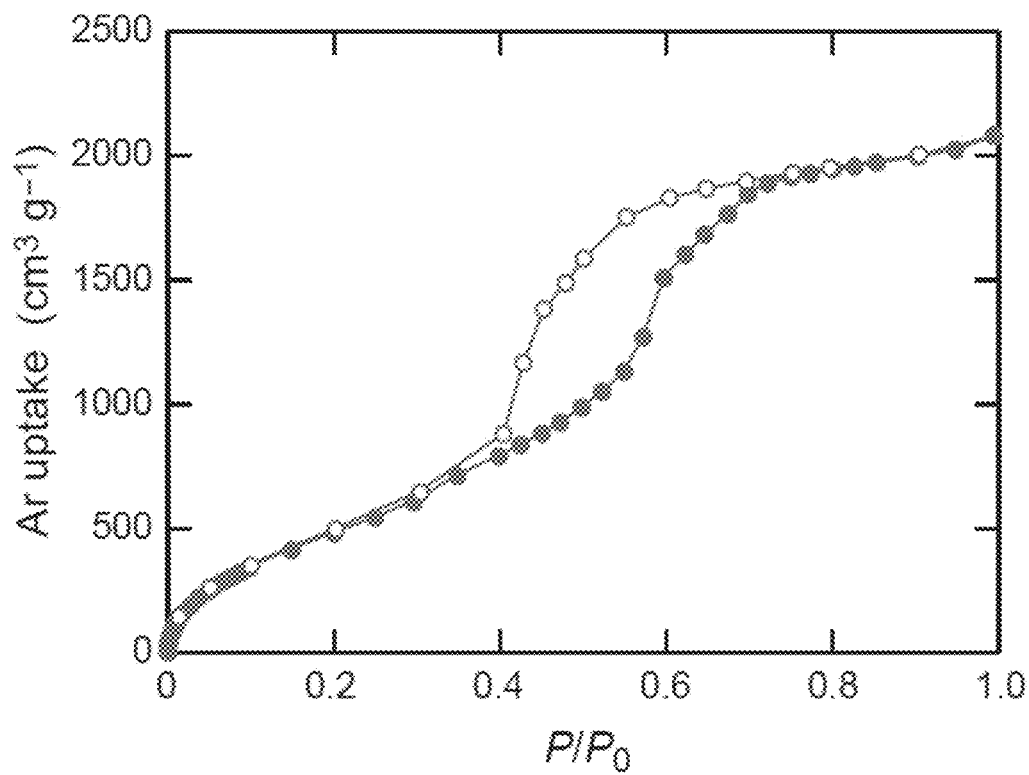
FIG. 56 provides an Ar isotherm of IRMOF-74-IX at 87 K. Filled and open symbols represent adsorption and desorption branches, respectively. The connecting curve is presented as a visual guide.
Figure 57:
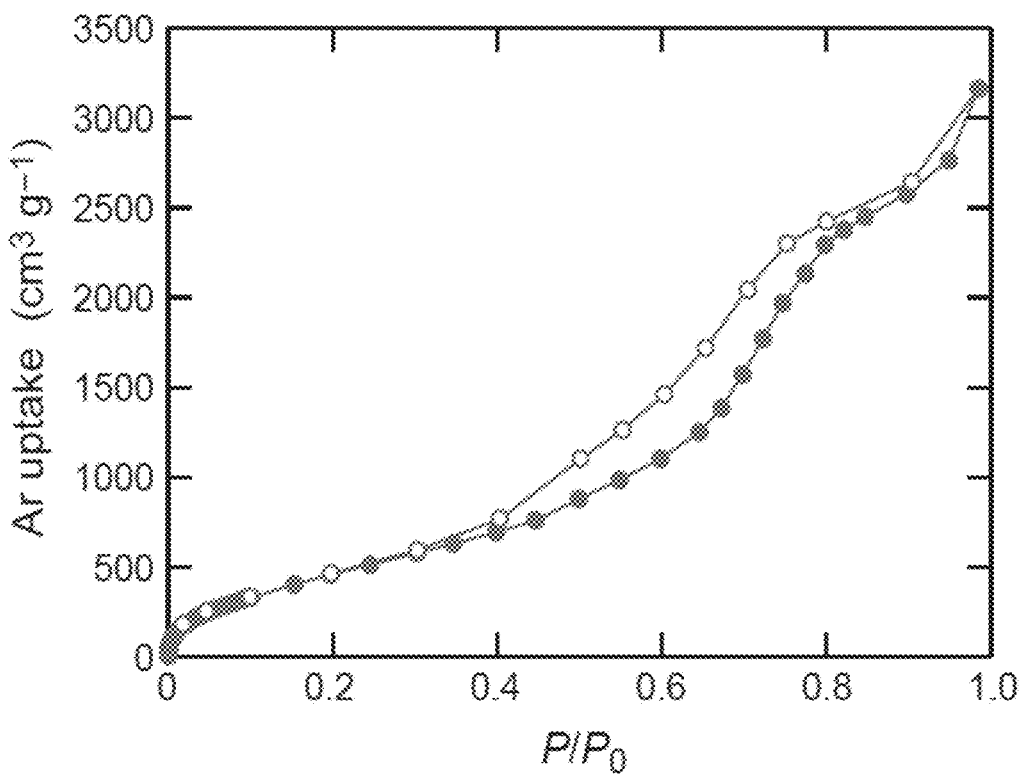
FIG. 57 provides an Ar isotherm of IRMOF-74-XI at 87 K. Filled and open symbols represent adsorption and desorption branches, respectively. The connecting curve is presented as a visual guide.

IRMOF-74-IX was chosen as illustrative example to demonstrate how the use of $^{13}$C CP/MAS NMR to analyze the activation and structural integrity of the IRMOF-74 series. $^{13}$C CP/MAS NMR spectra of the activated IRMOF-74-IX showed resonances at 174.8, 166.1 and 118.6, which were significantly shifted from their original positions of 176.0, 151.7, and 109.4, respectively, in the counterpart organic link spectra (FIG. 46). This indicated both the carboxylic and hydroxyl groups were involved in coordination, the same as observed in the parent IRMOF-74-I as well as the rest of the IRMOFs. Furthermore, no resonances were observed for any methanol or DMF, which were used for activation of the IRMOFs, indicating that IRMOF-74-IX was fully in its guest-free form. The $^{13}$C resonances for both the entire activated IRMOF-74 series and their corresponding free organic links are listed in Table 24.

and pore volume are available. Multiple measurements (≥3 times) were performed on different batches of each IRMOF with various weights, providing reproducible results with ±5% error. Ultrahigh-purity-grade Ar and He gases were used in all adsorption measurements. The Ar (87 K) isotherms were measured using a liquid argon bath (87 K). Ar isotherms of the IRMOFs-74 series is presented in FIGS. 47-57: IRMOF-74-I (FIG. 47); IRMOF-74-II (FIG. 48); IRMOF-74-III (FIG. 49); IRMOF-74-IV (FIG. 50); IRMOF-74-V (FIG. 51); IRMOF-74-V-hex (FIG. 52); IRMOF-74-VI (FIG. 53); IRMOF-74-VII (FIG. 54); IRMOF-74-VII-oeg (FIG. 55); IRMOF-74-IX (FIG. 56); and IRMOF-74-XI (FIG. 57).

A summary of the BET and Langmuir surface areas and pore volumes of IRMOFs is presented in Table 25.

TABLE 25

| | BET SA ($m^2 \cdot g^{-1}$) | Langmuir SA ($m^2 \cdot g^{-1}$) | Pore volume ($cm^3 \cdot g^{-1}$) |
|---|---|---|---|
| IRMOF-74-I | 1350 | 1600 | 0.60 |
| IRMOF-74-II | 2510 | 2940 | 1.04 |
| IRMOF-74-III | 2440 | 3750 | 1.23 |
| IRMOF-74-IV | 2480 | 5370 | 1.60 |
| IRMOF-74-V | 2230 | 6940 | 1.89 |
| IRMOF-74-V-hex | 1680 | 4450 | 1.29 |
| IRMOF-74-VI | 1600 | 5880 | 1.65 |
| IRMOF-74-VII | 1800 | 8320 | 2.12 |

TABLE 24

Summary of $^{13}$C CP/MAS NMR resonances of the IRMOF-74 series and its corresponding organic links.

Compound — Chemical shift δ (ppm)

IRMOFs

| Compound | | | | | | | | | | | | | | |
|---|---|---|---|---|---|---|---|---|---|---|---|---|---|---|
| IRMOF-74-I | 73.0 | 55.7 | 24.9 | | | | | | | | | | | |
| IRMOF-74-II | 74.0 | 66.0 | 42.2 | 32.6 | 19.5 | 18.0 | 14.1 | | | | | | | |
| IRMOF-74-III | 74.4 | 66.2 | 47.8 | 40.7 | 31.5 | 24.8 | 18.9 | 16.6 | 6.6 | | | | | |
| IRMOF-74-IV | 74.4 | 66.0 | 48.2 | 46.8 | 39.3 | 31.6 | 24.6 | 18.7 | 6.9 | | | | | |
| IRMOF-74-V | 73.6 | 66.2 | 48.5 | 39.8 | 31.8 | 24.4 | 17.5 | 6.4 | | | | | | |
| IRMOF-74-V-hex | 74.2 | 67.0 | 47.6 | 41.0 | 39.6 | 37.5 | 31.5 | 24.3 | 18.5 | 0.7 | 8.3 | 1.5 | 7.2 | 1.4 |
| IRMOF-74-VI | 74.5 | 65.9 | 48.3 | 39.9 | 31.8 | 24.2 | 18.7 | 6.6 | | | | | | |
| IRMOF-74-VII | 74.5 | 66.4 | 48.4 | 39.8 | 31.7 | 24.0 | 18.9 | 17.2 | 1.1 | 9.0 | 1.6 | 7.3 | 1.0 | |
| IRMOF-74-VII-oeg | 74.3 | 66.8 | 49.9 | 47.4 | 40.1 | 31.4 | 19.3 | 15.8 | 0.0 | 7.2 | 8.6 | | | |
| IRMOF-74-IX | 74.8 | 66.1 | 48.8 | 47.6 | 40.0 | 37.1 | 31.9 | 24.7 | 18.6 | 1.2 | 9.0 | 1.6 | 7.3 | 0.9 |
| IRMOF-74-XI | 74.8 | 66.6 | 48.0 | 39.9 | 31.8 | 18.5 | 0.0 | 1.6 | 8.5 | 3.3 | 1.6 | | | |

Organic Links

| | | | | | | | | | | | | | | |
|---|---|---|---|---|---|---|---|---|---|---|---|---|---|---|
| Link I | 74.4 | 53.0 | 17.6 | | | | | | | | | | | |
| Link II | 74.7 | 61.9 | 47.7 | 29.3 | 16.0 | 15.3 | 09.0 | | | | | | | |
| Link III | 76.2 | 62.7 | 50.2 | 37.0 | 31.1 | 26.4 | 19.2 | 06.4 | 0.6 | | | | | |
| Link IV | 75.6 | 61.7 | 50.3 | 49.4 | 39.1 | 31.0 | 19.4 | 08.6 | 8.3 | | | | | |
| Link V | 70.2 | 59.3 | 48.0 | 39.8 | 32.6 | 30.8 | 19.7 | 15.2 | 12.2 | 7.6 | | | | |
| Link V-hex | 75.7 | 61.6 | 49.8 | 39.3 | 31.0 | 19.6 | 09.7 | 1.0 | 1.2 | 9.2 | 3.6 | | | |
| Link VI | 75.6 | 61.8 | 49.0 | 39.7 | 32.7 | 31.0 | 18.7 | 09.8 | 7.9 | | | | | |
| Link VII | 75.4 | 61.6 | 49.8 | 39.6 | 31.6 | 18.6 | 09.7 | 0.1 | 1.9 | 8.7 | 3.5 | | | |
| Link VII-oeg | 72.4 | 61.7 | 51.3 | 49.1 | 39.5 | 36.1 | 34.2 | 30.9 | 22.9 | 19.7 | 16.9 | 10.6 | 0.8 | 8.7 .3 |
| Link IX | 76.0 | 61.7 | 50.3 | 39.7 | 37.0 | 31.9 | 19.6 | 09.4 | 3.7 | 0.1 | 2.4 | 8.2 | 3.4 | |
| Link XI | 76.2 | 61.8 | 50.2 | 40.0 | 36.8 | 32.2 | 30.2 | 18.9 | 09.3 | 9.9 | 3.4 | 8.3 | 3.4 | |

Gas Adsorption Measurements

Ar Adsorption Analyses:

Ar isotherms were recorded at 87 K on an Autosorb-1 automatic volumetric gas adsorption analyzer (Quantachrome, Boynton Beach, Fla.) with 50-100 mg of activated IRMOF-74. From the obtained isotherms where the adsorbed amount of gas is plotted to the pressure, specific surface areas of IRMOF-74 are calculated based on the BET and Langmuir models. Additionally, pore size distribution TABLE 25-continued

| | BET SA ($m^2 \cdot g^{-1}$) | Langmuir SA ($m^2 \cdot g^{-1}$) | Pore volume ($cm^3 \cdot g^{-1}$) |
|---|---|---|---|
| IRMOF-74-VII-oeg | 2230 | 3321 | 0.89 |
| IRMOF-74-IX | 1920 | 9410 | 2.51 |
| IRMOF-74-XI | 1760 | 9880 | 3.41 |

Inclusion Studies

General Methods:

Vitamin-$B_{12}$ and myoglobin (from equine heart, ≥90% (SDS-Page), essentially salt-free, lyophilized power) were purchased from Sigma Aldrich Chemical Co. Metal-organic polyhedra (MOP-18) was synthesized and activated according to a previously reported procedure. Methanol (HPLC grade) was purchased from EMD Science. Chloroform (HPLC grade, pentane stabilized) was purchased from Fisher Scientific International Inc. Green fluorescent protein (GFP) (Molecular weight: 27 kDa. sequence: (http:)www.uniprot.org/uniprot/P42212) and 0.1 M phosphate buffer solution (PBS) (pH 7.4). Ultraviolet-visual (UV-Vis) spectrophotometry measurements were performed on a Shimadzu UV1800 using 1 cm Hellma quartz optical cells. Inductively coupled optical emission spectroscopy (ICP-OES) measurements were conducted on a Thermo Jarrell Ash IRIS 1000 ICP-OES. Reference 1000 ppm standard solutions for ICP-OES of Mg, Co, Cu, and Fe were purchased from Fisher Scientific International Inc. Confocal microscopy imaging was performed on a Leica TCS-SP1 Confocal Microscope.

The inclusion of vitamin-$B_{12}$, MOP-18, myoglobin (Mb), and green fluorescent protein (GFP) through the pores aperture of IRMOF-74-IV, IRMOF-74-V, IRMOF-74-VI-Ioeg and IRMOF-74-IX respectively was monitored by absorption spectrophotometric technique. Solutions of vitamin-$B_{12}$ (Sigma Aldrich, ≥98.5%, 0.11 mM in methanol), MOP-18 (synthesized according to previously reported procedures, ref. 30), myoglobin (Sigma Aldrich, from equine heart, ≥90%) and green fluorescent protein (GFP) were prepared in such way that the absorbance was ≤1 at each molecule's characteristic wavelength. In general, 10 mg of the appropriate sized and freshly activated IRMOF-74 was immersed in a solution of the to-be-included species. The supernatant of this solution was extracted and placed in a 1 cm Hellma quartz optical cell and a UV-vis spectrum was recorded from 300 to 800 nm on a Shimadzu, UV1800 spectrophotometer. After each measurement, the solution was returned to the original mixture and this procedure was repeated periodically until absorbance remained constant indicating equilibrium was reached. The observed initial decrease in absorbance indicated inclusion of the molecules by IRMOF-74 crystals. As a control experiment, IRMOFs with pore apertures smaller than the to-be-included species were examined in a similar manner to rule out surface adhesion as the contributing factor to the decrease in absorbance evidenced in the UV-Vis spectrum. These spectral variations were reproducible when different batches were examined. Furthermore, in order to quantify the amount of molecules included within the pores, inductively coupled plasma-optical emission spectroscopy (ICP-OES) measurements were carried out on a Thermo Jarrell Ash IRIS 1000 ICP-OES for the metal containing included molecules. The ratios of [Mg]/[Co] (for $VB_{12} \subset$ IRMOF-74-IV), [Mg]/[Cu] (for MOP-18 $\subset$ IRMOF-74-V) and [Mg]/[Fe] (for Mb $\subset$ IRMOF-74-VIIoeg) were evaluated. The corresponding numbers of included molecules per IRMOF were calculated to be: one molecule of $VB_{12}$ per two unit cells of IRMOF-74-IV, one MOP-18 per six unit cells of IRMOF-74-V, and one Mb per five unit cells of IRMOF-74-VII-oeg.

The inclusion of vitamin-$B_{12}$ (0.11 mM in methanol), MOP-18 (0.01 mM in chloroform), myoglobin (6.6 µM in 0.1 M phosphate buffer), and GFP (3.3 µM in 0.1 M phosphate buffer) was followed by UV-Vis spectrophotometry. The decrease in concentration of these solutions in the presence of IRMOFs indicated their inclusion within the pore. Multiple experiments were carried out using varying concentrations of the to-be-included species and different amounts of IRMOF-74 demonstrating the reproducibility of the inclusion. Control experiments on the IRMOFs with smaller pore apertures or different pore environments ruled out the possibility of surface adhesion or inclusion within intercrystalline regions.

Figure 58:
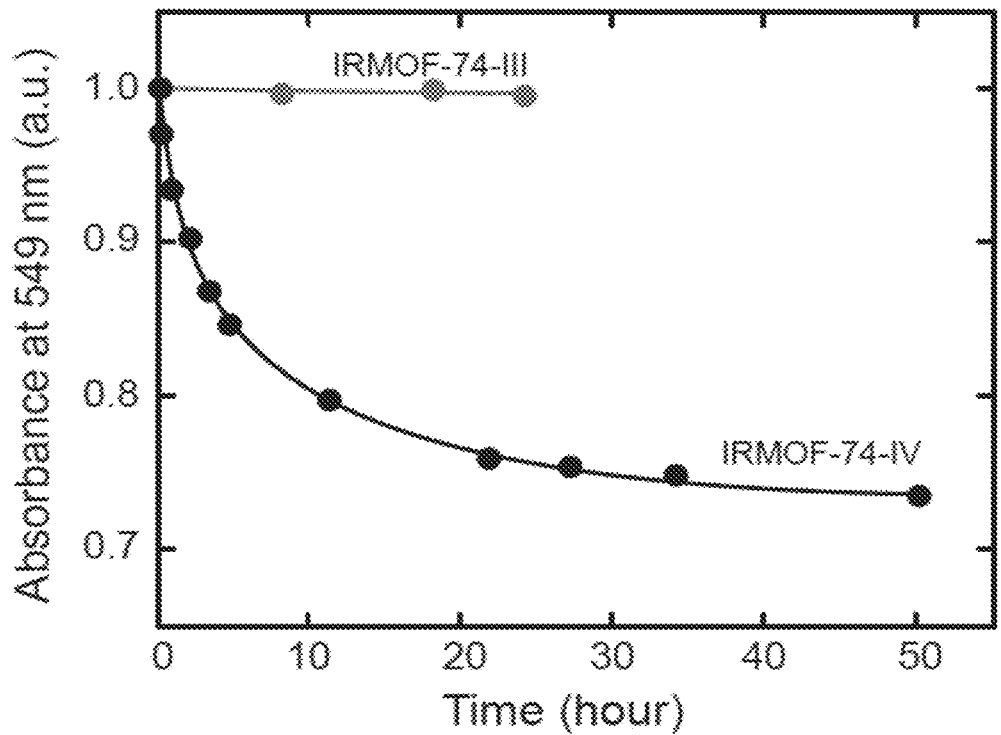
FIG. 58 presents the absorption variation at 549 nm for $VB_{12}$ in the presence of IRMOF-74-IV (black) and IRMOF-74-III (Top) as a function of time. Solvent: methanol; T=25.0(2)° C.; l=1 cm; $[VB_{12}]_0=1.1\times10^{-4}$ M.

Inclusion of Vitamin-$B_{12}$ into IRMOF-74-IV:

The inclusion of vitamin-$B_{12}$ ($VB_{12}$) molecules into IRMOF-74-IV was monitored through UV-Vis spectrophotometry. 10 mg of freshly activated IRMOF-74-IV was added to a solution of $VB_{12}$ ($1.1 \times 10^{-4}$ M) and was stirred at room temperature. 2 mL of the supernatant solution of $VB_{12}$ was extracted, and subsequently analyzed providing a spectrum (300-700 nm). After measuring, the solution was returned to the mixture and this procedure was repeated multiple times over a period of two days. FIG. 58 depicts the decrease in absorbance as a function of time at selected wavelength ($\alpha\beta$ band; $\lambda$=549 nm). The decrease in absorbance is attributed to the inclusion of $VB_{12}$ molecules into the IRMOF and saturation is reached after ~24 h. Moreover, a control experiment was performed on IRMOF-74-III, whose pore aperture is smaller than the size of $VB_{12}$. There was an observable lack of decrease in absorbance, which remained constant for at least 28 h indicating that decrease observed before was not a result of surface adhesion or inclusion within intercrystalline regions.

Figure 59:
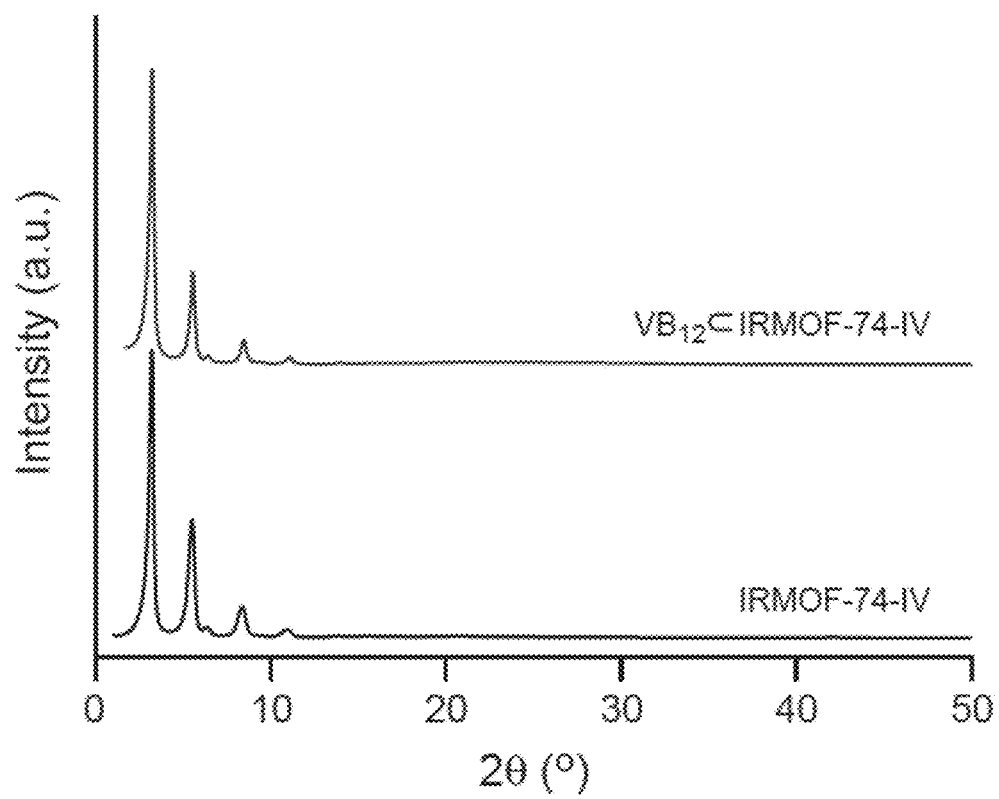
FIG. 59 provides PXRD patterns for IRMOF-74-IV (bottom) and $VB_{12} \subset$ IRMOF-74-IV (top).

Additional experiments of inductively coupled plasma optical emission spectroscopy (ICP-OES) of a washed and dried sample of $VB_{12} \subset$ IRMOF-74-IV resulted in a ratio of [Mg]/[Co]=32. This ratio corresponded to one molecule of $VB_{12}$ per two unit cells of IRMOF-74-IV. This value further supports the fact that the $VB_{12}$ molecules are included within the pore of IRMOF-74-IV. The PXRD recorded (FIG. 59) on the $VB_{12} \subset$ IRMOF-74-IV demonstrates that the crystallinity of the structural framework is maintained after inclusion has occurred.

Figure 60:
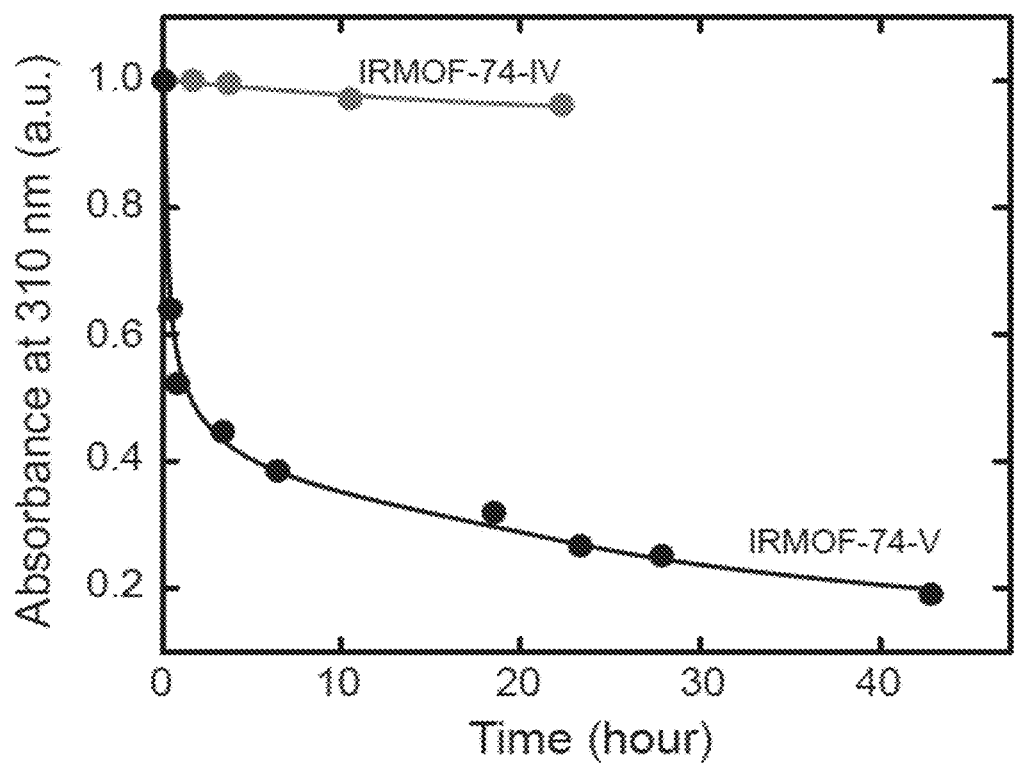
FIG. 60 presents the absorption variation at 310 nm for MOP-18 in the presence of IRMOF-74-IV (top) and IRMOF-74-V (bottom) as a function of time. Solvent: chloroform; T=25.0(2)° C.; l=1 cm; $[MOP-18]_0=1.0\times10^{-5}$ M.

Inclusion of MOP-18 into IRMOF-74-V:

Similar to the procedure described above for $VB_{12}$, the inclusion process of MOP-18 into IRMOF-74-V was performed by using UV-Vis spectrophotometry. The decrease in absorbance of the MOP-18 solution, centered at 310 nm, as a function of time was clearly observed and provides strong evidence for the inclusion process (FIG. 60). The absorbance of MOP-18 solution in the presence of IRMOF-74D, whose pore aperture is smaller than MOP-18, remains relatively constant for more than 35 h (FIG. 60).

Figure 61:
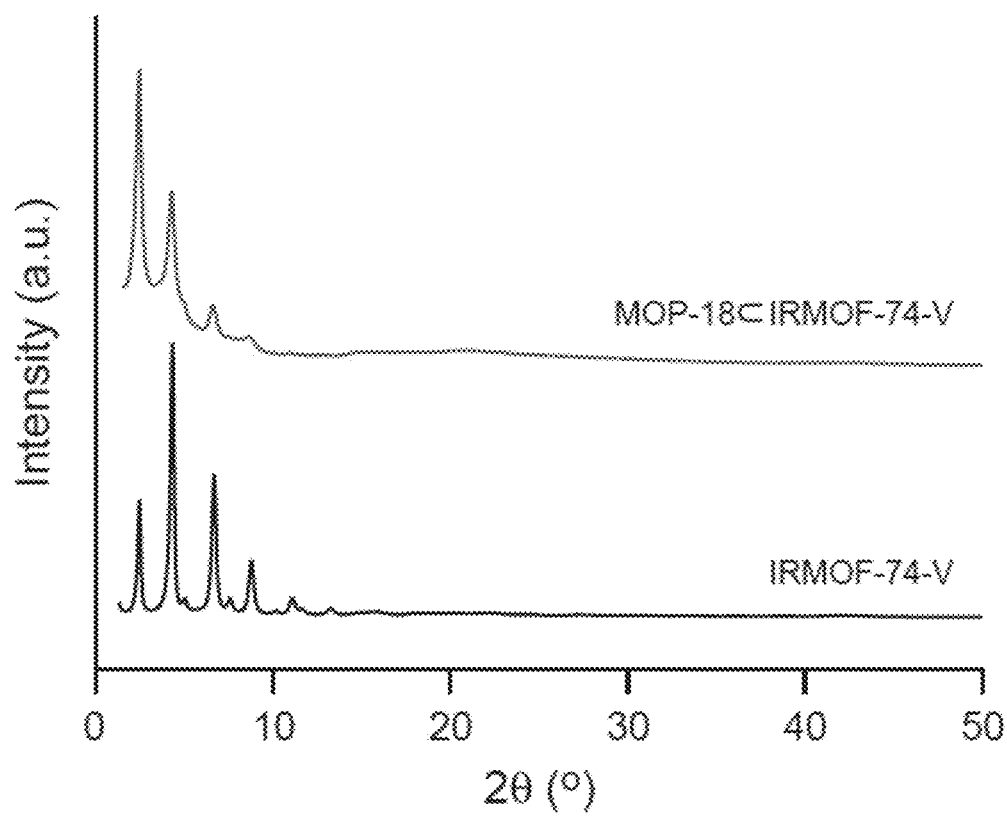
FIG. 61 provides PXRD patterns of IRMOF-74-V (bottom line) and MOP-18 $\subset$ IRMOF-74-V (top line).
Figure 62:
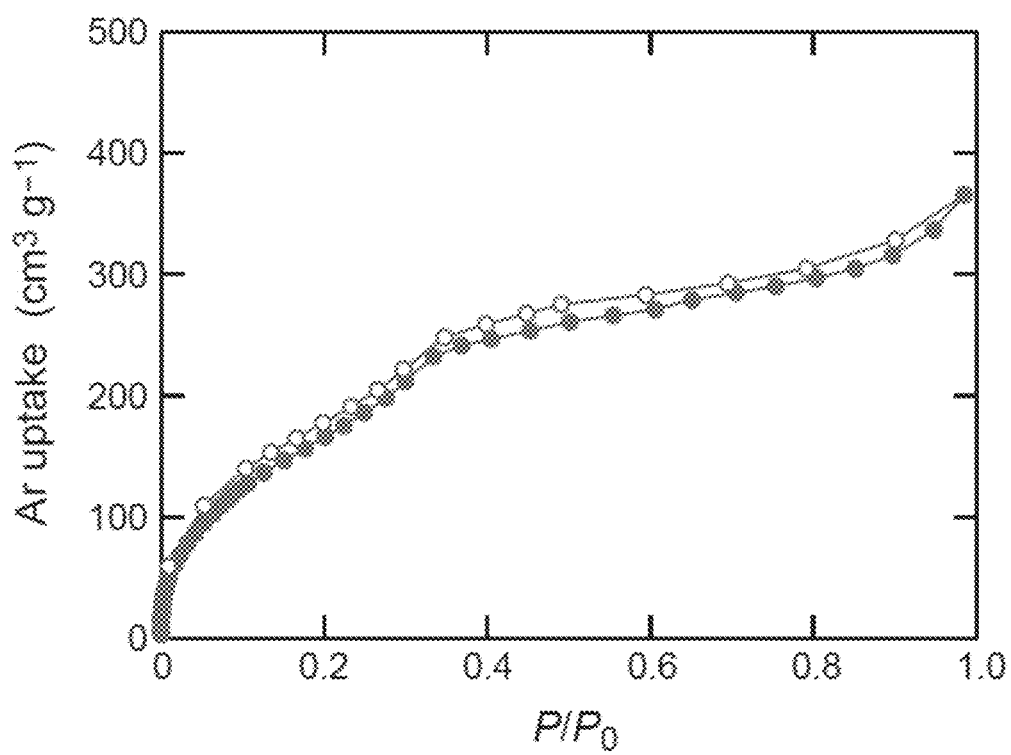
FIG. 62 provides an Ar isotherm of MOP-18 $\subset$ IRMOF-74-V at 87 K.
Figure 63:
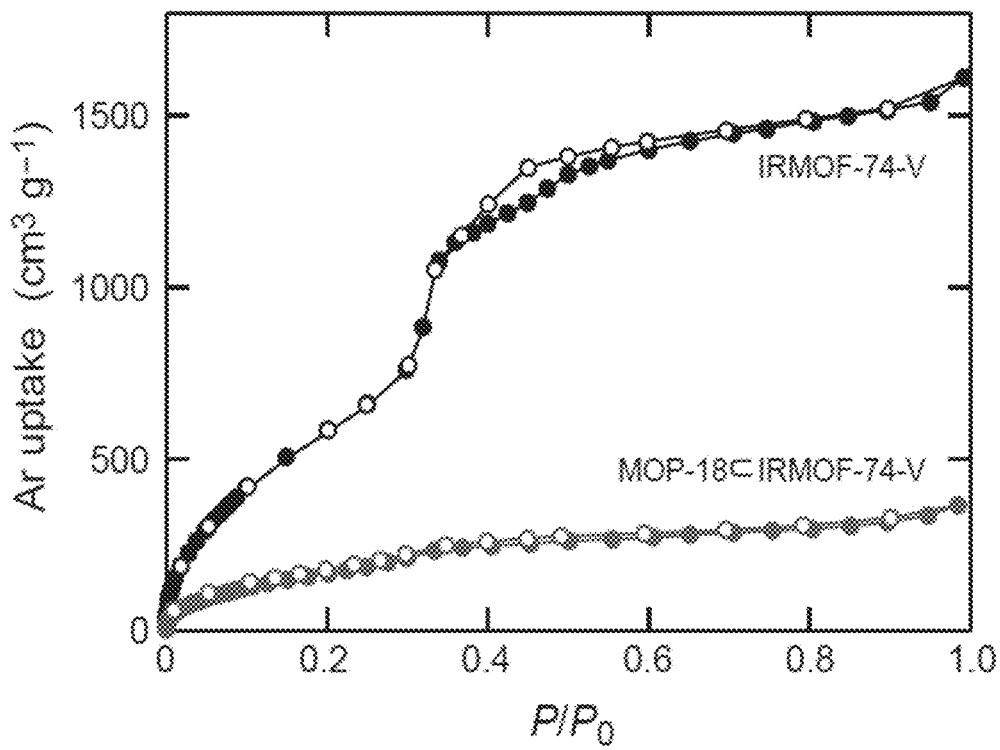
FIG. 63 provides an Ar isotherm overlay of IRMOF-74-V (top) and MOP-18 $\subset$ IRMOF-74-V (bottom) at 87 K.
Figure 64:
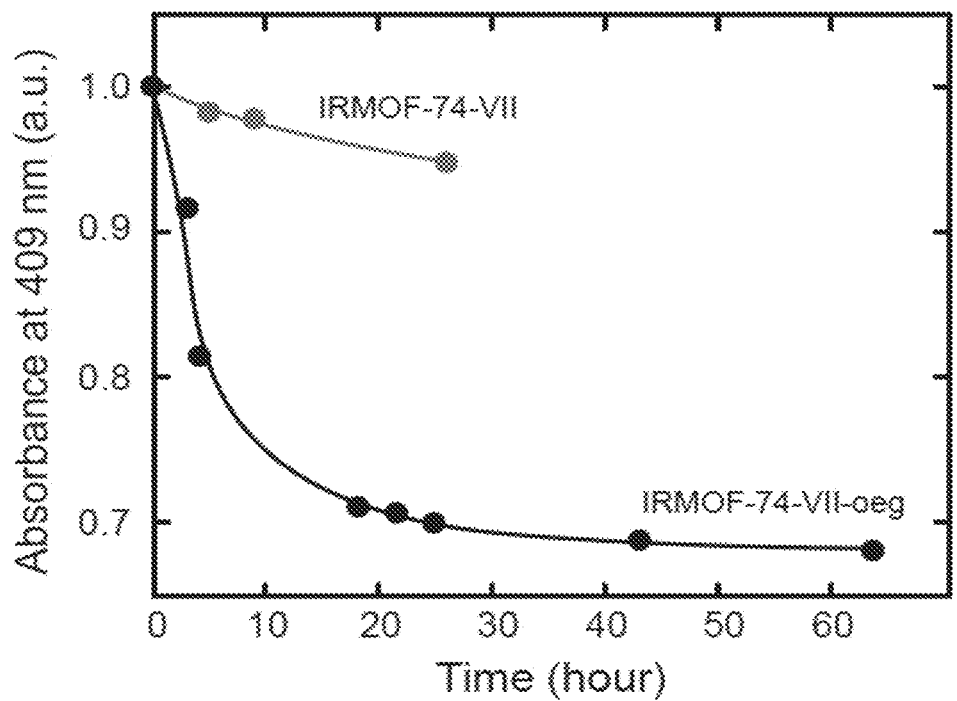
FIG. 64 presents the absorption variation at the Soret band (409 nm) for myoglobin in the presence of IRMOF-74VII-oeg as a function of time. Solvent: PBS; pH=7.4; T=25.0(2)° C.; l=1 cm; $[Mb]_0=6.6\times10^{-6}$ M.

The ICP-OES measurement of the washed and dried MOP-18 $\subset$ IRMOF-74-V sample afforded a ratio [Mg]/[Cu]=5.4 corresponding to one MOP-18 per six unit cells of IRMOF-74-V. Furthermore, the crystallinity of the structural framework is maintained throughout the inclusion process as evidenced by the PXRD recorded for the MOP-18 $\subset$ IRMOF-74-V (FIG. 61). Additionally, an Ar adsorption isotherm at 87K was measured for a dried sample of MOP-18 $\subset$ IRMOF-74-V (FIG. 62). The calculated BET surface area and pore volume decreased from 2230 $m^2 \cdot g^{-1}$ and 1.89 $cm^3 \cdot g^{-1}$ before inclusion, to 580 $m^2 \cdot g^{-1}$ and 0.35 $cm^3 \cdot g^{-1}$ after inclusion, respectively. A downshift in the step pressure, from $P/P_0$=0.33 to $P/P_0$=0.30, indicated a decrease in pore size, which further proves the inclusion of MOP-18 into the pore of IRMOF-74-V (FIG. 63).

Figure 65:
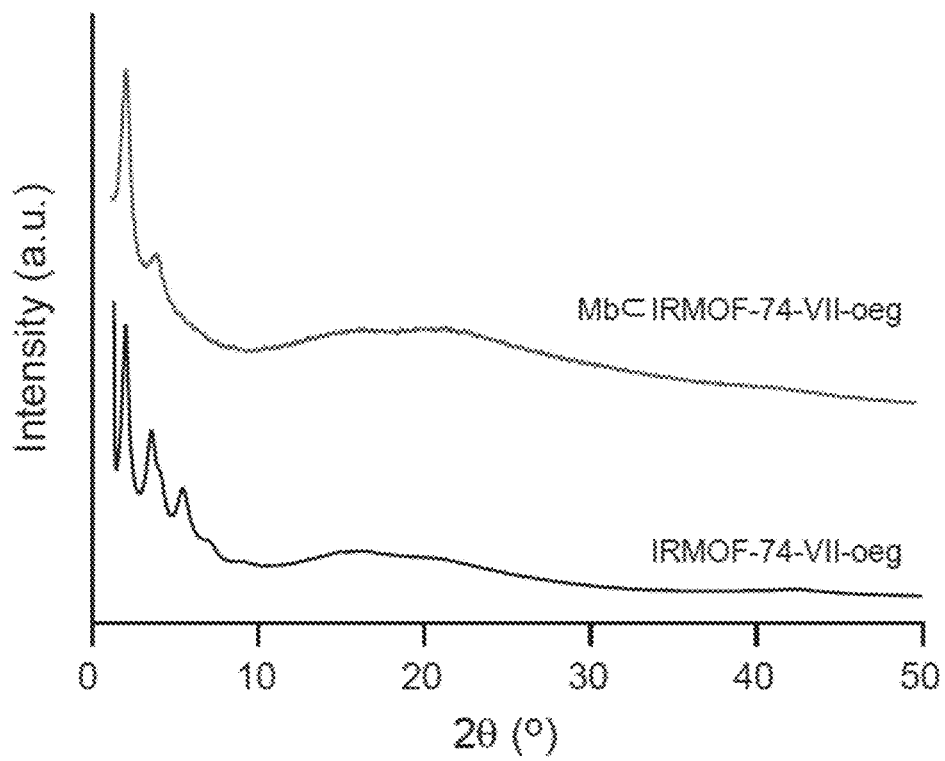
FIG. 65 provides PXRD patterns of IRMOF-74-VII-oeg (bottom) and Mb $\subset$ IRMOF-74-VII-oeg (top).

Inclusion of Myoglobin into IRMOF-74-VII-oeg:

Similar to before, 10 mg of freshly activated IRMOF-74-VII-oeg was added to a solution of myoglobin ($6.6 \times 10^{-6}$ M) that was prepared in a 0.1 M phosphate buffer solution (PBS). This suspension was periodically swirled at room temperature. The UV-Vis spectrum (600-250 nm) of the supernatant was recorded at different time points in order to monitor the decrease of the Soret band at 409 nm. The time to reach saturation was evidenced after ~60 h (FIG. 65). Similar to $VB_{12}$ and MOP-18 inclusion, a control experiment was performed with IRMOF-74-VII-hex, whose pore was tuned to afford a hydrophobic nature. Although, IRMOF-74-VII-hex has a slightly larger pore size than IRMOF-74-VII-oeg, the hydrophobic nature repels the hydrophilic surface of myoglobin resulting in a very slight decrease in absorbance over time. This demonstrates the ability to better tune the pore environment in order to include desired molecules.

Since Mb is comprised of an active site that has Fe, ICP-OES measurements were performed on a washed and dried sample of Mb ⊂ IRMOF-74-VII-oeg. A ratio of [Mg]/[Fe]=84 was determined, corresponding to one Mb per five unit cells of IRMOF-74-VII-oeg. Furthermore, the PXRD pattern recorded for Mb ⊂ IRMOF-74-VII-oeg reveals that the compound retains its crystallinity after the inclusion process (FIG. 65).

Figure 66:
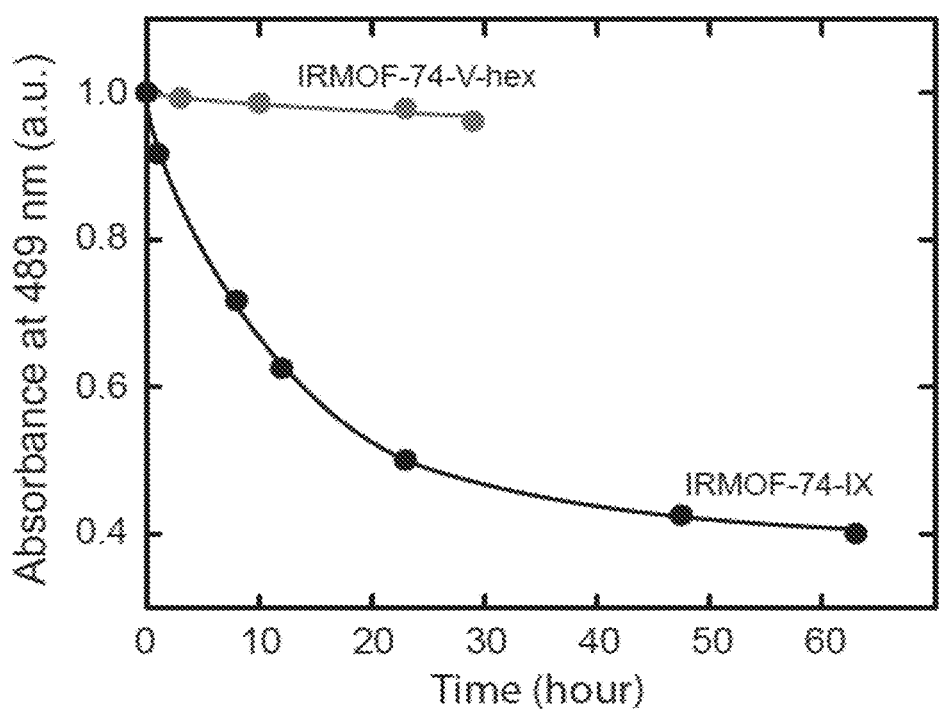
FIG. 66 presents the absorption variation at 489 nm of GFP in the presence of IRMOF-74-IX as a function of time. Solvent: PBS; pH=7.4; T=25.0(2)° C.; l=1 cm; $[GFP]_0=3.3\times10^{-6}$M.

Inclusion of Green Fluorescent Protein into IRMOF-74-IX:

The pore aperture of IRMOF-74-IX is of sufficient size for the inclusion of green fluorescent protein (GFP), which has a characteristic barrel-shaped structure and is highly stable in a wide variety of conditions. Similarly, the inclusion process was monitored by UV-Vis spectrophotometry; the decrease in absorbance of the supernatant at a selected wavelength (489 nm) was monitored and saturation was observed after more than 60 h. A control experiment was also carried out using IRMOF-74-V-hex, whose hydrophobic pore environment is identical to IRMOF-74-IX, albeit smaller. The absorbance of GFP solution in the presence of IRMOF-74-V-hex remains relatively constant for more than 30 h (FIG. 66). As is the case with the rest of the inclusion studies, IRMOF-74-IX maintained its crystallinity throughout the inclusion process as evidenced by the PXRD recorded for the GFP ⊂ IRMOF-74-IX sample (FIG. 67).

The advantageous feature of GFP is that it can emit a visible green fluorescence when it is in its native folded conformation. Therefore, confocal microscopy was employed to investigate whether GFP has undergone any conformational changes to its secondary structure when included within IRMOF-74-IX. Before scanning the GFP ⊂ IRMOF-74-IX, the sample was washed with fresh PBS until the supernatant was colorless in order to fully remove the surface adsorbed GFP. The obtained images of IRMOF-74-IX and GFP ⊂ IRMOF-74-IX are presented in FIG. 68. GFP ⊂ IRMOF-74-IX particles show an intense green luminescence indicating that the inclusion process has occurred without denaturation of the protein.

A number of embodiments of the disclosure have been described. Nevertheless, it will be understood that various modifications may be made without departing from the spirit and scope of the disclosure. Accordingly, other embodiments are within the scope of the following claims.

What is claimed is:

1. A composition comprising a pharmaceutically active agent and a MOF or IRMOF comprising the general structure M-L-M, wherein M comprises a metal and L is a linking moiety of Formula I:

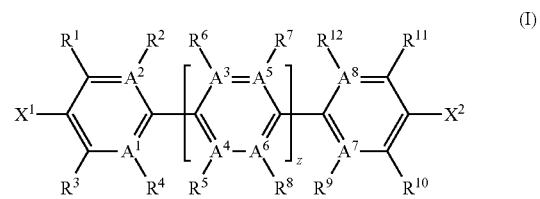

wherein,
$A^1$-$A^8$ are independently either N or C;
$X^1$ and $X^2$ are functional groups (FG);
$R^1$-$R^{12}$ are independently selected from the group comprising H, FG, $(C_1$-$C_{12})$alkyl, substituted $(C_1$-$C_{12})$ alkyl, $(C_1$-$C_{12})$alkenyl, substituted $(C_1$-$C_{12})$alkenyl, $(C_1$-$C_{12})$alkynyl, substituted $(C_1$-$C_{12})$alkynyl, hetero-$(C_1$-$C_{12})$alkyl, substituted hetero-$(C_1$-$C_{12})$alkyl, hetero-$(C_1$-$C_{12})$alkenyl, substituted hetero-$(C_1$-$C_{12})$alkenyl, hetero-$(C_1$-$C_{12})$alkynyl, substituted hetero-$(C_1$-$C_{12})$alkynyl, $(C_1$-$C_{12})$cycloalkyl, substituted $(C_1$-$C_{12})$ cycloalkyl, aryl, substituted aryl, heterocycle, substituted heterocycle, —$C(R^{13})_3$, —$CH(R^{13})_2$, —$CH_2R^{13}$, —$C(R^{13})_3$, —$CH(R^{14})_2$, —$CH_2R^{14}$, —$OC(R^{13})_3$, —$OCH(R^{13})_2$, —$OCH_2R^{14}$, —$OC(R^{14})_3$, —$OCH(R^{14})_2$, —$OCH_2(R^{14})$,

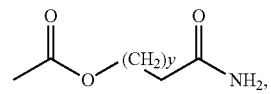

wherein $R^1$ and $R^2$ are linked together to form a substituted or unsubstituted ring selected from the group comprising cycloalkyl, aryl and heterocycle, and wherein $R^3$ and $R^4$ are linked together to form a substituted or unsubstituted ring selected from the group comprising cycloalkyl, aryl and heterocycle;
$R^{13}$ is selected from the group comprising FG, $(C_1$-$C_{12})$ alkyl, $(C_1$-$C_{12})$substituted alkyl, $(C_1$-$C_{12})$alkenyl, substituted $(C_1$-$C_{12})$alkenyl, $(C_1$-$C_{12})$alkynyl, substituted $(C_1$-$C_{12})$alkynyl, hetero-$(C_1$-$C_{12})$alkyl, substituted hetero-$(C_1$-$C_{12})$alkyl, hetero-$(C_1$-$C_{12})$alkenyl, substituted hetero-$(C_1$-$C_{12})$alkenyl, hetero-$(C_1$-$C_{12})$alkynyl, substituted hetero-$(C_1$-$C_{12})$alkynyl, hemiacetal, hemiketal, acetal, ketal, and orthoester;
$R^{14}$ is one or more substituted or unsubstituted rings selected from the group comprising cycloalkyl, aryl, and heterocycle;
y is a number from 0 to 3;
z is a number from 0 to 20; and
with the proviso that R is absent when bound to an A that is N; and
wherein the pharmaceutically active agent is located with pores of the MOF or IRMOF.

2. The composition of claim 1, wherein M is either a transition metal or an alkaline earth metal.

3. The composition of claim 1, wherein M is either Mg or Zn.

4. The composition of claim 3, wherein $X^1$ and $X^2$ are carboxylic acids.

5. The composition of claim 4, wherein $A^1$-$A^8$ are C.

6. The composition of claim 5, wherein
$R^1$ and $R^{10}$ are hydroxyls;
$R^2$-$R^5$, $R^7$, $R^9$, $R^{11}$ and $R^{12}$ are hydrogen; and
$R^6$ and $R^8$ are selected from the group consisting of $(C_1$-$C_{12})$alkyl, $(C_1$-$C_{12})$alkenyl, substituted $(C_1$-$C_{12})$ alkenyl, $(C_1$-$C_{12})$alkynyl, substituted $(C_1$-$C_{12})$alkynyl, hetero-$(C_1$-$C_{12})$alkyl, substituted hetero-$(C_1$-$C_{12})$alkyl, hetero-$(C_1-C_{12})$alkenyl, substituted hetero-$(C_1-C_{12})$alkenyl, hetero-$(C_1-C_{12})$alkynyl, and substituted hetero-$(C_1-C_{12})$alkynyl.

7. The composition of claim 6, wherein $R^6$ and $R^8$ are $(C_1-C_6)$alkyls.

8. The composition of claim 7, wherein z is a number from 1 to 15.

9. The composition of claim 1, wherein the MOF or IRMOF further comprises a post-framework reactant.

10. The composition of claim 9, wherein the post-framework reactant decreases the hydrophobicity of the framework.

11. The composition of claim 1, wherein at least one linking moiety comprises Formula I(a):

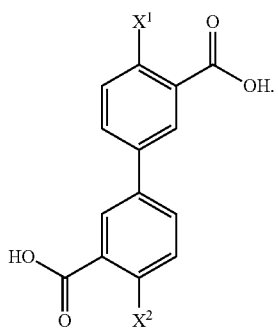

Formula I(a)

12. A composition comprising a pharmaceutically active agent and a MOF or IRMOF having the general structure M-L-M, wherein the pharmaceutically active agent is present in pores of the MOF or IRMOF, wherein M comprises a metal and L is a linking moiety, and wherein at least one linking moiety comprises Formula IV(a):

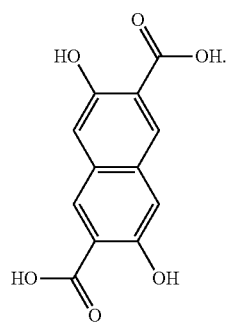

Formula IV(a)

13. A composition comprising a pharmaceutically active agent and a MOF or IRMOF having the general structure M-L-M, wherein the pharmaceutically active agent is present in pores of the MOF or IRMOF, wherein M comprises a metal and L is a linking moiety, and wherein at least one linking moiety comprises Formula IV(b):

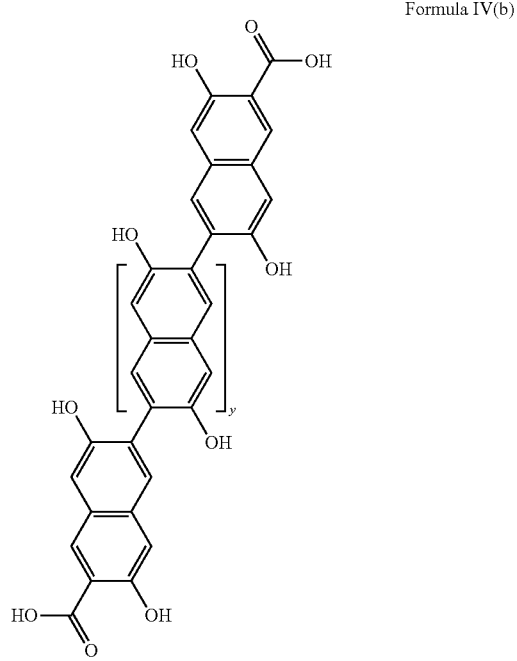

Formula IV(b)

wherein, y is a number from 0 to 20.

14. The composition of claim 1, wherein the pharmaceutically active agent is selected from the group consisting of a protein, a drug and a gas.

15. The composition of claim 12, wherein the pharmaceutically active agent is selected from the group consisting of a protein, a drug and a gas.

16. The composition of claim 13, wherein the pharmaceutically active agent is selected from the group consisting of a protein, a drug and a gas.

* * * * *